US010513694B2

(12) United States Patent
Duellman et al.

(10) Patent No.: US 10,513,694 B2
(45) Date of Patent: Dec. 24, 2019

(54) THIENOPYRROLE COMPOUNDS AND USES THEREOF

(71) Applicant: PROMEGA CORPORATION, Madison, WI (US)

(72) Inventors: Sarah Duellman, Fitchburg, WI (US); Matthew B. Robers, Madison, WI (US); Joel R. Walker, San Luis Obispo, CA (US); Wenhui Zhou, San Luis Obispo, CA (US); Chad Zimprich, Stoughton, WI (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

(21) Appl. No.: 15/192,420

(22) Filed: Jun. 24, 2016

(65) Prior Publication Data

US 2016/0376568 A1 Dec. 29, 2016

Related U.S. Application Data

(60) Provisional application No. 62/206,525, filed on Aug. 18, 2015, provisional application No. 62/184,714, filed on Jun. 25, 2015.

(51) Int. Cl.
C07D 493/04 (2006.01)
C07D 495/04 (2006.01)
C07D 209/42 (2006.01)
C12N 9/02 (2006.01)
C12Q 1/66 (2006.01)
G01N 33/58 (2006.01)
C07D 207/34 (2006.01)
C07D 491/048 (2006.01)
C07K 5/093 (2006.01)
G01N 33/542 (2006.01)
C07K 5/02 (2006.01)

(52) U.S. Cl.
CPC ......... C12N 9/0069 (2013.01); C07D 207/34 (2013.01); C07D 209/42 (2013.01); C07D 491/048 (2013.01); C07D 493/04 (2013.01); C07D 495/04 (2013.01); C07K 5/0222 (2013.01); C07K 5/0819 (2013.01); C12Q 1/66 (2013.01); C12Y 113/12007 (2013.01); G01N 33/542 (2013.01); G01N 33/581 (2013.01)

(58) Field of Classification Search
CPC .. C07D 209/42; C07D 491/04; C07D 493/04; C07D 495/04
See application file for complete search history.

(56) References Cited

U.S. PATENT DOCUMENTS

| 4,981,975 A | 1/1991 | Spang et al. |
| 5,340,801 A | 8/1994 | Ewing et al. |
| 5,814,471 A * | 9/1998 | Wood ............ C12N 9/0069 435/184 |
| 8,557,970 B2 | 10/2013 | Encell et al. |
| 8,669,103 B2 | 3/2014 | Binkowski et al. |
| 2008/0248511 A1 | 10/2008 | Daily et al. |
| 2012/0107849 A1 | 5/2012 | Klaubert et al. |
| 2012/0117667 A1 | 5/2012 | Klaubert et al. |
| 2013/0130289 A1 | 5/2013 | Benink et al. |
| 2015/0212078 A1 | 7/2015 | Zhou et al. |
| 2015/0307916 A1 | 10/2015 | Zhou et al. |
| 2016/0355523 A1 | 12/2016 | Levin et al. |

FOREIGN PATENT DOCUMENTS

| WO | WO 93/20099 | 10/1993 |
| WO | 03/044014 | 5/2003 |
| WO | 2003/040100 A1 | 5/2003 |
| WO | 2005/110410 | 11/2005 |
| WO | WO 2006055951 A2 | 5/2006 |
| WO | WO 2007054453 A2 | 5/2007 |
| WO | 2007/088277 | 8/2007 |
| WO | 2008/118445 | 10/2008 |
| WO | WO 2009000878 A1 | 12/2008 |
| WO | 2009/046165 | 4/2009 |
| WO | 2010/118208 | 10/2010 |
| WO | 2011/100359 | 8/2011 |
| WO | 2014/052653 | 4/2014 |
| WO | 2015/067302 A1 | 5/2015 |
| WO | 2016/210294 A1 | 12/2016 |
| WO | 2018/125992 A1 | 7/2018 |

OTHER PUBLICATIONS

Document No. 156:302194, retrieved from STN; entered in STN on Dec. 22, 2011.*
Document No. 155:115659, retrieved from STN; entered in STN on May 26, 2011.*
Document No. 151:51014, retrieved from STN; entered in STN on Apr. 23, 2009.*
Docujment No. 140:357208, retrieved from STN; entered in STN on May 3, 2004.*
Barrett, et al. Document No. 139:94263, retrieved from STN; entered in STN on Jul. 4, 2003.*
Langley et al., "Molecular Basis of beta-Galactosidase alpha-Complementation," PNAS 72:1254-1257 (1975).
Levit and Berger, "Ribonuclease S-Peptide, a Model for Molecular Recognition," J. Biol. Chem. 251:1333-1339 (1976).
Nazare et al., "Fragment Deconstruction of Small, Potent Factor Xa Inhibitors: Exploring the Superadditivity Energetics of Fragment Linking in Protein-Ligand Complexes", Angewandte Chemie International Edition, vol. 51, No. 4, Jan. 23, 2012, pp. 905-911.
Nisha et al., "Profiling 976 ToxCast Chemicals across 331 Enzymatic and Receptor Signaling Assays", XP002760866, retrieved from STN Database accession No. 2013:631295, Chemical Research in Toxicology , 26(6), pp. 878-895.
Beija et al., "Synthesis and applications of Rhodamine derivatives as fluorescent probes," Chem. Soc. Rev., 2009, 38, 2410-2433.

(Continued)

Primary Examiner — Shawquia Jackson
(74) Attorney, Agent, or Firm — Casimir Jones, S.C.; Anne M. Reynolds

(57) ABSTRACT

Thienopyrrole compounds that may inhibit *Oplophorus*-derived luciferases are disclosed, as well as compositions and kits comprising the thienopyrrole compounds, and methods of using the thienopyrrole compounds.

25 Claims, 36 Drawing Sheets

Specification includes a Sequence Listing.

(56) References Cited

OTHER PUBLICATIONS

Kvach et al., "Practical Synthesis of Isomerically Pure 5- and 6-Carboxytetramethylrhodamines, Useful Dyes for DNA Probes," Bioconjugate Chem. 2009, 20, 1673-1682.
Yu et al., "From Spirolactam Mixtures to Regioisomerically Pure 5- and 6-Rhodamines: A Chemodosimeter-Inspired Strategy," Org. Lett., 2012, 14 (8), pp. 2014-2017.
International Search Report and Written Opinion for Application No. PCT/US2016/039307 dated Sep. 14, 2016 (16 pages).
Hall et al., "Engineered Luciferase Reporter from a Deep Sea Shrimp Utilizing a Novel Imidazopyrazinone Substrate," ACS Chemical Biology, 2012, 7(11):1848-1857.
Lai et al., "Induced protein degradation: an emerging drug discovery paradigm," Nature Reviews Drug Discovery, 2017, 16(2):101-114.
Schena et al., "Modulating protein activity using tethered ligands with mutually exclusive biding sites," Nature Communications 6, 2015, Article No. 7830.
Walker et al., "Highly Potent Cell-Permeable and Impermeable NanoLuc Luciferase Inhibitors," ACS Chemical Biology, 2017, 12(4):1028-1037.
Yamaguchi et al., "Turn-ON fluorescent affinity labeling using a small bifunctional O-nitrobenzoxadiazole unit," Chemical Science, 2014, 5, 1021-1029.
International Search Report and Written Opinion for Application No. PCT/US2017/068686 dated Mar. 22, 2018 (14 pages).

\* cited by examiner

A

WZ141-89

| [inhibitor] | 15 min | 1.5 hr | 3 hr |
|---|---|---|---|
| | | RLU | |
| 100 μM | 9199 | 39835 | 78109 |
| 50 μM | 12384 | 43739 | 78050 |
| 25 μM | 14868 | 48293 | 86555 |
| 12.5 μM | 15802 | 45203 | 76954 |
| 7.25 μM | 16667 | 47168 | 83983 |
| 3.6 μM | 19679 | 53187 | 86724 |
| 1.8 μM | 20849 | 54163 | 88151 |
| 0 | 23061 | 54281 | 84519 |

B

WZ141-90

| [inhibitor] | 15 min | 1.5 hr | 3 hr |
|---|---|---|---|
| | | RLU | |
| 100 μM | 12525 | 41624 | 72121 |
| 50 μM | 13879 | 40551 | 69451 |
| 25 μM | 15885 | 41834 | 67746 |
| 12.5 μM | 17152 | 42802 | 68130 |
| 7.25 μM | 18265 | 44364 | 70010 |
| 3.6 μM | 18786 | 45342 | 70609 |
| 1.8 μM | 19968 | 48547 | 74874 |
| 0 | 21272 | 49474 | 75982 |

C

WZ141-91

| [inhibitor] | 15 min | 1.5 hr | 3 hr |
|---|---|---|---|
| | | RLU | |
| 100 μM | 14121 | 50681 | 90633 |
| 50 μM | 15454 | 48267 | 82610 |
| 25 μM | 17075 | 47086 | 80557 |
| 12.5 μM | 17805 | 47103 | 78131 |
| 7.25 μM | 18562 | 46951 | 77770 |
| 3.6 μM | 19657 | 48447 | 79251 |
| 1.8 μM | 19120 | 48316 | 80070 |
| 0 | 20326 | 49779 | 80791 |

FIGS. 6A-6C

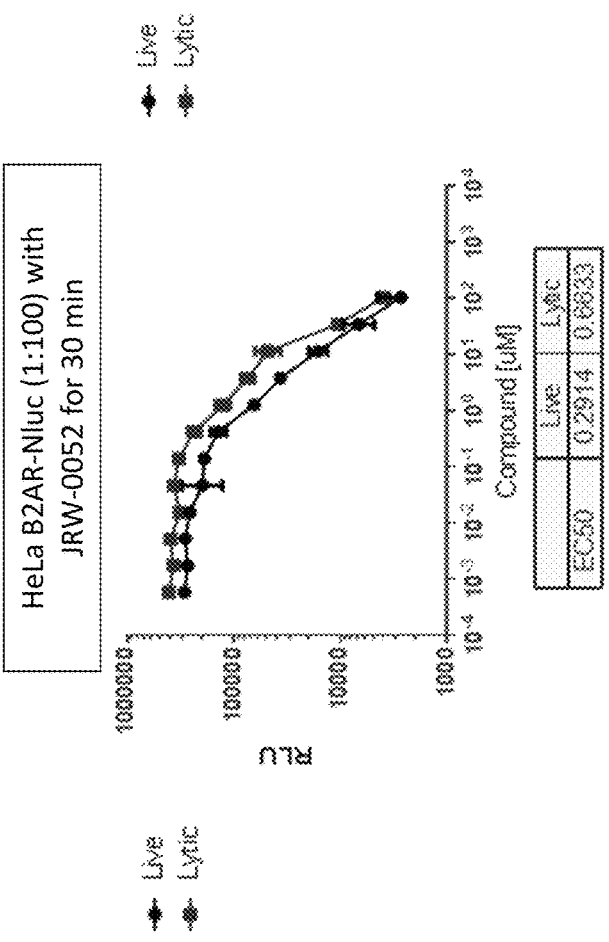
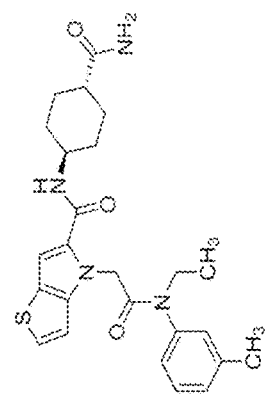
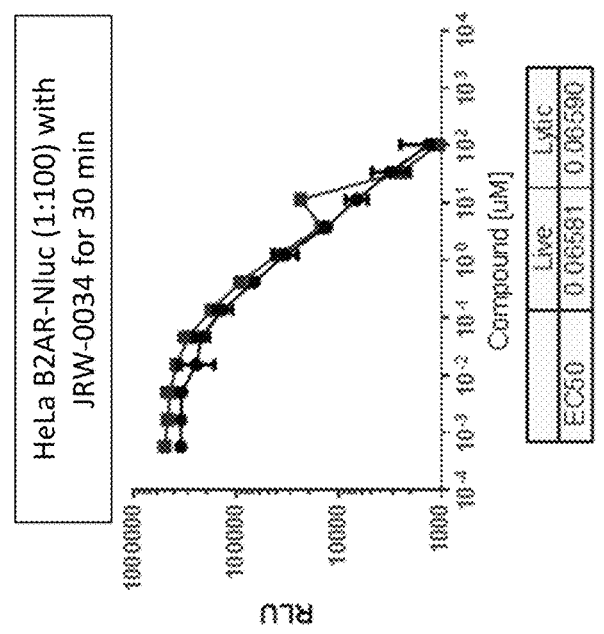
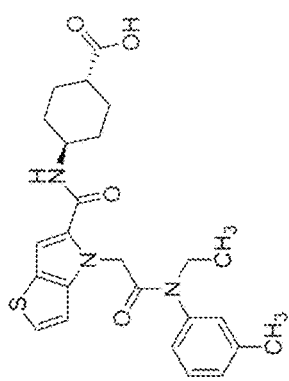
FIGS. 9C-9D

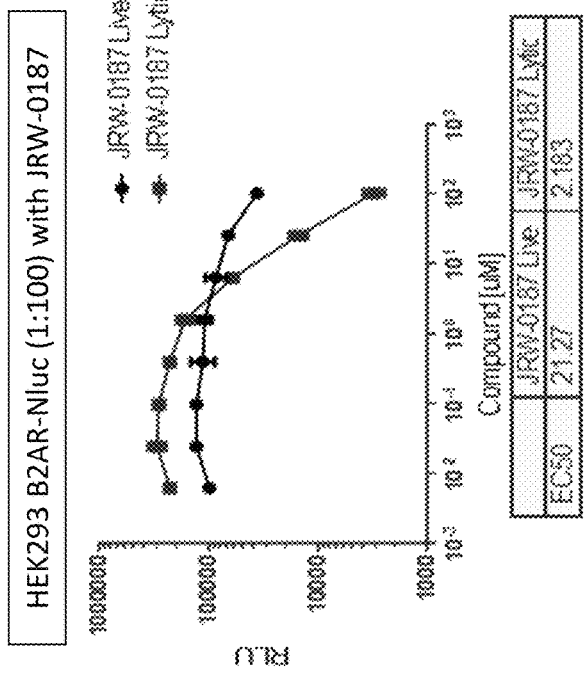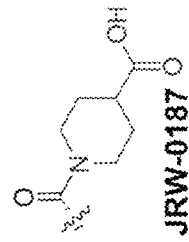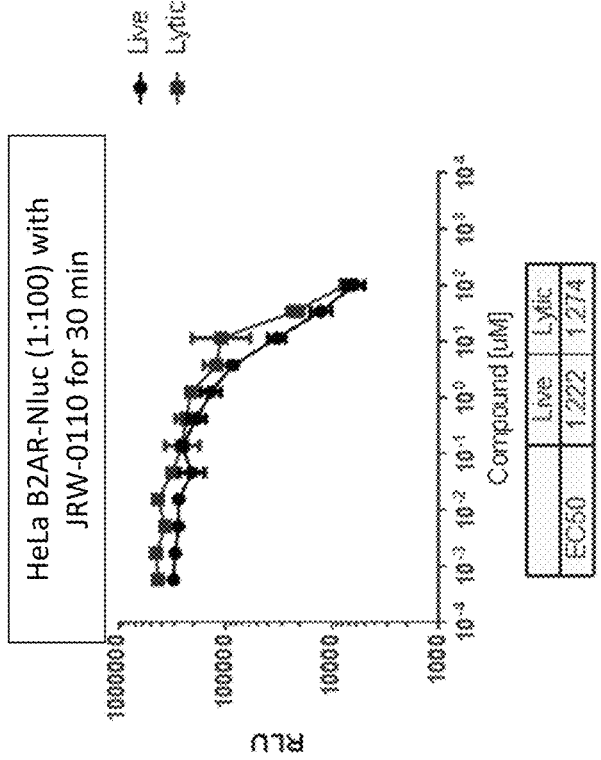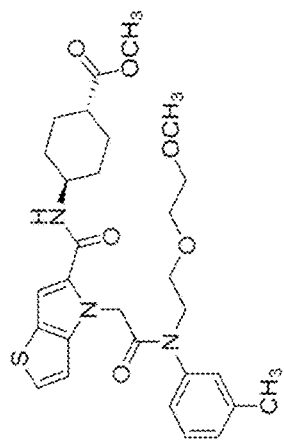
FIGS. 9E-9F

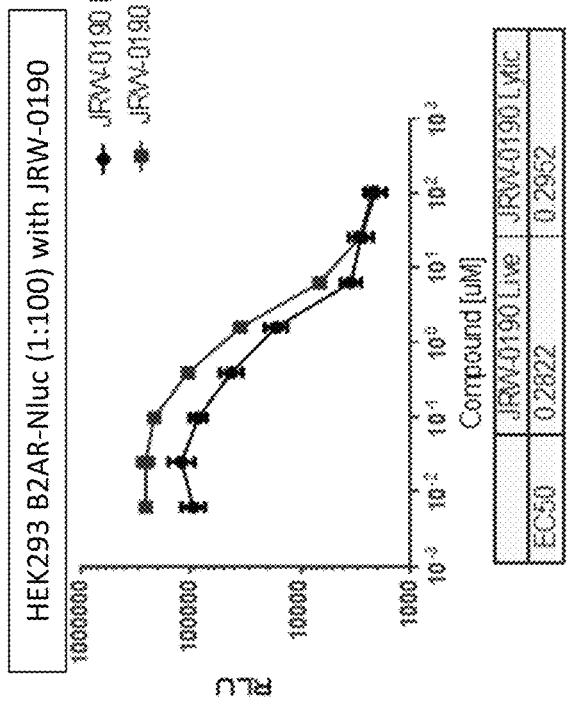
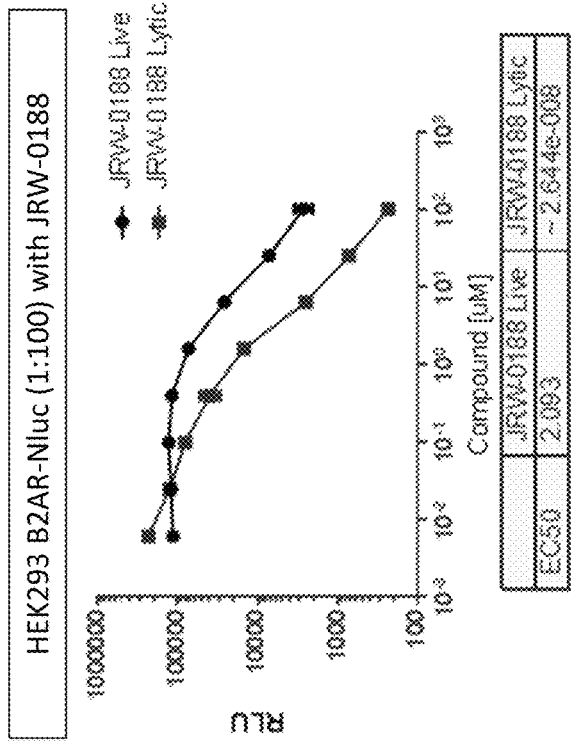
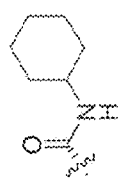
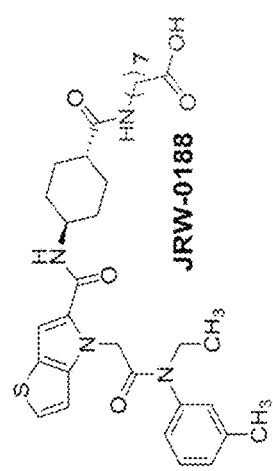
FIGS. 10A-10B

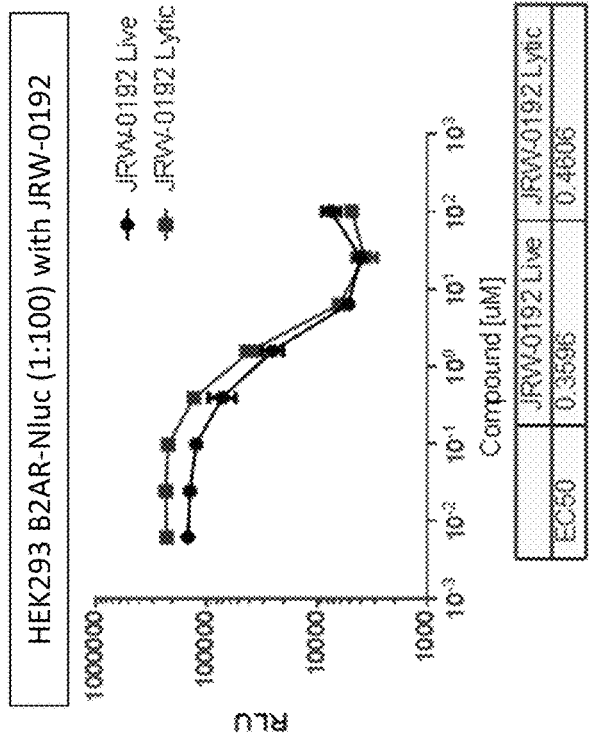
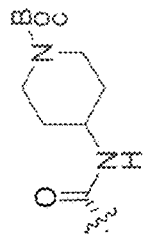
JRW-0192
D
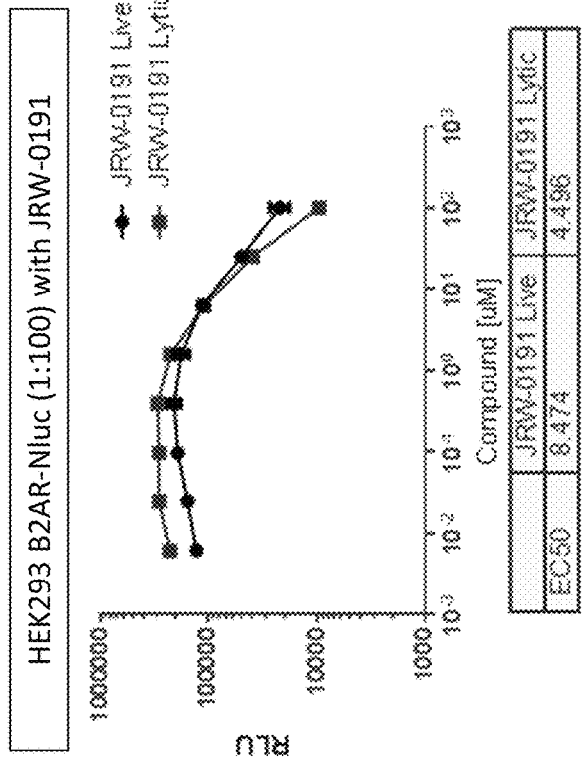
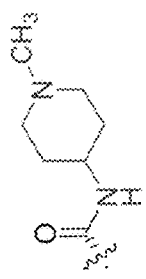
JRW-0191
C
FIGS. 10C-10D

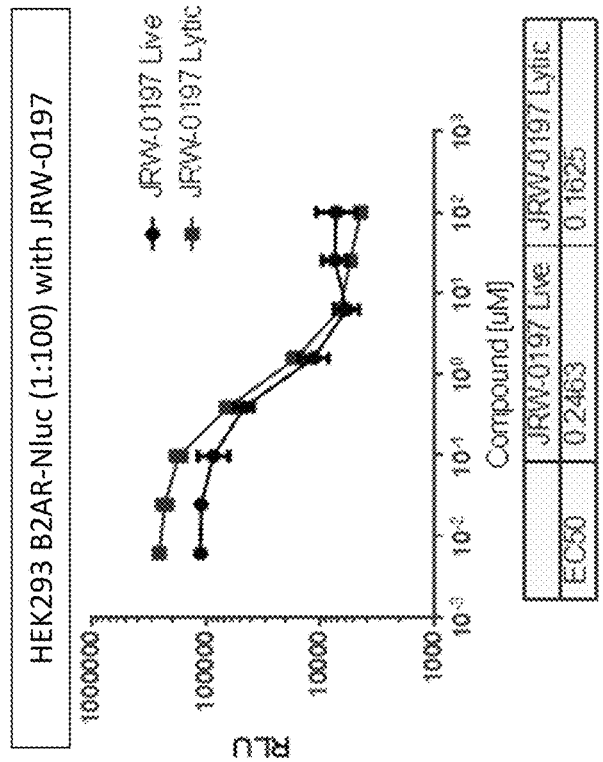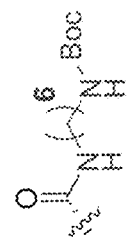
JRW-0197
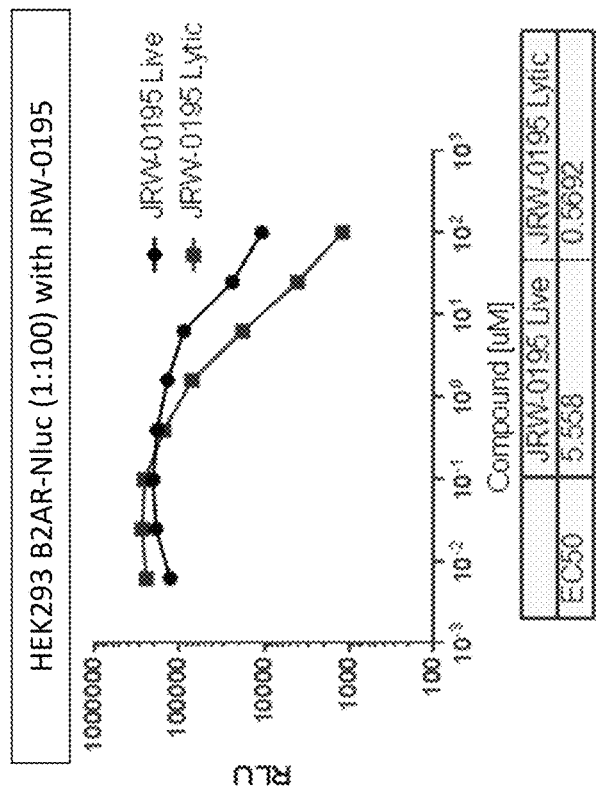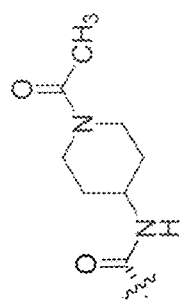
JRW-0195
FIGS. 10E-10F

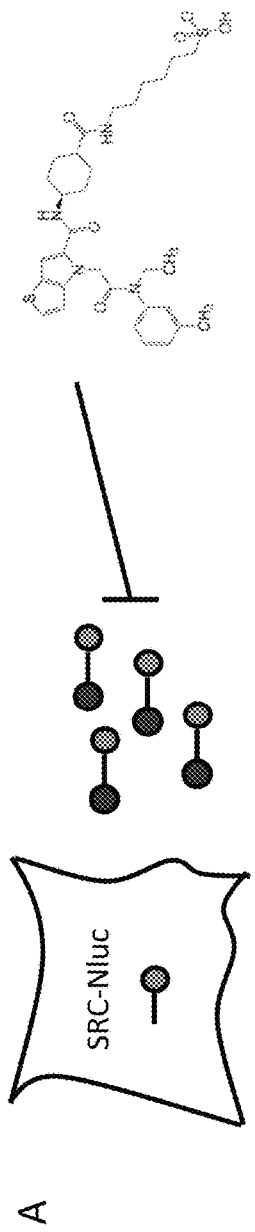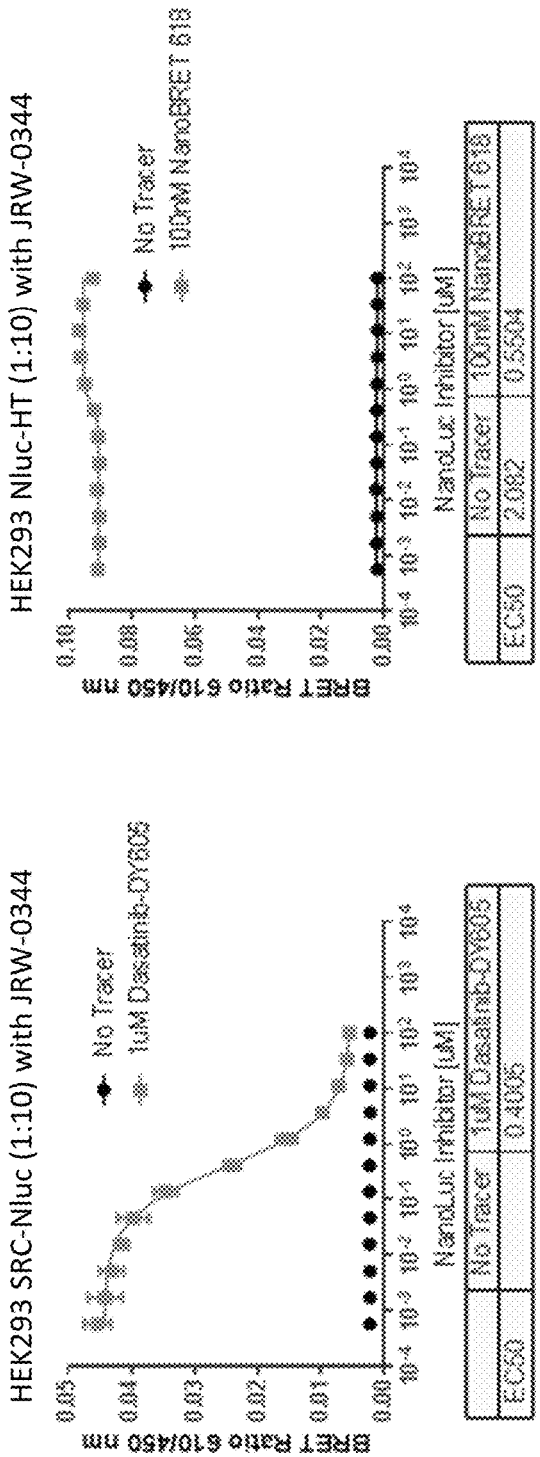
FIGS. 20A-20C

SEQUENCE LISTING

<160> NUMBER OF SEQ ID NOS: 2

<210> SEQ ID NO 1
<211> LENGTH: 169
<212> TYPE: PRT
<213> ORGANISM: Artificial Sequence
<220> FEATURE:
<223> OTHER INFORMATION: Synthetic Peptide - Native Mature Oplophorus
      luciferase

<400> SEQUENCE: 1

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

```
Gly Thr Leu Trp Asn Gly Asn Lys Ile Tyr Asp Glu Arg Leu Ile Asn
            130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165

<210> SEQ ID NO 2
<211> LENGTH: 171
<212> TYPE: PRT
<213> ORGANISM: Artificial Sequence
<220> FEATURE:
<223> OTHER INFORMATION: Synthetic Peptide - Nluc

<400> SEQUENCE: 2

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```

THIENOPYRROLE COMPOUNDS AND USES THEREOF

CROSS-REFERENCE TO RELATED APPLICATIONS

This application claims priority to U.S. Provisional Application No. 62/184,714, filed Jun. 25, 2015, and U.S. Provisional Application No. 62/206,525, filed on Aug. 18, 2015, the entire contents of each of which is incorporated herein by reference.

TECHNICAL FIELD

The present disclosure is directed to thienopyrrole compounds that may inhibit *Oplophorus*-derived luciferases.

BACKGROUND

Reporter molecules are routinely used to monitor molecular events in the fields of biology, biochemistry, immunology, cell biology, and molecular biology. Luciferases based on the luciferase secreted from the deep-sea shrimp, *Oplophorus gracilirostris*, may be used as reporter molecules and have been shown to have advantageous characteristics including broad substrate specificity, high activity, and high quantum yield. It may be further advantageous, in certain applications, to control the luminescent signal from *Oplophorus* luciferases.

SUMMARY

In one aspect, the disclosure provides a compound of formula (I), or a salt thereof:

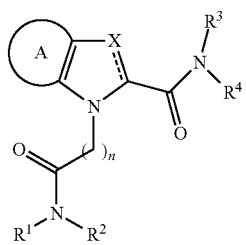

(I)

wherein:
the dashed line represents the presence or absence of a bond;
n is 0, 1, 2, 3, 4 or 5;
X is CH, N, O, or S;
wherein, when the dashed line represents the presence of a bond, X is CH or N,
and when the dashed line represents the absence of a bond, X is O or S;
A is an optionally substituted phenyl ring, or an optionally substituted 5- or 6-membered heteroaryl ring;
$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl; and
$R^3$ and $R^4$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring.

In one aspect, the disclosure provides a method of inhibiting an *Oplophorus*-derived luciferase the method comprising contacting the *Oplophorus*-derived luciferase with a compound described herein, such as a compound of formula (I), (Ia), (Ib), (Ib') or (II).

In one aspect, the disclosure provides a method of inhibiting an *Oplophorus*-derived luciferase, the method comprising contacting the *Oplophorus*-derived luciferase with a compound of formula (II):

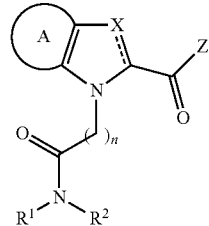

(II)

wherein:
the dashed line represents the presence or absence of a bond;
n is 0, 1, 2, 3, 4 or 5;
X is CH, N, O, or S;
wherein, when the dashed line represents the presence of a bond, X is CH or N,
and when the dashed line represents the absence of a bond, X is O or S;
A is an optionally substituted phenyl ring, or an optionally substituted 5- or 6-membered heteroaryl ring;
$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;
Z is selected from the group consisting of —$NR^3R^4$ and —$OR^5$; and
$R^3$, $R^4$ and $R^5$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring.

In one aspect, the disclosure provides a method for modulating luminescence of an *Oplophorus*-derived luciferase in a sample, the method comprising,
(a) contacting the sample with a coelenterazine substrate and a compound described herein, such as a compound of formula (I), (Ia), (Ib), (Ib') or (II); and
(b) detecting luminescence in the sample,
wherein the compound causes a decrease in the luminescence from the *Oplophorus*-derived luciferase.

In one aspect, the disclosure provides a method to detect an interaction between a first protein and a second protein in a sample, the method comprising:
(a) contacting a sample with a coelenterazine substrate a compound described herein, such as a compound of formula (I), (Ia), (Ib), (Ib') or (II), wherein the sample comprises:
(i) a first polynucleotide encoding a first fusion protein, wherein the first fusion protein comprises a first fragment of an *Oplophorus*-derived luciferase and a first protein; and
(ii) a second polynucleotide encoding a second fusion protein, wherein the second fusion protein comprises a second fragment of the *Oplophorus*-derived luciferase and a second protein; and
(b) detecting luminescence in the sample,
wherein the detection of luminescence indicates an interaction between the first protein and the second protein.

In one aspect, the disclosure provides a method to detect an interaction between a first protein and a second protein in a sample, the method comprising:
(a) contacting a sample with a coelenterazine substrate and a compound described herein, such as a compound of formula (I), (Ia), (Ib), (Ib') or (II), wherein the sample comprises:
(iii) a first polynucleotide encoding a first fusion protein, wherein the first fusion protein comprises an *Oplophorus*-derived luciferase and a first protein, wherein the *Oplophorus*-derived luciferase is a bioluminescent donor; and
(iv) a second polynucleotide encoding a second fusion protein, wherein the second fusion protein comprises a fluorescent acceptor molecule and a second protein;
(b) detecting bioluminescence resonance energy transfer (BRET) in the sample, indicating an interaction or close proximity of the bioluminescent donor and the fluorescence acceptor.

In one aspect, the disclosure provides a bioluminescence resonance energy transfer (BRET) system comprising: a first fusion protein including a first target protein and a bioluminescence donor molecule, wherein the bioluminescence donor molecule is an *Oplophorus*-derived luciferase; a second fusion protein including a second target protein and a fluorescent acceptor molecule; a coelenterazine substrate, and a compound described herein, such as a compound of formula (I), (Ia), (Ib), (Ib') or (II).

In one aspect, the disclosure provides a kit comprising:
(a) a compound described herein, such as a compound of formula (I), (Ia), (Ib), (Ib') or (II); and
(b) an *Oplophorus*-derived luciferase.

In one aspect, the disclosure provides a method for modulating luminescence of an *Oplophorus*-derived luciferase in a sample, the method comprising:
(a) contacting the sample with a coelenterazine substrate and a compound of formula (II):

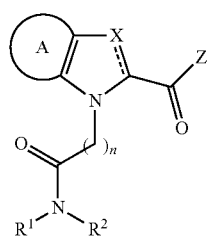

(II)

wherein:
the dashed line represents the presence or absence of a bond;
n is 0, 1, 2, 3, 4 or 5;
X is CH, N, O, or S;
  wherein, when the dashed line represents the presence of a bond, X is CH or N,
  and when the dashed line represents the absence of a bond, X is O or S;
A is an optionally substituted phenyl ring, or an optionally substituted 5- or 6-membered heteroaryl ring;
$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;
Z is selected from the group consisting of —$NR^3R^4$ and —$OR^5$; and
$R^3$, $R^4$ and $R^5$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring; and
(b) detecting luminescence in the sample,
wherein the compound of formula (II) causes a decrease in the luminescence from the *Oplophorus*-derived luciferase.

In one aspect, the disclosure provides a method to detect an interaction between a first protein and a second protein in a sample, the method comprising:
(a) contacting a sample with a coelenterazine substrate and a compound of formula (II):

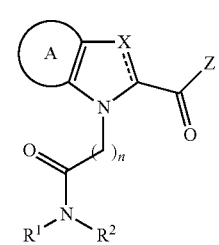

(II)

wherein:
the dashed line represents the presence or absence of a bond;
n is 0, 1, 2, 3, 4 or 5;
X is CH, N, O, or S;
  wherein, when the dashed line represents the presence of a bond, X is CH or N,
  and when the dashed line represents the absence of a bond, X is O or S;
A is an optionally substituted phenyl ring, or an optionally substituted 5- or 6-membered heteroaryl ring;
$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;

Z is selected from the group consisting of —NR³R⁴ and —OR⁵; and

R³, R⁴ and R⁵ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or R³ and R⁴, together with the nitrogen atom to which they are attached, together form an optionally substituted ring, wherein the sample comprises:

(v) a first polynucleotide encoding a first fusion protein, wherein the first fusion protein comprises a first fragment of an *Oplophorus*-derived luciferase and a first protein; and (vi) a second polynucleotide encoding a second fusion protein, wherein the second fusion protein comprises a second fragment of the *Oplophorus*-derived luciferase and a second protein; and (b) detecting luminescence in the sample, wherein the detection of luminescence indicates an interaction between the first protein and the second protein.

In one aspect, the disclosure provides a method to detect an interaction between a first protein and a second protein in a sample, the method comprising:

(a) contacting a sample with a coelenterazine substrate and a compound of formula (II):

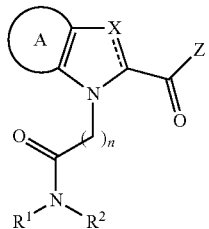

(II)

wherein:

the dashed line represents the presence or absence of a bond;

n is 0, 1, 2, 3, 4 or 5;

X is CH, N, O, or S;
wherein, when the dashed line represents the presence of a bond, X is CH or N,
and when the dashed line represents the absence of a bond, X is O or S;

A is an optionally substituted phenyl ring, or an optionally substituted 5- or 6-membered heteroaryl ring;

R¹ and R² are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;

Z is selected from the group consisting of —NR³R⁴ and —OR⁵; and

R³, R⁴ and R⁵ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or R³ and R⁴, together with the nitrogen atom to which they are attached, together form an optionally substituted ring, wherein the sample comprises:

(vii) a first polynucleotide encoding a first fusion protein, wherein the first fusion protein comprises an *Oplophorus*-derived luciferase and a first protein, wherein the *Oplophorus*-derived luciferase is a bioluminescent donor; and (viii) a second polynucleotide encoding a second fusion protein, wherein the second fusion protein comprises a fluorescent acceptor molecule and a second protein;

(b) detecting bioluminescence resonance energy transfer (BRET) in the sample, indicating an interaction or close proximity of the bioluminescent donor and the fluorescence acceptor.

In one aspect, the disclosure provides a bioluminescence resonance energy transfer (BRET) system comprising: a first fusion protein including a first target protein and a bioluminescence donor molecule, wherein the bioluminescence donor molecule is an *Oplophorus*-derived luciferase; a second fusion protein including a second target protein and a fluorescent acceptor molecule; a coelenterazine substrate, and a compound of formula (II):

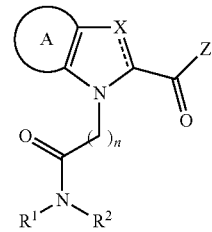

(II)

wherein:

the dashed line represents the presence or absence of a bond;

n is 0, 1, 2, 3, 4 or 5;

X is CH, N, O, or S;
wherein, when the dashed line represents the presence of a bond, X is CH or N,
and when the dashed line represents the absence of a bond, X is O or S;

A is an optionally substituted phenyl ring, or an optionally substituted 5- or 6-membered heteroaryl ring;

R¹ and R² are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;

Z is selected from the group consisting of —NR³R⁴ and —OR⁵; and

R³, R⁴ and R⁵ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring.

In one aspect, the disclosure provides a kit comprising:
(a) a compound of formula (II):

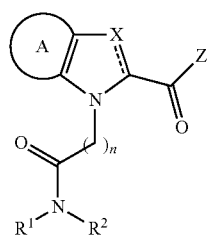

(II)

wherein:
the dashed line represents the presence or absence of a bond;
n is 0, 1, 2, 3, 4 or 5;
X is CH, N, O, or S;
  wherein, when the dashed line represents the presence of a bond, X is CH or N,
  and when the dashed line represents the absence of a bond, X is O or S;
A is an optionally substituted phenyl ring, or an optionally substituted 5- or 6-membered heteroaryl ring;
$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;
Z is selected from the group consisting of —$NR^3R^4$ and —$OR^5$; and
$R^3$, $R^4$ and $R^5$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring; and
(b) an *Oplophorus*-derived luciferase.

BRIEF DESCRIPTION OF THE DRAWINGS

FIGS. 6A-6C show that thienopyrrole compounds WZ141-89 (FIG. 6A), WZ141-90 (FIG. 6B), and WZ141-91 (FIG. 6C) inhibit Nluc in a dose- and time-dependent manner.

FIGS. 9A-9F show the permeability of the thienopyrrole compounds JRW-0044 (FIG. 9A), JRW-0013 (FIG. 9B), JRW-0034 (FIG. 9C), JRW-0052 (FIG. 9D), JRW-0110 (FIG. 9E), and JRW-0187 (FIG. 9F) using HEK293 or HeLa cells transiently transfected with a Beta-2 Adrenergic Receptor-Nluc fusion protein.

FIGS. 10A-10F show the permeability of the thienopyrrole compounds JRW-0188 (FIG. 10A), JRW-0190 (FIG. 10B), JRW-0191 (FIG. 10C), JRW-0192 (FIG. 10D), JRW-0195 (FIG. 10E), and JRW-0197 (FIG. 10F) using HEK293 or HeLa cells transiently transfected with a Beta-2 Adrenergic Receptor-Nluc fusion protein.

FIGS. 12A-12E show the ability of the thienopyrrole compounds to inhibit extracellular BRET. FIG. 12A shows a schematic diagram of spurious extracellular BRET assay design. FIGS. 12B-12E show compound response curves of the thienopyrrole compounds, JRW-0013 (FIG. 12B), JRW-0051 (FIG. 12C), JRW-0147 (FIG. 12D), and JRW-0187 (FIG. 12E) using the extracellular BRET assay.

FIG. 13A shows a schematic diagram of spurious extracellular Nluc assay design. FIGS. 13B-13E show compound response curves of the thienopyrrole compounds, JRW-0013 (FIG. 13B), JRW-0051 (FIG. 13C), JRW-0147 (FIG. 13D), and JRW-0187 (FIG. 13E) using the extracellular Nluc assay.

FIG. 15A shows a schematic diagram of SRC-Nluc assay design. FIGS. 15B-13C show compound response curves for Dasatinib-DY607 (FIG. 15B) and JRW-0147 (FIG. 15C).

FIGS. 20A-20C show the ability of the thienopyrrole compound JRW-0344 to inhibit extracellular luciferase activity. FIG. 20A shows a schematic diagram of the SRC-Nluc assay design. FIGS. 20B and 20C show compound response curves of the thienopyrrole compound JRW-0344 using the SRC-Nluc assay (FIG. 20B) or extracellular Nluc assay (FIG. 20C).

DETAILED DESCRIPTION

Figure 1:
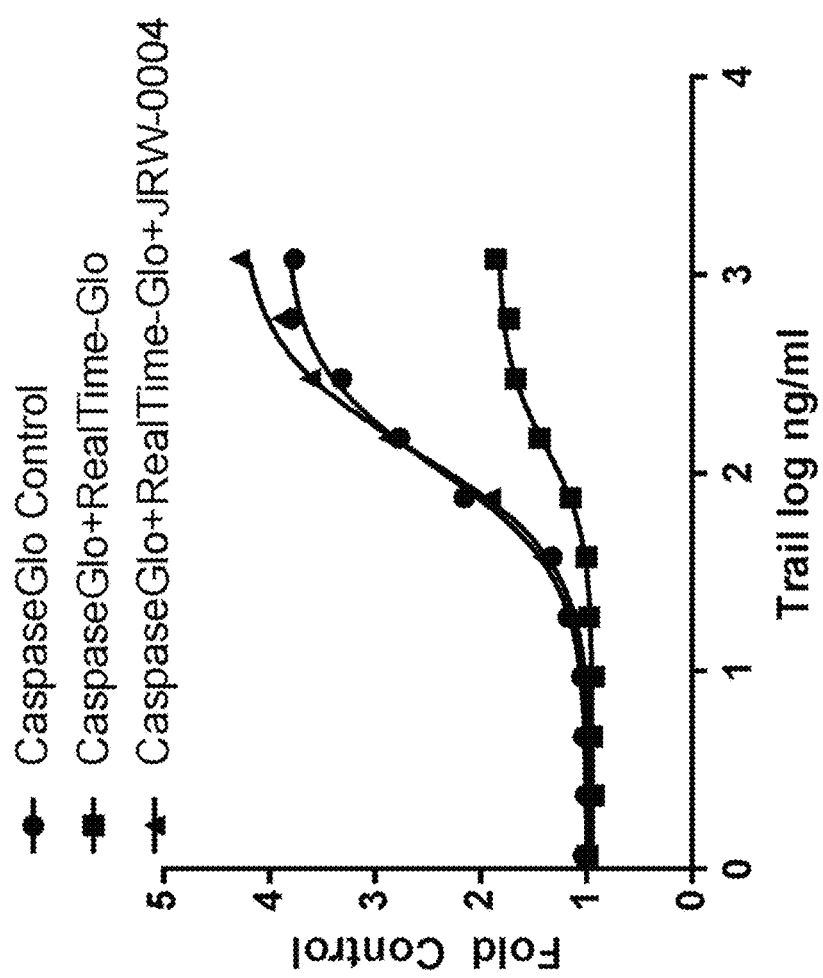
FIG. 1 shows the inhibition of NANOLUC® (Nluc) enzyme by JRW-0004 in a multiplex assay that combines RealTime-Glo and CASPASE-GLO® assay system.

Disclosed herein are thienopyrrole compounds that can selectively inhibit *Oplophorus*-derived luciferases, such as a luciferase of SEQ ID NO:2 (also interchangeably referred to herein as "NanoLuc", "Nluc," "Nluc luciferase," and "Nluc enzyme"). Due to their stabilities and their potential to be excreted from cells, it may be advantageous to use selective inhibitors to suppress the luminescence from *Oplophorus*-derived luciferases in certain applications. For example, in applications involving temporal multiplexing of multiple luminescent systems, it can be beneficial to have selective inhibitors for each system to allow for the measurement and/or detection of only one luminescent signal at a time. Additionally, in some plate-based assays, a certain amount of luciferase may be excreted from cells. An extracellular inhibitor compound would allow for luminescence from excreted luciferase to be selectively suppressed and may, therefore, help to improve the signal-to-noise ratio in certain assays.

Thienopyrrole compounds described herein have been found to be selective inhibitors for *Oplophorus* luciferases. The thienopyrrole compounds may compete for binding of the coelenterazine substrates of the luciferases and can be modified to produce both cell-permeable and cell-impermeable inhibitors.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "substituent" or "suitable substituent" is intended to mean a chemically acceptable functional group e.g., a moiety that does not negate the activity of the inventive compounds. Illustrative examples of suitable substituents include, but are not limited to halo groups, perfluoroalkyl groups, perfluoroalkoxy groups, alkyl groups, alkenyl groups, alkynyl groups, hydroxy groups, halo groups, oxo groups, mercapto groups, alkylthio groups, alkoxy groups, nitro groups, azidealkyl groups, sulfonic acid groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkyl-amino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. The substituents can be substituted by additional substituents. The substituents can also be in salt forms (e.g., a sulfonic acid group can be in the form of a sulfonate group.

As used herein, the term "alkenyl" refers a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. Alkenyl groups of the present invention may be unsubstituted or substituted by one or more suitable substituents, preferably 1 to 3 suitable substituents, as defined above.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkoxyalkoxy" refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkylene group, as defined herein. Representative examples of alkoxyalkoxy-alkyl include, but are not limited to, tert-butoxymethoxymethyl, ethoxymethoxymethyl, (2-methoxyethoxy)methyl, and 2-(2-methoxyethoxy)ethyl.

As used herein, the term "alkoxyalkyl" refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

As used herein, the term "alkoxycarbonyl" refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonyl-alkyl include, but are not limited to, ethoxycarbonylmethyl, 3-methoxycarbonylpropyl, 4-ethoxycarbonylbutyl, and 2-tert-butoxycarbonylethyl.

As used herein, the term "alkyl" refers to a linear or branched hydrocarbon radical, suitably having 1 to 30 carbon atoms, 1 to 12 carbon atoms, 1 to 10 carbon atoms, 1 to 8 carbon atoms, 1 to 6 carbon atoms, or 1 to 4 carbon atoms. The term "$C_1$-$C_8$-alkyl" is defined to include alkyl groups having 1, 2, 3, 4, 5, 6, 7 or 8 carbons in a linear or branched arrangement. For example, "$C_1$-$C_8$-alkyl" specifically includes methyl, ethyl, n-propyl, iso-propyl, n-butyl, sec-butyl, iso-butyl, tert-butyl, pentyl (e.g., n-pentyl), hexyl (e.g., n-hexyl), heptyl (e.g., n-heptyl) and octyl (e.g., n-octyl). The term "$C_1$-$C_6$-alkyl" is defined to include alkyl groups having 1, 2, 3, 4, 5, or 6 carbons in a linear or branched arrangement. For example, "$C_1$-$C_6$-alkyl" specifically includes methyl, ethyl, n-propyl, iso-propyl, n-butyl, sec-butyl, iso-butyl, tert-butyl, pentyl (e.g., n-pentyl), and hexyl (e.g., n-hexyl). The term "$C_1$-$C_4$-alkyl" is defined to include alkyl groups having 1, 2, 3, or 4 carbons in a linear or branched arrangement. For example, "$C_1$-$C_4$-alkyl" specifically includes methyl, ethyl, n-propyl, i-propyl, n-butyl, sec-butyl, iso-butyl and tert-butyl. Alkyl groups of the present invention may be unsubstituted or substituted by one or more suitable substituents, such as 1 to 3 suitable substituents, as defined above. For example, an alkyl group can be substituted with one or more halo substituents to form a haloalkyl group, or with one or more hydroxy substituents to form a hydroxyalkyl group, or with one or more alkoxy groups to form an alkoxyalkyl group.

As used herein, the term "alkylamino" refers to an alkyl group, as defined herein, appended to the parent molecular moiety through an amino group, as defined herein. Representative examples of alkylamino include, but are not limited to, methylamino, ethylamino, iso-propylamino, butylamino and sec-butylamino.

As used herein, the term "alkylaminoalkyl" refers to an alkyl group, as defined herein, appended to the parent molecular moiety through an aminoalkyl group, as defined herein. Representative examples of alkylaminoalkyl groups include, but are not limited to, methylaminoethyl and methylamino-2-propyl.

As used herein, the term "alkylcarbonyl" refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

As used herein, the term "alkylcarbonylalkyl" refers to an alkylcarbonyl group, as defined herein, appended to the parent molecular moiety through an alkyl group, as defined herein.

As used herein, the term "alkylcarbonylalkylamido" refers to an alkylcarbonyl group, as defined herein, appended to the parent molecular moiety through an alkylamido group, as defined herein.

The term "alkylene" means a divalent group derived from a saturated, straight or branched chain hydrocarbon of from 1 to 10 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, —$CH_2C(CH_3)_2$—, and —$CH_2CH(CH_3)CH_2$—.

As used herein, the term "alkynyl" refers to a straight or branched hydrocarbon radical having 2, 3, 4, 5, 6, 7, 8, 9 or 10 carbons, and having one or more carbon-carbon triple bonds. Alkynyl groups of the present invention include, but are not limited to, ethynyl, propynyl, and butynyl. Alkynyl groups of the present invention may be unsubstituted or substituted by one or more suitable substituents, preferably 1 to 3 suitable substituents, as defined above.

As used herein, the term "amido" refers to an amino group appended to the parent molecular moiety through a carbonyl group, as defined herein (i.e., —$CONH_2$). The term "alkylamido," as used herein, refers to an alkylamino group or dialkylamino group appended to the parent molecular moiety through a carbonyl group, as defined herein. Representative examples of alkylamido include, but are not limited to, methylaminocarbonyl, dimethylaminocarbonyl, ethylmethylaminocarbonyl, and n-hexylaminocarbonyl.

As used herein, the term "amino" refers to an —$NH_2$ group.

As used herein, the term "aminoalkyl" refers to at least one amino group, as defined herein, appended to the parent molecular moiety through an alkyl group, as defined herein. Representative examples of aminoalkyl include, but are not limited to, aminomethyl, 2-aminoethyl, 3-aminopropyl, 4-aminobutyl, 5-aminopentyl, and 6-aminohexyl.

As used herein, the term "aminoalkylamido" refers to at least one amino group, as defined herein, appended to the parent molecular moiety through an alkylamido group, as defined herein.

As used herein, the term "amino protecting group," refers to a moiety that prevents chemical reactions from occurring on the nitrogen atom to which that protecting group is attached. An amino protecting group must also be removable by a chemical reaction. Such groups are well known in the art and include those described in detail in Protecting Groups in Organic Synthesis, T. W. Greene and P. G. M. Wuts, 3rd edition, John Wiley & Sons, 1999, the entirety of which is incorporated herein by reference. Suitable amino protecting groups include, but are not limited to, carbobenzyloxy (—NHCO—$OCH_2C_6H_5$ or —NH-Cbz); t-butyloxycarbonyl (—NHCO—$OC(CH_3)_3$ or —NH-Boc); 9-fluorenylmethyloxycarbonyl (—NH—Fmoc), 2,2,2-trichloroethyloxycarbonyl (—NH-Troc), and allyloxycarbonyl (—NH-Alloc). (In each of the above, the —NH— represents the nitrogen from the amino group that is being protected.)

As used herein, the term "aminoluciferin" refers to (4S)-2-(6-amino-1,3-benzothiazol-2-yl)-4,5-dihydrothiazole-4-carboxylic acid, or a substituted analog of this molecule.

As used herein, the term "aryl" means monocyclic, bicyclic, or tricyclic aromatic radicals. Representative examples of the aryl groups include, but are not limited to, phenyl, dihydroindenyl, indenyl, naphthyl, dihydronaphthalenyl, and tetrahydronaphthalenyl. Aryl groups of the present invention may be optionally substituted by one or more suitable substituents, preferably 1 to 5 suitable substituents, as defined above.

As used herein, the term "arylalkyl" refers to an aryl group, as defined herein, appended to the parent molecular moiety through an alkyl group, as defined herein. Representative examples of arylalkyl include, but are not limited to, phenylmethyl (i.e. benzyl) and phenylethyl.

As used herein, the term "arylcarbonyl" refers to an aryl group, as defined herein, appended to the parent molecular moiety through a carbonyl group, as defined herein.

As used herein, the term "bioluminescence" or "luminescence" may refer to light produced as a result of a reaction between an enzyme and a substrate that generates light. Examples of such enzymes (bioluminescent enzymes) include *Oplophorus* luciferase, e.g., *Oplophorous gracilirostris*, firefly luciferase, e.g. *Photinus pyralis* or *Photuris pennsylvanica*, click beetle luciferase, *Renilla* luciferase, cypridina luciferase, *Aequorin* photoprotein, obelin photoprotein and the like.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "carboxy" refers to a —C(O)OH group.

As used herein, the term "carboxyalkyl" refers to a carboxy group as defined herein, appended to the parent molecular moiety through an alkyl group as defined herein.

As used herein, the term "carboxyalkylamido" refers to a carboxyalkyl group as defined herein, appended to the parent molecular moiety through an amido group as defined herein.

As used herein, the term "coelenterazine substrate" refers to a class of reporter molecules that luminesce when acted upon by a wide variety of bioluminescent proteins such as luciferases (e.g., marine luciferases). Coelenterazine substrates include coelenterazine as well as analogs and derivatives thereof.

As used herein, the term "cycloalkyl" refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups of the present invention may be unsubstituted or substituted by one or more suitable substituents, preferably 1 to 5 suitable substituents, as defined above.

As used herein, the term "cycloalkylalkyl" refers to a cycloalkyl group, as defined herein, appended to the parent molecular moiety through an alkyl group, as defined herein. Representative examples of cycloalkylalkyl include, but are not limited to, cyclohexylmethyl.

As used herein, the term "cycloalkylamido" refers to a cycloalkyl group, as defined herein, appended to the parent molecular moiety through an amido group, as defined herein.

As used herein, the term "dialkylamino" refers to two independently selected alkyl groups, as defined herein, appended to the parent molecular moiety through an amino group, as defined herein. Representative examples of dialkylamino include, but are not limited to, N,N-dimethylamino, N-ethyl-N-methylamino, and N-isopropyl-N-methylamino.

As used herein, the term "dialkylaminoalkyl" refers to a dialkylamino group, as defined herein, appended to the parent molecular moiety through an alkyl group, as defined herein. Representative examples of dialkylaminoalkyl include, but are not limited to, N,N-dimethylaminoethyl and N,N-methyl(2-propyl)aminoethyl.

As used herein, the term "dialkylaminoalkylamido" refers to a dialkylamino group, as defined herein, appended to the parent molecular moiety through an alkylamido group, as defined herein.

As used herein, the term "halogen" or "halo" refers to a fluoro, chloro, bromo or iodo radical.

As used herein, the term "haloalkoxy" refers to an alkoxy group, as defined herein, substituted by one, two, three, or four halogen atoms. Representative examples of haloalkoxy include, but are not limited to, chloromethoxy, 2-fluoroethoxy, trifluoromethoxy, and pentafluoroethoxy.

As used herein, the term "haloalkyl" refers to an alkyl group, as defined herein, substituted by one, two, three, or four halogen atoms. Representative examples of haloalkyl include, but are not limited to, chloromethyl, 2-fluoroethyl, trifluoromethyl, pentafluoroethyl, 2-chloro-3-fluoropentyl, and 4,4,4,-trifluorobutyl.

As used herein, the term "heteroaryl" refers to a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, and 5,6,7,8-tetrahydroquinolin-5-yl. Heteroaryl groups of the present invention may be unsubstituted or substituted by one or more suitable substituents, preferably 1 to 5 suitable substituents, as defined above.

As used herein, the term "heteroarylalkyl" refers to a heteroaryl group, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

As used herein, the term "heterocycle" or "heterocyclyl" refers to a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of oxygen, nitrogen, phosphorus and sulfur. The three- or four-membered ring contains zero or one double bond, and one heteroatom selected from the group consisting of oxygen, nitrogen, phosphorus and sulfur. The five-membered ring contains zero or one double bond and one, two or three heteroatoms selected from the group consisting of oxygen, nitrogen, phosphorus and sulfur. The six-membered ring contains zero, one or two double bonds and one, two, or three heteroatoms selected from the group consisting of oxygen, nitrogen, phosphorus and sulfur. The seven- and eight-membered rings contains zero, one, two, or three double bonds and one, two, or three heteroatoms selected from the group consisting of oxygen, nitrogen, phosphorus and sulfur. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, phosphinane, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, and 2,5-dioxo-pyrrolidinyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, 9-phosphabicyclo[3.3.1]nonane, 8-phosphabicyclo[3.2.1]octane, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), oxa-adamantane (2-oxatricyclo[3.3.1.1$^{3,7}$]decane), and 2,4,6-trioxa-8-phosphatricyclo[3.3.1.13,7]decane. Heterocyclic groups of the present invention may be unsubstituted or substituted by one or more suitable substituents, preferably 1 to 3 suitable substituents, as defined above. Heterocyclic groups of the present invention may be can contain one or more oxo groups (=O) or thioxo (=S) groups attached to the ring.

As used herein, the term "heterocyclylalkyl" refers to a heterocyclyl group, as defined herein, appended to the parent molecular moiety through an alkyl group, as defined herein. Representative examples of heterocyclylalkyl include, but are not limited to, piperidin-4-ylmethyl, piperazin-1-ylmethyl, 3-methyl-1-pyrrolidin-1-ylbutyl, (1R)-3-methyl-1-pyrrolidin-1-ylbutyl, (1S)-3-methyl-1-pyrrolidin-1-ylbutyl, and 3-morpholinopropyl.

As used herein, the term "heterocyclylamido" refers to a heterocyclyl group, as defined herein, appended to the parent molecular moiety through an amido group, as defined herein.

As used herein, the term "hydroxy" refers to an —OH group.

As used herein, the term "hydroxyalkoxy" refers to an alkoxy group, as defined herein, substituted by at least one hydroxy group. Representative examples of hydroxyalkoxy include, but are not limited to, hydroxyethoxy, and 2-hydroxypropoxy.

As used herein, the term "hydroxyalkyl" refers to an alkyl group, as defined herein, substituted by at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

The term "hydroxyalkylamido" as used herein refers to a hydroxyalkyl group attached to an amido group, e.g., -amido-alkyl-OH.

As used herein, the term "hydroxycarbonyl" refers to a hydroxy group, as defined herein, appended to the parent molecular moiety through a carbonyl group, as defined herein.

The term "luminescent enzyme," "bioluminescent enzyme," or "luciferase" as used interchangeably herein refers to a class of oxidative enzymes used in bioluminescence wherein the enzyme produces and emits light when given a substrate. The luciferase may be a naturally occurring, recombinant, or mutant luciferase that uses a luciferase substrate. The luciferase substrate may be luciferin, a luciferin derivative or analog, a preluciferin derivative or analog, a coelenterazine, or a coelenterazine derivative or analog. The luminescent enzyme, if naturally occurring, may be obtained easily by the skilled person from an organism. If the luminescent enzyme is one that occurs naturally or is a recombinant or mutant luminescent enzyme, e.g. one which retains activity in a luciferase-coelenterazine or luciferase-luciferin reaction of a naturally occurring luminescent enzyme, it can be obtained readily from a culture of bacteria, yeast, mammalian cells, insect cells, plant cells, or the like, transformed to express a nucleic acid encoding the luminescent enzyme. Further, the recombinant or mutant luminescent enzyme can be derived from an in vitro cell-free system using a nucleic acid encoding the luciferase. Suitable luminescent enzymes include luciferases derived from bioluminescent decapods, such as from the Oplophoroidea (e.g. *Oplophorus*-derived luciferases), beetle luciferases (e.g., *Photinus pyralis, Photuris pennsylvanica*, etc.), marine organisms such as cnidarians (e.g., *Renilla* luciferase), Aristeidae, Solenoceridae, Luciferidae, Sergestidae, Pasipheidae and Thalassocarididae decapoda families, copepod luciferases, such as *Gaussia* luciferase, such as *Gaussia princeps* luciferase, *Metridia* luciferases, such as *Metridia longa* and *Metridia pacifica* luciferases, *Vargula* luciferases, such as *Vargula hilgendorfii* luciferase, *Pleuromamma xiphias* luciferase, and photoproteins, such as *Aequorin*, and variants, recombinants, and mutants thereof.

A "luminescent reaction mixture" contains materials that will allow the luminescent enzyme to generate a light signal, i.e., luminescence. The mixture may also contain the enzyme, e.g., the luciferase enzyme or luciferase. The materials, and the particular concentrations and/or amounts, needed to generate a luminescent signal will vary depending on the luminescent enzyme used as well as the type of assay being performed. Often other materials will be added to the solution including: a buffer to maintain the reaction at the proper pH, an additive such as PRIONEX or Bovine serum albumin (BSA) to help maintain enzyme activity, reducing agents, detergents, etc.

As used herein, the term "methylenedioxy" refers to a —OCH$_2$O— group wherein the oxygen atoms of the methylenedioxy are attached to the parent molecular moiety through two adjacent carbon atoms.

As used herein, the terms "*Oplophorus* luciferase" and "*Oplophorus*-derived luciferase" are used interchangeably and refer to a luciferase secreted from the deep-sea shrimp *Oplophorus gracihrostris* (e.g., SEQ ID NO: 1), including wild-type, variants, and mutants thereof. For example, suitable *Oplophorus* luciferase variants are described in U.S. Pat. Nos. 8,557,970 and 8,669,103, each of which is incorporated herein by reference in its entirety. Exemplary *Oplophorus*-derived luciferases include, for example, that of SEQ ID NO: 2 (also interchangeably referred to herein as "Nano-Luc", "Nluc," "Nluc luciferase," and "Nluc enzyme").

As used herein, the term "oxo" refers to a double bonded oxygen (=O) radical wherein the bond partner is a carbon atom. Such a radical can also be thought as a carbonyl group.

The term "peptide" or "polypeptide" refers to a sequence of at least two amino acids. In some embodiments, a peptide may contain no more than 80 amino acids, or no more than 35 amino acids, no more than 10 amino acids, or no more than 5 amino acids.

As used herein, the term "reporter moiety" may refer to a moiety that, under appropriate conditions, directly or indirectly generates a detectable signal. Exemplary reporter moieties include, but are not limited to, fluorophores, luminescent molecules, dyes, radiolabels and substrates for enzymes such as luciferase. In some embodiments, a reporter moiety may indirectly generate a detectable signal, for example, when the reporter moiety is a substrate for an enzyme. The reaction of the enzyme with the substrate then produces a detectable signal such as fluorescence or luminescence. As used herein, the term "bioluminescent reporter moiety" may refer to a moiety that is a substrate for a luciferase. For example, the bioluminescent reporter moiety can be a luciferin, a luciferin derivative, e.g., pre-luciferin, aminoluciferin, quionolyl-luciferin, napthyl luciferin, fluoroluciferin, chloroluciferin, precursors of luciferin derivatives, a coelenterazine or a coelenterazine derivative or analog, e.g., furimazine. The luminescent signal generated may be detected using a luminometer. As used herein, the term "fluorescent reporter moiety" may refer to a moiety that fluoresces. For example, the fluorescent reporter moiety may be a flurophore, such as coumarin, R110, fluoroscein, DDAO, resorufin, cresyl violet, sily xanthene, or carbopyronine. Fluorescence may be detected using a fluorometer.

A prefix attached to a multi-component substituent only applies to the first component it precedes. To illustrate, the term "cycloalkylalkyl" contains two components: alkyl and cycloalkyl. Thus, the $C_1$-$C_6$-prefix on $C_1$-$C_6$-cycloalkylalkyl means that the alkyl component of the cycloalkylalkyl contains from 1 to 6 carbon atoms; the $C_1$-$C_6$-prefix does not describe the cycloalkyl component. To illustrate further, the term "halo-$C_1$-$C_6$-alkyl" refers to halomethyl, haloethyl, halopropyl, halobutyl, halopentyl, or halohexyl. To illustrate further, the prefix "halo" on haloalkoxyalkyl indicates that only the alkoxy component of the alkoxyalkyl substituent is substituted with one or more halogen radicals. If the halogen substitution may only occur on the alkyl component, the substituent would instead be described as "alkoxyhaloalkyl."

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted," a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

When a substituent is referred to as "unsubstituted" or not referred to as "substituted" or "optionally substituted," it means that the substituent does not have any substituents. If a substituent is described as being "optionally substituted," the substituent may be either (1) unsubstituted or (2) substituted. If a substituent is described as being optionally substituted with up to a particular number of non-hydrogen radicals, that substituent may be either (1) unsubstituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

If substituents are described as being "independently selected" from a group, each substituent is selected independent of the other. Each substituent, therefore, may be identical to or different from the other substituent(s).

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Thienopyrrole Compounds

Provided herein are thienopyrrole compounds that may inhibit *Oplophorus*-derived luciferases and/or *Oplophorus*-derived luciferase activity. The thienopyrrole compounds include compounds of formula (I) and salts thereof:

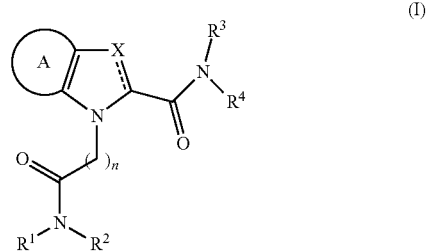

(I)

wherein:
the dashed line represents the presence or absence of a bond;
n is 0, 1, 2, 3, 4 or 5;
X is CH, N, O, or S;
  wherein, when the dashed line represents the presence of a bond, X is CH or N,
  and when the dashed line represents the absence of a bond, X is O or S;
A is an optionally substituted phenyl ring, or an optionally substituted 5- or 6-membered heteroaryl ring;

$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl; and $R^3$ and $R^4$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring.

In some embodiments, the dashed line represents the presence of a bond, and X is CH.

In some embodiments, n is 1.

In some embodiments, A is a phenyl ring. In some embodiments, A is a 5-membered heteroaryl ring. In some embodiments, A is a thienyl ring. In some embodiments, A is a furanyl ring.

In some embodiments, 1e is selected from the group consisting of hydrogen, $C_1$-$C_8$ alkyl, halo-$C_1$-$C_8$-alkyl, alkoxyalkoxyalkyl and arylalkyl. For example, in some embodiments, $R^1$ is selected from the group consisting of hydrogen, ethyl, n-hexyl, 2-(2-methoxyethoxy)ethyl and benzyl. In some embodiments, 1e is ethyl.

In some embodiments, $R^2$ is optionally substituted aryl. For example, in some embodiments, $R^2$ is substituted phenyl. $R^2$ is phenyl substituted with one substituent selected from the group consisting of $C_1$-$C_4$ alkyl, cyano, amido, $C_1$-$C_4$ alkoxy, and hydroxyalkyl. In some embodiments, $R^2$ is phenyl substituted with one methyl group (e.g., m-tolyl).

In some embodiments, $R^1$ is $C_1$-$C_4$ alkyl and $R^2$ is optionally substituted phenyl. In some embodiments, 1e is ethyl and $R^2$ is m-tolyl.

In some embodiments, $R^3$ and $R^4$, together with the nitrogen atom to which they are attached, together form an optionally substituted ring. In some embodiments, $R^3$ and $R^4$, together with the nitrogen atom to which they are attached, together form an optionally substituted monocyclic heterocycle. In some embodiments, the optionally substituted monocyclic heterocycle is selected from the group consisting of optionally substituted pyrrolidine, piperidine and piperazine. In some embodiments, the optionally substituted monocyclic heterocycle is selected from the group consisting of unsubstituted pyrrolidine, unsubstituted piperidine, piperidine substituted with one substituent (e.g., alkoxycarbonyl such as ethoxycarbonyl), or piperazine substituted with one substituent (e.g., $C_1$-$C_4$ alkyl such as methyl).

In some embodiments, $R^3$ is hydrogen.

In some embodiments, $R^4$ is selected from the group consisting of unsubstituted $C_1$-$C_8$ alkyl (e.g., methyl), halo-$C_1$-$C_8$-alkyl, carboxy-$C_1$-$C_8$-alkyl (e.g., —$(CH_2)_7$—COOH), $C_1$-$C_4$-alkoxycarbonyl-$C_1$-$C_8$-alkyl (e.g., —$(CH_2)_7$—COOCH$_3$), optionally substituted phenyl (below), optionally substituted $C_5$-$C_6$ cycloalkyl (e.g., unsubstituted cyclopentyl, unsubstituted cyclohexyl, or substituted cyclohexyl), optionally substituted heterocyclyl (e.g., unsubstituted piperidinyl, piperidinyl substituted with tert-butoxycarbonyl, alkoxycarbonylalkylcarbonyl such as —CO—$(CH_2)_4$—COOCH$_3$), or carboxyalkylcarbonyl such as —CO—$(CH_2)_4$—COOH), optionally substituted heteroarylalkyl (e.g., pyridyl-$C_1$-$C_4$-alkyl such as —$CH_2$-pyridyl), and optionally substituted heterocyclylalkyl (e.g., morpholino-$C_1$-$C_4$-alkyl such as —$(CH_2)_3$-morpholino). For example, in some embodiments, $R^4$ is phenyl that is unsubstituted or substituted with one substituent, such as a substituent selected from the group consisting of $C_1$-$C_4$-alkoxycarbonyl (e.g., —C(O)OCH$_3$) and $C_1$-$C_4$-alkoxycarbonyl-$C_1$-$C_4$-alkyl (e.g., —$CH_2$—C(O)CH$_2$CH$_3$).

In some embodiments, $R^4$ is cyclohexyl substituted with one substituent selected from the group consisting of carboxy, $C_1$-$C_4$-alkoxycarbonyl (e.g., —C(O)OCH$_3$), $C_1$-$C_8$-alkylamido (e.g., —C(O)NH—$(CH_2)_3$CH$_3$ or —C(O)NH—$(CH_2)_5$CH$_3$), hydroxy-$C_1$-$C_8$-alkylamido (e.g., —C(O)NH—$(CH_2)_2$OH or —C(O)NH—$(CH_2)_6$OH), amido (i.e. —CONH$_2$), optionally substituted amino-$C_1$-$C_8$-alkylamido (e.g., —C(O)NH—$(CH_2)_6$NH$_2$), $C_1$-$C_4$-dialkylamino-$C_1$-$C_8$-alkylamido (e.g., —C(O)NH—$(CH_2)_2$N(CH$_3$)$_2$), carboxy-$C_1$-$C_8$-alkylamido (e.g., —C(O)NH—$(CH_2)_3$COOH, —C(O)NH—$(CH_2)_5$COOH or —C(O)NH—$(CH_2)_7$COOH), sulfonic acid-$C_1$-$C_8$-alkylamido (e.g., —C(O)NH—$(CH_2)_6$SO$_3$H), sulfonate-$C_1$-$C_8$-alkylamido (e.g., —C(O)NH—$(CH_2)_6$SO$_3$—), $C_1$-$C_4$-alkylcarbonyl-$C_1$-$C_8$-alkylamido (e.g., —C(O)NH—$(CH_2)_3$COOCH$_3$, —C(O)NH—$(CH_2)_5$COOCH$_3$ or —C(O)NH—$(CH_2)_7$COOCH$_3$), optionally substituted $C_3$-$C_6$-cycloalkylamido (e.g., —C(O)NH—cyclohexyl, —C(O)NH-cyclohexyl-COOH or —C(O)NH-cyclohexyl-COOCH$_3$), and heterocyclylamido (e.g., —C(O)NH-piperidinyl, unsubstituted or substituted with methyl, tert-butoxycarbonyl or acetyl). For example, in some embodiments, $R^4$ is optionally substituted amino-$C_1$-$C_8$-alkylamido (e.g., —C(O)NH—$(CH_2)_6$NH$_2$), wherein the amino group is protected with an amino protecting group (e.g., tert-butoxycarbonyl), or wherein the amino group is protonated to form a salt (e.g., a hydrochloride salt), or wherein the amino group is further functionalized with a fluorophore (e.g., fluorescein) or a polypeptide (e.g., an -Asp-Asp-Asp peptide, which may be acetylated at the terminus).

In some embodiments, the compound has formula (Ia):

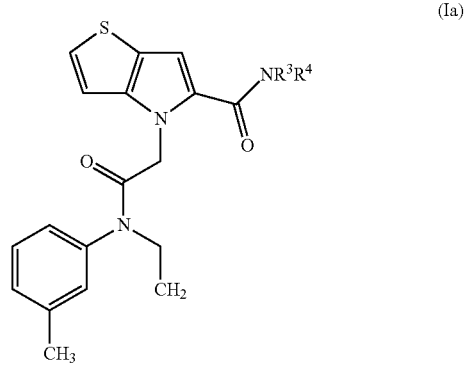

(Ia)

wherein $R^3$ and $R^4$ are as defined in any of the embodiments described above for formula (I).

In some embodiments compound has formula (Ib):

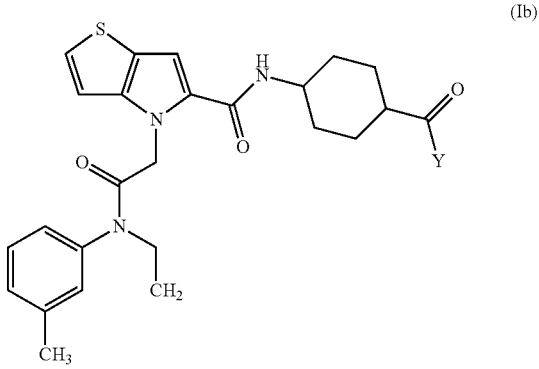

(Ib)

wherein:
Y is selected from the group consisting of —NR$^a$R$^b$ and —OR$^c$;
R$^a$ and R$^b$ are each independently selected from the group consisting of hydrogen, optionally substituted $C_1$-$C_8$ alkyl, optionally substituted $C_3$-$C_8$-cycloalkyl, and optionally substituted heterocyclyl; or R$^a$ and R$^b$, together with the nitrogen atom to which they are attached, together form an optionally substituted ring; and
R$^c$ is selected from the group consisting of hydrogen and optionally substituted $C_1$-$C_4$ alkyl.

In some embodiments, Y is —OR$^c$. In some embodiments, R$^c$ is selected from the group consisting of hydrogen and methyl.

In some embodiments, Y is —NR$^a$R$^b$.

In some embodiments, R$^a$ is hydrogen. In some embodiments, R$^b$ is selected from the group consisting of hydrogen, optionally substituted $C_1$-$C_8$ alkyl, optionally substituted $C_3$-$C_8$-cycloalkyl, and optionally substituted heterocyclyl. In some embodiments, R$^b$ is selected from the group consisting of hydrogen, unsubstituted $C_1$-$C_6$ alkyl (e.g., n-butyl or n-hexyl), hydroxyalkyl (e.g., hydroxy-$C_1$-$C_6$-alkyl, such as —(CH$_2$)$_2$OH or —(CH$_2$)$_6$OH), optionally substituted aminoalkyl (e.g., amino-$C_1$-$C_6$-alkyl, such as —(CH$_2$)$_6$NH$_2$), dialkylaminoalkyl (e.g., $C_1$-$C_4$-dialkylamino-$C_1$-$C_8$-alkylamido, such as —C(O)NH—(CH$_2$)$_2$N(CH$_3$)$_2$), carboxyalkyl (e.g., carboxy-$C_1$-$C_8$-alkyl, such as —(CH$_2$)$_3$COOH, —(CH$_2$)$_5$COOH or —(CH$_2$)$_7$COOH), sulfonic acid-$C_1$-$C_8$-alkyl (e.g., —(CH$_2$)$_6$SO$_3$H), sulfonate-$C_1$-$C_8$-alkyl (e.g., —(CH$_2$)$_6$SO$_3^-$), alkylcarbonylalkyl (e.g., $C_1$-$C_4$-alkylcarbonyl-$C_1$-$C_8$-alkylamido, such as —(CH$_2$)$_3$COOCH$_3$, —(CH$_2$)$_5$COOCH$_3$ or —(CH$_2$)$_7$COOCH$_3$), optionally substituted $C_3$-$C_6$-cycloalkyl (e.g., -cyclohexyl, -cyclohexyl-COOH or -cyclohexyl-COOCH$_3$), and optionally substituted six-membered heterocyclyl (e.g., unsubstituted or substituted with methyl, tert-butoxycarbonyl or acetyl). For example, in some embodiments, R$^b$ is optionally substituted amino-$C_1$-$C_8$-alkyl (e.g., —(CH$_2$)$_6$NH$_2$), wherein the amino group is protected with an amino protecting group (e.g., tert-butoxycarbonyl), or wherein the amino group is protonated to form a salt (e.g., a hydrochloride salt), or wherein the amino group is further functionalized with a fluorophore (e.g., fluorescein) or a polypeptide (e.g., an -Asp-Asp-Asp peptide, which may be acetylated at the terminus).

In some embodiments R$^a$ and R$^b$, together with the nitrogen atom to which they are attached, together form an optionally substituted ring. In some embodiments, R$^a$ and R$^b$, together with the nitrogen atom to which they are attached, together form an optionally substituted monocyclic heterocycle. In some embodiments, the optionally substituted monocyclic heterocycle is optionally substituted piperidine. In some embodiments, the monocyclic heterocycle is selected from the group consisting of unsubstituted piperidine and piperidine substituted with one substituent (e.g., carboxyl or alkoxycarbonyl such as —C(O)OCH$_2$CH$_3$).

In some embodiments, the compound has the following formula (Ib')

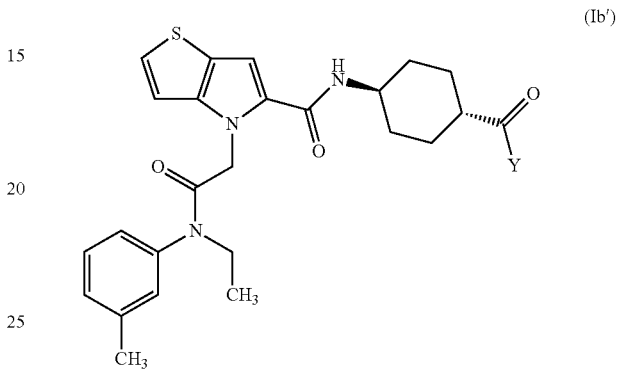

(Ib')

wherein Y is as defined in any of the embodiments described above for formula (Ib).

Suitable compounds include the following:
N-cyclohexyl-4-(2-(ethyl(m-tolyl)amino)-2-oxoethyl)-4H-thieno[3,2-b]pyrrole-5-carboxamide;
N-ethyl-2-(5-(pyrrolidine-1-carbonyl)-4H-thieno[3,2-b]pyrrol-4-yl)-N-(m-tolyl)acetamide;
N-ethyl-2-(5-(piperidine-1-carbonyl)-4H-thieno[3,2-b]pyrrol-4-yl)-N-(m-tolyl)acetamide;
ethyl 1-(4-(2-(ethyl(m-tolyl)amino)-2-oxoethyl)-4H-thieno[3,2-b]pyrrole-5-carbonyl)piperidine-4-carboxylate;
4-(2-(ethyl(m-tolyl)amino)-2-oxoethyl)-N-phenyl-4H-thieno[3,2-b]pyrrole-5-carboxamide;
ethyl 2-(4-(4-(2-(ethyl(m-tolyl)amino)-2-oxoethyl)-4H-thieno[3,2-b]pyrrole-5-carboxamido)phenyl)acetate;
methyl 3-(4-(2-(ethyl(m-tolyl)amino)-2-oxoethyl)-4H-thieno[3,2-b]pyrrole-5-carboxamido)benzoate;
methyl-cis-4-(4-(2-(ethyl(m-tolyl)amino)-2-oxoethyl)-4H-thieno[3,2-b]pyrrole-5-carboxamido)cyclohexane-1-carboxylate;
8-(4-(2-(ethyl(m-tolyl)amino)-2-oxoethyl)-4H-thieno[3,2-b]pyrrole-5-carboxamido)octanoic acid;
6-(4-(4-(2-(ethyl(m-tolyl)amino)-2-oxoethyl)-4H-thieno[3,2-b]pyrrole-5-carboxamido)piperidin-1-yl)-6-oxohexanoic acid;
trans-methyl-4-(4-(2-(ethyl(m-tolyl)amino)-2-oxoethyl)-4H-thieno[3,2-b]pyrrole-5-carboxamido)cyclohexane-1-carboxylate;
trans-4-(4-(2-(ethyl(m-tolyl)amino)-2-oxoethyl)-4H-thieno[3,2-b]pyrrole-5-carboxamido)cyclohexane-1-carboxylic acid;
N-(trans-4-(butylcarbamoyl)cyclohexyl)-4-(2-(ethyl(m-tolyl)amino)-2-oxoethyl)-4H-thieno[3,2-b]pyrrole-5-carboxamide;
4-(2-(ethyl(m-tolyl)amino)-2-oxoethyl)-N-(trans-4-((2-hydroxyethyl)carbamoyl)cyclohexyl)-4H-thieno[3,2-b]pyrrole-5-carboxamide;
N-(trans-4-((2-(dimethylamino)ethyl)carbamoyl)cyclohexyl)-4-(2-(ethyl(m-tolyl)amino)-2-oxoethyl)-4H-thieno[3,2-b]pyrrole-5-carboxamide;

4-(trans-4-(4-(2-(ethyl(m-tolyl)amino)-2-oxoethyl)-4H-thieno[3,2-b]pyrrole-5-carboxamido)cyclohexane-1-carboxamido)butanoic acid;

N-(trans-4-carbamoylcyclohexyl)-4-(2-(ethyl(m-tolyl)amino)-2-oxoethyl)-4H-thieno[3,2-b]pyrrole-5-carboxamide;

4-(2-(ethyl(m-tolyl)amino)-2-oxoethyl)-N-(trans-4-(hexylcarbamoyl)cyclohexyl)-4H-thieno[3,2-b]pyrrole-5-carboxamide;

ethyl 1-(trans-4-(4-(2-(ethyl(m-tolyl)amino)-2-oxoethyl)-4H-thieno[3,2-b]pyrrole-5-carboxamido)cyclohexane-1-carbonyl)piperidine-4-carboxylate;

methyl 6-(trans-4-(4-(2-(ethyl(m-tolyl)amino)-2-oxoethyl)-4H-thieno[3,2-b]pyrrole-5-carboxamido)cyclohexane-1-carboxamido)hexanoate;

6-(trans-4-(4-(2-(ethyl(m-tolyl)amino)-2-oxoethyl)-4H-thieno[3,2-b]pyrrole-5-carboxamido)cyclohexane-1-carboxamido)hexanoic acid;

1-(trans-4-(4-(2-(ethyl(m-tolyl)amino)-2-oxoethyl)-4H-thieno[3,2-b]pyrrole-5-carboxamido)cyclohexane-1-carbonyl)piperidine-4-carboxylic acid;

8-(trans-4-(4-(2-(ethyl(m-tolyl)amino)-2-oxoethyl)-4H-thieno[3,2-b]pyrrole-5-carboxamido)cyclohexane-1-carboxamido)octanoic acid;

N-(trans-4-(cyclohexylcarbamoyl)cyclohexyl)-4-(2-(ethyl(m-tolyl)amino)-2-oxoethyl)-4H-thieno[3,2-b]pyrrole-5-carboxamide;

4-(2-(ethyl(m-tolyl)amino)-2-oxoethyl)-N-(trans-4-((1-methylpiperidin-4-yl)carbamoyl)cyclohexyl)-4H-thieno[3,2-b]pyrrole-5-carboxamide;

tert-butyl 4-(trans-4-(4-(2-(ethyl(m-tolyl)amino)-2-oxoethyl)-4H-thieno[3,2-b]pyrrole-5-carboxamido)cyclohexane-1-carboxamido)piperidine-1-carboxylate;

4-(2-(ethyl(m-tolyl)amino)-2-oxoethyl)-N-(trans-4-(piperidin-4-ylcarbamoyl)cyclohexyl)-4H-thieno[3,2-b]pyrrole-5-carboxamide;

N-(trans-4-((1-acetylpiperidin-4-yl)carbamoyl)cyclohexyl)-4-(2-(ethyl(m-tolyl)amino)-2-oxoethyl)-4H-thieno[3,2-b]pyrrole-5-carboxamide;

tert-butyl(6-(trans-4-(4-(2-(ethyl(m-tolyl)amino)-2-oxoethyl)-4H-thieno[3,2-b]pyrrole-5-carboxamido)cyclohexane-1-carboxamido)hexyl)carbamate;

N-(trans-4-((6-(3',6'-dihydroxy-3-oxo-3H-spiro[isobenzofuran-1,9'-xanthene]-5(6)-carboxamido)hexyl)carbamoyl)cyclohexyl)-4-(2-(ethyl(m-tolyl)amino)-2-oxoethyl)-4H-thieno[3,2-b]pyrrole-5-carboxamide;

N-(trans-4-((6-aminohexyl)carbamoyl)cyclohexyl)-4-(2-(ethyl(m-tolyl)amino)-2-oxoethyl)-4H-thieno[3,2-b]pyrrole-5-carboxamide hydrochloride;

4-(2-(ethyl(m-tolyl)amino)-2-oxoethyl)-N-(trans-4-((6-hydroxyhexyl)carbamoyl)cyclohexyl)-4H-thieno[3,2-b]pyrrole-5-carboxamide;

methyl-trans-4-(trans-4-(4-(2-(ethcyl(m-tolyl)amino)-2-oxoethyl)-4H-thieno[3,2-b]pyrrole-5-carboxamido)cyclohexane-1-carboxamido)cyclohexane-1-carboxylate;

trans-4-(trans-4-(4-(2-(ethyl(m-tolyl)amino)-2-oxoethyl)-4H-thieno[3,2-b]pyrrole-5-carboxamido)cyclohexane-1-carboxamido)cyclohexane-1-carboxylic acid;

(11S,14S,17S)-17-acetamido-11,14-bis(carboxymethyl)-1-(trans-4-(4-(2-(ethyl(m-tolyl)amino)-2-oxoethyl)-4H-thieno[3,2-b]pyrrole-5-carboxamido)cyclohexyl)-1,10,13,16-tetraoxo-2,9,12,15-tetraazanonadecan-19-oic acid;

4-(2-(ethyl(m-tolyl)amino)-2-oxoethyl)-N-methyl-4H-thieno[3,2-b]pyrrole-5-carboxamide;

N-cyclopentyl-4-(2-(ethyl(m-tolyl)amino)-2-oxoethyl)-4H-thieno[3,2-b]pyrrole-5-carboxamide;

4-(2-(ethyl(m-tolyl)amino)-2-oxoethyl)-N-(pyridin-4-ylmethyl)-4H-thieno[3,2-b]pyrrole-5-carboxamide;

4-(2-(ethyl(m-tolyl)amino)-2-oxoethyl)-N-(3-morpholinopropyl)-4H-thieno[3,2-b]pyrrole-5-carboxamide;

N-ethyl-2-(5-(4-methylpiperazine-1-carbonyl)-4H-thieno[3,2-b]pyrrol-4-yl)-N-(m-tolyl)acetamide;

methyl 4-(2-oxo-2-(m-tolylamino)ethyl)-4H-thieno[3,2-b]pyrrole-5-carboxylate;

N-cyclohexyl-4-(2-oxo-2-(m-tolylamino)ethyl)-4H-thieno[3,2-b]pyrrole-5-carboxamide;

N-cyclohexyl-4-(2-((2-(2-methoxyethoxy)ethyl)(m-tolyl)amino)-2-oxoethyl)-4H-thieno[3,2-b]pyrrole-5-carboxamide;

methyl-trans-4-(4-(2-((2-(2-methoxyethoxy)ethyl)(m-tolyl)amino)-2-oxoethyl)-4H-thieno[3,2-b]pyrrole-5-carboxamido)cyclohexane-1-carboxylate;

methyl 4-(2-(hexyl(m-tolyl)amino)-2-oxoethyl)-4H-thieno[3,2-b]pyrrole-5-carboxylate;

N-cyclohexyl-4-(2-(hexyl(m-tolyl)amino)-2-oxoethyl)-4H-thieno[3,2-b]pyrrole-5-carboxamide;

methyl-trans-4-(4-(2-(hexyl(m-tolyl)amino)-2-oxoethyl)-4H-thieno[3,2-b]pyrrole-5-carboxamido)cyclohexane-1-carboxylate;

methyl 4-(2-(benzyl(m-tolyl)amino)-2-oxoethyl)-4H-thieno[3,2-b]pyrrole-5-carboxylate;

6-(cis-4-(4-(2-(ethyl(m-tolyl)amino)-2-oxoethyl)-4H-thieno[3,2-b]pyrrole-5-carboxamido)cyclohexane-1-carboxamido)hexanoic acid;

methyl 6-(trans-4-((4-(2-(ethyl(m-tolyl)amino)-2-oxoethyl)-4H-thieno[3,2-b]pyrrole-5-carboxamido)methyl)cyclohexane-1-carboxamido)hexanoate;

6-(trans-4-((4-(2-(ethyl(m-tolyl)amino)-2-oxoethyl)-4H-thieno[3,2-b]pyrrole-5-carboxamido)methyl)cyclohexane-1-carboxamido)hexanoic acid;

sodium 6-(trans-4-(4-(2-(ethyl(m-tolyl)amino)-2-oxoethyl)-4H-thieno[3,2-b]pyrrole-5-carboxamido)cyclohexane-1-carboxamido)hexane-1-sulfonate;

potassium 6-(trans-4-(4-(2-(ethyl(m-tolyl)amino)-2-oxoethyl)-4H-thieno[3,2-b]pyrrole-5-carboxamido)cyclohexane-1-carboxamido)hexane-1-sulfonate;

trans-4-(4-(2-(hexyl(m-tolyl)amino)-2-oxoethyl)-4H-thieno[3,2-b]pyrrole-5-carboxamido)cyclohexane-1-carboxylic acid;

methyl trans-4-(4-(2-(ethyl(phenyl)amino)-2-oxoethyl)-4H-thieno[3,2-b]pyrrole-5-carboxamido)cyclohexane-1-carboxylate;

methyl trans-4-(4-(2-((3-cyanophenyl)(ethyl)amino)-2-oxoethyl)-4H-thieno[3,2-b]pyrrole-5-carboxamido)cyclohexane-1-carboxylate;

methyl trans-4-(4-(2-((3-carbamoylphenyl)(ethyl)amino)-2-oxoethyl)-4H-thieno[3,2-b]pyrrole-5-carboxamido)cyclohexane-1-carboxylate;

methyl trans-4-(4-(2-(ethyl(3-ethylphenyl)amino)-2-oxoethyl)-4H-thieno[3,2-b]pyrrole-5-carboxamido)cyclohexane-1-carboxylate;

methyl trans-4-(4-(2-(ethyl(3-methoxyphenyl)amino)-2-oxoethyl)-4H-thieno[3,2-b]pyrrole-5-carboxamido)cyclohexane-1-carboxylate;

methyl trans-4-(4-(2-(ethyl(o-tolyl)amino)-2-oxoethyl)-4H-thieno[3,2-b]pyrrole-5-carboxamido)cyclohexane-1-carboxylate;

methyl trans-4-(4-(2-(6-methyl-3,4-dihydroquinolin-1(2H)-yl)-2-oxoethyl)-4H-thieno[3,2-b]pyrrole-5-carboxamido)cyclohexane-1-carboxylate;

methyl trans-4-(4-(2-(ethyl(p-tolyl)amino)-2-oxoethyl)-4H-thieno[3,2-b]pyrrole-5-carboxamido)cyclohexane-1-carboxylate;

methyl trans-4-(4-(2-(ethyl(4-(hydroxymethyl)phenyl)amino)-2-oxoethyl)-4H-thieno[3,2-b]pyrrole-5-carboxamido)cyclohexane-1-carboxylate;
methyl trans-4-(1-(2-(ethyl(m-tolyl)amino)-2-oxoethyl)-1H-indole-2-carboxamido)cyclohexane-1-carboxylate;
methyl trans-4-(1-(2-(ethyl(m-tolyl)amino)-2-oxoethyl)-6-methoxy-1H-indole-2-carboxamido)cyclohexane-1-carboxylate;
methyl trans-4-(4-(2-(ethyl(m-tolyl)amino)-2-oxoethyl)-4H-furo[3,2-b]pyrrole-5-carboxamido)cyclohexane-1-carboxylate;
4-(2-(ethyl(3-ethylphenyl)amino)-2-oxoethyl)-N-(trans-4-(6-hydroxyhexyl)carbamoyl)cyclohexyl)-4H-thieno[3,2-b]pyrrole-5-carboxamide;
sodium 6-(trans-4-(4-(2-(ethyl(3-ethylphenyl)amino)-2-oxoethyl)-4H-thieno[3,2-b]pyrrole-5-carboxamido)cyclohexane-1-carboxamido)hexane-1-sulfonate;
methyl trans-4-(4-(2-(ethyl(3-isopropylphenyl)amino)-2-oxoethyl)-4H-thieno[3,2-b]pyrrole-5-carboxamido)cyclohexane-1-carboxylate;
methyl trans-4-(4-(2-(ethyl(3-(hydroxymethyl)phenyl)amino)-2-oxoethyl)-4H-thieno[3,2-b]pyrrole-5-carboxamido)cyclohexane-1-carboxylate;
methyl trans-4-(4-(2-((3-(bromomethyl)phenyl)(ethyl)amino)-2-oxoethyl)-4H-thieno[3,2-b]pyrrole-5-carboxamido)cyclohexane-1-carboxylate;
methyl trans-4-(4-(2-((3-(dimethylamino)phenyl)(ethyl)amino)-2-oxoethyl)-4H-thieno[3,2-b]pyrrole-5-carboxamido)cyclohexane-1-carboxylate;
methyl trans-4-(4-(2-(ethyl(3-isobutylphenyl)amino)-2-oxoethyl)-4H-thieno[3,2-b]pyrrole-5-carboxamido)cyclohexane-1-carboxylate;
methyl trans-4-(1-(2-(ethyl(3-ethylphenyl)amino)-2-oxoethyl)-1H-indole-2-carboxamido)cyclohexane-1-carboxylate;
1-(2-(ethyl(3-ethylphenyl)amino)-2-oxoethyl)-N-(trans-4-(6-hydroxyhexyl)carbamoyl)cyclohexyl)-1H-indole-2-carboxamide;
sodium 6-(trans-4-(1-(2-(ethyl(3-ethylphenyl)amino)-2-oxoethyl)-1H-indole-2-carboxamido)cyclohexane-1-carboxamido)hexane-1-sulfonate;
methyl trans-4-(1-(2-(ethyl(m-tolyl)amino)-2-oxoethyl)-1H-pyrrole-2-carboxamido)cyclohexane-1-carboxylate; and
methyl trans-4-(6-(2-(ethyl(m-tolyl)amino)-2-oxoethyl)-6H-thieno[2,3-b]pyrrole-5-carboxamido)cyclohexane-1-carboxylate.

(1) Salt Forms

A thienopyrrole compound described herein can be in the form of a salt. A neutral form of the compound may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as $Ca^{2+}$ and $Mg^{2+}$, and other cations. Examples of suitable organic cations include, but are not limited to, ammonium ion (i.e., $NH_4^+$) and substituted ammonium ions (e.g., $NH_3R_1^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular thienopyrrole compound herein also includes salt forms thereof.

(2) Isomers

Certain thienopyrrole compounds may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r- forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as "isomers" (or "isomeric forms").

In some embodiments, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In some embodiments, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In some embodiments, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Thienopyrrole compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, $-OCH_3$, is not to be construed as a reference to its structural isomer, a hydroxymethyl group, $-CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_3$-alkyl or propyl includes n-propyl and iso-propyl; $C_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

3. *Oplophorus* Luciferases

The thienopyrrole compounds of the present invention may be used to inhibit *Oplophorus*-derived luciferases. The thienopyrrole compounds may inhibit the luciferase activity of the *Oplophorus*-derived luciferases. The *Oplophorus*-derived luciferase may be a wild-type *Oplophorus* luciferase or a variant of an *Oplophorus* luciferase, such as a luciferase of SEQ ID NO:2. *Oplophorus* luciferase variants are described in U.S. Pat. Nos. 8,557,970 and 8,669,103, each of which is incorporated herein by reference in its entirety.

The polypeptide sequence of the mature 19 kDa subunit of the naturally-occurring form of the *Oplophorus gracilirostris* luciferase is provided in SEQ ID NO: 1. An exemplary polypeptide sequence for a synthetic *Oplophorus*-derived luciferase, which can be used in the methods described herein, is provided in SEQ ID NO: 2 (also interchangeably referred to herein as "NanoLuc", "Nluc," "Nluc luciferase," and "Nluc enzyme").

4. Coelenterazine Substrates

The thienopyrrole compounds of the present invention may be used to inhibit luciferase activity by competing or interfering with a coelenterazine or coelenterazine-derivative substrate from binding to a luciferase. Coelenterazine substrates are a class of reporter molecules that luminesce when acted upon by luciferases and other bioluminescent proteins. Examples of coelenterazine substrates include but are not limited to: coelenterazine; coelenterazine derivatives and/or analogs such as 2-furanylmethyl-deoxy-coelenterazine (furimazine), coelenterazine-n, coelenterazine-f, coelenterazine-h, coelenterazine-hcp, coelenterazine-cp, coelenterazine-c, coelenterazine-e, coelenterazine-fcp, bis-deoxycoelenterazine ("coelenterazine-hh"), coelenterazine-i, coelenterazine-icp, coelenterazine-v, and 2-methyl-coelenterazine, in addition to those disclosed in WO 2003/040100, U.S. Patent Publication No. 2008/0248511, and U.S. Patent Publication No. US 2012/0117667; pro-coelenterazines (i.e. compounds that are not substrates for a non-luminescent enzyme, which converts the compound to a substrate for a luciferase), quinone-masked coelenterazines, and the like. Further examples of coelenterazine substrates are described in, for example, U.S. Publication No. 2012/0107849, U.S. Publication No. 2013/0130289, U.S. patent application Ser. No. 14/608,910, and U.S. patent application Ser. No. 14/609,372, each of which is incorporated herein by reference.

5. Methods of Inhibiting *Oplophorus* Luciferase Activity

The disclosed thienopyrrole compounds may be used in methods to inhibit *Oplophorus* luciferase activity. The method may include contacting a thienopyrrole compound disclosed herein (e.g., a compound of formula (I), (Ia), (Ib) or (Ib')) to a cell expressing or containing an *Oplophorus*-derived luciferase, wherein the disclosed compounds may selectively inhibit the *Oplophorus*-derived luciferase. The disclosed thienopyrrole compounds may be used in assays that are used detect the presence or activity of enzymes using *Oplophorus* luciferases, to selectively inhibit the signal from the *Oplophorus* luciferase. For example, they may be used in a bioluminogenic method which employs an *Oplophorus* luciferase and a coelenterazine or coelenterazine-derivative substrate to detect one or more molecules in a sample, e.g., a protein of interest (e.g., an enzyme, a binding partner, a ligand, etc.), a cofactor for an enzymatic reaction, an enzyme substrate, an enzyme inhibitor, an enzyme activator, or OH radicals, or one or more conditions, e.g., redox conditions. While the coelenterazine substrate serves as a substrate for the *Oplophorus* luciferase, the claimed thienopyrrole compounds may serve to inhibit the luciferase to selectively suppress the luminescent signal in embodiments in which such suppression may be desired, such as in applications involving temporal multiplexing of multiple bioluminescent systems, or in some plate-based luminescent assays. For example, the thienopyrrole compounds may be used to inhibit intracellular and/or extracellular *Oplophorus* luciferase activities.

(1) Thienopyrrole Compounds

As discussed above, the methods may include contacting a thienopyrrole compound disclosed herein (e.g., a compound of formula (I), (Ia), (Ib) or (Ib')) to a cell expressing an *Oplophorus*-derived luciferase, wherein the disclosed compounds may selectively inhibit the *Oplophorus*-derived luciferase. In addition to compounds of formulae (I), (Ia), (Ib) and (Ib'), compounds that can be used in the methods described herein also include compounds of formula (II), or salts thereof:

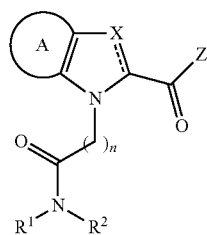

wherein:
the dashed line represents the presence or absence of a bond;
n is 0, 1, 2, 3, 4 or 5;
X is CH, N, O, or S;
  wherein, when the dashed line represents the presence of a bond, X is CH or N,
  and when the dashed line represents the absence of a bond, X is O or S;
A is an optionally substituted phenyl ring, or an optionally substituted 5- or 6-membered heteroaryl ring;
$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;
Z is selected from the group consisting of —$NR^3R^4$ and —$OR^5$; and
$R^3$, $R^4$ and $R^5$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring.

In some embodiments, n is 1.
In some embodiments, the dashed line represents the presence of a bond, and X is CH.
In some embodiments, A is a phenyl ring. In some embodiments, A is a 5-membered heteroaryl ring. In some embodiments, A is a thienyl ring. In some embodiments, A is a furanyl ring.

In some embodiments, 1e is selected from the group consisting of hydrogen, $C_1$-$C_8$ alkyl, halo-$C_1$-$C_8$-alkyl, alkoxyalkoxyalkyl and arylalkyl. For example, in some embodiments, $R^1$ is selected from the group consisting of hydrogen, ethyl, n-hexyl, 2-(2-methoxyethoxy)ethyl and benzyl. In some embodiments, 1e is ethyl.

In some embodiments, $R^2$ is optionally substituted aryl. For example, in some embodiments, $R^2$ is substituted phenyl. $R^2$ is phenyl substituted with one substituent selected from the group consisting of $C_1$-$C_4$ alkyl, cyano, amido, $C_1$-$C_4$ alkoxy, and hydroxyalkyl. In some embodiments, $R^2$ is phenyl substituted with one methyl group (e.g., m-tolyl).

In some embodiments, $R^1$ is $C_1$-$C_4$ alkyl and $R^2$ is optionally substituted phenyl. In some embodiments, 1e is ethyl and $R^2$ is m-tolyl.

In some embodiments, Z is —$NR^3R^4$.
In some embodiments, $R^3$ and $R^4$, together with the nitrogen atom to which they are attached, together form an optionally substituted ring. In some embodiments, $R^3$ and $R^4$, together with the nitrogen atom to which they are attached, together form an optionally substituted monocyclic heterocycle. In some embodiments, the optionally substituted monocyclic heterocycle is selected from the group consisting of optionally substituted pyrrolidine, piperidine and piperazine. In some embodiments, the optionally substituted monocyclic heterocycle is selected from the group consisting of unsubstituted pyrrolidine, unsubstituted piperidine, piperidine substituted with one substituent (e.g., alkoxycarbonyl such as ethoxycarbonyl), or piperazine substituted with one substituent (e.g., $C_1$-$C_4$ alkyl such as methyl).

In some embodiments, $R^3$ is hydrogen.
In some embodiments, $R^4$ is selected from the group consisting of unsubstituted $C_1$-$C_8$ alkyl (e.g., methyl), carboxy-$C_1$-$C_8$-alkyl (e.g., —$(CH_2)_7$—COOH), $C_1$-$C_4$-alkoxycarbonyl-$C_1$-$C_8$-alkyl (e.g., —$(CH_2)_7$—$COOCH_3$), optionally substituted phenyl (below), optionally substituted $C_5$-$C_6$ cycloalkyl (e.g., unsubstituted cyclopentyl, unsubstituted cyclohexyl, or substituted cyclohexyl), optionally substituted heterocyclyl (e.g., unsubstituted piperidinyl, piperidinyl substituted with tert-butoxycarbonyl, alkoxycarbonylalkylcarbonyl such as —CO—$(CH_2)_4$—$COOCH_3$), or carboxyalkylcarbonyl such as —CO—$(CH_2)_4$—COOH), optionally substituted heteroarylalkyl (e.g., pyridyl-$C_1$-$C_4$-alkyl such as —$CH_2$-pyridyl), and optionally substituted heterocyclylalkyl (e.g., morpholino-$C_1$-$C_4$-alkyl such as —$(CH_2)_3$-morpholino). For example, in some embodiments, $R^4$ is phenyl that is unsubstituted or substituted with one substituent, such as a substituent selected from the group consisting of $C_1$-$C_4$-alkoxycarbonyl (e.g., —$C(O)OCH_3$) and $C_1$-$C_4$-alkoxycarbonyl-$C_1$-$C_4$-alkyl (e.g., —$CH_2$—$C(O)CH_2CH_3$).

In some embodiments, $R^4$ is cyclohexyl substituted with one substituent selected from the group consisting of carboxy, $C_1$-$C_4$-alkoxycarbonyl (e.g., —$C(O)OCH_3$), $C_1$-$C_8$-alkylamido (e.g., —$C(O)NH$—$(CH_2)_3CH_3$ or —$C(O)NH$—$(CH_2)_5CH_3$), hydroxy-$C_1$-$C_8$-alkylamido (e.g., —$C(O)NH$—$(CH_2)_2OH$ or —$C(O)NH$—$(CH_2)_6OH$), amido (i.e. —$CONH_2$), optionally substituted amino-$C_1$-$C_8$-alkylamido (e.g., —$C(O)NH$—$(CH_2)_6NH_2$), $C_1$-$C_4$-dialkylamino-$C_1$-$C_8$-alkylamido (e.g., —$C(O)NH$—$(CH_2)_2N(CH_3)_2$), carboxy-$C_1$-$C_8$-alkylamido (e.g., —$C(O)NH$—$(CH_2)_3COOH$, —$C(O)NH$—$(CH_2)_5COOH$ or —$C(O)NH$—$(CH_2)_7COOH$), sulfonic acid-$C_1$-$C_8$-alkylamido (e.g., —$C(O)NH$—$(CH_2)_6SO_3H$), sulfonate-$C_1$-$C_8$-alkylamido (e.g., —$C(O)NH$—$(CH_2)_6SO_3$—), $C_1$-$C_4$-alkylcarbonyl-$C_1$-$C_8$-alkylamido (e.g., —$C(O)NH$—$(CH_2)_3COOCH_3$, —$C(O)NH$—$(CH_2)_5COOCH_3$ or —$C(O)NH$—$(CH_2)_7COOCH_3$), optionally substituted $C_3$-$C_6$-cycloalkylamido (e.g., —$C(O)NH$— cyclohexyl, —$C(O)NH$-cyclohexyl-COOH or —$C(O)NH$-cyclohexyl-$COOCH_3$), and heterocyclylamido (e.g., —$C(O)NH$-piperidinyl, unsubstituted or substituted with methyl, tert-butoxycarbonyl or acetyl). For example, in some embodiments, $R^4$ is optionally substituted amino-$C_1$-$C_8$-alkylamido (e.g., —$C(O)NH$—$(CH_2)_6NH_2$), wherein the amino group is protected with an amino protecting group (e.g., tert-butoxycarbonyl), or wherein the amino group is protonated to form a salt (e.g., a hydrochloride salt), or wherein the amino group is further functionalized with a fluorophore (e.g., fluorescein) or a polypeptide (e.g., an -Asp-Asp-Asp peptide, which may be acetylated at the terminus).

In some embodiments, Z is —OR$^5$. In some embodiments, R$^5$ is H. In some embodiments, R$^5$ is optionally substituted C$_1$-C$_4$ alkyl (e.g., methyl).

(2) Use of Cell-Impermeable Thienopyrrole Compounds

In certain embodiments, the methods disclosed herein include contacting a sample (e.g., a cell) with a mixture of a cell-permeable coelenterazine substrate and a compound described herein that is modified such that it is cell-impermeable. In such embodiments, the disclosed thienopyrrole compounds and methods may be used to build up the initial brightness of a high-throughput screening operation assay format, and then selectively inhibit any luciferases that may be excreted from cells, to selectively inhibit luminescence that may occur outside of the cells. Such methods may provide for a more selective signal within cells. Examples of cell-impermeable thienopyrrole compounds include JRW-0051, JRW-0147, and JRW-0187.

(3) Use of Cell-Permeable Thienopyrrole Compounds

In certain embodiments, the methods disclosed herein include contacting a sample (e.g., a cell) with a mixture of a cell-permeable coelenterazine substrate and a compound described herein that is cell-permeable. In such embodiments, the disclosed thienopyrrole compounds can enter in to cells and selectively inhibit an *Oplophorus* luciferase therein. Such methods may be advantageous in multiplexing assays that involve use of two or more luciferases, and may allow for inhibition of luminescence from an *Oplophorus* luciferase so as to selectively view luminescence from another luciferase inside the cell. Examples of cell-permeable thienopyrrole compounds include JRW-0013 and JRW-0138.

(4) Use with Transcriptional Reporters

The disclosed thienopyrrole compounds may be used with genetic transcriptional reporter systems. In certain embodiments, provided is a method for measuring the activity of a promoter in a sample, wherein the promoter is operably linked to a gene encoding an *Oplophorus*-derived luciferase or a variant thereof. The method includes (a) contacting the sample with a coelenterazine substrate; (b) determining the activity of the promoter by measuring luminescence of the sample, wherein the sample comprises the promoter. The method can further include a step of contacting the sample with a thienopyrrole compound described herein, to selectively inhibit the luminescence. The promoter may be operably linked to the gene via a translational or transcriptional fusion. A biological pathway of interest, for example, may be examined by treating a cell that comprises the promoter, which is operably linked to a gene encoding the luciferase, with an inducer agent of the pathway. This promoter activity may then be measured and monitored to study any correlation between the activity of the promoter and the pathway of interest, as well as obtain kinetic measurements relating to gene expression (e.g. inducibility, repression and activation). The thienopyrrole compound described herein can be used to selectively inhibit the luminescence.

(5) Multiplexing

The disclosed thienopyrrole compounds may be used to inhibit *Oplophorus* luciferases as applied to temporal multiplexing with other luciferases and assays. In some embodiments, the *Oplophorus*-derived luciferase or variant thereof may be multiplexed with another enzyme (e.g. a luciferase) that emits light at a different wavelength, e.g., green firefly luciferase, e.g., *Photinus pyralis* (e.g., Luc2; Promega Corp) or red click beetle luciferase (CHROMA-LUC™ luciferase; Promega Corp.). For example, if an *Oplophorus* luciferase is used as a functional reporter, then the green firefly luciferase or red CHROMA-LUC™ luciferase could be used to control for non-specific effects on genetic regulation or to normalize for transfection efficiency. In some embodiments, luminescence generated from the *Oplophorus* luciferase (approximately 460 nm) and red CHROMA-LUC (approximately 610 nm) can be easily resolved using a luminometer with wavelength-discriminating filters, enabling the measurement of both signals from the same sample. In such embodiments, a thienopyrrole compound described herein can be used to selectively inhibit the *Oplophorus* luciferase, such that the signal from the other luciferase can be selectively viewed.

In another example, an *Oplophorus* luciferase could be used as a transcriptional reporter and paired with a luciferase that emits light at a different wavelength contained in an assay reagent. In another example, an *Oplophorus* luciferase may be used with one or more additional luciferases, where the luminescence of each luciferase may be separately measured through the use of selective enzyme inhibitors. For example, the luminescence of the *Oplophorus* luciferase may be measured upon addition of appropriate substrates and buffers, followed by measurement of a second luciferase upon a subsequent addition of appropriate substrates and buffers and one or more thienopyrrole compounds described herein, which are selective for the an *Oplophorus* luciferase. In another example, the *Oplophorus* luciferase contained in an assay reagent may be used for measuring a specific aspect of cellular physiology, for example ATP to estimate cell viability or caspase activity to estimate cellular apoptosis.

(6) Bioluminescence Resonance Energy Transfer (BRET)

The disclosed thienopyrrole compounds may be used in any method in which an *Oplophorus* luciferase is used for detecting ligand-protein and/or protein-protein interactions. In various embodiments, the *Oplophorus* luciferase may be used to transfer energy to an energy acceptor. One such method is Bioluminescence Resonance Energy Transfer (BRET). With respect to BRET, energy transfer from a bioluminescent donor to a fluorescent acceptor results in a shift in the spectral distribution of the emission of light. This energy transfer may enable real-time monitoring of protein-protein or ligand-protein interaction in vitro or in vivo. In some embodiments, the BRET method may be an Nluc-Mediated Bioluminescence Resonance Energy Transfer (such as NanoBRET) Assay for ligand-protein and protein-protein interactions. NANOBRET comprises two different methods: 1) using HALOTAG and Nluc-based technologies, Bioluminescence Resonance Energy Transfer (BRET) to detect protein-protein and/or ligand-protein interactions may be achieved with increased signal and decreased spectral overlap; and 2) using Nluc luciferase fused to a protein of interest and a fluorescent tracer to detect ligand-receptor interaction in living cells.

In some embodiments, the luminescent enzymes (i.e. *Oplophorus* luciferases) used in BRET analysis can be used to determine if two molecules are capable of binding to each other or co-localize in a cell. For example, a luminescent enzyme can be used as a bioluminescence donor molecule, which is combined with a molecule or protein of interest to create a first fusion protein. In various embodiments, the first fusion protein contains a luminescent enzyme and a protein of interest. In various embodiments, the first fusion proteins containing the luminescent enzyme can be used in BRET analysis to detect protein/protein interaction in systems including but not limited to cell lysates, intact cells, and living animals. In various embodiments, HALOTAG can be used as a fluorescent acceptor molecule. In some embodiments, HALOTAG can be fused to a second protein of interest or to a luminescent enzyme. For example, a luminescent enzyme can be fused to HALOTAG, expressed in cells or animals, and labeled with a fluorescent HALOTAG ligand such as HALOTAG TMR ligand. The fusion can subsequently be excited to fluoresce in the presence of a cell-permeant luminescent enzyme substrate. In some embodiments, BRET may be performed using luminescent enzymes in combination with fluorescent proteins, including but not limited to Green Fluorescent Protein (GFP) or Red Fluorescent Protein (RFP) or fluorescent labels including fluorescein, rhodamine green, Oregon green, or Alexa 488, to name a few non-limiting examples.

In some embodiments, quenching the signal from excreted Nluc can improve the signal to noise ratio when using the NanoBRET plate assay.

In certain embodiments, a cell-permeable thienopyrrole compound may be used to inhibit intracellular BRET. In certain embodiments, a cell-impermeable thienopyrrole compound may be used to inhibit extracellular BRET. In certain embodiments, a cell-impermeable thienopyrrole compound may be used in a target engagement model.

(7) Protein Proximity Assays for Live Cells or Lytic Formats

In some embodiments, *Oplophorus* luciferases may be used in circularly permuted (CP) or straight split (SS) luminescent enzyme fusion proteins to measure protein proximity. The *Oplophorus* luciferase is permuted or split via insertion of a protease substrate amino acid sequence (e.g., TEV) to generate low bioluminescence. The inactive luciferase is tethered (e.g., via genetic fusion) to a monitor protein. A potential interacting protein is tethered (e.g., via genetic fusion) to a protease (e.g., TEV). When the two monitor proteins interact or are in sufficient proximity (e.g., via a constitutive interaction, a drug stimulus or a pathway response), the luminescent enzyme is cleaved to generate increased bioluminescence activity. The example may be applied to measurements of protein proximity in cells or in biochemical assays.

(8) Protein Complementation Assays

In some embodiments, the disclosed thienopyrrole compounds may be used to inhibit an *Oplophorus* luciferase when such a luciferase is used in other methods for detecting ligand-protein and protein-protein interactions or proximity, such as the protein complementation assay (PCA) or enzyme fragmentation assay. Protein complementation assays (PCA) provide a means to detect the interaction of two biomolecules, e.g., polypeptides. PCA utilizes two fragments of the same protein, e.g., enzyme, that when brought into close proximity with each other can reconstitute into a functional, active protein. In some embodiments, the NANOBIT® technology (Promega Corporation) may be used to detect molecular proximity by virtue of the reconstitution of a luminescent enzyme via the binding interaction of enzyme components or subunits. NANOBIT utilizes a non-luminescent peptide (NLPep) and non-luminescent polypeptide (NLPoly) derived from the *Oplophorus* luciferase variant, Nluc luciferase. The NLPep and NLPoly are fused to proteins of interest. If the proteins of interest interact, NLPep and NLPoly interact to reconstitute a full-length *Oplophorus* luciferase enzyme.

For example, a luminescent enzyme can be separated into two fragments at a site(s) tolerant to separation and each fragment of the separated luminescent enzyme can be fused to one of a pair of polypeptides of interest believed to interact, e.g., FKBP and FRB. If the two polypeptides of interest do in fact interact, the luminescent enzyme fragments, for example, then come into close proximity with each other to reconstitute the functional, active luminescent enzyme. In some embodiments, the activity of the reconstituted luminescent enzyme can then be detected and measured. In some embodiments, the split luminescent enzyme can be used in a more general complementation system similar to lac-Z (Langley et al., *PNAS* 72:1254-1257 (1975)) or ribonuclease S (Levit and Berger, *J. Biol. Chem.* 251:1333-1339 (1976)). In some embodiments, a luminescent enzyme fragment (designated "A") known to complement with another luminescent enzyme fragment ("B") can be fused to a target protein, and the resulting fusion can be monitored via luminescence in a cell or cell lysate containing fragment B. In some embodiments, the source of fragment B could be the same cell (e.g., if the gene for fragment B is integrated into the genome of the cell or is contained on another plasmid within the cell) or it could be a lysate or purified protein derived from another cell. In some embodiments, this same fusion protein (fragment A) could be captured or immobilized using a fusion between fragment B and a polypeptide such as HALOTAG capable of attachment to a solid support. In some embodiments, luminescence can be used to demonstrate successful capture or to quantify the amount of material captured.

(9) Dimerization Assay

In some embodiments, the disclosed thienopyrrole compounds may be used with full-length circularly permuted luminescent enzymes fused to respective binding partners, e.g., FRB and FKBP, and used in a protein complementation-type assay. The key difference between the method disclosed herein and traditional protein complementation is that there was no complementation, but rather there was dimerization of two full length enzymes, e.g., circularly permuted luminescent enzymes.

Briefly, the circularly permuted reporter proteins similarly configured for low activity are fused to both of the fusion protein partners. For example, each fusion partner may be linked to identically structured, permuted reporters. Interaction of the fusion partners brought the permuted reporters into close proximity, thereby allowing reconstitution of a hybrid reporter having higher activity.

6. Sample

The disclosed thienopyrrole compounds may be used with samples containing biological components. The sample may comprise cells. The sample may comprise heterogeneous mixtures of components (including intact cells, cell extracts, cell lysates, bacteria, viruses, organelles, exosomes, and mixtures thereof) or a single component or homogeneous group of components (e.g., natural or synthetic amino acid, nucleic acid or carbohydrate polymers, or lipid membrane complexes). The thienopyrrole compounds may be generally non-toxic to living cells and other biological components within the concentrations of use.

The sample may include an animal (e.g., a vertebrate), a plant, a fungus, physiological fluid (e.g., blood, plasma, urine, mucous secretions and the like), a cell, a cell lysate, a cell supernatant, or a purified fraction of a cell (e.g., a subcellular fraction). In certain embodiments, the sample may be a cell. In some embodiments, the sample may be a live cell. The cell may be a eukaryotic cell, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule. The cell may or may not express a luciferase. The cells may have been genetically modified via recombinant techniques.

7. Kits

Disclosed are kits for determining the presence or activity of one or more enzymes (e.g., an *Oplophorus* or *Oplophorus* variant luciferase). The kit may include one or more of the following: a compound or composition of the invention that may inhibit the *Oplophorus* or *Oplophorus* variant luciferase, a coelenterazine or coelenterazine-derivative substrate, an *Oplophorus* or *Oplophorus* variant luciferase, instructions for carrying out a luminescence assay, and reaction buffer(s). The reaction buffers may be present in individual formulations for the non-luciferase enzyme reactions and the luminescent enzyme reactions or in a single formulation for a single step assay. The kits may also contain other inhibitors, activators and/or enhancers for the non-luciferase enzyme(s). The kits may also contain a positive and/or negative control for the assay.

8. Examples

General Synthesis Procedure A: To a solution of ester intermediate (1eq) in dioxane/water (4:1), lithium hydroxide (5eq) was added. The suspension was heated to 60° C. until starting material was consumed (monitored by LCMS or TLC analysis). The reaction mixture was cooled and acidified with HCl (2M) until pH 3. The suspension was partitioned between ethyl acetate and water. The organic layer was dried over anhydrous sodium sulfate and filtered. The filtrate was then concentrated. The residue was purified by column chromatography (silica, dichloromethane/methanol) to afford the desired product.

General Synthesis Procedure B: To a solution of carboxylate intermediate (1eq) in dimethylformamide, the requisite amine (or amine hydrochloride), hydroxybenzotriazole (2eq), 1-ethyl-3-(3-dimethylaminopropyl)carbodiimide (2eq) and diisopropylethylamine (3eq) was added. The mixture was heated to 60° C. until starting material was consumed (monitored by LCMS or TLC analysis). The reaction mixture cooled, diluted with ethyl acetate, and washed with water. The organic layer was dried over anhydrous sodium sulfate and filtered. The filtrate was then concentrated. The residue was purified by column chromatography (silica, dichloromethane/methanol or heptane/ethyl acetate) to afford the desired product.

Example 1

General Syntheses of Compounds of Formula (Ia)

Compounds of formula (Ia) can be generally synthesized according to Scheme 1.

Scheme 1.

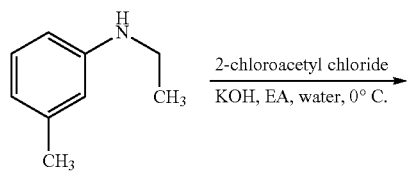

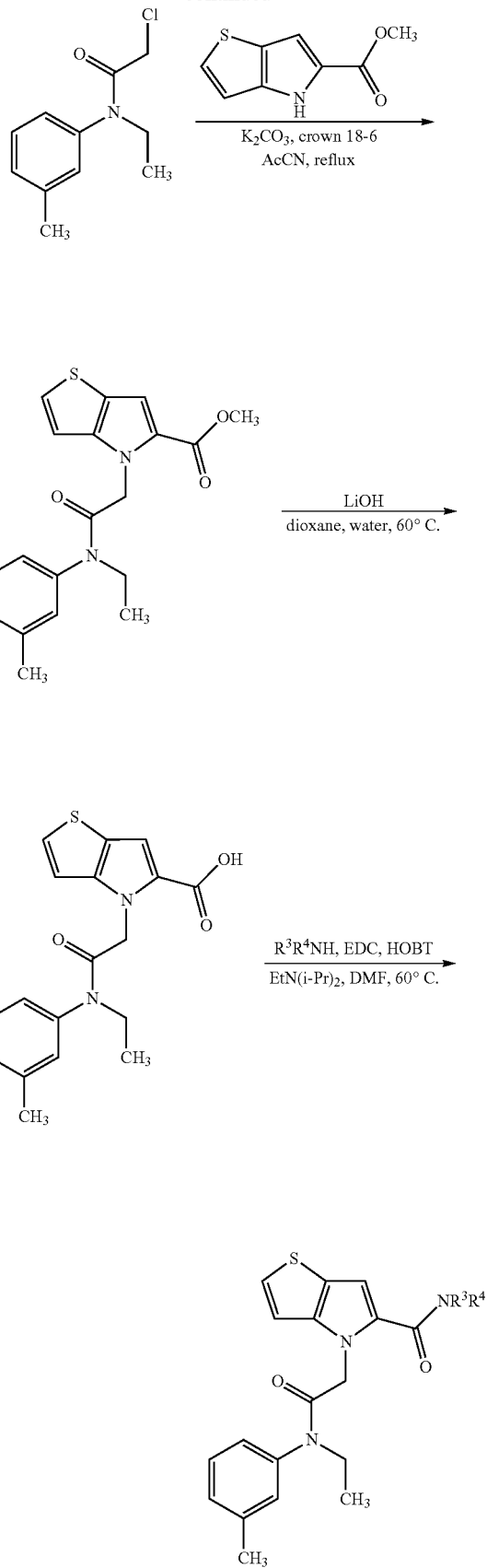

2-chloro-N-ethyl-N-(m-tolyl)acetamide (JRW-0003)

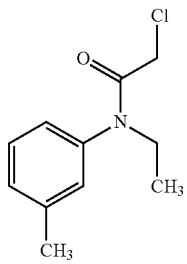

To a solution of N-ethyl-3-methylaniline (2.0 g, 14.8 mmol) in ethyl acetate (25 mL), water (12 mL) was added. The biphasic solution was cooled to 0° C., and potassium hydroxide (2.49 g, 44.4 mmol) added in one motion. 2-Chloroacetyl chloride (2.5 g, 1.8 mL, 22.2 mmol) was added dropwise over 10 min. The mixture was stirred for 1 h, diluted with water, and extracted with ethyl acetate. The organic layer was dried over anhydrous sodium sulfate and filtered. The filtrate was then concentrated to afford crude product (3.2 g) as a mobile oil. ESI MS m/z 212 [M+H]$^+$.

methyl 4-(2-(ethyl(m-tolyl)amino)-2-oxoethyl)-4H-thieno[3,2-b]pyrrole-5-carboxylate (JRW-0004)

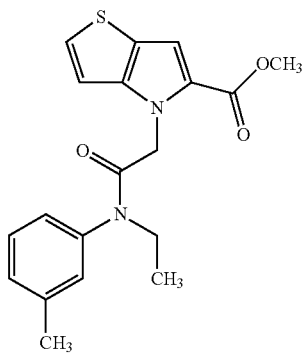 [SMILES: CCN(C(=O)Cn1c(C(=O)OC)cc2sccc21)c1cccc(C)c1]

To a solution of 2-chloro-N-ethyl-N-(m-tolyl)acetamide (14.8 mmol) in acetonitrile (100 mL), methyl 4H-thieno[3,2-b]pyrrole-5-carboxylate (2.28 g, 12.6 mmol), potassium carbonate (2.09 g, 15.1 mmol) and 18-crown-6 (166 mg, 0.63 mmol) was added. The mixture was heated to reflux for 5 h, and the reaction was concentrated under vacuum to ~20 mL volume. The suspension was diluted with water, filtered, and washed with water. The solid was dried under vacuum to afford crude product (4.6 g) as a light brown solid. $^1$H NMR (300 MHz, DMSO-d$_6$) δ 7.53 (d, J=5.4, 1H), 7.46-7.36 (m, 1H), 7.35-7.11 (m, 5H), 4.92 (s, 2H), 3.74 (s, 3H), 3.67-3.53 (m, 2H), 2.37 (s, 3H), 1.00 (t, J=6.6, 3H); ESI MS m/z 357 [M+H]$^+$.

4-(2-(ethyl(m-tolyl)amino)-2-oxoethyl)-4H-thieno[3,2-b]pyrrole-5-carboxylic acid (WZ-141-74)

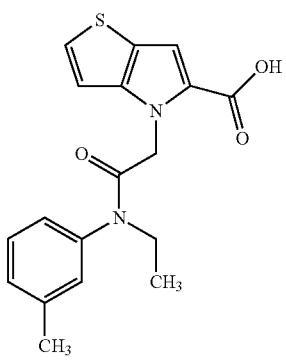

Following general procedure A, methyl 4-(2-(ethyl(m-tolyl)amino)-2-oxoethyl)-4H-thieno[3,2-b]pyrrole-5-carboxylate (2.0 g, 5.6 mmol) was reacted with lithium hydroxide (671 mg 28.0 mmol) to afford the desired product (1.8 g, 93%) as a light yellow solid. $^1$H NMR (300 MHz, DMSO-d$_6$) δ 12.45 (s, 1H), 7.49 (d, J=5.4, 1H), 7.44-7.37 (m, 1H), 7.33-7.12 (m, 4H), 7.09 (s, 1H), 4.91 (s, 2H), 3.71-3.54 (m, 2H), 2.36 (s, 3H), 1.08-0.94 (s, 3H); ESI MS m/z 343 [M+H]$^+$.

Example 2

N-cyclohexyl-4-(2-(ethyl(m-tolyl)amino)-2-oxoethyl)-4H-thieno[3,2-b]pyrrole-5-carboxamide (JRW-0006)

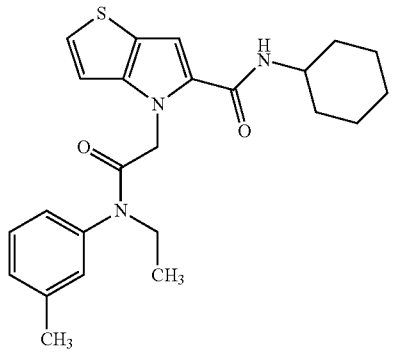 [SMILES: CCN(C(=O)Cn1c(C(=O)NC2CCCCC2)cc2sccc21)c1cccc(C)c1]

Following general procedure B, 4-(2-(ethyl(m-tolyl)amino)-2-oxoethyl)-4H-thieno[3,2-b]pyrrole-5-carboxylic acid (75 mg, 0.22 mmol) was reacted with cyclohexylamine (43 mg 0.44 mmol) to afford the desired product (50 mg, 54%) as a white solid. $^1$H NMR (300 MHz, DMSO-d$_6$) δ 7.83 (d, J=8.1, 1H), 7.44-7.16 (m, 5H), 7.13-7.06 (m, 2H), 4.96 (s, 2H), 3.75-3.52 (m, 2H), 2.36 (s, 3H), 1.84-1.51 (m, 5H), 1.37-1.17 (m, 6H), 1.05-0.93 (m, 3H); ESI MS m/z 424 [M+H]$^+$; HPLC >99% (AUC), T$_R$ 7.02 min; UV (MeOH) λ$_{max}$ 289 nm, ε25,200.

Example 3

N-ethyl-2-(5-(pyrrolidine-1-carbonyl)-4H-thieno[3,2-b]pyrrol-4-yl)-N-(m-tolyl)acetamide (JRW-0008)

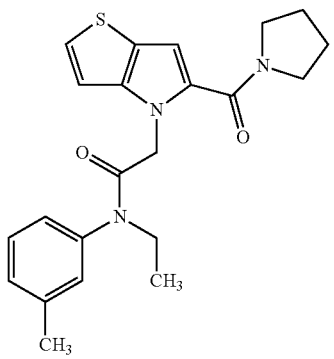 [SMILES: CCN(C(=O)Cn1c(C(=O)N2CCCC2)cc2sccc21)c1cccc(C)c1]

Following general procedure B, 4-(2-(ethyl(m-tolyl)amino)-2-oxoethyl)-4H-thieno[3,2-b]pyrrole-5-carboxylic acid (75 mg, 0.22 mmol) was reacted with pyrrolidine (43 mg 0.44 mmol) to afford the desired product (70 mg, 81%) as an off-white solid. $^1$H NMR (300 MHz, DMSO-$d_6$) δ 7.45-7.16 (m, 5H), 7.06 (d, J=5.2, 1H), 6.83 (s, 1H), 4.83 (s, 2H), 3.77-3.32 (m, 6H), 2.36 (s, 3H), 1.91-1.75 (m, 4H), 1.06-0.92 (m, 3H); ESI MS m/z 396 [M+H]$^+$; HPLC 97.3% (AUC), $T_R$ 6.24 min; UV (MeOH) $\lambda_{max}$ 288 nm, ε 21,773.

Example 4

N-ethyl-2-(5-(piperidine-1-carbonyl)-4H-thieno[3,2-b]pyrrol-4-yl)-N-(m-tolyl)acetamide (JRW-0009)

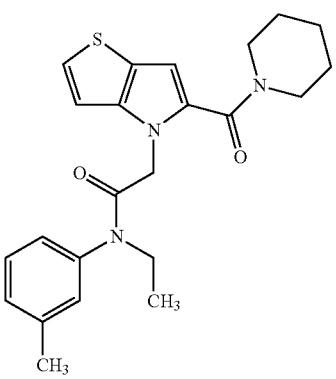 [SMILES: CCN(C(=O)Cn1c(C(=O)N2CCCCC2)cc2sccc21)c1cccc(C)c1]

Following general procedure B, 4-(2-(ethyl(m-tolyl)amino)-2-oxoethyl)-4H-thieno[3,2-b]pyrrole-5-carboxylic acid (80 mg, 0.23 mmol) was reacted with piperidine (40 mg 0.47 mmol) to afford the desired product (90 mg, 94%) as an orange gum. $^1$H NMR (300 MHz, DMSO-$d_6$) δ 7.52-7.13 (m, 5H), 7.05 (d, J=5.2, 1H), 6.58 (s, 1H), 4.75 (s, 2H), 3.68-3.45 (m, 6H), 2.37 (s, 3H), 1.69-1.42 (m, 6H), 1.00 (t, J=6.9, 3H); ESI MS m/z 410 [M+H]$^+$; HPLC 98.8% (AUC), $T_R$ 5.91 min; UV (MeOH) $\lambda_{max}$ 284 nm, ε 24,598.

Example 5 ethyl 1-(4-(2-(ethyl(m-tolyl)amino)-2-oxoethyl)-4H-thieno[3,2-b]pyrrole-5-carbonyl)piperidine-4-carboxylate (JRW-0012)

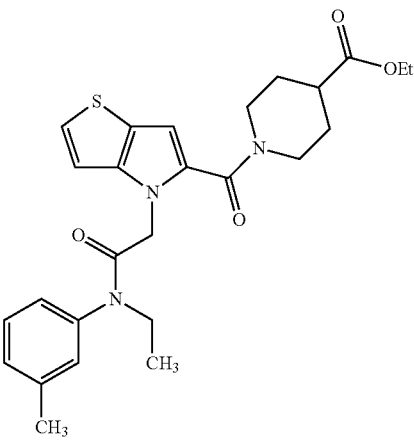 [SMILES: CCOC(=O)C1CCN(C(=O)c2cc3sccc3n2CC(=O)N(CC)c2cccc(C)c2)CC1]

Following general procedure B, 4-(2-(ethyl(m-tolyl)amino)-2-oxoethyl)-4H-thieno[3,2-b]pyrrole-5-carboxylic acid (120 mg, 0.35 mmol) was reacted with ethyl piperidine-4-carboxylate (110 mg 0.70 mmol) to afford the desired product (160 mg, 94%) as a white foam. $^1$H NMR (300 MHz, DMSO-$d_6$) δ 7.47-7.36 (m, 1H), 7.32 (d, J=5.3, 1H), 7.29-7.14 (m, 3H), 7.07 (d, J=5.3, 1H), 6.61 (s, 1H), 4.75 (s, 2H), 4.22 (d, J=13.2, 2H), 4.06 (q, J=7.1, 2H), 3.68-3.52 (m, 2H), 3.18-2.94 (m, 2H), 2.70-2.55 (m, 1H), 2.37 (s, 3H), 1.90-1.78 (m, 2H), 1.62-1.48 (m, 2H), 1.17 (t, J=7.1, 3H), 0.98 (t, J=6.8, 3H); ESI MS m/z 482 [M+H]$^+$; HPLC >99% (AUC), $T_R$ 7.25 min; UV (MeOH) $\lambda_{max}$ 286 nm, ε 20,009

Example 6

4-(2-(ethyl(m-tolyl)amino)-2-oxoethyl)-N-phenyl-4H-thieno[3,2-b]pyrrole-5-carboxamide (JRW-0143)

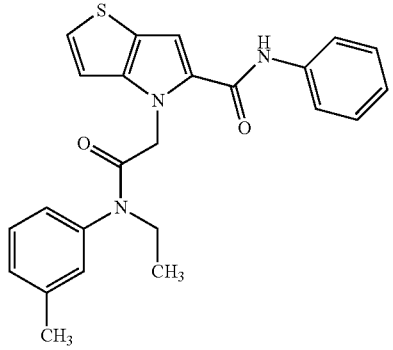 [SMILES: CCN(C(=O)Cn1c(C(=O)Nc2ccccc2)cc2sccc21)c1cccc(C)c1]

Following general procedure B, 4-(2-(ethyl(m-tolyl)amino)-2-oxoethyl)-4H-thieno[3,2-b]pyrrole-5-carboxylic acid (50 mg, 0.15 mmol) was reacted with aniline (16 mg 0.18 mmol) to afford the desired product (30 mg, 49%) as a foam. $^1$H NMR (300 MHz, DMSO-$d_6$) δ 9.93 (s, 1H), 7.74-7.68 (m, 2H), 7.49-7.19 (m, 9H), 7.16 (d, J=5.3, 1H), 7.05 (t, J=7.4, 1H), 4.99 (s, 2H), 3.67-3.52 (m, 2H), 2.37 (s, 3H), 1.06-0.92 (m, 3H); ESI MS m/z 418 [M+H]$^+$; HPLC 85.4% (AUC), T$_R$ 6.04 min; UV (EtOH) $\lambda_{max}$ 306 nm, ε 27,330.

Example 7 ethyl 2-(4-(4-(2-(ethyl(m-tolyl)amino)-2-oxoethyl)-4H-thieno[3,2-b]pyrrole-5-carboxamido)phenyl)acetate (JRW-0152)

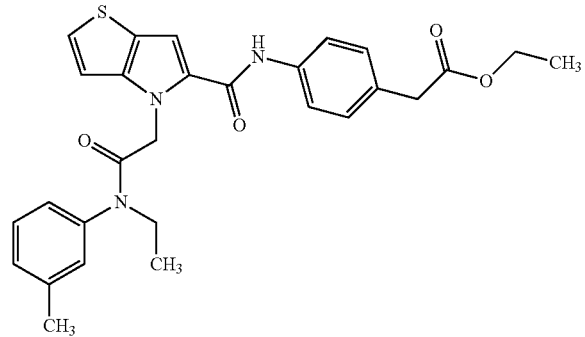 [SMILES: CCOC(=O)Cc1ccc(NC(=O)c2cc3sccc3n2CC(=O)N(CC)c2cccc(C)c2)cc1]

To a solution of 4-(2-(ethyl(m-tolyl)amino)-2-oxoethyl)-4H-thieno[3,2-b]pyrrole-5-carboxylic acid (50 mg, 0.15 mmol) in DMF (3 mL), ethyl 2-(4-aminophenyl)acetate (31 mg, 0.18 mmol), HATU (111 mg, 0.29 mmol) and diisopropylethylamine (56 mg, 0.44 mmol) was added. The reaction was heated to 60° C. for 18 h. The reaction mixture cooled, diluted with ethyl acetate, and washed with water. The organic layer was dried over anhydrous sodium sulfate and filtered. The filtrate was then concentrated. The residue was purified by column chromatography (silica, heptane/ethyl acetate) to afford the desired product (28 mg, 38%) as an orange solid. $^1$H NMR (300 MHz, DMSO-d$_6$) δ 9.93 (s, 1H), 7.64 (d, J=7.6, 2H), 7.50-7.11 (m, 9H), 4.99 (s, 2H), 4.06 (q, J=6.4 Hz, 2H), 3.60 (s, 4H), 2.37 (s, 3H), 1.17 (t, J=7.2, 3H), 0.98 (t, J=6.4, 3H); ESI MS m/z 476 [M+H]$^+$; HPLC 97.2% (AUC), T$_R$ 7.61 min; UV (EtOH) $\lambda_{max}$ 308 nm, ε 34,350.

Example 8 methyl 3-(4-(2-(ethyl(m-tolyl)amino)-2-oxoethyl)-4H-thieno[3,2-b]pyrrole-5-carboxamido)benzoate (JRW-0151)

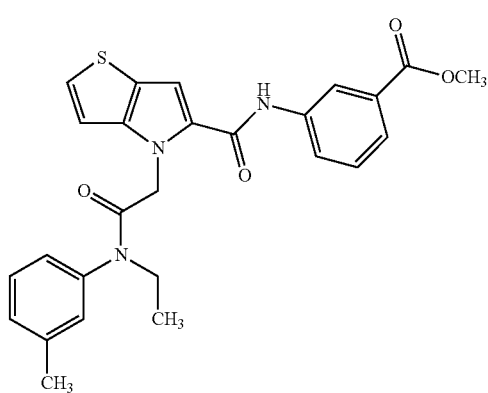 [SMILES: CCN(C(=O)Cn1c(C(=O)Nc2cccc(C(=O)OC)c2)cc2sccc21)c1cccc(C)c1]

To a solution of 4-(2-(ethyl(m-tolyl)amino)-2-oxoethyl)-4H-thieno[3,2-b]pyrrole-5-carboxylic acid (50 mg, 0.15 mmol) in DMF (3 mL), methyl 3-aminobenzoate (33 mg, 0.22 mmol), HATU (111 mg, 0.29 mmol) and diisopropylethylamine (56 mg, 0.44 mmol). The reaction was heated to 60° C. for 18 h. The reaction mixture cooled, diluted with ethyl acetate, and washed with water. The organic layer was dried over anhydrous sodium sulfate and filtered. The filtrate was then concentrated. The residue was purified by column chromatography (silica, heptane/ethyl acetate) to afford the desired product (30 mg, 43%) as a light yellow solid. $^1$H NMR (300 MHz, DMSO-d$_6$) δ 10.15 (s, 1H), 8.42-8.38 (m, 1H), 8.00 (d, J=8.2, 1H), 7.67-7.63 (m, 1H), 7.56-7.10 (m, 8H), 5.00 (s, 2H), 3.86 (s, 3H), 3.67-3.55 (m, 2H), 2.38 (s, 3H), 0.99 (t, J=6.7, 3H); ESI MS m/z 476 [M+H]$^+$; HPLC 98.3% (AUC), T$_R$ 7.52 min; UV (EtOH) $\lambda_{max}$ 309 nm, ε 37,302.

Example 9 methyl-cis-4-(4-(2-(ethyl(m-tolyl)amino)-2-oxoethyl)-4H-thieno[3,2-b]pyrrole-5-carboxamido)cyclohexane-1-carboxylate (JRW-0041)

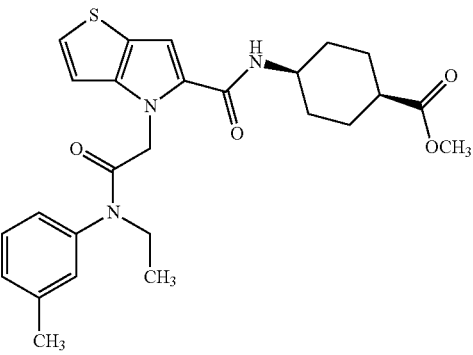 [SMILES: CCN(C(=O)Cn1c(C(=O)N[C@H]2CC[C@@H](C(=O)OC)CC2)cc2sccc21)c1cccc(C)c1]

Following general procedure B, 4-(2-(ethyl(m-tolyl)amino)-2-oxoethyl)-4H-thieno[3,2-b]pyrrole-5-carboxylic acid (150 mg, 0.44 mmol) was reacted with methyl cis-4-aminocyclohexane-1-carboxylate hydrochloride (127 mg, 0.66 mmol) to afford the desired product (186 mg, 88%) as a white foam. $^1$H NMR (300 MHz, DMSO-d$_6$) δ 7.82 (d, J=7.8, 1H), 7.45-7.33 (m, 2H), 7.32-7.16 (m, 3H), 7.12 (s, 1H), 7.08 (d, J=5.3, 1H), 4.95 (s, 2H), 3.85-3.70 (m, 1H), 3.68-3.53 (m, 5H), 2.63-2.56 (m, 1H), 2.36 (s, 3H), 2.08-1.92 (m, 2H), 1.69-1.43 (m, 6H), 1.08-0.95 (m, 3H); ESI MS m/z 482 [M+H]$^+$; HPLC >99% (AUC), T$_R$ 7.16 min; UV (MeOH) $\lambda_{max}$ 288 nm, ε 24,998.

Example 10

6-(cis-4-(4-(2-(ethyl(m-tolyl)amino)-2-oxoethyl)-4H-thieno[3,2-b]pyrrole-5-carboxamido)cyclohexane-1-carboxamido)hexanoic acid (JRW-0264)

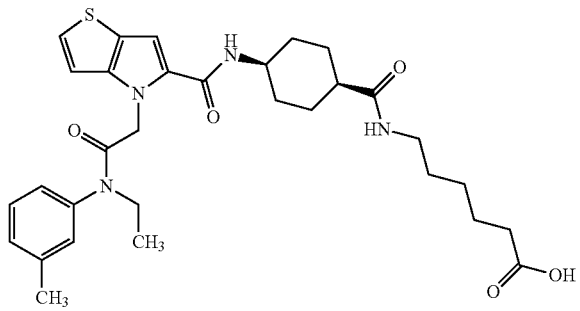 [SMILES: CCN(C(=O)Cn1c(C(=O)N[C@H]2CC[C@@H](C(=O)NCCCCCC(=O)O)CC2)cc2sccc21)c1cccc(C)c1]

Step 1. cis-4-(4-(2-(ethyl(m-tolyl)amino)-2-oxoethyl)-4H-thieno[3,2-b]pyrrole-5-carboxamido)cyclohexane-1-carboxylic acid (JRW-0261)

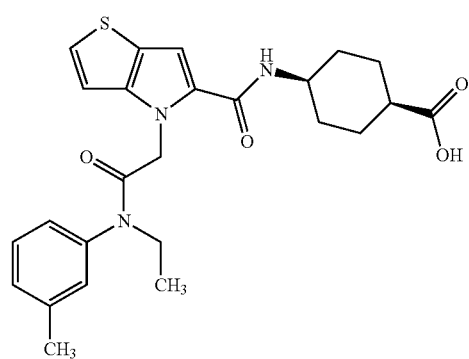 [SMILES: CCN(C(=O)Cn1c(C(=O)N[C@H]2CC[C@@H](C(=O)O)CC2)cc2sccc21)c1cccc(C)c1]

Following general procedure A, methyl-cis-4-(4-(2-(ethyl(m-tolyl)amino)-2-oxoethyl)-4H-thieno[3,2-b]pyrrole-5-carboxamido)cyclohexane-1-carboxylate (160 mg, 0.33 mmol) was reacted with lithium hydroxide (40 mg, 1.66 mmol) to afford crude product as a light brown solid. ESI MS m/z 468 [M+H]$^+$.

Step 2. methyl 6-(cis-4-(4-(2-(ethyl(m-tolyl)amino)-2-oxoethyl)-4H-thieno[3,2-b]pyrrole-5-carboxamido)cyclohexane-1-carboxamido)hexanoate (JRW-0262)

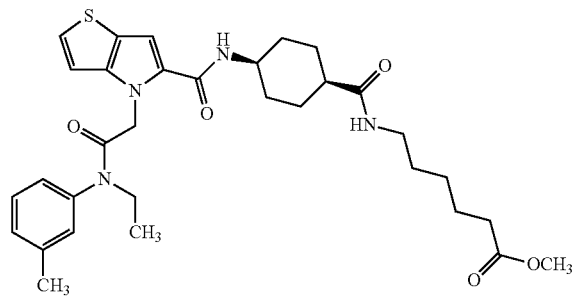 [SMILES: CCN(C(=O)Cn1c(C(=O)N[C@H]2CC[C@@H](C(=O)NCCCCCC(=O)OC)CC2)cc2sccc21)c1cccc(C)c1]

Following general procedure B, cis-4-(4-(2-(ethyl(m-tolyl)amino)-2-oxoethyl)-4H-thieno[3,2-b]pyrrole-5-carboxamido)cyclohexane-1-carboxylic acid (68 mg, 0.15 mmol) was reacted with methyl 6-aminohexanoate hydrochloride (40 mg, 0.22 mmol) to afford the desired product (63 mg, 72%) as a light red foam. ESI MS m/z 595 [M+H]$^+$.

Step 3. 6-(cis-4-(4-(2-(ethyl(m-tolyl)amino)-2-oxoethyl)-4H-thieno[3,2-b]pyrrole-5-carboxamido)cyclohexane-1-carboxamido)hexanoic acid (JRW-0264)

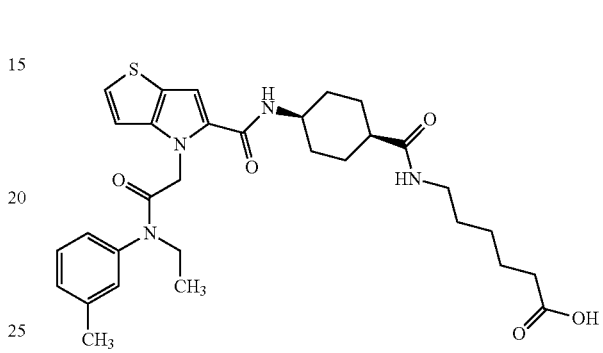

Following general procedure A, methyl 6-(cis-4-(4-(2-(ethyl(m-tolyl)amino)-2-oxoethyl)-4H-thieno[3,2-b]pyrrole-5-carboxamido)cyclohexane-1-carboxamido)hexanoate (60 mg, 0.10 mmol) was reacted with lithium hydroxide (12 mg, 0.50 mmol) to afford the desired product (56 mg, 95%) as a light red foam. $^1$H NMR (300 MHz, DMSO-d$_6$) δ 11.96 (s, 1H), 7.77 (d, J=7.2, 1H), 7.61 (t, J=5.5, 1H), 7.45-7.33 (m, 2H), 7.33-7.14 (m, 4H), 7.08 (d, J=5.5, 1H), 4.95 (s, 2H), 3.92-3.74 (m, 1H), 3.67-3.56 (m, 2H), 3.01 (dd, J=6.8, 12.6, 2H), 2.36 (s, 3H), 2.27-2.10 (m, 3H), 1.94-1.79 (m, 2H), 1.78-1.64 (m, 2H), 1.60-1.31 (m, 8H), 1.30-1.18 (m, 2H), 1.06-0.94 (m, 3H).; ESI MS m/z 581 [M+H]$^+$; HPLC 97.8% (AUC), T$_R$ 5.50 min; UV (EtOH) λ$_{max}$ 289 nm, ε 18,873.

Example 11

8-(4-(2-(ethyl(m-tolyl)amino)-2-oxoethyl)-4H-thieno[3,2-b]pyrrole-5-carboxamido)octanoic acid (JRW-0198)

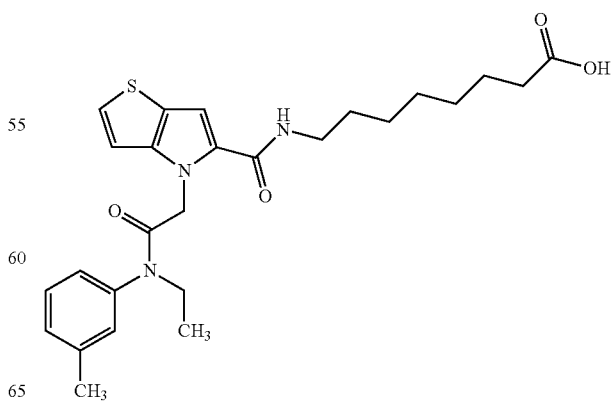

Step 1. methyl 8-(4-(2-(ethyl(m-tolyl)amino)-2-oxoethyl)-4H-thieno[3,2-b]pyrrole-5-carboxamido)octanoate (JRW-0196)

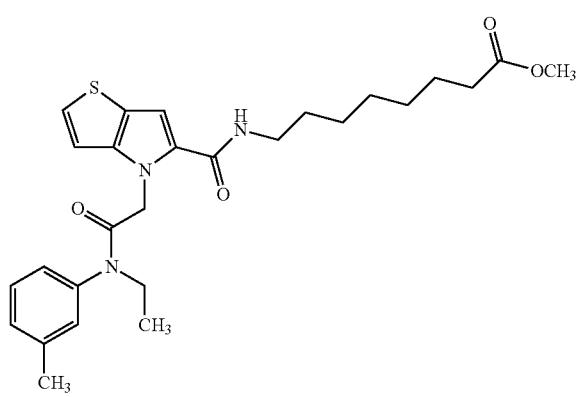 [SMILES: CCN(C(=O)Cn1c(C(=O)NCCCCCCCC(=O)OC)cc2sccc21)c1cccc(C)c1]

Following general procedure B, 4-(2-(ethyl(m-tolyl)amino)-2-oxoethyl)-4H-thieno[3,2-b]pyrrole-5-carboxylic acid (50 mg, 0.15 mmol) was reacted with methyl 8-aminooctanoate hydrochloride (46 mg, 0.22 mmol) to afford the desired product (72 mg, 99%) as an oil. ESI MS m/z 498 [M+H]$^+$.

Step 2. 8-(4-(2-(ethyl(m-tolyl)amino)-2-oxoethyl)-4H-thieno[3,2-b]pyrrole-5-carboxamido)octanoic acid (JRW-0198)

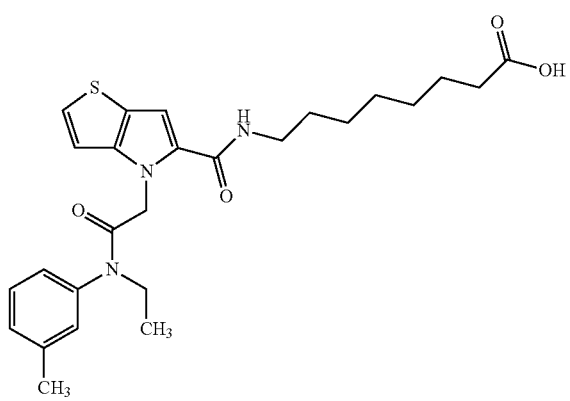 [SMILES: CCN(C(=O)Cn1c(C(=O)NCCCCCCCC(=O)O)cc2sccc21)c1cccc(C)c1]

Following general procedure A, methyl 8-(4-(2-(ethyl(m-tolyl)amino)-2-oxoethyl)-4H-thieno[3,2-b]pyrrole-5-carboxamido)octanoate (72 mg, 0.14 mmol) was reacted with lithium hydroxide (17 mg, 0.72 mmol) to afford the desired product (47 mg, 67%) as a white foam. $^1$H NMR (300 MHz, DMSO-d$_6$) δ 11.91 (s, 1H), 8.09 (t, J=5.3, 1H), 7.47-7.16 (m, 5H), 7.09 (d, J=5.3, 1H), 7.03 (s, 1H), 4.96 (s, 2H), 3.72-3.52 (m, 2H), 3.16 (dd, J=6.4, 12.8, 2H), 2.36 (s, 3H), 2.17 (t, J=7.3, 2H), 1.60-1.40 (m, 4H), 1.36-1.18 (m, 6H), 1.08-0.93 (m, 3H); ESI MS m/z 484 [M+H]$^+$; HPLC 99.4% (AUC), T$_R$ 5.43 min; UV (EtOH) λ$_{max}$ 288 nm, ε 24,627.

Example 12

6-(4-(4-(2-(ethyl(m-tolyl)amino)-2-oxoethyl)-4H-thieno[3,2-b]pyrrole-5-carboxamido)piperidin-1-yl)-6-oxohexanoic acid (JRW-0208)

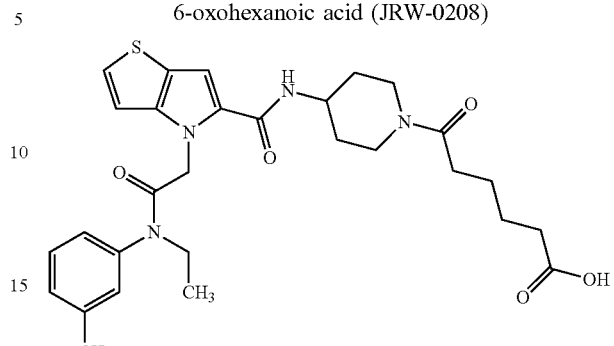

Step 1. tert-butyl 4-(4-(2-(ethyl(m-tolyl)amino)-2-oxoethyl)-4H-thieno[3,2-b]pyrrole-5-carboxamido)piperidine-1-carboxylate (JRW-0203)

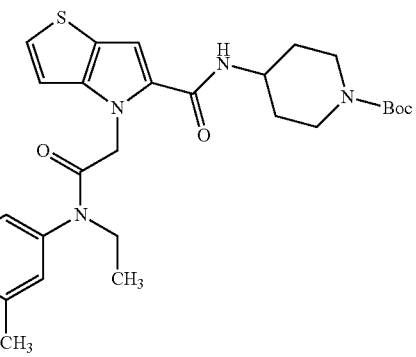

Following general procedure B, 4-(2-(ethyl(m-tolyl)amino)-2-oxoethyl)-4H-thieno[3,2-b]pyrrole-5-carboxylic acid (75 mg, 0.22 mmol) was reacted with tert-butyl 4-aminopiperidine-1-carboxylate (66 mg, 0.33 mmol) to afford the desired product (120 mg, quant) as a white foam. ESI MS m/z 525 [M+H]$^+$.

Step 2. 4-(2-(ethyl(m-tolyl)amino)-2-oxoethyl)-N-(piperidin-4-yl)-4H-thieno[3,2-b]pyrrole-5-carboxamide (JRW-0204)

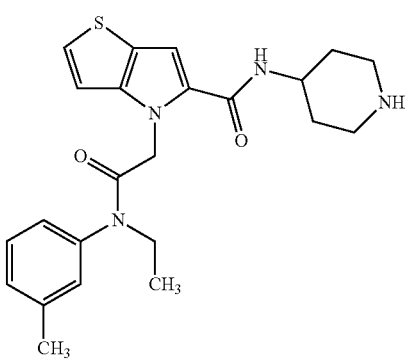 [SMILES: CCN(C(=O)Cn1c(C(=O)NC2CCNCC2)cc2sccc21)c1cccc(C)c1]

To a solution of tert-butyl 4-(4-(2-(ethyl(m-tolyl)amino)-2-oxoethyl)-4H-thieno[3,2-b]pyrrole-5-carboxamido)piperidine-1-carboxylate (120 mg, 0.22 mmol) in dichloromethane (5 mL), trifluoroacetic acid (1 mL) was added. The reaction stirred at RT for 1 h. The mixture was diluted with toluene and concentrated under vacuum (3×) to afford crude product (170 mg) of light brown oil. ESI MS m/z 425 [M+H]$^+$.

Step 3. methyl 6-(4-(4-(2-(ethyl(m-tolyl)amino)-2-oxoethyl)-4H-thieno[3,2-b]pyrrole-5-carboxamido)piperidin-1-yl)-6-oxohexanoate (JRW-0206)

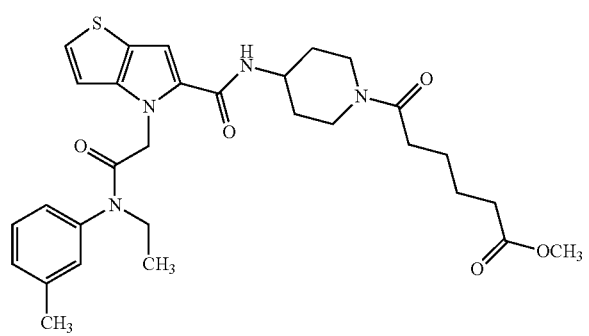 [SMILES: CCN(C(=O)Cn1c(C(=O)NC2CCN(C(=O)CCCCC(=O)OC)CC2)cc2sccc21)c1cccc(C)c1]

To a solution of 4-(2-(ethyl(m-tolyl)amino)-2-oxoethyl)-N-(piperidin-4-yl)-4H-thieno[3,2-b]pyrrole-5-carboxamide (0.22 mmol) in dichloromethane (5 mL) cooled to 0° C., methyl 6-chloro-6-oxohexanoate (49 mg, 0.27 mmol) and diisopropylethylamine (147 mg, 1.1 mmol) was added. The reaction stirred at 0° C. for 30 min. The mixture was diluted with dichloromethane and water, and the layers were separated. The organic layer was dried over anhydrous sodium sulfate and filtered. The filtrate was concentrated. The residue was purified by column chromatography (silica, dichloromethane/methanol) to afford the desired product (100 mg, 77%) as a white foam. ESI MS m/z 567 [M+H]$^+$.

Step 4. 6-(4-(4-(2-(ethyl(m-tolyl)amino)-2-oxoethyl)-4H-thieno[3,2-b]pyrrole-5-carboxamido)piperidin-1-yl)-6-oxohexanoic acid (JRW-0208)

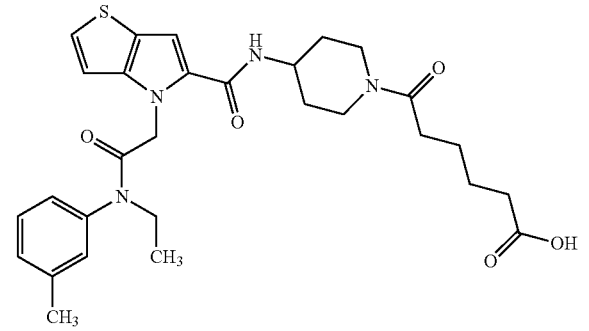 [SMILES: CCN(C(=O)Cn1c(C(=O)NC2CCN(C(=O)CCCCC(=O)O)CC2)cc2sccc21)c1cccc(C)c1]

Following general procedure A, methyl 6-(4-(4-(2-(ethyl(m-tolyl)amino)-2-oxoethyl)-4H-thieno[3,2-b]pyrrole-5-carboxamido)piperidin-1-yl)-6-oxohexanoate (100 mg, 0.18 mmol) was reacted with lithium hydroxide (2 1mg 0.88 mmol) to afford the desired product (98 mg, quant.) as a white foam. $^1$H NMR (300 MHz, DMSO-d$_6$) δ 11.96 (s, 1H), 7.93 (d, J=7.9, 1H), 7.46-7.34 (m, 2H), 7.33-7.17 (m, 3H), 7.12-7.06 (m, 2H), 4.96 (s, 2H), 4.39-4.26 (m, 1H), 4.05- 3.75 (m, 2H), 3.68-3.54 (m, 2H), 3.17-3.00 (m, 1H), 2.73-2.57 (m, 1H), 2.42-2.25 (m, 5H), 2.24-2.12 (m, 2H), 1.86-1.67 (m, 2H), 1.55-1.11 (m, 6H), 1.07-0.93 (m, 3H); ESI MS m/z 553 [M+H]$^+$; HPLC 98.8% (AUC), T$_R$ 5.30 min; UV (MeOH) λ$_{max}$ 289 nm, ε 23,015.

Example 13 methyl 6-(trans-4-((4-(2-(ethyl(m-tolyl)amino)-2-oxoethyl)-4H-thieno[3,2-b]pyrrole-5-carboxamido)methyl)cyclohexane-1-carboxamido)hexanoate (JRW-0267)

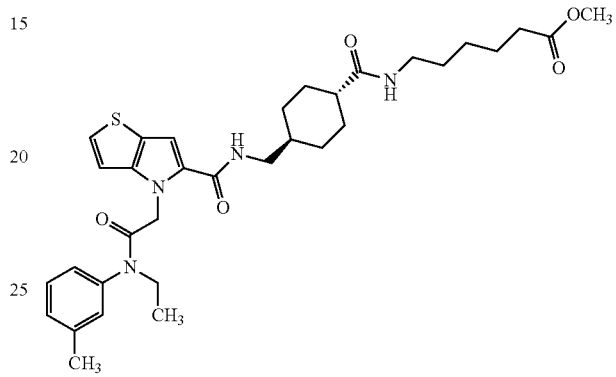

Following general procedure B, 4-(2-(ethyl(m-tolyl)amino)-2-oxoethyl)-4H-thieno[3,2-b]pyrrole-5-carboxylic acid (133 mg, 0.39 mmol) was reacted with methyl 6-(trans-4-(aminomethyl)cyclohexane-1-carboxamido)hexanoate (111 mg, 0.39 mmol) to afford the desired product (180 mg, 76%) as a white foam. $^1$H NMR (300 MHz, DMSO-d$_6$) δ 8.09 (t, J=5.6, 1H), 7.61 (t, J=5.5, 1H), 7.66-7.56 (m, 2H), 7.32-7.16 (m, 3H), 7.14-6.99 (m, 2H), 4.96 (s, 2H), 3.67-3.46 (m, 5H), 3.07-2.92 (m, 4H), 2.37 (s, 3H), 2.25 (t, J=7.4, 2H), 2.08-1.93 (m, 1H), 1.83-1.60 (m, 4H), 1.56-1.12 (m, 10H), 1.08-0.80 (m, 5H); ESI MS m/z 609 [M+H]$^+$; HPLC >99% (AUC), T$_R$ 5.95 min; UV (EtOH) λ$_{max}$ 288 nm, ε 20,078.

Example 14

6-(trans-4-((4-(2-(ethyl(m-tolyl)amino)-2-oxoethyl)-4H-thieno[3,2-b]pyrrole-5-carboxamido)methyl)cyclohexane-1-carboxamido)hexanoic acid (JRW-0268)

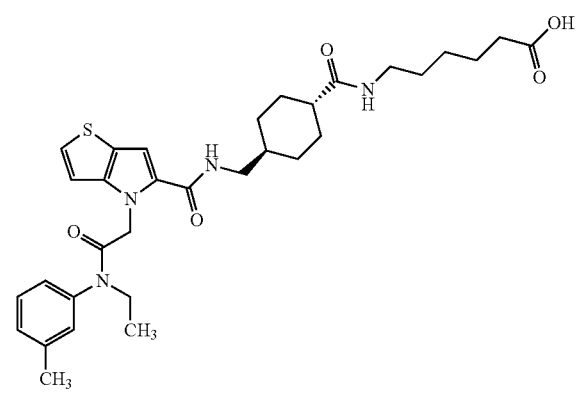 [SMILES: CCN(C(=O)Cn1c(C(=O)NC[C@H]2CC[C@H](C(=O)NCCCCCC(=O)O)CC2)cc2sccc21)c1cccc(C)c1]

Following general procedure A, methyl 6-(trans-4-((4-(2-(ethyl(m-tolyl)amino)-2-oxoethyl)-4H-thieno[3,2-b]pyrrole-5-carboxamido)methyl)cyclohexane-1-carboxamido)hexanoate (165 mg, 0.27 mmol) was reacted with lithium hydroxide (32 mg 3.4 mmol) to afford the desired product (115 mg, 71%) as a white foam. $^1$H NMR (300 MHz, DMSO-d$_6$) δ 11.93 (s, 1H), 8.14-8.04 (m, 1H), 7.61 (t, J=5.3, 1H), 7.46-7.16 (m, 5H), 7.13-6.98 (m, 2H), 4.96 (s, 2H), 3.68-3.53 (m, 2H), 3.08-2.92 (m, 4H), 2.36 (s, 3H), 2.15 (t, J=7.2, 2H), 2.07-1.92 (m, 1H), 1.80-1.63 (m, 4H), 1.54-1.14 (m, 10H), 1.08-0.79 (m, 5H); ESI MS m/z 595 [M+H]$^+$; HPLC >99% (AUC), T$_R$ 5.44 min; UV (EtOH) λ$_{max}$ 289 nm, ε 25,604.

Example 15

General Synthesis of Compounds of Formula (Ib)

Compounds of formula (Ib) can be generally synthesized according to Scheme 2.

Scheme 2.

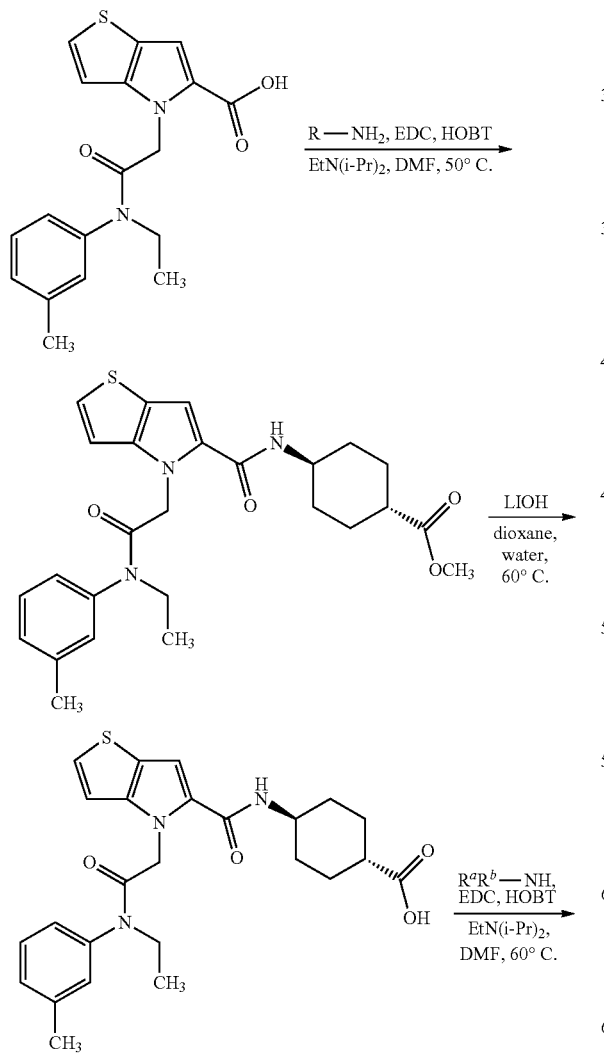

Example 16 trans-methyl-4-(4-(2-(ethyl(m-tolyl)amino)-2-oxoethyl)-4H-thieno[3,2-b]pyrrole-5-carboxamido)cyclohexane-1-carboxylate (JRW-0013)

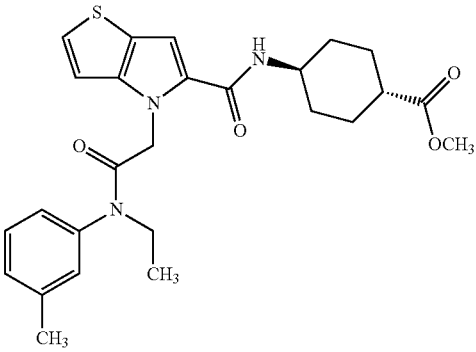 [SMILES: CCN(C(=O)Cn1c(C(=O)N[C@H]2CC[C@H](C(=O)OC)CC2)cc2sccc21)c1cccc(C)c1]

Following general procedure B, 4-(2-(ethyl(m-tolyl)amino)-2-oxoethyl)-4H-thieno[3,2-b]pyrrole-5-carboxylic acid (100 mg, 0.29 mmol) was reacted with methyl trans-4-aminocyclohexane-1-carboxylate (84 mg 0.44 mmol) to afford the desired product (103 mg, 73%) as a white foam. $^1$H NMR (300 MHz, DMSO-d$_6$) δ 7.89 (d, J=7.9, 1H), 7.46-7.36 (m, 2H), 7.34-7.15 (m, 3H), 7.12-7.04 (m, 2H), 4.96 (s, 2H), 3.72-3.46 (s, 6H), 2.36 (s, 3H), 2.32-2.18 (m, 1H), 2.03-1.77 (m, 4H), 1.52-1.20 (m, 4H), 1.06-0.95 (m, 3H); ESI MS m/z 482 [M+H]$^+$; HPLC 99.0% (AUC), T$_R$ 7.75 min; UV (MeOH) λ$_{max}$ 289 nm, ε 26,100.

Example 17 trans-4-(4-(2-(ethyl(m-tolyl)amino)-2-oxoethyl)-4H-thieno[3,2-b]pyrrole-5-carboxamido)cyclohexane-1-carboxylic acid (JRW-0034)

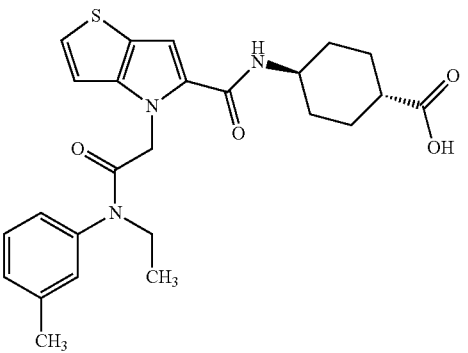 [SMILES: CCN(C(=O)Cn1c(C(=O)N[C@H]2CC[C@H](C(=O)O)CC2)cc2sccc21)c1cccc(C)c1]

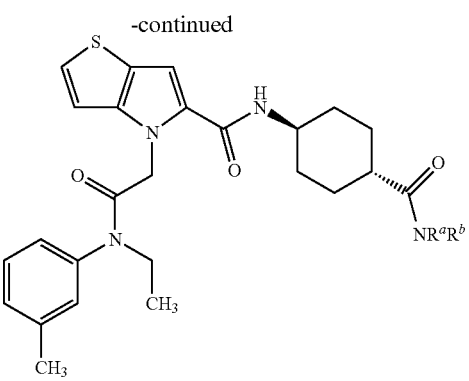

Following general procedure A, trans-methyl-4-(4-(2-(ethyl(m-tolyl)amino)-2-oxoethyl)-4H-thieno[3,2-b]pyrrole-5-carboxamido)cyclohexane-1-carboxylate (55 mg, 0.11 mmol) was reacted with lithium hydroxide (14 mg, 0.57 mmol) to afford the desired product (50 mg, 93%) as a white solid. $^1$H NMR (300 MHz, DMSO-$d_6$) δ 11.99 (s, 1H), 7.92-7.84 (m, 1H), 7.44-7.19 (m, 5H), 7.12-7.04 (m, 2H), 4.97 (s, 2H), 3.73-3.52 (m, 3H), 2.36 (s, 3H), 2.22-2.06 (m, 1H), 1.98-1.76 (m, 4H), 1.47-1.21 (m, 4H), 1.08-0.93 (m, 3H); ESI MS m/z 468 [M+H]$^+$; HPLC 99.4% (AUC), $T_R$ 5.81 min; UV (MeOH) $\lambda_{max}$ 290 nm, ε 26,502.

Example 18

N-(trans-4-(butylcarbamoyl)cyclohexyl)-4-(2-(ethyl(m-tolyl)amino)-2-oxoethyl)-4H-thieno[3,2-b]pyrrole-5-carboxamide (JRW-0042)

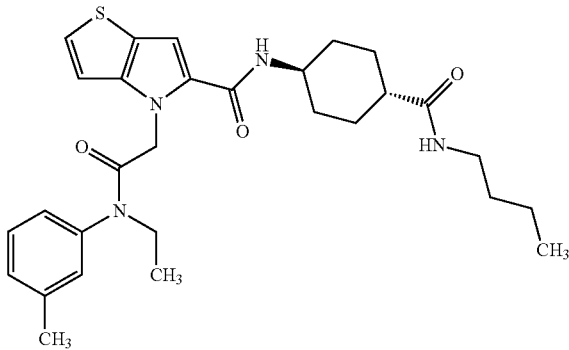 [SMILES: CCCCNC(=O)[C@H]1CC[C@H](NC(=O)c2cc3sccc3n2CC(=O)N(CC)c2cccc(C)c2)CC1]

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (50 mg, 0.11 mmol) was reacted with butylamine (9 mg, 0.13 mmol) to afford the desired product (50 mg, 89%) as a white solid. $^1$H NMR (300 MHz, DMSO-$d_6$) δ 7.82 (d, J=8.1, 1H), 7.65-7.57 (m, 1H), 7.46-7.11 (m, 5H), 7.06-6.98 (m, 2H), 4.91 (s, 2H), 3.66-3.45 (m, 3H), 2.96 (q, J=6.0 Hz, 2H), 2.32 (s, 3H), 2.05-1.92 (m, 1H), 1.85-1.60 (m, 4H), 1.50-1.10 (m, 9H), 1.02-0.90 (m, 3H), 0.80 (t, J=7.2, 3H); ESI MS m/z 523 [M+H]$^+$; HPLC 99.6% (AUC), $T_R$ 6.52 min; UV (MeOH) $\lambda_{max}$ 288 nm, ε 28,364.

Example 19

4-(2-(ethyl(m-tolyl)amino)-2-oxoethyl)-N-(trans-4-((2-hydroxyethyl)carbamoyl)cyclohexyl)-4H-thieno[3,2-b]pyrrole-5-carboxamide (JRW-0043)

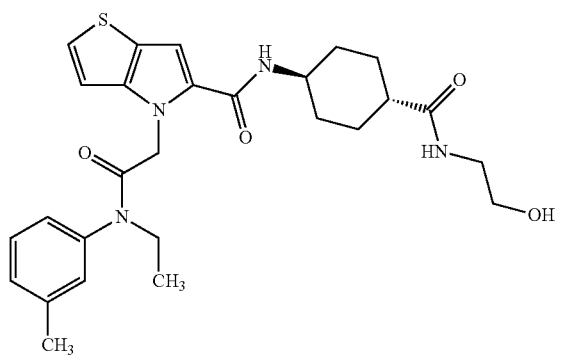 [SMILES: CCN(C(=O)Cn1c(C(=O)N[C@H]2CC[C@H](C(=O)NCCO)CC2)cc2sccc21)c1cccc(C)c1]

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (50 mg, 0.11 mmol) was reacted with ethanolamine (7 mg, 0.13 mmol) to afford the desired product (48 mg, 88%) as a white foam. $^1$H NMR (300 MHz, DMSO-$d_6$) δ 7.86 (d, J=7.8, 1H), 7.69 (t, J=5.4, 1H), 7.45-7.18 (m, 5H), 7.13-7.04 (m, 2H), 4.96 (s, 2H), 4.60 (t, J=5.5, 1H), 3.75-3.54 (m, 3H), 3.36 (q, J=5.9, 2H), 3.08 (q, J=5.9, 2H), 2.37 (s, 3H), 2.14-2.00 (m, 1H), 1.90-1.69 (m, 4H), 1.52-1.10 (m, 4H), 1.08-0.94 (m, 3H); ESI MS m/z 511 [M+H]$^+$; HPLC 99.7% (AUC), $T_R$ 6.52 min; UV (MeOH) $\lambda_{max}$ 289 nm, ε 24,966.

Example 20

N-(trans-4-((2-(dimethylamino)ethyl)carbamoyl)cyclohexyl)-4-(2-(ethyl(m-tolyl)amino)-2-oxoethyl)-4H-thieno[3,2-b]pyrrole-5-carboxamide (JRW-0044)

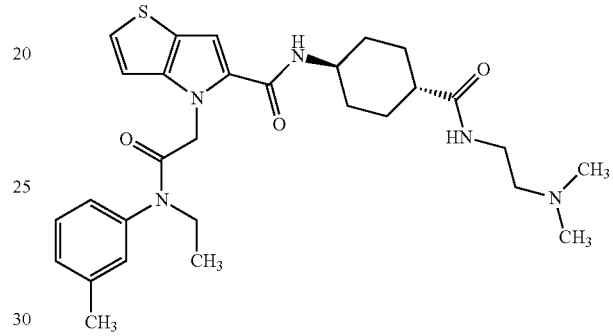

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (50 mg, 0.11 mmol) was reacted with ethanolamine (18 mg, 0.21 mmol) to afford the desired product (45 mg, 78%) as a light red solid. $^1$H NMR (300 MHz, DMSO-$d_6$) δ 7.87 (d, J=8.1, 1H), 7.62 (t, J=5.5, 1H), 7.45-7.35 (m, 2H), 7.33-7.17 (m, 3H), 7.12-7.05 (m, 2H), 4.97 (s, 2H), 3.73-3.54 (m, 3H), 3.10 (q, J=6.4, 2H), 2.37 (s, 3H), 2.24 (t, J=6.4, 2H), 2.15-2.00 (m, 7H), 1.88-1.691.78 (m, 4H), 1.53-1.19 (m, 4H), 1.08-0.94 (m, 3H); ESI MS m/z 538 [M+H]$^+$; HPLC 99.4% (AUC), $T_R$ 4.31 min; UV (MeOH) $\lambda_{max}$ 289 nm, ε 29,980.

Example 21

4-(trans-4-(4-(2-(ethyl(m-tolyl)amino)-2-oxoethyl)-4H-thieno[3,2-b]pyrrole-5-carboxamido)cyclohexane-1-carboxamido)butanoic acid (JRW-0051)

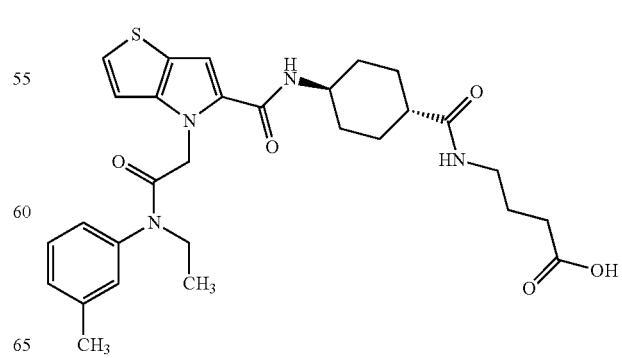

Step 1. methyl 4-(trans-4-(4-(2-(ethyl(m-tolyl)amino)-2-oxoethyl)-4H-thieno[3,2-b]pyrrole-5-carboxamido)cyclohexane-1-carboxamido)butanoate (JRW-0050)

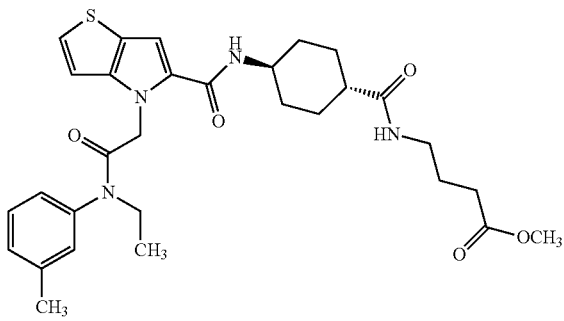 [SMILES: CCN(C(=O)Cn1c(C(=O)N[C@H]2CC[C@H](C(=O)NCCCC(=O)OC)CC2)cc2sccc21)c1cccc(C)c1]

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (50 mg, 0.11 mmol) was reacted with methyl 4-aminobutanoate (15 mg, 0.13 mmol) to afford crude product (80 mg) as a white glass. ESI MS m/z 567 [M+H]+.

Step 2. 4-(trans-4-(4-(2-(ethyl(m-tolyl)amino)-2-oxoethyl)-4H-thieno[3,2-b]pyrrole-5-carboxamido)cyclohexane-1-carboxamido)butanoic acid (JRW-0051)

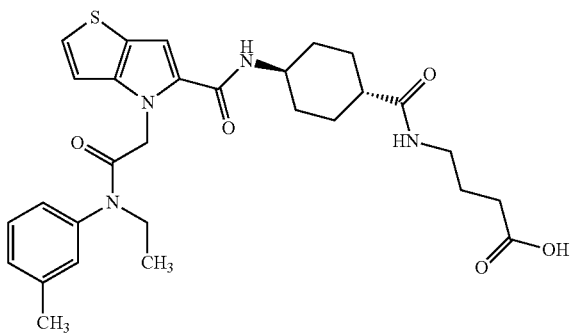 [SMILES: CCN(C(=O)Cn1c(C(=O)N[C@H]2CC[C@H](C(=O)NCCCC(=O)O)CC2)cc2sccc21)c1cccc(C)c1]

Following general procedure A, methyl 4-(trans-4-(4-(2-(ethyl(m-tolyl)amino)-2-oxoethyl)-4H-thieno[3,2-b]pyrrole-5-carboxamido)cyclohexane-1-carboxamido)butanoate (60 mg, 0.10 mmol) was reacted with lithium hydroxide (13 mg, 0.53 mmol) to afford the desired product (55 mg, 93%) as a white solid. $^1$H NMR (300 MHz, DMSO-$d_6$) δ 11.97 (s, 1H), 7.82 (d, J=7.7, 1H), 7.66 (t, J=5.4, 1H), 7.40-7.29 (m, 2H), 7.27-7.13 (m, 3H), 7.07-7.00 (m, 2H), 4.92 (s, 2H), 3.68-3.48 (m, 3H), 3.03-2.92 (m, 2H), 2.32 (s, 3H), 2.14 (t, J=7.3, 2H), 2.06-1.93 (m, 1H), 1.85-1.64 (m, 4H), 1.62-1.47 (m, 2H), 1.47-1.15 (m, 4H), 1.05-0.88 (m, 3H); ESI MS m/z 553 [M+H]+; HPLC >99% (AUC), T$_R$ 5.17 min; UV (MeOH) λ$_{max}$ 289 nm, ε 24,710.

Example 22

N-(trans-4-carbamoylcyclohexyl)-4-(2-(ethyl(m-tolyl)amino)-2-oxoethyl)-4H-thieno[3,2-b]pyrrole-5-carboxamide (JRW-0052)

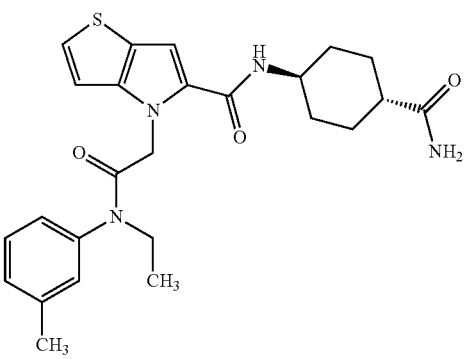 [SMILES: CCN(C(=O)Cn1c(C(=O)N[C@H]2CC[C@H](C(N)=O)CC2)cc2sccc21)c1cccc(C)c1]

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (50 mg, 0.11 mmol) was reacted with ammonia (1.1 mL, 0.5M, 0.21 mmol) to afford the desired product (45 mg, 90%) as a white solid. $^1$H NMR (300 MHz, DMSO-$d_6$) δ 7.82 (d, J=8.2, 1H), 7.40-7.29 (m, 2H), 7.28-7.08 (m, 4H), 7.06-6.98 (m, 2H), 6.61 (s, 1H), 4.91 (s, 2H), 3.67-3.49 (m, 3H), 2.31 (s, 3H), 2.03-1.91 (m, 1H), 1.82-1.68 (m, 4H), 1.47-1.14 (m, 4H), 1.03-0.88 (s, 3H); ESI MS m/z 467 [M+H]+; HPLC >99% (AUC), T$_R$ 5.11 min; UV (MeOH) λ$_{max}$ 289 nm, ε 25,213.

Example 23

4-(2-(ethyl(m-tolyl)amino)-2-oxoethyl)-N-(trans-4-(hexylcarbamoyl)cyclohexyl)-4H-thieno[3,2-b]pyrrole-5-carboxamide (JRW-0138)

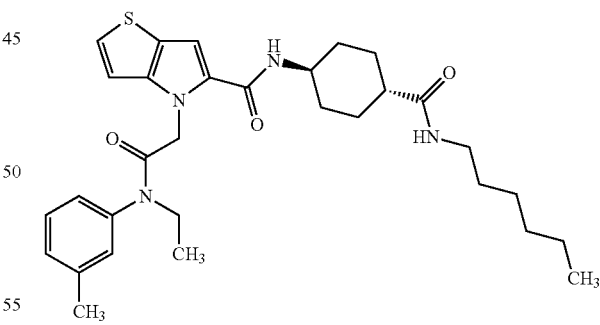

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (50 mg, 0.11 mmol) was reacted with hexylamine (13 mg, 0.13 mmol) to afford the desired product (50 mg, 85%) as a white solid. $^1$H NMR (300 MHz, DMSO-$d_6$) δ 7.88 (d, J=8.1, 1H), 7.67 (t, J=5.6, 1H), 7.45-7.34 (m, 2H), 7.33-7.18 (m, 3H), 7.12-7.04 (m, 2H), 4.96 (s, 2H), 3.72-3.52 (m, 3H), 2.99 (dd, J=6.5, 12.6, 2H), 2.36 (s, 3H), 2.10-1.96 (m, 1H), 1.88-1.68 (m, 4H), 1.52-1.16 (m, 12H), 1.08-0.92 (m, 3H), 0.88-0.78 (m, 3H); ESI MS m/z 551 [M+H]+; HPLC 99.4% (AUC), T$_R$ 6.54 min; UV (EtOH) λ$_{max}$ 292 nm, ε 29,535.

Example 24 ethyl 1-(trans-4-(4-(2-(ethyl(m-tolyl)amino)-2-oxoethyl)-4H-thieno[3,2-b]pyrrole-5-carboxamido)cyclohexane-1-carbonyl)piperidine-4-carboxylate (JRW-0140)

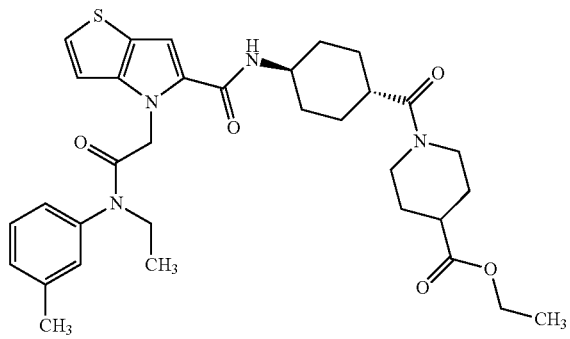 [SMILES: CCOC(=O)C1CCN(C(=O)[C@H]2CC[C@H](NC(=O)c3cc4sccc4n3CC(=O)N(CC)c3cccc(C)c3)CC2)CC1]

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (50 mg, 0.11 mmol) was reacted with ethyl piperidine-4-carboxylate (20 mg, 0.13 mmol) to afford the desired product (60 mg, 92%) as a clear semi-solid. $^1$H NMR (300 MHz, DMSO-d$_6$) δ 7.92 (d, J=7.8, 1H), 7.45 -7.34 (m, 2H), 7.32-7.18 (m, 3H), 7.12-7.05 (m, 2H), 4.96 (s, 2H), 4.23 (d, J=12.7, 1H), 4.05 (q, J=7.1, 2H), 3.87 (d, J=12.7, 1H), 3.72-3.52 (m, 3H), 3.18-3.02 (m, 1H), 2.76-2.51 (m, 3H), 2.36 (s, 3H), 1.93-1.63 (m, 6H), 1.56-1.26 (m, 6H), 1.16 (t, J=6.0 Hz, 3H), 1.07-0.93 (m, 3H); ESI MS m/z 607 [M+H]+; HPLC 99.5% (AUC), T$_R$ 6.01 min; UV (EtOH) λ$_{max}$ 290 nm, ε 29,325.

Example 25 methyl 6-(trans-4-(4-(2-(ethyl(m-tolyl)amino)-2-oxoethyl)-4H-thieno[3,2-b]pyrrole-5-carboxamido)cyclohexane-1-carboxamido)hexanoate (JRW-0145)

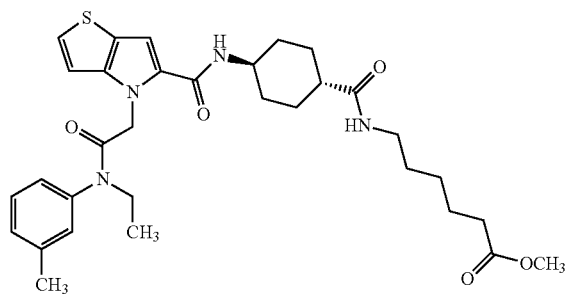 [SMILES: CCN(C(=O)Cn1c(C(=O)N[C@H]2CC[C@H](C(=O)NCCCCCC(=O)OC)CC2)cc2sccc21)c1cccc(C)c1]

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (50 mg, 0.11 mmol) was reacted with methyl 6-aminohexanoate (23 mg, 0.13 mmol) to afford the desired product (60 mg, 94%) as a white solid. $^1$H NMR (300 MHz, DMSO-d$_6$) δ 7.88 (d, J=8.1, 1H), 7.68 (t, J=5.6, 1H), 7.44-7.34 (m, 2H), 7.32-7.17 (m, 3H), 7.12-7.03 (m, 2H), 4.95 (s, 2H), 3.73-3.50 (m, 6H), 2.98 (dd, J=6.6, 12.5, 2H), 2.36 (s, 3H), 2.26 (t, J=7.4, 2H), 2.08-1.95 (m, 1H), 1.87-1.67 (m, 4H), 1.57-1.15 (m, 10H), 1.05-0.93 (m, 3H); ESI MS m/z 595 [M+H]+; HPLC 99.4% (AUC), T$_R$ 6.24 min; UV (EtOH) λ$_{max}$ 288 nm, ε 26,555.

Example 26

6-(trans-4-(4-(2-(ethyl(m-tolyl)amino)-2-oxoethyl)-4H-thieno[3,2-b]pyrrole-5-carboxamido)cyclohexane-1-carboxamido)hexanoic acid (JRW-0147)

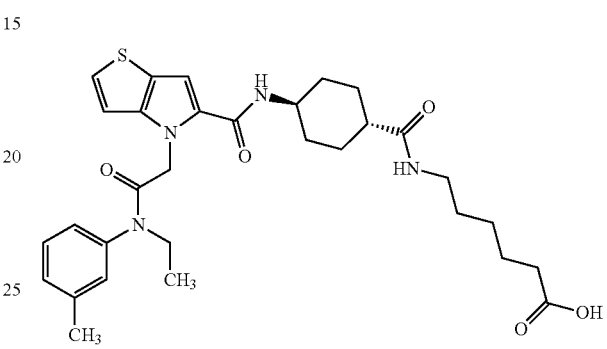

Following general procedure A, methyl 6-(trans-4-(4-(2-(ethyl(m-tolyl)amino)-2-oxoethyl)-4H-thieno[3,2-b]pyrrole-5-carboxamido)cyclohexane-1-carboxamido)hexanoate (53 mg, 0.089 mmol) was reacted with lithium hydroxide (10 mg, 0.44 mmol) to afford the desired product (50 mg, 96%) as a white solid. $^1$H NMR (300 MHz, DMSO-d$_6$) δ 11.98 (s, 1H), 7.88 (d, J=7.6, 1H), 7.72-7.63 (m, 1H), 7.44-7.33 (m, 2H), 7.32-7.18 (m, 3H), 7.12-7.04 (m, 2H), 4.95 (s, 2H), 3.72-3.52 (m, 3H), 3.04-2.93 (m, 2H), 2.36 (s, 3H), 2.16 (t, J=7.1, 2H), 2.10-1.93 (m, 1H), 1.88-1.67 (m, 4H), 1.55-1.10 (m, 10H), 1.08-0.92 (m, 3H); ESI MS m/z 581 [M+H]+; HPLC >99% (AUC), T$_R$ 5.49 min; UV (EtOH) λ$_{max}$ 288 nm, ε 23,738.

Example 27

1-(trans-4-(4-(2-(ethyl(m-tolyl)amino)-2-oxoethyl)-4H-thieno[3,2-b]pyrrole-5-carboxamido)cyclohexane-1-carbonyl)piperidine-4-carboxylic acid (JRW-0187)

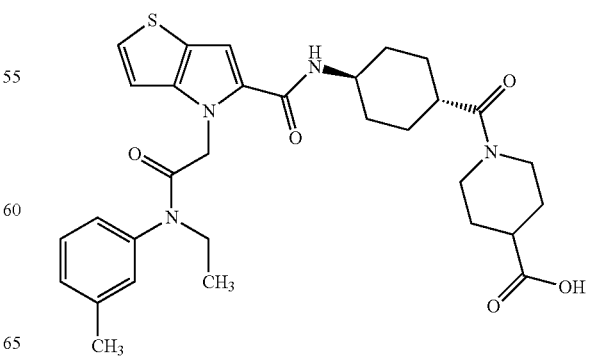

Following general procedure A, ethyl 1-(trans-4-(4-(2-(ethyl(m-tolyl)amino)-2-oxoethyl)-4H-thieno[3,2-b]pyrrole-5-carboxamido)cyclohexane-1-carbonyl)piperidine-4-carboxylate (60 mg, 0.099 mmol) was reacted with lithium hydroxide (12 mg, 0.49 mmol) to afford the desired product (45 mg, 78%) as a white solid. $^1$H NMR (300 MHz, DMSO-d$_6$) δ 12.20 (s, 1H), 7.90 (d, J=7.5, 1H), 7.45-7.33 (m, 2H), 7.32-7.18 (m, 3H), 7.08 (s, 2H), 4.96 (s, 2H), 4.28-4.15 (m, 1H), 3.92-3.79 (m, 1H), 3.70-3.52 (m, 3H), 3.15-3.00 (m, 1H), 2.75-2.60 (m, 1H), 2.36 (s, 3H), 1.92-1.63 (m, 7H), 1.56-1.25 (m, 7H), 1.08-0.95 (m, 3H); ESI MS m/z 579 [M+H]$^+$; HPLC 99.5% (AUC), T$_R$ 4.45 min; UV (EtOH) λ$_{max}$ 289 nm, ε23,470.

Example 28

8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (JRW-0188)

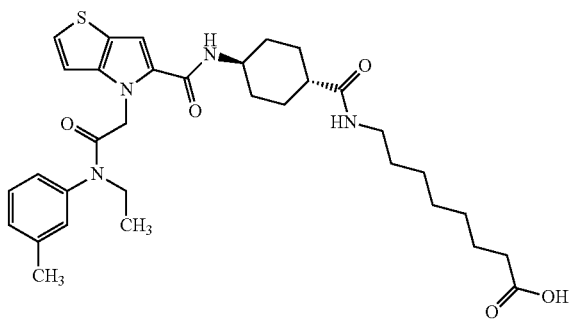 [SMILES: CCN(C(=O)Cn1c(C(=O)N[C@H]2CC[C@H](C(=O)NCCCCCCCC(=O)O)CC2)cc2sccc21)c1cccc(C)c1]

Step 1. methyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate (JRW-0186)

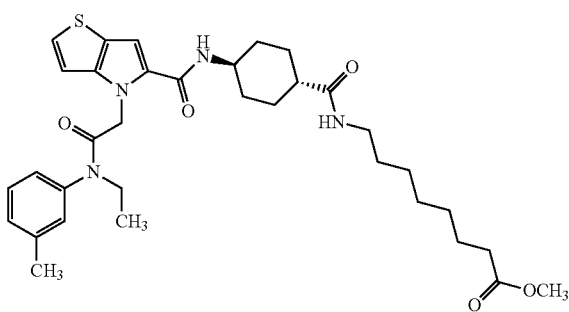 [SMILES: CCN(C(=O)Cn1c(C(=O)N[C@H]2CC[C@H](C(=O)NCCCCCCCC(=O)OC)CC2)cc2sccc21)c1cccc(C)c1]

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (50 mg, 0.11 mmol) was reacted with methyl 8-aminooctanoate (27 mg, 0.13 mmol) to afford the desired product (55 mg, 82%) as an oil. ESI MS m/z 623 [M+H]$^+$.

Step 2. 8-(trans-4-(4-(2-(ethyl(m-tolyl)amino)-2-oxoethyl)-4H-thieno[3,2-b]pyrrole-5-carboxamido)cyclohexane-1-carboxamido)octanoic acid (JRW-0188)

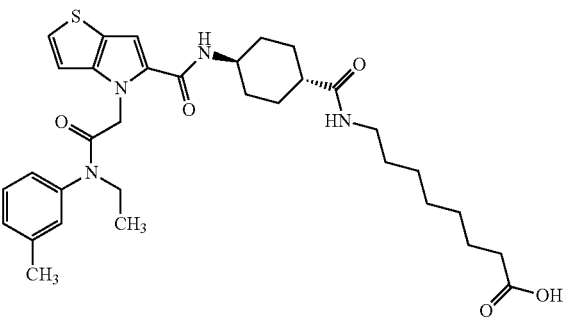 [SMILES: CCN(C(=O)Cn1c(C(=O)N[C@H]2CC[C@H](C(=O)NCCCCCCCC(=O)O)CC2)cc2sccc21)c1cccc(C)c1]

Following general procedure A, methyl 8-(trans-4-(4-(2-(ethyl(m-tolyl)amino)-2-oxoethyl)-4H-thieno[3,2-b]pyrrole-5-carboxamido)cyclohexane-1-carboxamido)octanoate (50 mg, 0.080 mmol) was reacted with lithium hydroxide (9 mg, 0.40 mmol) to afford the desired product (45 mg, 92%) as a white foam. $^1$H NMR (300 MHz, DMSO-d$_6$) δ 11.92 (s, 1H), 7.87 (d, J=7.8, 1H), 7.70-7.61 (m, 1H), 7.45-7.14 (m, 5H), 7.10-7.03 (m, 2H), 4.96 (s, 2H), 3.72-3.54 (m, 3H), 3.05-2.93 (m, 2H), 2.37 (s, 3H), 2.22-2.12 (m, 2H), 2.10-1.98 (m, 1H), 1.91-1.66 (m, 4H), 1.55-1.10 (m, 14H), 1.08-0.93 (m, 3H); ESI MS m/z 609 [M+H]$^+$; HPLC 96.9% (AUC), T$_R$ 4.97 min; UV (EtOH) λ$_{max}$ 289 nm, ε 25,824.

Example 29

N-(trans-4-(cyclohexylcarbamoyl)cyclohexyl)-4-(2-(ethyl(m-tolyl)amino)-2-oxoethyl)-4H-thieno[3,2-b]pyrrole-5-carboxamide (JRW-0190)

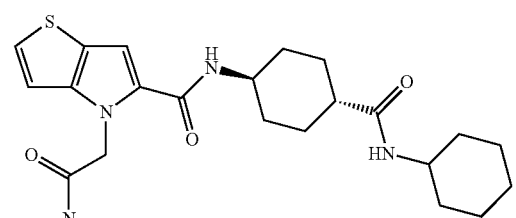

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (50 mg, 0.11 mmol) was reacted with cyclohexylamine (16 mg, 0.16 mmol) to afford the desired product (55 mg, 94%) as a white solid. $^1$H NMR (300 MHz, DMSO-d$_6$) δ 7.95-7.82 (m, 1H), 7.66-7.16 (m, 6H), 7.12-7.04 (m, 2H), 4.97 (s, 2H), 3.76-3.40 (m, 4H), 2.36 (s, 3H), 2.11-1.96 (m, 1H), 1.90-1.60 (m, 8H), 1.59-0.91 (m, 13H); ESI MS m/z 549 [M+H]$^+$; HPLC 99.5% (AUC), T$_R$ 5.98 min; UV (EtOH) λ$_{max}$ 288 nm, ε 25,407.

Example 30

4-(2-(ethyl(m-tolyl)amino)-2-oxoethyl)-N-(trans-4-((1-methylpiperidin-4-yl)carbamoyl)cyclohexyl)-4H-thieno[3,2-b]pyrrole-5-carboxamide (JRW-0191)

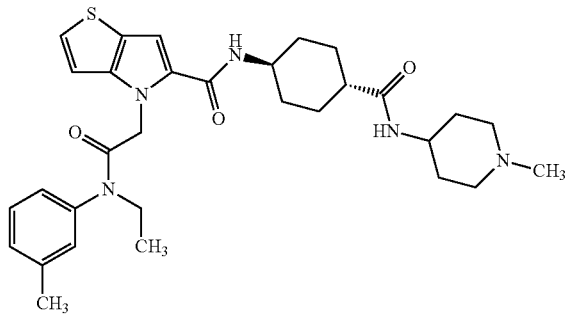 [SMILES: CCN(C(=O)Cn1c(C(=O)N[C@H]2CC[C@H](C(=O)NC3CCN(C)CC3)CC2)cc2sccc21)c1cccc(C)c1]

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (50 mg, 0.11 mmol) was reacted with 1-methylpiperidin-4-amine (18 mg, 0.16 mmol) to afford the desired product (47 mg, 78%) as a white solid. $^1$H NMR (300 MHz, DMSO-$d_6$) δ 7.87 (d, J=8.1, 1H), 7.58 (d, J=7.6, 1H), 7.50-7.16 (m, 5H), 7.13-7.04 (m, 2H), 4.96 (s, 2H), 3.75-3.38 (m, 4H), 2.73-2.61 (m, 2H), 2.36 (s, 3H), 2.22-1.96 (m, 5H), 1.96-1.58 (m, 8H), 1.53-1.19 (m, 6H), 1.08-0.97 (s, 3H); ESI MS m/z 564 [M+H]$^+$; HPLC 98.8% (AUC), $T_R$ 3.35 min; UV (EtOH) $\lambda_{max}$ 289 nm, ε 30,051.

Example 31 tert-butyl 4-(trans-4-(4-(2-(ethyl(m-tolyl)amino)-2-oxoethyl)-4H-thieno[3,2-b]pyrrole-5-carboxamido)cyclohexane-1-carboxamido)piperidine-1-carboxylate (JRW-0192)

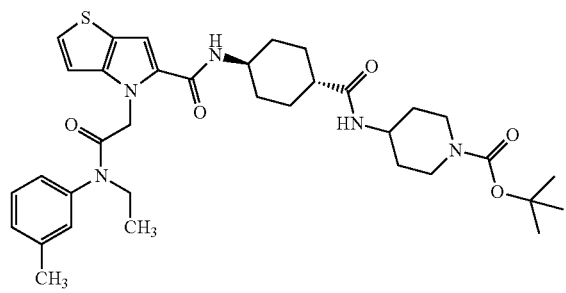 [SMILES: CCN(C(=O)Cn1c(C(=O)N[C@H]2CC[C@H](C(=O)NC3CCN(C(=O)OC(C)(C)C)CC3)CC2)cc2sccc21)c1cccc(C)c1]

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (84 mg, 0.18 mmol) was reacted with tert-butyl 4-aminopiperidine-1-carboxylate (54 mg, 0.27 mmol) to afford the desired product (115 mg, 99%) as a white solid. $^1$H NMR (300 MHz, DMSO-$d_6$) δ 7.93-7.83 (m, 1H), 7.68-7.58 (m, 1H), 7.45-7.16 (m, 5H), 7.13-7.03 (m, 2H), 4.96 (s, 2H), 3.96-3.46 (m, 6H), 2.93-2.70 (m, 2H), 2.36 (s, 3H), 2.09-1.95 (m, 1H), 1.88-1.60 (m, 6H), 1.55-1.08 (m, 15H), 1.06-0.93 (m, 3H); ESI MS m/z 650 [M+H]$^+$; HPLC 99.6% (AUC), $T_R$ 5.87 min; UV (EtOH) $\lambda_{max}$ 288 nm, ε 31,128.

Example 32

4-(2-(ethyl(m-tolyl)amino)-2-oxoethyl)-N-(trans-4-(piperidin-4-ylcarbamoyl)cyclohexyl)-4H-thieno[3,2-b]pyrrole-5-carboxamide (JRW-0194)

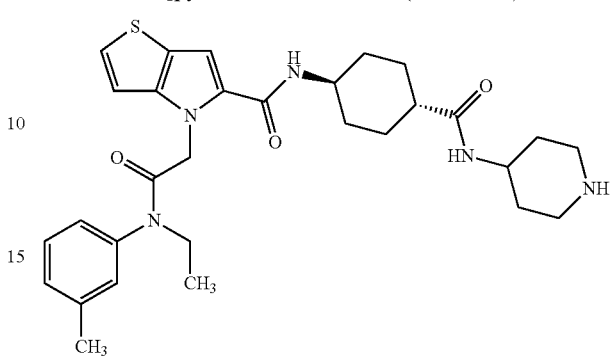

To a solution of tert-butyl 4-(trans-4-(4-(2-(ethyl(m-tolyl)amino)-2-oxoethyl)-4H-thieno[3,2-b]pyrrole-5-carboxamido)cyclohexane-1-carboxamido)piperidine-1-carboxylate (105 mg, 0.16 mmol) in dichloromethane (5 mL), trifluoroacetic acid (1 mL) was added. The reaction was stirred at RT for 2 h. The mixture was diluted with toluene and concentrated under vacuum (3×) to afford crude product (150 mg) of white foam. ESI MS m/z 550 [M+H]$^+$.

Example 33

N-(trans-4-((1-acetylpiperidin-4-yl)carbamoyl)cyclohexyl)-4-(2-(ethyl(m-tolyl)amino)-2-oxoethyl)-4H-thieno[3,2-b]pyrrole-5-carboxamide (JRW-0195)

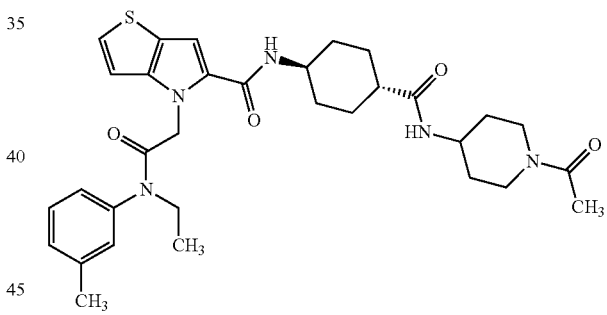

To a solution of 4-(2-(ethyl(m-tolyl)amino)-2-oxoethyl)-N-(trans-4-(piperidin-4-ylcarbamoyl)cyclohexyl)-4H-thieno[3,2-b]pyrrole-5-carboxamide (0.16 mmol) in dichloromethane (5 mL) cooled to 0° C., acetyl chloride (25 mg, 0.32 mmol) and diisopropylethylamine (104 mg, 0.81 mmol) was added. The reaction stirred and warmed to RT overnight. The mixture was diluted with dichloromethane and water, and the layers were separated. The organic layer was dried over anhydrous sodium sulfate and filtered. The filtrate was then concentrated. The residue was purified by column chromatography (silica, dichloromethane/methanol) to afford the desired product (84 mg, 88%) as a white solid. $^1$H NMR (300 MHz, DMSO-$d_6$) δ 7.87 (d, J=7.6, 1H), 7.67 (d, J=7.6, 1H), 7.46-7.32 (m, 2H), 7.33-7.17 (m, 3H), 7.13-7.03 (m, 2H), 4.96 (s, 2H), 4.22-4.08 (m, 1H), 3.81-3.52 (m, 5H), 3.15-3.00 (m, 1H), 2.70 (t, J=11.9, 1H), 2.36 (s, 3H), 2.11-1.94 (m, 4H), 1.91-1.59 (m, 6H), 1.52-1.09 (m, 6H), 1.06-0.91 (m, 3H); ESI MS m/z 592 [M+H]$^+$; HPLC 99.8% (AUC), $T_R$ 4.09 min; UV (EtOH) $\lambda_{max}$ 288 nm, ε 26,034.

Example 34 tert-butyl (6-(trans-4-(4-(2-(ethyl(m-tolyl)amino)-2-oxoethyl)-4H-thieno[3,2-b]pyrrole-5-carboxamido)cyclohexane-1-carboxamido)hexyl)carbamate (JRW-0197)

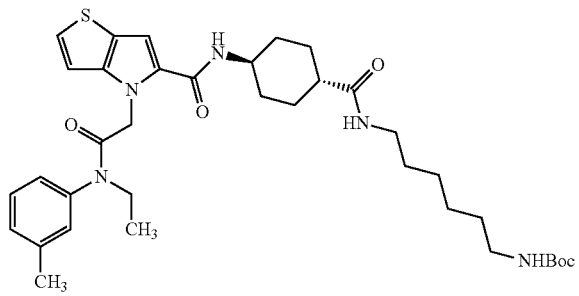 [SMILES: CCN(C(=O)Cn1c(C(=O)N[C@H]2CC[C@H](C(=O)NCCCCCCNC(=O)OC(C)(C)C)CC2)cc2sccc21)c1cccc(C)c1]

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (115 mg, 0.25 mmol) was reacted with tert-butyl (6-aminohexyl)carbamate (80 mg, 0.37 mmol) to afford the desired product (150 mg, 91%) as a white foam. $^1$H NMR (300 MHz, DMSO-$d_6$) δ 7.87 (d, J=8.0, 1H), 7.65 (t, J=5.1, 1H), 7.45-7.33 (m, 2H), 7.32-7.17 (m, 3H), 7.12-7.06 (m, 2H), 6.77-6.68 (m, 1H), 4.96 (s, 2H), 3.72-3.53 (m, 3H), 3.03-2.93 (m, 2H), 2.87 (dd, J=6.0, 12.6, 2H), 2.36 (s, 3H), 2.12-1.96 (m, 1H), 1.88-1.68 (m, 4H), 1.51-1.16 (m, 21H), 1.06-0.93 (m, 3H); ESI MS m/z 666 [M+H]$^+$; HPLC 99.7% (AUC), $T_R$ 4.11 min; UV (EtOH) $\lambda_{max}$ 288 nm, ε 21,608.

Example 35

N-(trans-4-((6-(3',6'-dihydroxy-3-oxo-3H-spiro[isobenzofuran-1,9'-xanthene]-5(6)-carboxamido)hexyl)carbamoyl)cyclohexyl)-4-(2-(ethyl(m-tolyl)amino)-2-oxoethyl)-4H-thieno[3,2-b]pyrrole-5-carboxamide (JRW-0200)

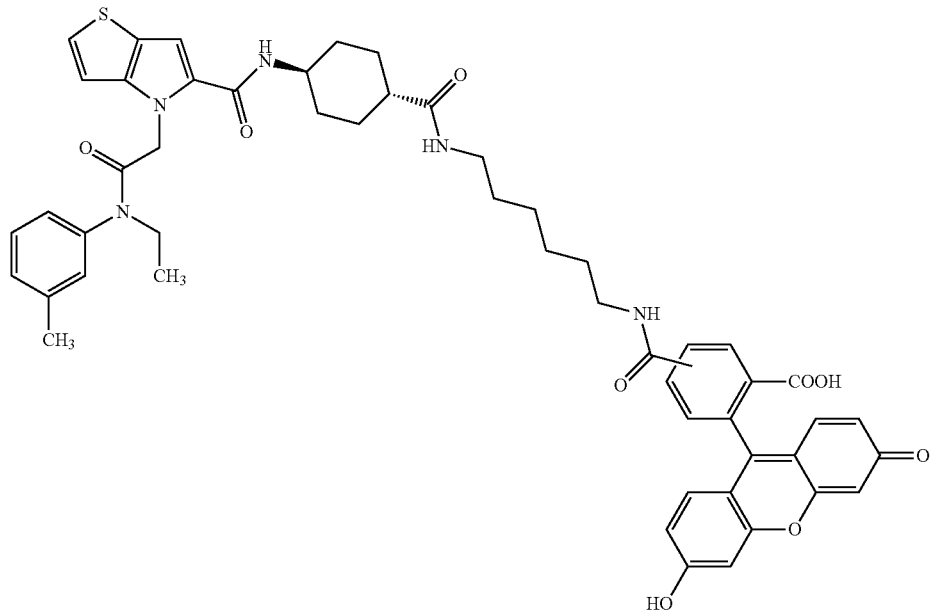

Step 1. N-(trans-4-((6-aminohexyl)carbamoyl)cyclohexyl)-4-(2-(ethyl(m-tolyl)amino)-2-oxoethyl)-4H-thieno[3,2-b]pyrrole-5-carboxamide (JRW-0199)

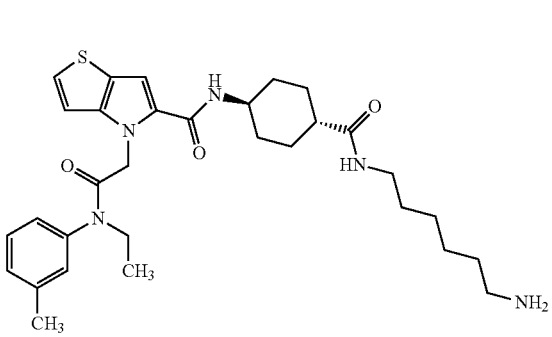 [SMILES: CCN(C(=O)Cn1c(C(=O)N[C@H]2CC[C@H](C(=O)NCCCCCCN)CC2)cc2sccc21)c1cccc(C)c1]

To a solution of tert-butyl (6-(trans-4-(4-(2-(ethyl(m-tolyl)amino)-2-oxoethyl)-4H-thieno[3,2-b]pyrrole-5-carboxamido)cyclohexane-1-carboxamido)hexyl)carbamate (150 mg, 0.22 mmol) in dichloromethane (5 mL), trifluoroacetic acid (1 mL) was added. The reaction stirred at RT for 5 h. The mixture was diluted with toluene and concentrated under vacuum (3×) to afford crude product (150 mg) of clear oil. ESI MS m/z 566 [M+H]$^+$.

Step 2. N-(trans-4-((6-(3',6'-dihydroxy-3-oxo-3H-spiro[isobenzofuran-1,9'-xanthene]-5(6)-carboxamido)hexyl)carbamoyl)cyclohexyl)-4-(2-(ethyl(m-tolyl)amino)-2-oxoethyl)-4H-thieno[3,2-b]pyrrole-5-carboxamide (JRW-0200)

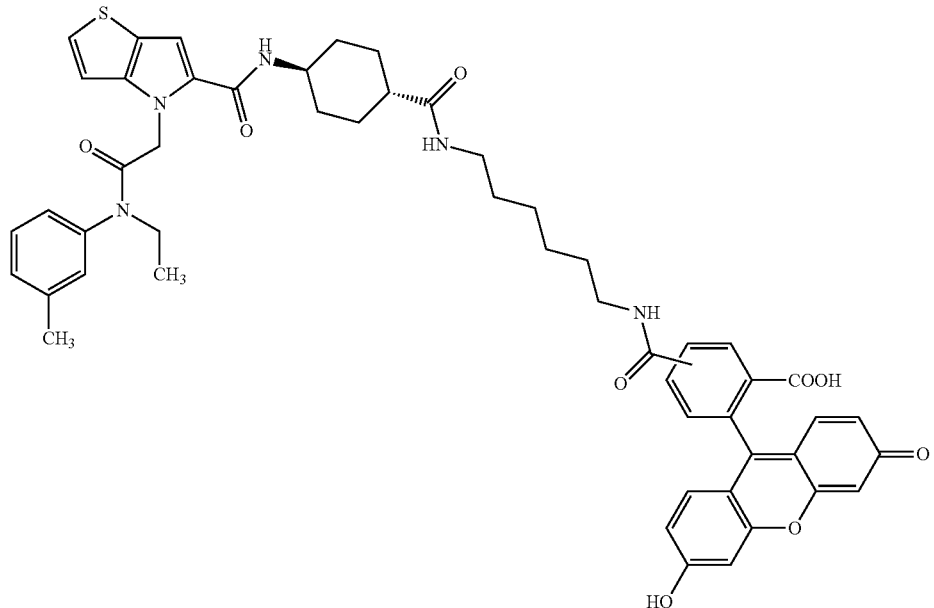

To a solution of N-(trans-4-((6-aminohexyl)carbamoyl)cyclohexyl)-4-(2-(ethyl(m-tolyl)amino)-2-oxoethyl)-4H-thieno[3,2-b]pyrrole-5-carboxamide (0.22 mmol) in DMF (3 mL), 2,5-dioxopyrrolidin-1-yl 3',6'-dihydroxy-3-oxo-3H-spiro[isobenzofuran-1,9'-xanthene]-5(6)-carboxylate[5(6)-FAM-SE] (106 mg, 0.22 mmol) and diisopropylethylamine (145 mg, 1.1 mmol) was added. The reaction was stirred at RT for 1 h. The reaction mixture was acidified (0.1M HCl), diluted with water, and extracted with 3:1 CHCl$_3$/isopropanol. The organic layer was dried over anhydrous sodium sulfate and filtered. The filtrate was then concentrated. The residue was purified by column chromatography (silica, dichloromethane/methanol) to afford the desired product (145 mg, 69%) as an orange solid. $^1$H NMR (300 MHz, DMSO-d$_6$) δ 10.12 (s, 2H), 8.78 (t, J=5.5, 1H, isomer A), 8.64 (t, J=5.7, 1H, isomer B), 8.44 (s, 1H, isomer A), 8.23 (dd, J=1.5, 8.1, 1H, isomer A), 8.15 (dd, J=1.3, 8.1, 1H, isomer B), 8.05 (d, J=8.1, 1H, isomer B), 7.87 (d, J=8.0, 1H), 7.72-7.60 (m, 1H), 7.44-7.32 (m, 3H), 7.32-7.17 (m, 3H), 7.12-7.04 (m, 2H), 6.70-6.65 (m, 2H), 6.61-6.49 (m, 4H), 4.96 (s, 2H), 3.70-3.52 (m, 3H), 3.32-3.23 (m, 2H), 3.22-3.12 (m, 1H), 3.08-2.91 (m, 2H), 2.36 (s, 3H), 2.11-1.95 (m, 1H), 1.89-1.65 (m, 4H), 1.61-1.16 (m, 11H), 1.06-0.92 (m, 3H); ESI MS m/z 925 [M+H]$^+$; HPLC 97.1% (AUC), T$_R$ 6.16, 6.26 min; UV (MeOH) λ$_{max}$ 284 nm, ε 31,419.

Example 36

N-(trans-4-((6-aminohexyl)carbamoyl)cyclohexyl)-4-(2-(ethyl(m-tolyl)amino)-2-oxoethyl)-4H-thieno[3,2-b]pyrrole-5-carboxamide hydrochloride (JRW-0241)

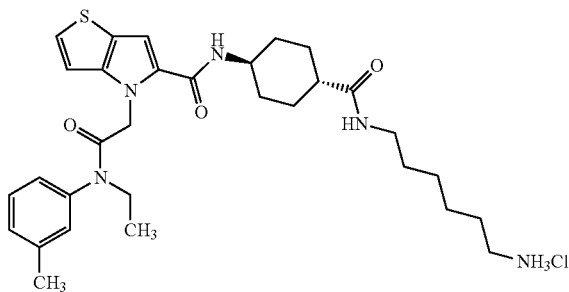

To a solution of tert-butyl (6-(trans-4-(4-(2-(ethyl(m-tolyl)amino)-2-oxoethyl)-4H-thieno[3,2-b]pyrrole-5-carboxamido)cyclohexane-1-carboxamido)hexyl)carbamate (100 mg, 0.15 mmol) in dichloromethane (5 mL), trifluoroacetic acid (1 mL) was added. The reaction stirred at RT for 1 h. The mixture was diluted with toluene and concentrated under vacuum (3×). The residue was dissolved in methanol and HCl (2 mL, 1M in ether) was added. The solution was evaporated to afford the desired product (95 mg, quant.) of white solid. $^1$H NMR (300 MHz, DMSO-d$_6$) δ 8.02-7.68 (m, 5H), 7.45-7.34 (m, 2H), 7.33-7.15 (m, 3H), 7.12-7.05 (m, 2H), 4.97 (s, 2H), 3.74-3.51 (m, 3H), 3.01 (dd, J=6.5, 12.5, 2H), 2.79-2.66 (m, 2H), 2.36 (s, 3H), 2.11-1.97 (m, 1H), 1.88-1.68 (m, 4H), 1.59-1.17 (m, 12H), 1.02-0.94 (m, 3H);

ESI MS m/z 566 [M+H]$^+$; HPLC 99.0% (AUC), T$_R$ 4.47 min; UV (MeOH) $\lambda_{max}$ 289 nm, ε 23,213.

Example 37

4-(2-(ethyl(m-tolyl)amino)-2-oxoethyl)-N-(trans-4-((6-hydroxyhexyl)carbamoyl)cyclohexyl)-4H-thieno[3,2-b]pyrrole-5-carboxamide (JRW-0242)

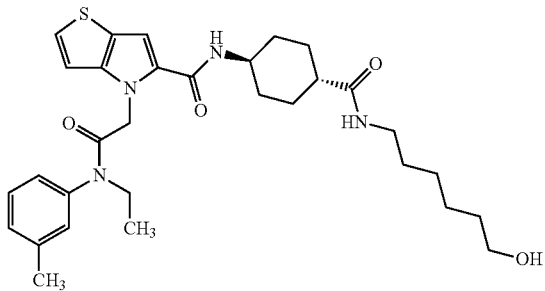 [SMILES: CCN(C(=O)Cn1c(C(=O)N[C@H]2CC[C@H](C(=O)NCCCCCCO)CC2)cc2sccc21)c1cccc(C)c1]

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (150 mg, 0.32 mmol) was reacted with 6-aminohexan-1-ol (56 mg, 0.48 mmol) to afford the desired product (160 mg, 88%) as a white foam. $^1$H NMR (300 MHz, DMSO-d$_6$) δ 7.87 (d, J=7.4, 1H), 7.73-7.59 (s, 1H), 7.48-7.15 (m, 5H), 7.13-7.02 (m, 2H), 4.96 (s, 2H), 4.35-4.23 (m, 1H), 3.73-3.50 (m, 3H), 3.43-3.30 (m, 2H), 3.05-2.94 (m, 2H), 2.37 (s, 3H), 2.10-1.95 (m, 1H), 1.90-1.65 (m, 4H), 1.55-1.13 (m, 12H), 1.09-0.90 (s, 3H); ESI MS m/z 567 [M+H]$^+$; HPLC >99% (AUC), T$_R$ 5.48 min; UV (MeOH) $\lambda_{max}$ 289 nm, ε 26,356.

Example 38

Sodium 6-(trans-4-(4-(2-(ethyl(m-tolyl)amino)-2-oxoethyl)-4H-thieno[3,2-b]pyrrole-5-carboxamido)cyclohexane-1-carboxamido)hexane-1-sulfonate (JRW-0344)

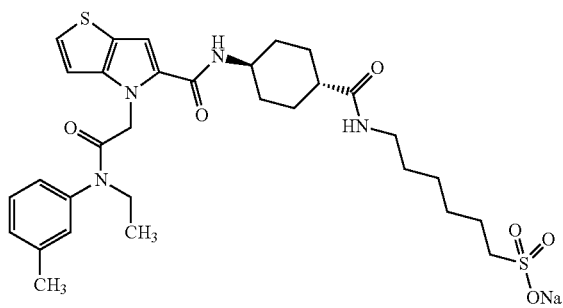

Step 1. 4-(2-(ethyl(m-tolyl)amino)-2-oxoethyl)-N-(trans-4-((6-iodohexyl)carbamoyl)cyclohexyl)-4H-thieno[3,2-b]pyrrole-5-carboxamide (JRW-0342)

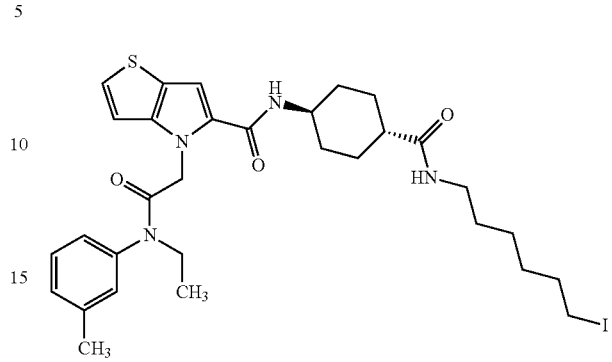

To a solution of imidazole (36 mg, 0.53 mmol), triphenylphosphine (138 mg, 0.53 mmol), and iodine (134 mg, 0.53 mmol), 4-(2-(ethyl(m-tolyl)amino)-2-oxoethyl)-N-(trans-4-((6-hydroxyhexyl)carbamoyl)cyclohexyl)-4H-thieno[3,2-b]pyrrole-5-carboxamide (100 mg, 0.18 mmol) dissolved in THF (5 mL) was added. The solution stirred for 1 h at RT. The reaction was diluted with ethyl acetate and quenched with a 10% Na$_2$S$_2$O$_3$ solution. The mixture was diluted with ethyl acetate and water, and the layers were separated. The organic layer was washed with a 10% Na$_2$S$_2$O$_3$ solution and brine, dried over anhydrous sodium sulfate, and filtered. The filtrate was then concentrated. The residue was partially purified by column chromatography (silica, dichloromethane/methanol) to afford crude product as a white solid. ESI MS m/z 677 [M+H]$^+$.

Step 2. Sodium 6-(trans-4-(4-(2-(ethyl(m-tolyl)amino)-2-oxoethyl)-4H-thieno[3,2-b]pyrrole-5-carboxamido)cyclohexane-1-carboxamido)hexane-1-sulfonate (JRW-0344)

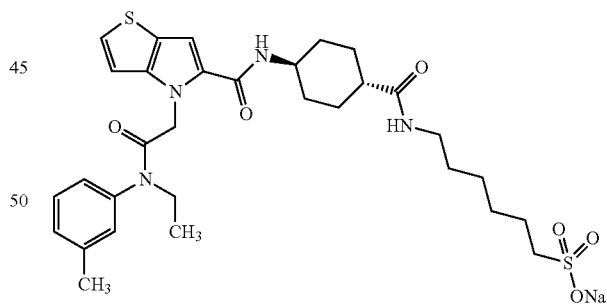

To a solution of 4-(2-(ethyl(m-tolyl)amino)-2-oxoethyl)-N-(trans-4-((6-iodohexyl)carbamoyl)cyclohexyl)-4H-thieno[3,2-b]pyrrole-5-carboxamide (0.18 mmol) in ethanol (5 mL), sodium sulfite (66 mg, 0.53 mmol) and water (3 mL) was added. The mixture was heated to 75° C. for 2 h. The reaction was concentrated, and the residue was purified by column chromatography (silica, dichloromethane/methanol) to afford the desired product (100 mg, 90%) as a white solid. $^1$H NMR (300 MHz, DMSO-d$_6$) δ 7.87 (d, J=8.0, 1H), 7.67 (t, J=5.5, 1H), 7.49-7.17 (m, 5H), 7.13-7.05 (m, 2H), 4.97 (s, 2H), 3.72-3.54 (m, 3H), 3.05-2.93 (m, 2H), 2.40-2.28 (m, 5H), 2.12-1.96 (m, 1H), 1.88-1.68 (m, 4H), 1.62-1.14 (m, 12H), 1.05-0.93 (m, 3H); ESI MS m/z 631 [M+H]+; HPLC >99% (AUC), $T_R$ 4.56 min; UV (MeOH) $\lambda_{max}$ 288 nm, ε 21,072.

Example 39

Potassium 6-(trans-4-(4-(2-(ethyl(m-tolyl)amino)-2-oxoethyl)-4H-thieno[3,2-b]pyrrole-5-carboxamido)cyclohexane-1-carboxamido)hexane-1-sulfonate (JRW-0348)

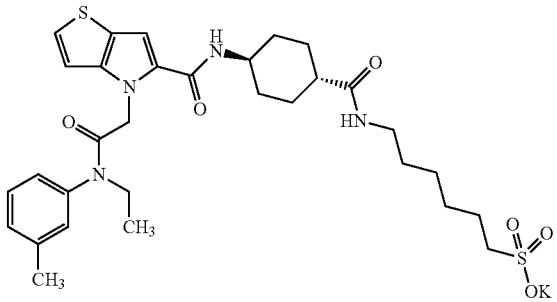

To a solution of 6-(trans-4-(4-(2-(ethyl(m-tolyl)amino)-2-oxoethyl)-4H-thieno[3,2-b]pyrrole-5-carboxamido)cyclohexane-1-carboxamido)hexane-1-sulfonic acid (50 mg, 0.08 mmol) in water (25 mL), DowEx 50WX4 (potassium charged) was added. The suspension stirred at RT for 10 min. The mixture was filtered, and the filtrate was concentrated by lyophilization to afford the desired product (48 mg, 90%) as a white solid. 1H NMR (300 MHz, DMSO-d6) δ 7.83 (d, J=8.1, 1H), 7.62 (t, J=5.5, 1H), 7.47-7.15 (m, 5H), 7.10-7.04 (m, 2H), 4.97 (s, 2H), 3.71-3.54 (m, 3H), 3.05-2.94 (m, 2H), 2.41-2.31 (m, 5H), 2.15-1.96 (m, 1H), 1.90-1.70 (m, 4H), 1.61-1.16 (m, 12H), 1.06-0.95 (m, 3H); ESI MS m/z 631 [M+H]+; HPLC >99% (AUC), $T_R$ 4.55 min; UV (MeOH) $\lambda_{max}$ 289 nm, ε 19,812.

Example 40 methyl-trans-4-(trans-4-(4-(2-(ethyl(m-tolyl)amino)-2-oxoethyl)-4H-thieno[3,2-b]pyrrole-5-carboxamido)cyclohexane-1-carboxamido)cyclohexane-1-carboxylate (JRW-0243)

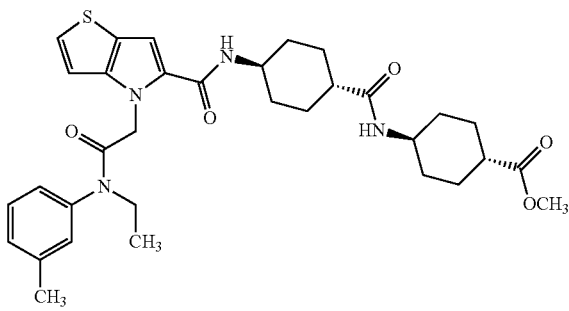 [SMILES: CCN(C(=O)Cn1c(C(=O)N[C@H]2CC[C@H](C(=O)N[C@H]3CC[C@H](C(=O)OC)CC3)CC2)cc2sccc21)c1cccc(C)c1]

Following general procedure B, trans-4-(4-(2-(ethyl(m-tolyl)amino)-2-oxoethyl)-4H-thieno[3,2-b]pyrrole-5-carboxamido)cyclohexane-1-carboxylic acid (75 mg, 0.16 mmol) was reacted with methyl trans-4-aminocyclohexane-1-carboxylate hydrochloride (46 mg, 0.24 mmol) to afford the desired product (89 mg, 91%) as a white solid. 1H NMR (300 MHz, DMSO-d6) δ 7.86 (d, J=8.5, 1H), 7.58 (d, J=7.8, 1H), 7.47-7.33 (m, 2H), 7.32-7.18 (m, 3H), 7.11-7.04 (m, 2H), 4.96 (s, 2H), 3.72-3.53 (m, 6H), 3.52-3.35 (m, 1H), 2.36 (s, 3H), 2.29-2.16 (m, 1H), 2.08-1.95 (m, 1H), 1.95-1.65 (m, 8H), 1.53-1.06 (m, 8H), 1.05-0.93 (m, 3H); ESI MS m/z 607 [M+H]+; HPLC 99.7% (AUC), $T_R$ 6.27 min; UV (MeOH) $\lambda_{max}$ 288 nm, ε 24,192.

Example 41 trans-4-(trans-4-(4-(2-(ethyl(m-tolyl)amino)-2-oxoethyl)-4H-thieno[3,2-b]pyrrole-5-carboxamido)cyclohexane-1-carboxamido)cyclohexane-1-carboxylic acid (JRW-0245)

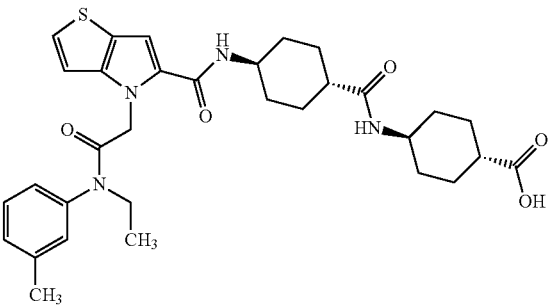 [SMILES: CCN(C(=O)Cn1c(C(=O)N[C@H]2CC[C@H](C(=O)N[C@H]3CC[C@H](C(=O)O)CC3)CC2)cc2sccc21)c1cccc(C)c1]

Following general procedure A, methyl-trans-4-(trans-4-(4-(2-(ethcyl(m-tolyl)amino)-2-oxoethyl)-4H-thieno[3,2-b]pyrrole-5-carboxamido)cyclohexane-1-carboxamido)cyclohexane-1-carboxylate (80 mg, 0.13 mmol) was reacted with lithium hydroxide (16 mg, 0.66 mmol) to afford the desired product (66 mg, 84%) as a white solid. 1H NMR (300 MHz, DMSO-d6) δ 12.00 (s, 1H), 7.86 (d, J=8.1, 1H), 7.57 (d, J=7.6, 1H), 7.45-7.33 (m, 2H), 7.32-7.15 (m, 3H), 7.12-7.03 (m, 2H), 4.97 (s, 2H), 3.73-3.52 (m, 3H), 3.52-3.35 (m, 1H), 2.36 (s, 3H), 2.19-1.95 (m, 2H), 1.94-1.65 (m, 8H), 1.51-1.05 (m, 8H), 1.05-0.94 (m, 3H); ESI MS m/z 593 [M+H]+; HPLC 98.4% (AUC), $T_R$ 5.51 min; UV (MeOH) $\lambda_{max}$ 288 nm, ε 24,976.

Example 42

(11S,14S,17S)-17-acetamido-11,14-bis(carboxymethyl)-1-(trans-4-(4-(2-(ethyl(m-tolyl)amino)-2-oxoethyl)-4H-thieno[3,2-b]pyrrole-5-carboxamido)cyclohexyl)-1,10,13,16-tetraoxo-2,9,12,15-tetraazanonadecan-19-oic acid (JRW-0251)

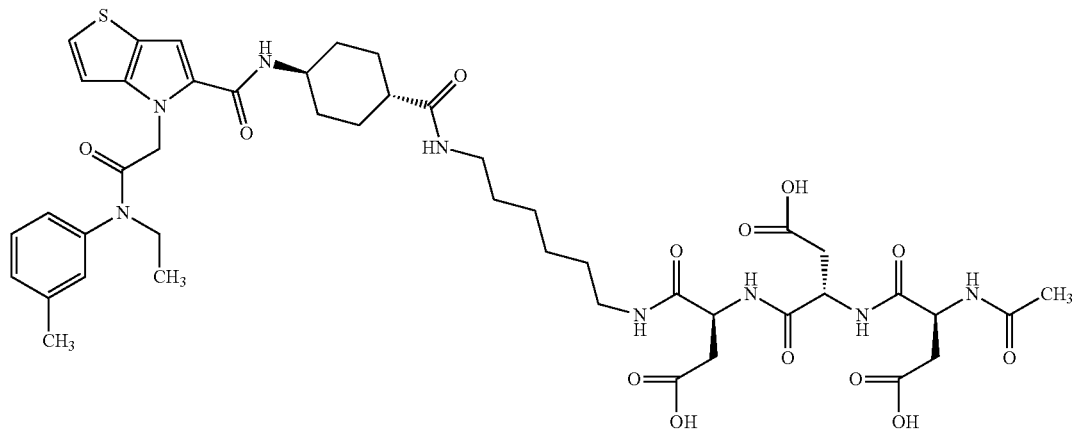 [SMILES: CCN(C(=O)Cn1c(C(=O)N[C@H]2CC[C@H](C(=O)NCCCCCCNC(=O)[C@H](CC(=O)O)NC(=O)[C@H](CC(=O)O)NC(=O)[C@H](CC(=O)O)NC(C)=O)CC2)cc2sccc21)c1cccc(C)c1]

Step 1. tert-butyl (11S,14S,17S)-17-acetamido-11,14-bis(2-(tert-butoxy)-2-oxoethyl)-1-(trans-4-(4-(2-(ethyl(m-tolyl)amino)-2-oxoethyl)-4H-thieno[3,2-b]pyrrole-5-carboxamido)cyclohexyl)-1,10,13,16-tetraoxo-2,9,12,15-tetraazanonadecan-19-oate (JRW-0249)

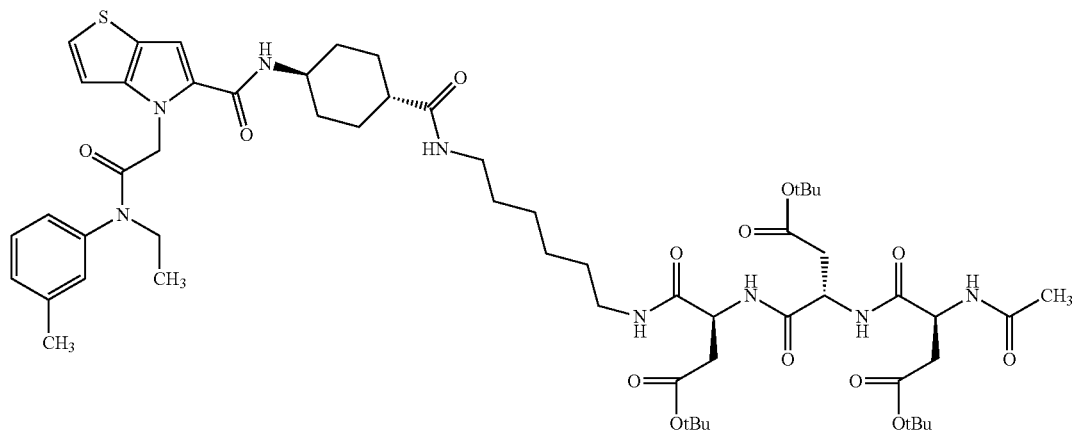 [SMILES: CCN(C(=O)Cn1c(C(=O)N[C@H]2CC[C@H](C(=O)NCCCCCCNC(=O)[C@H](CC(=O)OC(C)(C)C)NC(=O)[C@H](CC(=O)OC(C)(C)C)NC(=O)[C@H](CC(=O)OC(C)(C)C)NC(C)=O)CC2)cc2sccc21)c1cccc(C)c1]

Following general procedure B, (S)-2-((S)-2-((S)-2-acetamido-4-(tert-butoxy)-4-oxobutanamido)-4-(tert-butoxy)-4-oxobutanamido)-4-(tert-butoxy)-4-oxobutanoic acid (81 mg, 0.14 mmol) was reacted with N-(trans-4-((6-aminohexyl)carbamoyl)cyclohexyl)-4-(2-(ethyl(m-tolyl)amino)-2-oxoethyl)-4H-thieno[3,2-b]pyrrole-5-carboxamide hydrochloride (85 mg, 0.14 mmol) to afford the desired product (125 mg, 78%) as a light yellow solid. ESI MS m/z 1122 [M+H]$^+$.

Step 2. (11S,14S,17S)-17-acetamido-11,14-bis(carboxymethyl)-1-(trans-4-(4-(2-(ethyl(m-tolyl)amino)-2-oxoethyl)-4H-thieno[3,2-b]pyrrole-5-carboxamido)cyclohexyl)-1,10,13,16-tetraoxo-2,9,12,15-tetraazanonadecan-19-oic acid (JRW-0251)

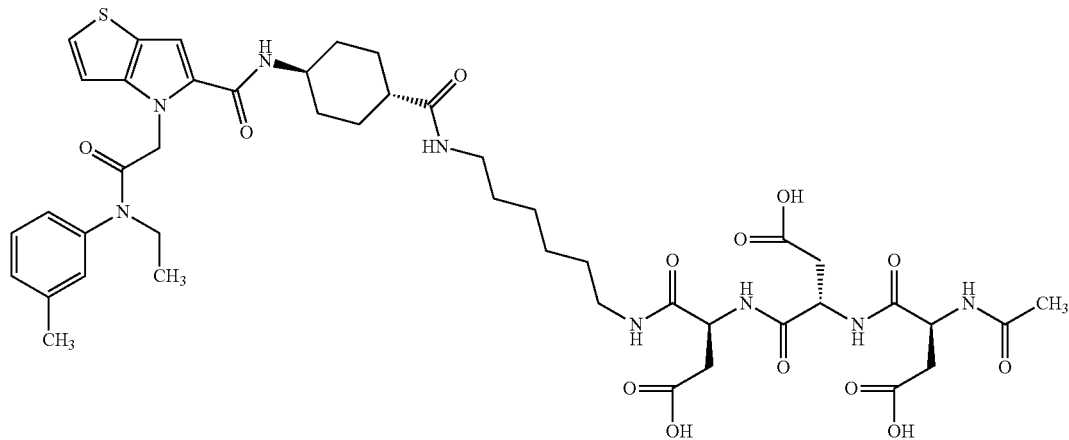 [SMILES: CCN(C(=O)Cn1c(C(=O)N[C@H]2CC[C@H](C(=O)NCCCCCCNC(=O)[C@H](CC(=O)O)NC(=O)[C@H](CC(=O)O)NC(=O)[C@H](CC(=O)O)NC(C)=O)CC2)cc2sccc21)c1cccc(C)c1]

To a solution of tert-butyl (11S,14S,17S)-17-acetamido-11,14-bis(2-(tert-butoxy)-2-oxoethyl)-1-(trans-4-(4-(2-(ethyl(m-tolyl)amino)-2-oxoethyl)-4H-thieno[3,2-b]pyrrole-5-carboxamido)cyclohexyl)-1,10,13,16-tetraoxo-2,9,12,15-tetraazanonadecan-19-oate (120 mg, 0.11 mmol) in dichloromethane (10 mL), trifluoroacetic acid (1 mL) was added. The reaction stirred at RT for 18 h. The mixture was diluted with toluene and concentrated under vacuum (3×). The residue was purified by column chromatography (silica, dichloromethane/methanol) to afford the desired product (68 mg, 66%) as a white solid. $^1$H NMR (300 MHz, DMSO-$d_6$) δ 12.31 (s, 3H), 8.45-8.18 (m, 2H), 7.95-7.83 (m, 2H), 7.66 (t, J=5.5, 1H), 7.52-7.17 (m, 6H), 7.11-7.04 (m, 2H), 4.96 (s, 2H), 4.55-4.35 (m, 3H), 3.71-3.52 (m, 2H), 3.06-2.90 (m, 4H), 2.75-2.60 (m, 3H), 2.60-2.42 (m, 4H), 2.36 (s, 3H), 2.09-1.96 (m, 1H), 1.89-1.66 (m, 7H), 1.53-1.13 (m, 12H), 1.06-0.93 (m, 3H); ESI MS m/z 953 [M+H]$^+$; HPLC 93.8% (AUC), $T_R$ 4.74 min; UV (MeOH) $\lambda_{max}$ 289 nm, ε 24,417.

Example 43

Alternate Syntheses of Compounds of Formula (Ia)

Compounds of formula (Ia) can also be generally synthesized according to Scheme 3.

Scheme 3.

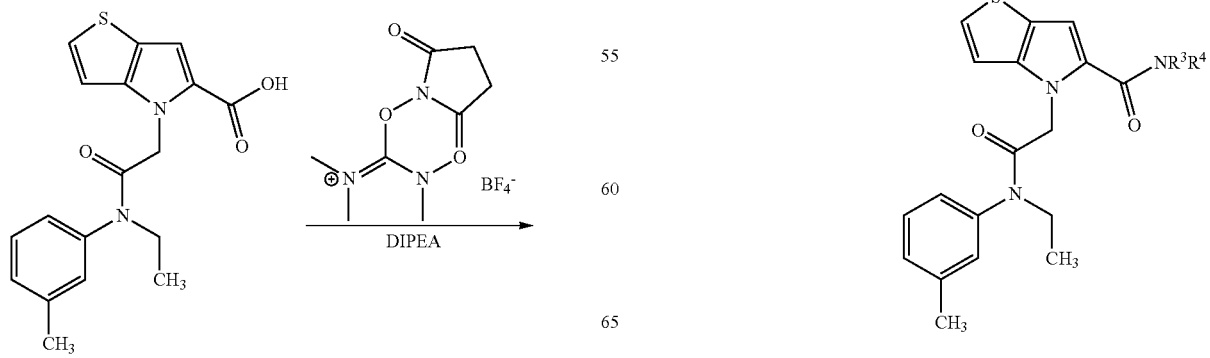

Example 44

4-(2-(ethyl(m-tolyl)amino)-2-oxoethyl)-N-methyl-4H-thieno[3,2-b]pyrrole-5-carboxamide (WZ-141-84)

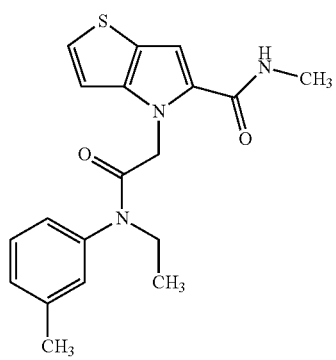

Step 1. 2,5-dioxopyrrolidin-1-yl 4-(2-(ethyl(m-tolyl)amino)-2-oxoethyl)-4H-thieno[3,2-b]pyrrole-5-carboxylate (WZ-141-82)

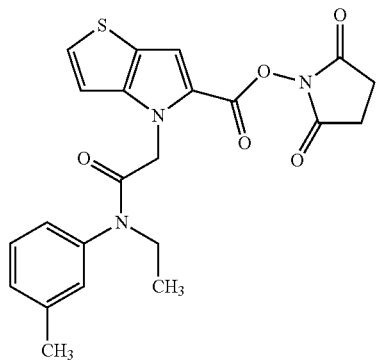 [SMILES: CCN(C(=O)Cn1c(C(=O)ON2C(=O)CCC2=O)cc2sccc21)c1cccc(C)c1]

4-(2-(Ethyl(m-tolyl)amino)-2-oxoethyl)-4H-thieno[3,2-b]pyrrole-5-carboxylic acid (0.44 g, 1.28 mmol) and TSTU (1.16 g, 3.85 mol) was dissolved in 15 ml of methylene chloride and 15 ml of acetonitrile. DIPEA (0.996 g, 7.71 mmol) was slowly added at room temperature, and the resultant mixture was stirred at room temperature for 30 minutes. The reaction mixture was diluted by 100 ml of methylene chloride, washed twice with 30% citric acid and twice with water, and dried over $Na_2SO_4$. The organic solvent was concentrated to 30 ml solution. Without further purification, a portion of the solution was used directly in next step.

Step 2. 4-(2-(ethyl(m-tolyl)amino)-2-oxoethyl)-N-methyl-4H-thieno[3,2-b]pyrrole-5-carboxamide (WZ-141-84)

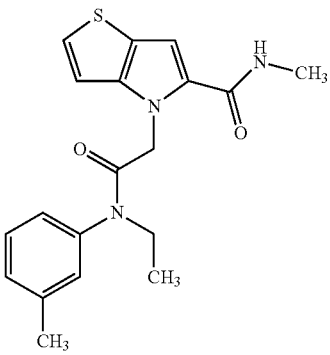 [SMILES: CCN(C(=O)Cn1c(C(=O)NC)cc2sccc21)c1cccc(C)c1]

To the above 10 ml of crude of 2,5-dioxopyrrolidin-1-yl 4-(2-(ethyl(m-tolyl)amino)-2-oxoethyl)-4H-thieno[3,2-b]pyrrole-5-carboxylate (WZ141-82)(150 mg, 0.34 mmol), methyl amine (40%)(0.53 g, 6.83 mmol) was added, and the resulted mixture was stirred at room temperature for 30 minutes. After removing solvent, the compound was purified by flash column using heptane/ethyl acetate as eluent to give the desired product in a quantitative yield. $^1$H NMR (300 MHz, $CD_2Cl_2$) δ 7.5-6.8 (m, 7H), 4.95 (s, 2H), 3.76 (m, 2H), 2.91 (d, 3H), 2.43 (s, 3H), 1.10 (t, 3H); ESI MS m/z 356 [M+H]$^+$; HPLC 99.6% at 254 nm.

Example 45

N-cyclopentyl-4-(2-(ethyl(m-tolyl)amino)-2-oxoethyl)-4H-thieno[3,2-b]pyrrole-5-carboxamide (WZ-141-88)

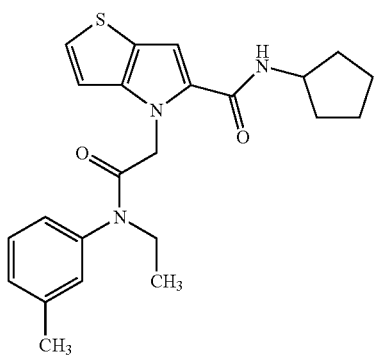 [SMILES: CCN(C(=O)Cn1c(C(=O)NC2CCCC2)cc2sccc21)c1cccc(C)c1]

The compound WZ141-88 was synthesized by employing the similar method for preparation of 4-(2-(ethyl(m-tolyl)amino)-2-oxoethyl)-N-methyl-4H-thieno[3,2-b]pyrrole-5-carboxamide (WZ141-84). $^1$H NMR (300 MHz, DMSO-$d_6$) δ 7.96 (d, 1H), 7.5-7.1 (m, 6H), 6.8 (d, 1H), 4.90 (s, 2H), 4.61 (m, 1H), 3.63 (m, 2H), 2.38 (s, br, 3H), 1.9-1.4 (m, 8H), 1.00 (t, 3H); ESI MS m/z 410 [M+H]$^+$; HPLC purity 99.1% at 254 nm.

Example 46

4-(2-(ethyl(m-tolyl)amino)-2-oxoethyl)-N-(pyridin-4-ylmethyl)-4H-thieno[3,2-b]pyrrole-5-carboxamide (WZ-141-89)

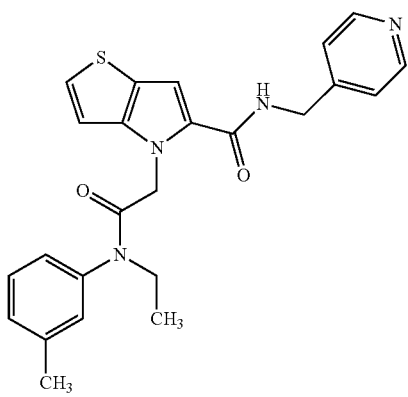 [SMILES: CCN(C(=O)Cn1c(C(=O)NCc2ccncc2)cc2sccc21)c1cccc(C)c1]

The compound WZ141-89 was synthesized by employing the above similar method for preparation of 4-(2-(ethyl(m-tolyl)amino)-2-oxoethyl)-N-methyl-4H-thieno[3,2-b]pyrrole-5-carboxamide (WZ141-84). $^1$H NMR (300 MHz, DMSO-$d_6$) δ 8.79 (t, 1H), 8.46 (d, 2H), 7.45-7.05 (m, 8H), 4.92 (s, 2H), 4.41 (d, 2H), 3.58 (m, 2H), 2.32 (s, 3H), 1.10 (t, 3H); ESI MS m/z 433 [M+H]+; HPLC purity 94.2% at 254 nm.

Example 47

4-(2-(ethyl(m-tolyl)amino)-2-oxoethyl)-N-(3-morpholinopropyl)-4H-thieno[3,2-b]pyrrole-5-carboxamide (WZ-141-90)

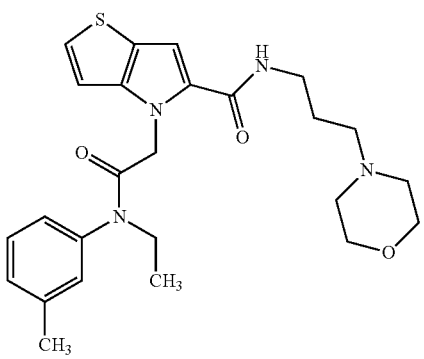 [SMILES: CCN(C(=O)Cn1c(C(=O)NCCCN2CCOCC2)cc2sccc21)c1cccc(C)c1]

The compound WZ141-90 was synthesized by employing the similar method for preparation of 4-(2-(ethyl(m-tolyl)amino)-2-oxoethyl)-N-methyl-4H-thieno[3,2-b]pyrrole-5-carboxamide (WZ141-84). $^1$H NMR (300 MHz, DMSO-$d_6$) δ 8.12 (d, 2H), 7.4-7.0 (m, 6H), 4.93 (s, 2H), 3.7-3.4 (m, 6H), 3.4-3.2 (m, 2H), 2.4-2.2 (s, 9H), 1.7-1.5 (m, 2H), 1.10 (t, 3H); ESI MS m/z 469 [M+H]+; HPLC purity 98.0% at 254 nm.

Example 48

N-ethyl-2-(5-(4-methylpiperazine-1-carbonyl)-4H-thieno[3,2-b]pyrrol-4-yl)-N-(m-tolyl)acetamide (WZ-141-91)

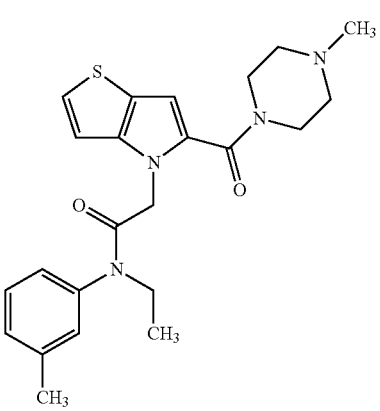 [SMILES: CCN(C(=O)Cn1c(C(=O)N2CCN(C)CC2)cc2sccc21)c1cccc(C)c1]

The compound WZ141-91 was synthesized by employing the similar method for preparation of 4-(2-(ethyl(m-tolyl)amino)-2-oxoethyl)-N-methyl-4H-thieno[3,2-b]pyrrole-5-carboxamide (WZ141-84). $^1$H NMR (300 MHz, DMSO-$d_6$) δ 7.44 (d, 1H), 7.3-7.1 (m, 3H), 7.03 (d, 1H), 6.26 (s, 1H), 4.68 (s, 2H), 3.7-3.5 (m, 6H), 2.35 (s, 3H), 2.32 (m, 4H), 2.18 (s, 3H), 1.10 (t, 3H); ESI MS m/z 425 [M+H]+; HPLC purity 96.0% at 254 nm.

Example 49

Syntheses of Compounds of Formula (Ic)

Compounds of formula (Ic) can be generally synthesized according to Scheme 4.

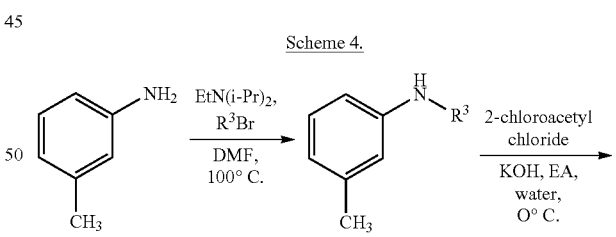

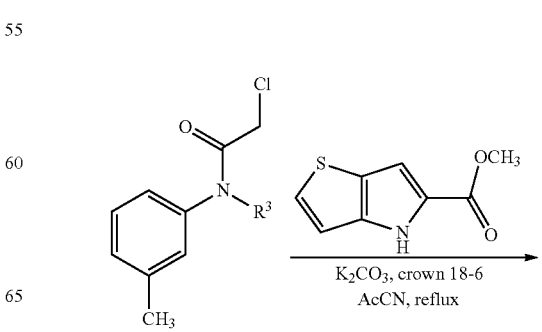

-continued

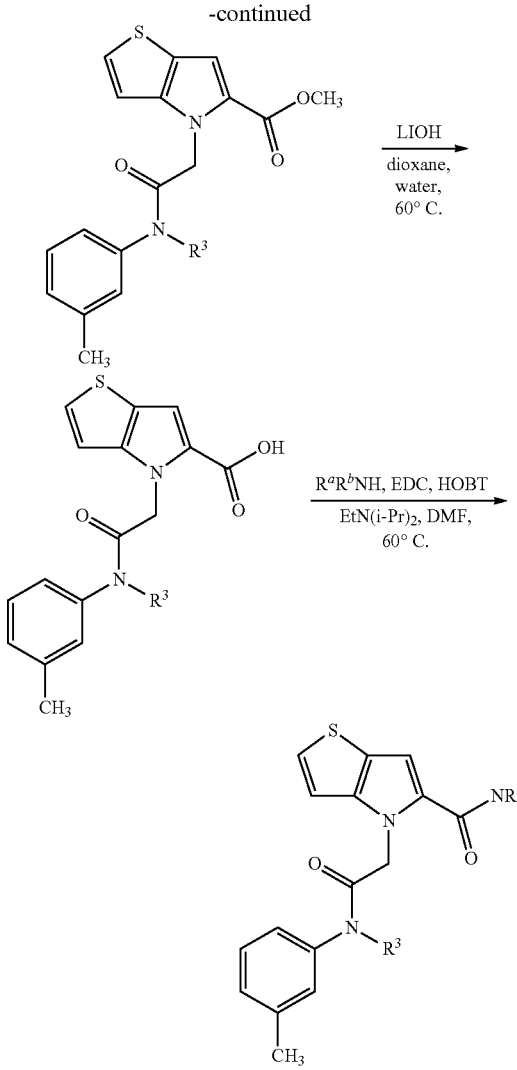

Example 50 methyl 4-(2-oxo-2-(m-tolylamino)ethyl)-4H-thieno[3,2-b]pyrrole-5-carboxylate (JRW-0077)

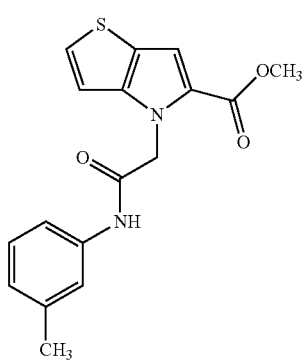 [SMILES: COC(=O)c1cc2sccc2n1CC(=O)Nc1cccc(C)c1]

To a solution of 2-chloro-N-(m-tolyl)acetamide (500 mg, 2.7 mmol) in acetonitrile (20 mL), methyl 4H-thieno[3,2-b]pyrrole-5-carboxylate (411 mg, 2.3 mmol), potassium carbonate (376 mg, 2.7 mmol) and 18-crown-6 (30 mg, 0.11 mmol) was added. The reaction was heated to reflux for 1.5 h. The mixture was diluted with ethyl acetate and water, and the layers were separated. The organic layer was dried over anhydrous sodium sulfate and filtered. The filtrate was then concentrated. The residue was purified by column chromatography (silica, heptane/ethyl acetate) to afford the desired product (530 mg, 71%) as a light brown solid. $^1$H NMR (300 MHz, DMSO-$d_6$) δ 10.21 (s, 1H), 7.57 (d, J=5.4, 1H), 7.42 (s, 1H), 7.37-7.30 (m, 1H), 7.27 (d, J=5.4, 1H), 7.23 (s, 1H), 7.16 (t, J=7.8, 1H), 6.85 (d, J=7.8, 1H), 5.31 (s, 2H), 3.73 (s, 3H), 2.24 (s, 3H); ESI MS m/z 329 [M+H]$^+$; HPLC 99.6% (AUC), $T_R$ 6.32 min; UV (MeOH) $\lambda_{max}$ 288 nm, ε 29,177.

Example 51

N-cyclohexyl-4-(2-oxo-2-(m-tolylamino)ethyl)-4H-thieno[3,2-b]pyrrole-5-carboxamide (JRW-0081)

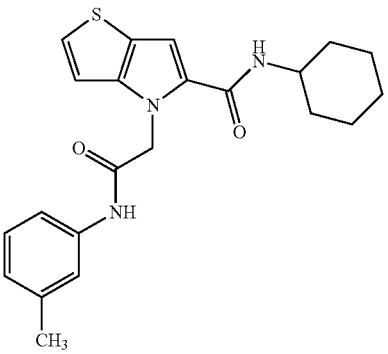 [SMILES: Cc1cccc(NC(=O)Cn2c(C(=O)NC3CCCCC3)cc3sccc32)c1]

Step 1. 4-(2-oxo-2-(m-tolylamino)ethyl)-4H-thieno[3,2-b]pyrrole-5-carboxylic acid (JRW-0080)

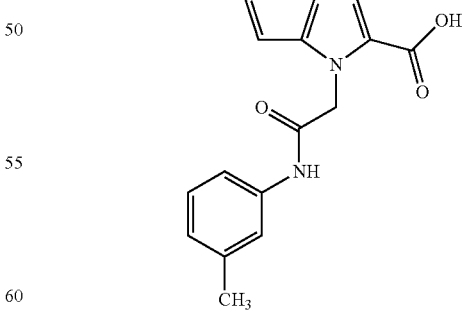

Following general procedure A, methyl 4-(2-oxo-2-(m-tolylamino)ethyl)-4H-thieno[3,2-b]pyrrole-5-carboxylate (130 mg, 0.39 mmol) was reacted with lithium hydroxide (47 mg 2.0 mmol) to afford crude product as a light brown solid.

Step 2. N-cyclohexyl-4-(2-oxo-2-(m-tolylamino)
ethyl)-4H-thieno[3,2-b]pyrrole-5-carboxamide
(JRW-0081)

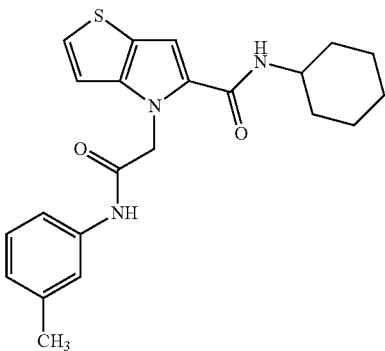 [SMILES: Cc1cccc(NC(=O)Cn2c(C(=O)NC3CCCCC3)cc3sccc32)c1]

Following general procedure B, 4-(2-oxo-2-(m-tolylamino)ethyl)-4H-thieno[3,2-b]pyrrole-5-carboxylic acid (120 mg, 0.38 mmol) was reacted with cyclohexylamine (56 mg, 0.57 mmol) to afford the desired product (47 mg, 31%) as a white solid. $^1$H NMR (300 MHz, DMSO-d$_6$) δ 10.13 (s, 1H), 7.95 (d, J=8.1, 1H), 7.43-7.38 (m, 2H), 7.33 (d, J=8.1, 1H), 7.23-7.10 (m, 3H), 6.84 (d, J=7.5, 1H), 5.30 (s, 2H), 3.75-3.58 (m, 1H), 2.24 (s, 3H), 1.85-1.53 (m, 5H), 1.35-1.00 (m, 5H); ESI MS m/z 396 [M+H]$^+$; HPLC 94.7% (AUC), T$_R$ 7.34 min; UV (MeOH) 285 nm, ε 28,066.

Example 52

N-cyclohexyl-4-(2-((2-(2-methoxyethoxy)ethyl)(m-tolyl)amino)-2-oxoethyl)-4H-thieno[3,2-b]pyrrole-5-carboxamide (JRW-0109)

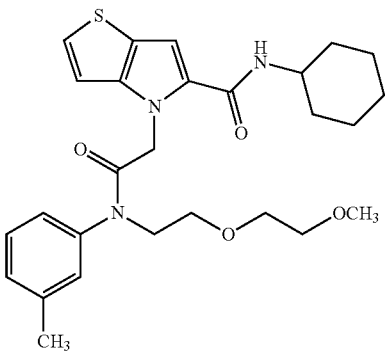 [SMILES: COCCOCCN(C(=O)Cn1c(C(=O)NC2CCCCC2)cc2sccc21)c1cccc(C)c1]

Step 1. N-(2-(2-methoxyethoxy)ethyl)-3-methylaniline (JRW-0101)

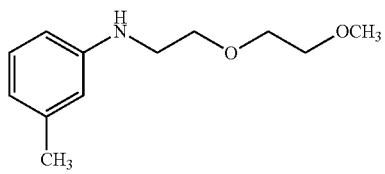

To a solution of m-toluidine (1.0 g, 9.3 mmol) in DMF (10 mL), 1-bromo-2-(2-methoxyethoxy)ethane (0.85 g, 4.6 mmol) and diisopropylamine (1.2 g, 0.93 mmol) was added. The mixture was heated to 100° C. for 4 h. The mixture was diluted with ethyl acetate and water, and the layers were separated. The organic layer was dried over anhydrous sodium sulfate and filtered. The filtrate was then concentrated. The residue was purified by column chromatography (silica, heptane/ethyl acetate) to afford the desired product (650 mg, 66%) as an oil. $^1$H NMR (300 MHz, CDCl$_3$) δ 7.07 (t, J=7.5, 1H), 6.56 (d, J=7.5, 1H), 6.52-6.45 (m, 2H), 3.71 (t, J=5.3, 2H), 3.67-3.62 (m, 2H), 3.60-3.52 (m, 2H), 3.31 (t, J=5.3, 2H), 2.28 (s, 3H); ESI MS m/z 210 [M+H]$^+$.

Step 2. 2-chloro-N-(2-(2-methoxyethoxy)ethyl)-N-(m-tolyl)acetamide (JRW-0104)

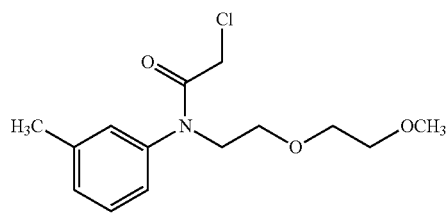 [SMILES: COCCOCCN(C(=O)CCl)c1cccc(C)c1]

To a solution of N-(2-(2-methoxyethoxy)ethyl)-3-methylaniline (650 mg, 3.1 mmol) in ethyl acetate (15 mL), water (5 mL) was added. The biphasic solution was cooled to 0° C. and potassium hydroxide (522 mg, 9.3 mmol) was added in one motion. 2-Chloroacetyl chloride (526 mg, 4.7 mmol) was added dropwise over 10 min. The mixture was stirred for 2.5 h, diluted with water, and extracted with ethyl acetate. The organic layer was dried over anhydrous sodium sulfate and filtered. The filtrate was then concentrated to afford crude product (830 mg) as light red oil. $^1$H NMR (300 MHz, CDCl$_3$) δ 7.34-7.25 (m, 1H), 7.18 (d, J=7.7, 1H), 7.15-7.03 (m, 2H), 3.89 (t, J=5.8, 2H), 3.83 (s, 2H), 3.65 (t, J=5.8, 2H), 3.62-3.55 (m, 2H), 3.54-3.46 (m, 2H), 2.37 (s, 3H); ESI MS m/z 286 [M+H]$^+$.

Step 3. methyl 4-(2-((2-(2-methoxyethoxy)ethyl)(m-tolyl)amino)-2-oxoethyl)-4H-thieno[3,2-b]pyrrole-5-carboxylate (JRW-0105)

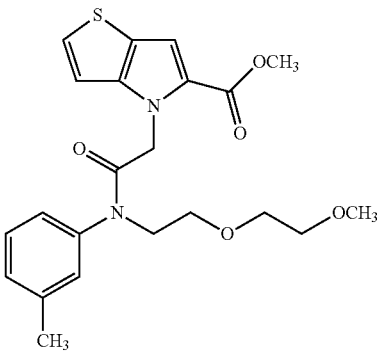 [SMILES: COCCOCCN(C(=O)Cn1c(C(=O)OC)cc2sccc21)c1cccc(C)c1]

To a solution of 2-chloro-N-(2-(2-methoxyethoxy)ethyl)-N-(m-tolyl)acetamide (830 mg, 2.9 mmol) in acetonitrile (20 mL), methyl 4H-thieno[3,2-b]pyrrole-5-carboxylate (438 mg, 2.4 mmol), potassium carbonate (400 mg, 2.9 mmol) and 18-crown-6 (32 mg, 0.12 mmol) was added. The mixture was heated to reflux for 18 h. The mixture was diluted with ethyl acetate and water, and the layers were separated. The organic layer was dried over anhydrous sodium sulfate and filtered. The filtrate was then concentrated. The residue was purified by column chromatography (silica, heptane/ethyl acetate) to afford crude product (1.3 g) as a thick oil. ESI MS m/z 430 [M+H]$^+$.

Step 4. 4-(2-((2-(2-methoxyethoxy)ethyl)(m-tolyl)amino)-2-oxoethyl)-4H-thieno[3,2-b]pyrrole-5-carboxylic acid (JRW-0107)

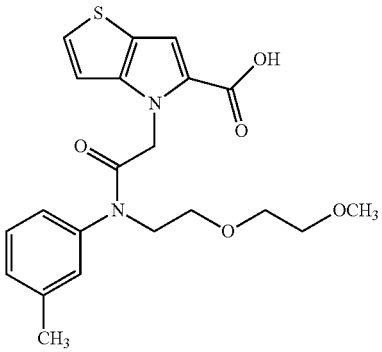 [SMILES: COCCOCCN(C(=O)Cn1c(C(=O)O)cc2sccc21)c1cccc(C)c1]

Following general procedure A, methyl 4-(2-((2-(2-methoxyethoxy)ethyl)(m-tolyl)amino)-2-oxoethyl)-4H-thieno[3,2-b]pyrrole-5-carboxylate (2.4 mmol) was reacted with lithium hydroxide (287 mg, 12.0 mmol) to afford crude product (1.0 g, quant.) as a light yellow solid. ESI MS m/z 417 [M+H]$^+$.

Step 5. N-cyclohexyl-4-(2-((2-(2-methoxyethoxy)ethyl)(m-tolyl)amino)-2-oxoethyl)-4H-thieno[3,2-b]pyrrole-5-carboxamide (JRW-0109)

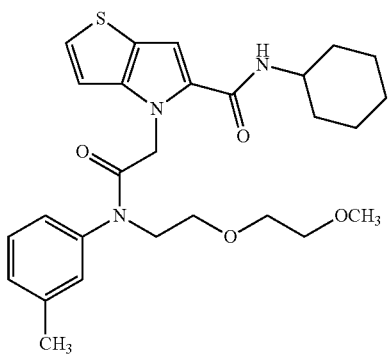 [SMILES: COCCOCCN(C(=O)Cn1c(C(=O)NC2CCCCC2)cc2sccc21)c1cccc(C)c1]

Following general procedure B, 4-(2-((2-(2-methoxyethoxy)ethyl)(m-tolyl)amino)-2-oxoethyl)-4H-thieno[3,2-b]pyrrole-5-carboxylic acid (120 mg, 0.28 mmol) was reacted with cyclohexylamine (42 mg, 0.43 mmol) to afford the desired product (120 mg, 83%) as a white gum. $^1$H NMR (300 MHz, DMSO-d$_6$) δ 7.96-7.85 (m, 1H), 7.48-7.30 (m, 4H), 7.30-7.20 (m, 1H), 7.17-7.07 (m, 2H), 5.01 (s, 2H), 3.82-3.62 (m, 3H), 3.56-3.35 (m, 6H), 3.25 (s, 3H), 2.38 (s, 3H), 1.90-1.54 (m, 5H), 1.41-1.04 (m, 5H); ESI MS m/z 498 [M+H]$^+$; HPLC 96.0% (AUC), T$_R$ 7.38 min; UV (EtOH) λ$_{max}$ 289 nm, ε 25,434.

Example 53

Methyl-trans-4-(4-(2-((2-(2-methoxyethoxy)ethyl)(m-tolyl)amino)-2-oxoethyl)-4H-thieno[3,2-b]pyrrole-5-carboxamido)cyclohexane-1-carboxylate (JRW-0110)

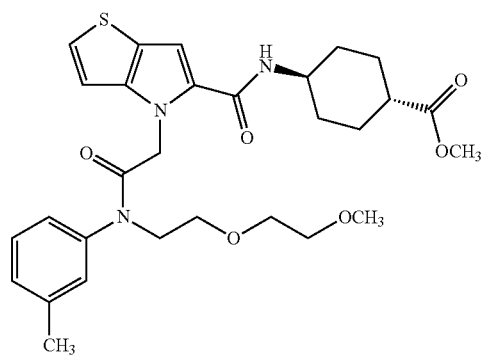 [SMILES: COCCOCCN(C(=O)Cn1c(C(=O)N[C@H]2CC[C@H](C(=O)OC)CC2)cc2sccc21)c1cccc(C)c1]

Following general procedure B, 4-(2-((2-(2-methoxyethoxy)ethyl)(m-tolyl)amino)-2-oxoethyl)-4H-thieno[3,2-b]pyrrole-5-carboxylic acid (120 mg, 0.28 mmol) was reacted with methyl trans-4-aminocyclohexane-1-carboxylate (68 mg, 0.43 mmol) to afford the desired product (140 mg, 87%) as a white gum. $^1$H NMR (300 MHz, DMSO-d$_6$) δ 7.94 (d, J=7.8, 1H), 7.46-7.20 (m, 5H), 7.15-7.04 (m, 2H), 5.00 (s, 2H), 3.78-3.65 (m, 3H), 3.60 (s, 3H), 3.52-3.35 (m, 6H), 3.23 (s, 3H), 2.38 (s, 3H), 2.34-2.20 (m, 1H), 2.02-1.81 (m, 4H), 1.53-1.22 (m, 4H); ESI MS m/z 556 [M+H]$^+$; HPLC 98.7% (AUC), T$_R$ 6.60 min; UV (MeOH) λ$_{max}$ 289 nm, ε 23,567.

Example 54 methyl 4-(2-(hexyl(m-tolyl)amino)-2-oxoethyl)-4H-thieno[3,2-b]pyrrole-5-carboxylate (JRW-0142)

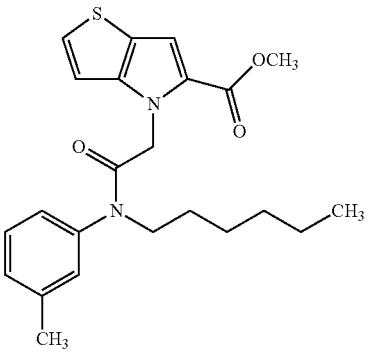 [SMILES: CCCCCCN(C(=O)Cn1c(C(=O)OC)cc2sccc21)c1cccc(C)c1]

Step 1. 2-chloro-N-hexyl-N-(m-tolyl)acetamide (JRW-0141)

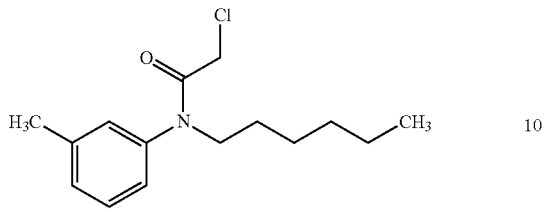

To a solution of N-hexyl-3-methylaniline (500 mg, 2.6 mmol) in ethyl acetate (15 mL), water (5 mL) was added. The biphasic solution was cooled to 0° C., and potassium hydroxide (440 mg, 7.8 mmol) added in one motion. 2-Chloroacetyl chloride (442 mg, 3.9 mmol) was added dropwise over 10 min. The mixture was stirred for 1 h, diluted with water, and extracted with ethyl acetate. The organic layer was dried over anhydrous sodium sulfate and filtered. The filtrate was then concentrated to afford crude product (730 mg) as light red oil. $^1$H NMR (300 MHz, CDCl$_3$) δ 7.32 (t, J=8.0, 1H), 7.24-7.17 (m, 1H), 7.04-6.97 (m, 2H), 3.80 (s, 2H), 3.74-3.61 (m, 2H), 2.38 (s, 3H), 1.59-1.41 (m, 2H), 1.37-1.16 (m, 6H), 0.92-0.80 (m, 3H); ESI MS m/z 268 [M+H]$^+$.

Step 2. methyl 4-(2-(hexyl(m-tolyl)amino)-2-oxoethyl)-4H-thieno[3,2-b]pyrrole-5-carboxylate (JRW-0142)

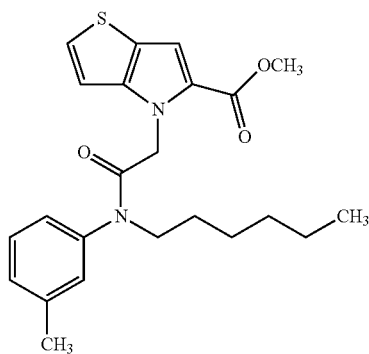 [SMILES: CCCCCCN(C(=O)Cn1c(C(=O)OC)cc2sccc21)c1cccc(C)c1]

To a solution of 2-chloro-N-hexyl-N-(m-tolyl)acetamide (700 mg, 2.6 mmol) in acetonitrile (20 mL), methyl 4H-thieno[3,2-b]pyrrole-5-carboxylate (394 mg, 2.2 mmol), potassium carbonate (361 mg, 2.6 mmol) and 18-crown-6 (29 mg, 0.11 mmol) was added. The mixture was heated to reflux for 18 h. The mixture was diluted with ethyl acetate and water, and the layers were separated. The organic layer was dried over anhydrous sodium sulfate and filtered. The filtrate was the concentrated. The residue was purified by column chromatography (silica, heptane/ethyl acetate) to afford the desired product (780 mg, 86%) as a white solid. $^1$H NMR (300 MHz, DMSO-d$_6$) δ 7.53 (d, J=5.4, 1H), 7.41 (t, J=7.7, 1H), 7.33-7.11 (m, 5H), 4.93 (s, 2H), 3.74 (s, 3H), 3.58 (t, J=6.0 Hz, 2H), 2.37 (s, 3H), 1.48-1.30 (m, 2H), 1.28-1.15 (m, 6H), 0.81 (t, J=6.7, 3H); ESI MS m/z 413 [M+H]$^+$; HPLC 97.1% (AUC), T$_R$ 7.18 min; UV (EtOH) λ$_{max}$ 289 nm, ε 26,840.

Example 55

N-cyclohexyl-4-(2-(hexyl(m-tolyl)amino)-2-oxoethyl)-4H-thieno[3,2-b]pyrrole-5-carboxamide (JRW-0148)

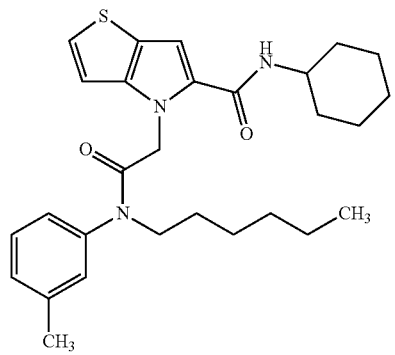

Step 1. 4-(2-(hexyl(m-tolyl)amino)-2-oxoethyl)-4H-thieno[3,2-b]pyrrole-5-carboxylic acid (JRW-0149)

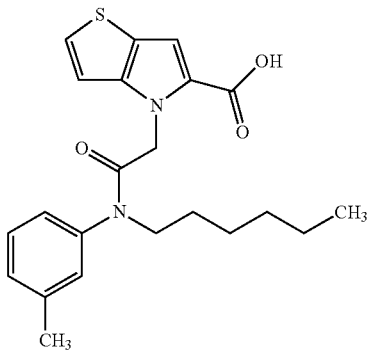 [SMILES: CCCCCCN(C(=O)Cn1c(C(=O)O)cc2sccc21)c1cccc(C)c1]

Following general procedure A, methyl 4-(2-(hexyl(m-tolyl)amino)-2-oxoethyl)-4H-thieno[3,2-b]pyrrole-5-carboxylate (300 mg, 0.73 mmol) was reacted with lithium hydroxide (87 mg, 3.6 mmol) to afford crude product (300 mg) as a light yellow solid. ESI MS m/z 399 [M+H]$^+$.

Step 2. N-cyclohexyl-4-(2-(hexyl(m-tolyl)amino)-2-oxoethyl)-4H-thieno[3,2-b]pyrrole-5-carboxamide (JRW-0148)

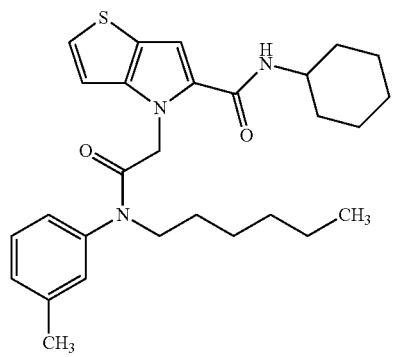 [SMILES: CCCCCCN(C(=O)Cn1c(C(=O)NC2CCCCC2)cc2sccc21)c1cccc(C)c1]

Following general procedure B, 4-(2-(hexyl(m-tolyl)amino)-2-oxoethyl)-4H-thieno[3,2-b]pyrrole-5-carboxylic acid (50 mg, 0.12 mmol) was reacted with cyclohexylamine (15 mg, 0.15 mmol) to afford the desired product (60 mg, 99%) as a white foam. $^1$H NMR (300 MHz, DMSO-$d_6$) δ 7.85 (d, J=8.2, 1H), 7.46-7.16 (m, 5H), 7.12-7.06 (m, 2H), 4.96 (s, 2H), 3.75-3.60 (m, 1H), 3.56 (t, J=6.7, 2H), 2.36 (s, 3H), 1.84-1.52 (m, 5H), 1.43-1.04 (m, 13H), 0.81 (t, J=6.9, 3H); ESI MS m/z 480 [M+H]$^+$; HPLC 98.1% (AUC), $T_R$ 8.62 min; UV (EtOH) $λ_{max}$ 288 nm, ε 24,544.

Example 56 methyl-trans-4-(4-(2-(hexyl(m-tolyl)amino)-2-oxoethyl)-4H-thieno[3,2-b]pyrrole-5-carboxamido)cyclohexane-1-carboxylate (JRW-0149)

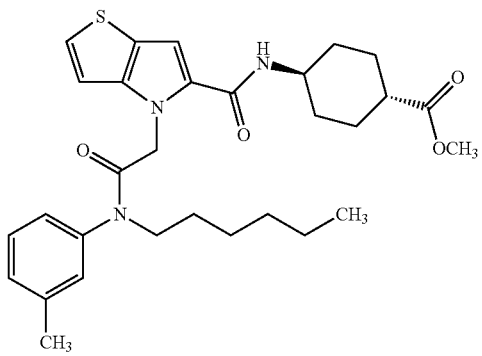 [SMILES: CCCCCCN(C(=O)Cn1c(C(=O)N[C@H]2CC[C@H](C(=O)OC)CC2)cc2sccc21)c1cccc(C)c1]

Following general procedure B, 4-(2-(hexyl(m-tolyl)amino)-2-oxoethyl)-4H-thieno[3,2-b]pyrrole-5-carboxylic acid (50 mg, 0.12 mmol) was reacted with methyl trans-4-aminocyclohexane-1-carboxylate (24 mg, 0.15 mmol) to afford the desired product (65 mg, 96%) as a white foam. $^1$H NMR (300 MHz, DMSO-$d_6$) δ 7.91 (d, J=8.0, 1H), 7.44-7.33 (m, 2H), 7.33-7.17 (m, 3H), 7.12-7.06 (m, 2H), 4.96 (s, 2H), 3.75-3.47 (m, 6H), 2.36 (s, 3H), 2.31-2.20 (m, 1H), 1.99-1.78 (m, 4H), 1.51-1.10 (m, 12H), 0.81 (t, J=6.9, 3H); ESI MS m/z 538 [M+H]$^+$; HPLC 99.8% (AUC), $T_R$ 8.17 min; UV (EtOH) $λ_{max}$ 289 nm, ε 26,509.

Example 57

Trans-4-(4-(2-(hexyl(m-tolyl)amino)-2-oxoethyl)-4H-thieno[3,2-b]pyrrole-5-carboxamido)cyclohexane-1-carboxylic acid (JRW-0260)

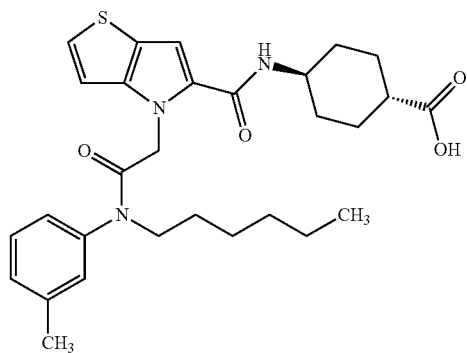 [SMILES: CCCCCCN(C(=O)Cn1c(C(=O)N[C@H]2CC[C@H](C(=O)O)CC2)cc2sccc21)c1cccc(C)c1]

Following general procedure A, methyl-trans-4-(4-(2-(hexyl(m-tolyl)amino)-2-oxoethyl)-4H-thieno[3,2-b]pyrrole-5-carboxamido)cyclohexane-1-carboxylate (58 mg, 0.11 mmol) was reacted with lithium hydroxide (13 mg, 0.54 mmol) to afford the desired product (55 mg, 97%) as a white foam. $^1$H NMR (300 MHz, DMSO-$d_6$) δ 12.03 (s, 1H), 7.88 (d, J=7.8, 1H), 7.46-7.17 (m, 5H), 7.12-7.06 (m, 2H), 4.97 (s, 2H), 3.74-3.48 (m, 3H), 2.36 (s, 3H), 2.19-2.05 (m, 1H), 2.00-1.77 (m, 4H), 1.48-1.09 (m, 12H), 0.88-0.77 (m, 3H).; ESI MS m/z 524 [M+H]$^+$; HPLC >99% (AUC), $T_R$ 7.42 min; UV (EtOH) $λ_{max}$ 288 nm, ε24,240.

Example 58 methyl 4-(2-(benzyl(m-tolyl)amino)-2-oxoethyl)-4H-thieno[3,2-b]pyrrole-5-carboxylate (WZ-141-86)

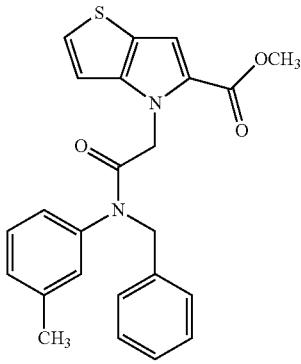 [SMILES: COC(=O)c1cc2sccc2n1CC(=O)N(Cc1ccccc1)c1cccc(C)c1]

Step 1. N-benzyl-2-chloro-N-(m-tolyl)acetamide (WZ-141-85)

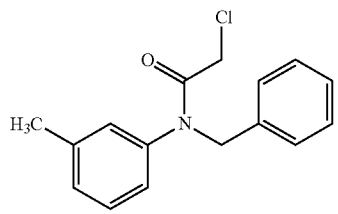 [SMILES: Cc1cccc(N(Cc2ccccc2)C(=O)CCl)c1]

To the solution of N-benzyl-3-methylaniline (1.35 g, 6.84 mmol) and TEA (0.761 g, 7.53 mmol) in 50 ml methylene chloride, 2-chloroacetyl chloride (0.772 g, 0.772 mmol) at 0° C. was slowly added. The resultant mixture was stirred at 0° C. for 30 minutes and then overnight at RT. The mixture was diluted to 100 ml methylene chloride and washed with water three times, and organic layer was dried over Na$_2$SO$_4$. After removing the solvent, the compound was purified by flash column chromatography using heptane and ethyl acetate as solvent to give the yellowish product in a yield of 74%. $^1$H NMR (300 MHz, CD$_2$Cl$_2$) δ 7.6-6.7 (m, 9H), 4.89 (s, 2H), 3.71 (s, 2H), 2.31 (s, 3H); ESI MS m/z 274 [M+H]$^+$.

Step 2. methyl 4-(2-(benzyl(m-tolyl)amino)-2-oxo-ethyl)-4H-thieno[3,2-b]pyrrole-5-carboxylate (WZ-141-86)

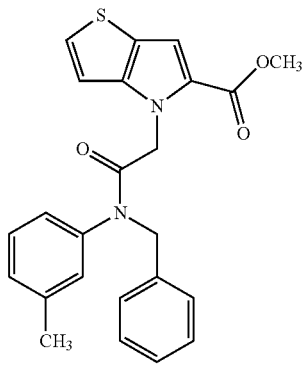 [SMILES: COC(=O)c1cc2sccc2n1CC(=O)N(Cc1ccccc1)c1cccc(C)c1]

The mixture of N-benzyl-2-chloro-N-(m-tolyl)acetamide (1.36 g, 4.97 mmol), methyl 4H-thieno[3,2-b]pyrrole-5-carboxylate (0.6 g, 3.31 mmol), 18-crown-6 ether (0.262 g, 0.993 mmol) and $K_2CO_3$ (0.915 g, 6.62 mmol) in 50 ml of acetonitrile was heated to reflux overnight. Upon cooling, the majority of solvent was removed under vacuum, and the residue was dissolved in methylene chloride (100 ml) and washed with water. The organic layer was dried over $Na_2SO_4$. After removing solvent, the compound was purified by flash column using heptane and ethyl acetate as solvent to give the pale white product in a yield of 95%. $^1$H NMR (300 MHz, DMSO-$d_6$) δ 7.57 (s, 1H), 7.4-7.1 (m, 11H), 5.06 (s, 2H), 4.83 (s, 2H), 3.79 (s, 3H), 2.31 (s, 3H); ESI MS m/z 419 [M+H]$^+$; HPLC purity 94.3% at 254 nm.

Scheme 5.

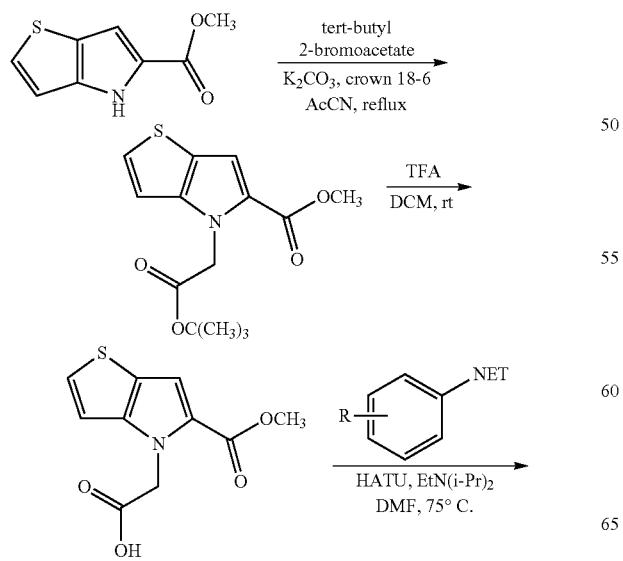

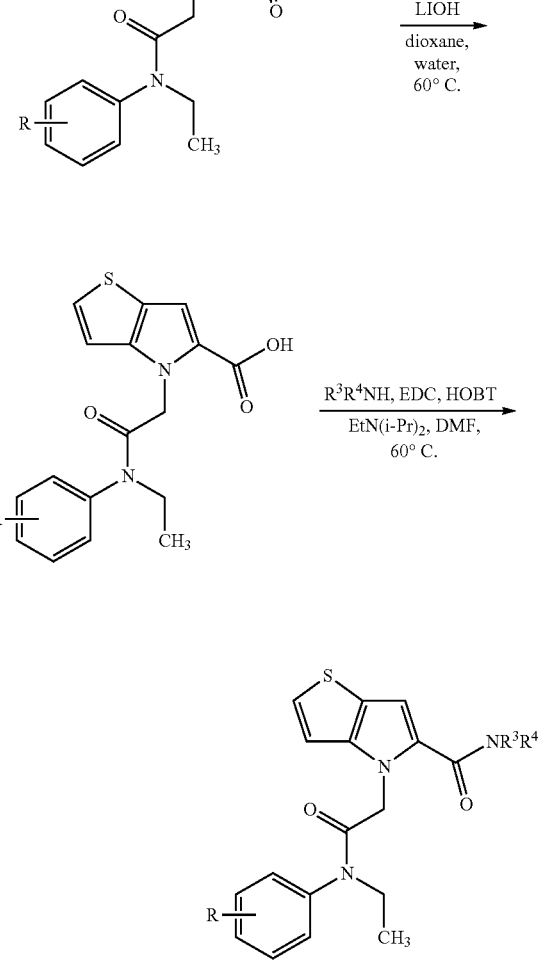

Example 59

Methyl trans-4-(4-(2-(ethyl(phenyl)amino)-2-oxo-ethyl)-4H-thieno[3,2-b]pyrrole-5-carboxamido)cyclohexane-1-carboxylate (JRW-0318)

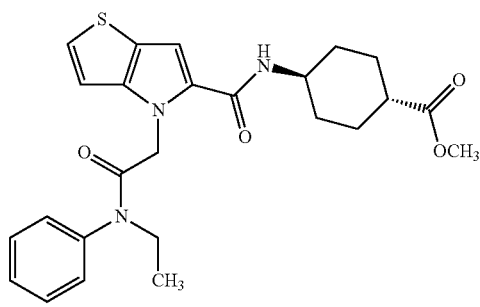 [SMILES: CCN(C(=O)Cn1c(C(=O)N[C@H]2CC[C@H](C(=O)OC)CC2)cc2sccc21)c1ccccc1]

Step 1. methyl 4-(2-(tert-butoxy)-2-oxoethyl)-4H-thieno[3,2-b]pyrrole-5-carboxylate (JRW-0277)

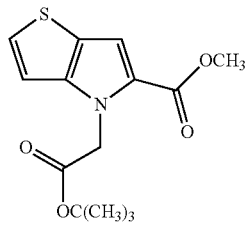

To a solution of methyl 4H-thieno[3,2-b]pyrrole-5-carboxylate (1.4 g, 7.73 mmol) in acetonitrile (30 mL), potassium carbonate (1.28 g, 9.28 mmol), 18-crown-6 ether (102 mg, 0.38 mmol), and tert-butyl 2-bromoacetate (1.81 g, 9.28 mmol) was added. The suspension was heated to 75° C. for 18 h. The mixture was diluted with ethyl acetate and water, and the layers were separated. The organic layer was dried over anhydrous sodium sulfate and filtered. The filtrate was then concentrated. The residue was purified by column chromatography (silica, heptane/ethyl acetate) to afford the desired product (2.1 g, 91%) as a light yellow solid. $^1$H NMR (300 MHz, CDCl$_3$) δ 7.34 (d, J=5.4, 1H), 7.22 (d, J=0.7, 1H), 6.87 (dd, J=0.7, 5.4, 1H), 5.11 (s, 2H), 3.84 (s, 3H), 1.46 (s, 9H); ESI MS m/z 296 [M+H]$^+$.

Step 2. 2-(5-(methoxycarbonyl)-4H-thieno[3,2-b]pyrrol-4-yl)acetic acid (JRW-0288)

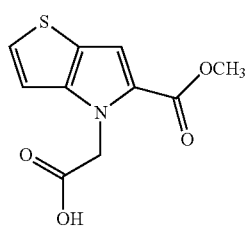 [SMILES: COC(=O)c1cc2sccc2n1CC(=O)O]

To a solution of methyl 4-(2-(tert-butoxy)-2-oxoethyl)-4H-thieno[3,2-b]pyrrole-5-carboxylate (1.92 g, 6.50 mmol) in DCM (20 mL), trifluoroacetic acid (2 mL) was added. The solution stirred at RT for 4 h, then the mixture was concentrated. Toluene was added to the residue and concentrated to obtained crude product as a white solid. $^1$H NMR (300 MHz, CDCl$_3$) δ 7.38 (d, J=5.4, 1H), 7.24 (s, 1H), 6.89 (d, J=5.4, 1H), 5.24 (s, 2H), 3.86 (s, 3H); ESI MS m/z 240 [M+H]$^+$.

Step 3. Methyl 4-(2-(ethyl(phenyl)amino)-2-oxoethyl)-4H-thieno[3,2-b]pyrrole-5-carboxylate (JRW-0294)

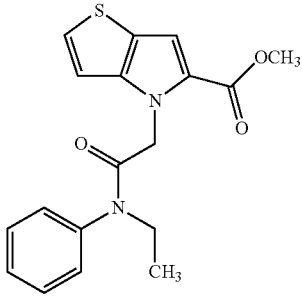 [SMILES: CCN(C(=O)Cn1c(C(=O)OC)cc2sccc21)c1ccccc1]

To a solution of 2-(5-(methoxycarbonyl)-4H-thieno[3,2-b]pyrrol-4-yl)acetic acid (100 mg, 0.42 mmol) in DMF (3 mL), N-ethylaniline (101 mg, 0.84 mmol), HATU (318 mg, 0.84 mmol), and diisopropylethylamine (108 mg, 0.84 mmol) was added. The reaction was heated to 75° C. for 18 h. The reaction mixture cooled, diluted with ethyl acetate, and washed with water. The organic layer was dried over anhydrous sodium sulfate and filtered. The filtrate was then concentrated. The residue was purified by column chromatography (silica, heptane/ethyl acetate) to afford the desired product (86 mg, 60%) as a white solid. $^1$H NMR (300 MHz, CDCl$_3$) δ 7.57-7.21 (m, 6H), 7.16 (s, 1H), 6.80 (d, J=5.5, 1H), 4.95 (s, 2H), 3.87-3.68 (m, 5H), 1.13 (t, J=7.2, 3H); ESI MS m/z 343 [M+H]$^+$.

Step 4. 4-(2-(ethyl(phenyl)amino)-2-oxoethyl)-4H-thieno[3,2-b]pyrrole-5-carboxylic acid (JRW-309)

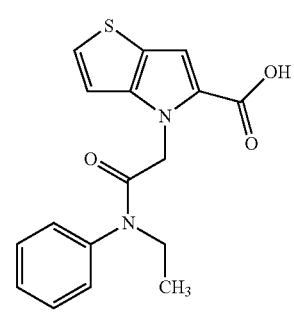 [SMILES: CCN(C(=O)Cn1c(C(=O)O)cc2sccc21)c1ccccc1]

Following general procedure A, methyl 4-(2-(ethyl(phenyl)amino)-2-oxoethyl)-4H-thieno[3,2-b]pyrrole-5-carboxylate (86 mg, 0.25 mmol) was reacted with lithium hydroxide (30 mg, 1.3 mmol) to afford crude product (82 mg) as a light brown solid. ESI MS m/z 329 [M+H]$^+$.

Step 5. Methyl trans-4-(4-(2-(ethyl(phenyl)amino)-2-oxoethyl)-4H-thieno[3,2-b]pyrrole-5-carboxamido)cyclohexane-1-carboxylate (JRW-0318)

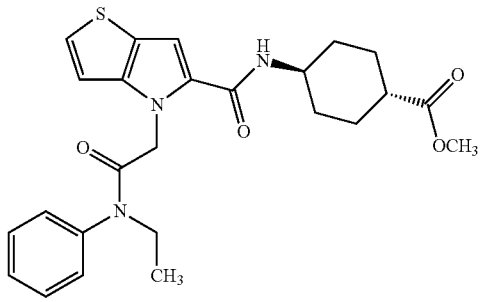 [SMILES: CCN(C(=O)Cn1c(C(=O)N[C@H]2CC[C@H](C(=O)OC)CC2)cc2sccc21)c1ccccc1]

Following general procedure B, 4-(2-(ethyl(phenyl)amino)-2-oxoethyl)-4H-thieno[3,2-b]pyrrole-5-carboxylic acid (80 mg, 0.24 mmol) was reacted with methyl trans-4-aminocyclohexane-1-carboxylate (56 mg, 0.29 mmol) to afford the desired product (81 mg, 71%) as a white solid. $^1$H NMR (300 MHz, DMSO-$d_6$) δ 7.89 (d, J=7.9, 1H), 7.60-7.28 (m, 6H), 7.04-7.13 (m, 2H), 4.95 (s, 2H), 3.73-3.52 (m, 5H), 2.31-2.18 (m, 1H), 2.03-1.78 (m, 4H), 1.50-1.20 (m, 4H), 1.07-0.93 (s, 3H); ESI MS m/z 468 [M+H]$^+$; HPLC 97.7% (AUC), $T_R$ 6.51 min; UV (EtOH) $\lambda_{max}$ 289 nm, ε 28,274.

Example 60

Methyl trans-4-(4-(2-((3-cyanophenyl)(ethyl)amino)-2-oxoethyl)-4H-thieno[3,2-b]pyrrole-5-carboxamido)cyclohexane-1-carboxylate (JRW-0321)

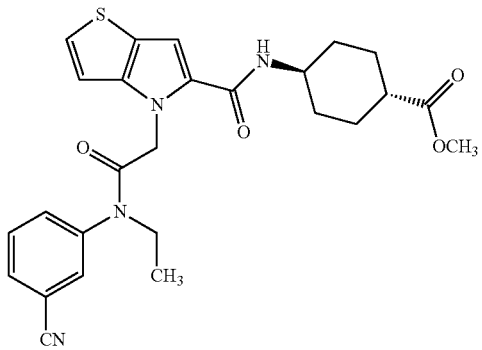 [SMILES: CCN(C(=O)Cn1c(C(=O)N[C@H]2CC[C@H](C(=O)OC)CC2)cc2sccc21)c1cccc(C#N)c1]

Step 1. 2-chloro-N-(3-cyanophenyl)-N-ethylacetamide (JRW-0313)

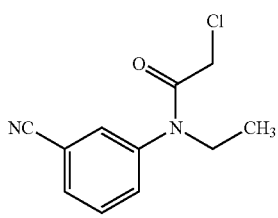

To a solution of 3-(ethylamino)benzonitrile (60 mg, 0.41 mmol) in ethyl acetate (7 mL), water (3 mL) was added. The biphasic solution was cooled to 0° C., and potassium hydroxide (69 mg, 1.2 mmol) was added in one motion. 2-Chloroacetyl chloride (69 mg, 0.62 mmol) was added dropwise over 10 min. The mixture was stirred for 2 h, diluted with water, and extracted with ethyl acetate. The organic layer was dried over anhydrous sodium sulfate and filtered. The filtrate was then concentrated to afford crude product (98 mg) as an oil. $^1$H NMR (300 MHz, CDCl$_3$) δ 7.81-7.42 (m, 4H), 3.84-3.70 (m, 4H), 1.15 (t, J=7.2, 3H); ESI MS m/z 223 [M+H]$^+$.

Step 2. Methyl 4-(2-((3-cyanophenyl)(ethyl)amino)-2-oxoethyl)-4H-thieno[3,2-b]pyrrole-5-carboxylate (JRW-0316)

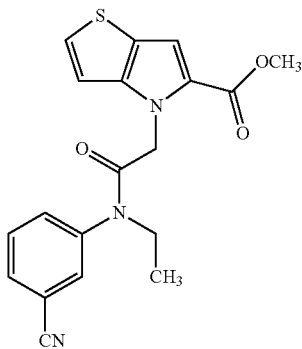 [SMILES: CCN(C(=O)Cn1c(C(=O)OC)cc2sccc21)c1cccc(C#N)c1]

To a solution of methyl 4H-thieno[3,2-b]pyrrole-5-carboxylate (68 mg, 0.37 mmol) in acetonitrile (5 mL), potassium carbonate (62 mg, 0.45 mmol), 18-crown-6 ether (5 mg, 0.019 mmol), and 2-chloro-N-(3-cyanophenyl)-N-ethylacetamide (98 mg, 0.45 mmol) was added. The suspension was heated to 75° C. for 18 h. The mixture was diluted with ethyl acetate and water, and the layers were separated. The organic layer was dried over anhydrous sodium sulfate and filtered. The filtrate was then concentrated. The residue was purified by column chromatography (silica, heptane/ethyl acetate) to afford the desired product (94 mg, 68%) as a white foam. $^1$H NMR (300 MHz, CDCl$_3$) δ 7.71-7.62 (m, 1H), 7.61-7.49 (m, 3H), 7.33 (d, J=5.4, 1H), 7.12 (s, 1H), 6.82 (d, J=5.4, 1H), 4.98 (s, 2H), 3.87-3.70 (m, 5H), 1.14 (t, J=7.1, 3H); ESI MS m/z 368 [M+H]$^+$.

Step 3. 4-(2-((3-cyanophenyl)(ethyl)amino)-2-oxoethyl)-4H-thieno[3,2-b]pyrrole-5-carboxylic acid (JRW-0319-1) and 4-(2-((3-carbamoylphenyl)(ethyl)amino)-2-oxoethyl)-4H-thieno[3,2-b]pyrrole-5-carboxylic acid (JRW-0319-2)

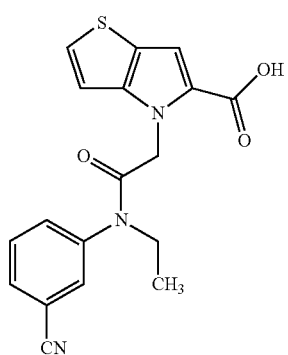

-continued

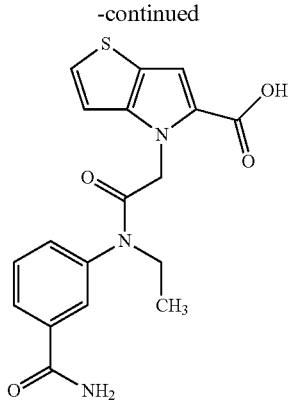

Following general procedure A, methyl 4-(2-((3-cyanophenyl)(ethyl)amino)-2-oxoethyl)-4H-thieno[3,2-b]pyrrole-5-carboxylate (90 mg, 0.24 mmol) was reacted with lithium hydroxide (12 mg, 0.49 mmol). The two products were separated by column chromatography (silica, dichloromethane/methanol) to afford the nitrile (61 mg) and the amide (31 mg) as white solids. ESI MS m/z 354 [M+H]$^+$ and m/z 372 [M+H]$^+$.

Step 4. Methyl trans-4-(4-(24(3-cyanophenyl)(ethyl)amino)-2-oxoethyl)-4H-thieno[3,2-b]pyrrole-5-carboxamido)cyclohexane-1-carboxylate (JRW-0321)

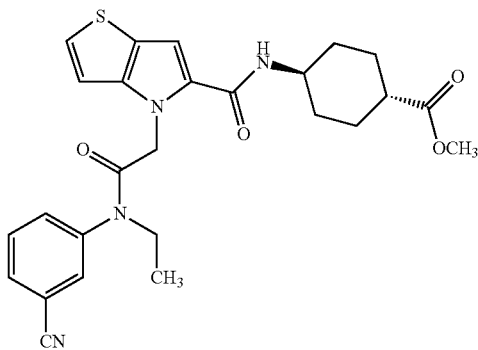 [SMILES: CCN(C(=O)Cn1c(C(=O)N[C@H]2CC[C@H](C(=O)OC)CC2)cc2sccc21)c1cccc(C#N)c1]

Following general procedure B, 4-(2-((3-cyanophenyl)(ethyl)amino)-2-oxoethyl)-4H-thieno[3,2-b]pyrrole-5-carboxylic acid (60 mg, 0.17 mmol) was reacted with methyl trans-4-aminocyclohexane-1-carboxylate (56 mg, 0.29 mmol) to afford the desired product (68 mg, 81%) as a white foam. $^1$H NMR (300 MHz, DMSO-$d_6$) δ 8.02-7.59 (m, 5H), 7.38 (d, J=5.3, 1H), 7.17-7.03 (m, 2H), 5.02 (s, 2H), 3.77-3.55 (m, 6H), 2.32-2.18 (m, 1H), 1.99-1.79 (m, 4H), 1.54-1.20 (m, 4H), 1.10-0.95 (m, 3H); ESI MS m/z 493 [M+H]$^+$; HPLC 98.3% (AUC), T$_R$ 6.12 min; UV (EtOH) λ$_{max}$ 289 nm, ε 26,802.

Example 61

Methyl trans-4-(4-(2-((3-carbamoylphenyl)(ethyl)amino)-2-oxoethyl)-4H-thieno[3,2-b]pyrrole-5-carboxamido)cyclohexane-1-carboxylate (JRW-0322)

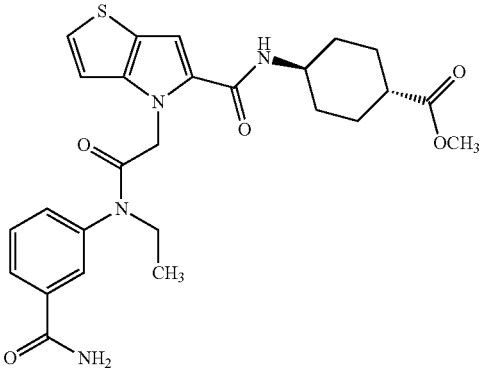 [SMILES: CCN(C(=O)Cn1c(C(=O)N[C@H]2CC[C@H](C(=O)OC)CC2)cc2sccc21)c1cccc(C(N)=O)c1]

Following general procedure B, 4-(2-((3-carbamoylphenyl)(ethyl)amino)-2-oxoethyl)-4H-thieno[3,2-b]pyrrole-5-carboxylic acid (30 mg, 0.08 mmol) was reacted with methyl trans-4-aminocyclohexane-1-carboxylate (19 mg, 0.10 mmol) to afford the desired product (33 mg, 80%) as a white foam. $^1$H NMR (300 MHz, DMSO-$d_6$) δ 8.05 (s, 1H), 7.97-7.83 (m, 3H), 7.72-7.43 (m, 3H), 7.37 (d, J=5.4, 1H), 7.12-7.05 (m, 2H), 4.98 (s, 2H), 3.75-3.54 (m, 6H), 2.32-2.18 (m, 1H), 1.99-1.79 (m, 4H), 1.53-1.22 (m, 4H), 1.10-0.95 (m, 3H); ESI MS m/z 511 [M+H]$^+$; HPLC 98.2% (AUC), T$_R$ 4.81 min; UV (EtOH) λ$_{max}$ 289 nm, ε 28,223.

Example 62

Methyl trans-4-(4-(2-(ethyl(3-ethylphenyl)amino)-2-oxoethyl)-4H-thieno[3,2-b]pyrrole-5-carboxamido)cyclohexane-1-carboxylate (JRW-0326)

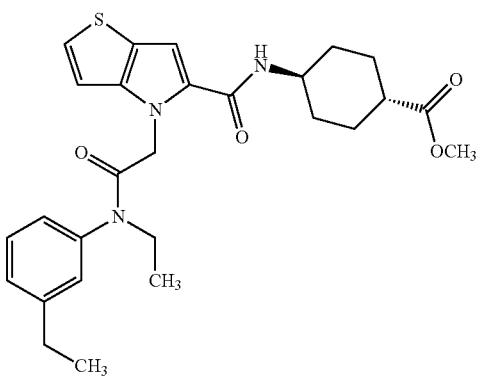 [SMILES: CCc1cccc(N(CC)C(=O)Cn2c(C(=O)N[C@H]3CC[C@H](C(=O)OC)CC3)cc3sccc32)c1]

Step 1. Methyl 4-(2-(ethyl(3-ethylphenyl)amino)-2-oxoethyl)-4H-thieno[3,2-b]pyrrole-5-carboxylate (JRW-0298)

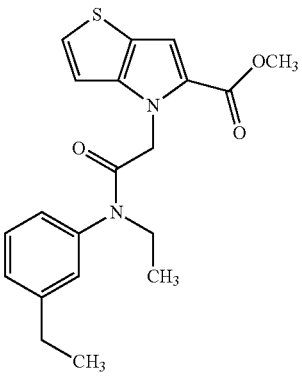 [SMILES: CCc1cccc(N(CC)C(=O)Cn2c(C(=O)OC)cc3sccc32)c1]

To a solution of 2-(5-(methoxycarbonyl)-4H-thieno[3,2-b]pyrrol-4-yl)acetic acid (100 mg, 0.42 mmol) in DMF (3 mL), N,3-diethylaniline (94 mg, 0.63 mmol), HATU (318 mg, 0.84 mmol), and diisopropylethylamine (162 mg, 1.25 mmol) was added. The reaction was heated to 85° C. for 18 h. The reaction mixture cooled, diluted with ethyl acetate, and washed with water. The organic layer was dried over anhydrous sodium sulfate and filtered. The filtrate was then concentrated. The residue was purified by column chromatography (silica, heptane/ethyl acetate) to afford the desired product (107 mg, 69%) as an orange foam. $^1$H NMR (300 MHz, CDCl$_3$) δ 7.38 (t, J=7.9, 1H), 7.31-7.20 (m, 2H), 7.17-7.10 (m, 3H), 6.81 (d, J=5.4, 1H), 4.98 (s, 2H), 3.84-3.67 (m, 5H), 2.71 (q, J=7.6, 2H), 1.29 (t, J=7.6, 3H), 1.13 (t, J=7.2, 3H); ESI MS m/z 371 [M+H]$^+$.

Step 2. 4-(2-(ethyl(3-ethylphenyl)amino)-2-oxoethyl)-4H-thieno[3,2-b]pyrrole-5-carboxylic acid (JRW-0323)

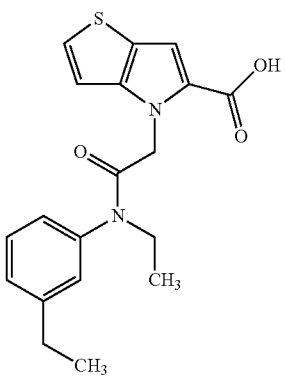 [SMILES: CCc1cccc(N(CC)C(=O)Cn2c(C(=O)O)cc3sccc32)c1]

Following general procedure A, methyl 4-(2-(ethyl(3-ethylphenyl)amino)-2-oxoethyl)-4H-thieno[3,2-b]pyrrole-5-carboxylate (100 mg, 0.27 mmol) was reacted with lithium hydroxide (19 mg, 0.81 mmol) to afford crude product (100 mg) as a light yellow solid. ESI MS m/z 357 [M+H]$^+$.

Step 3. Methyl trans-4-(4-(2-(ethyl(3-ethylphenyl)amino)-2-oxoethyl)-4H-thieno[3,2-b]pyrrole-5-carboxamido)cyclohexane-1-carboxylate (JRW-0326)

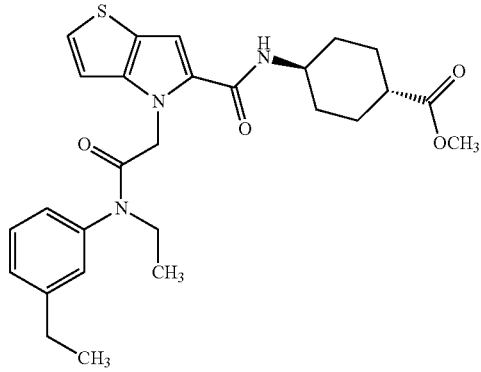

Following general procedure B, 4-(2-(ethyl(3-ethylphenyl)amino)-2-oxoethyl)-4H-thieno[3,2-b]pyrrole-5-carboxylic acid (100 mg, 0.28 mmol) was reacted with methyl trans-4-aminocyclohexane-1-carboxylate (65 mg, 0.34 mmol) to afford the desired product (105 mg, 75%) as a white foam. $^1$H NMR (300 MHz, DMSO-d$_6$) δ 7.90 (d, J=7.9, 1H), 7.51-7.19 (m, 5H), 7.13-7.04 (m, 2H), 4.95 (s, 2H), 3.74-3.54 (m, 5H), 2.73-2.61 (m, 2H), 2.32-2.18 (m, 1H), 2.01-1.78 (m, 4H), 1.51-1.14 (m, 7H), 1.08-0.95 (s, 3H); ESI MS m/z 496 [M+H]$^+$; HPLC 97.6% (AUC), T$_R$ 7.37 min; UV (MeOH) λ$_{max}$ 288 nm, ε 27,343.

Example 63

4-(2-(Ethyl(3-ethylphenyl)amino)-2-oxoethyl)-N-(trans-4-((6-hydroxyhexyl)carbamoyl)cyclohexyl)-4H-thieno[3,2-b]pyrrole-5-carboxamide (JRW-0429)

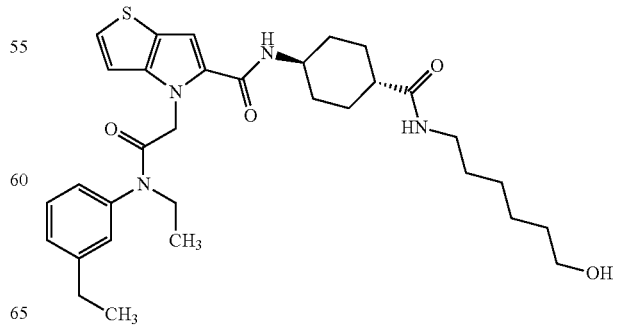

Step 1. Trans-4-(4-(2-(ethyl(3-ethylphenyl)amino)-2-oxoethyl)-4H-thieno[3,2-b]pyrrole-5-carboxamido)cyclohexane-1-carboxylic acid (JRW-0427)

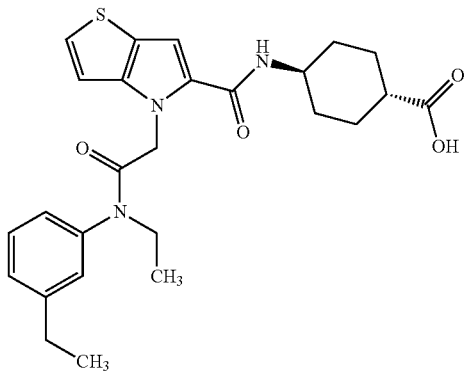 [SMILES: CCc1cccc(N(CC)C(=O)Cn2c(C(=O)N[C@H]3CC[C@H](C(=O)O)CC3)cc3sccc32)c1]

Following general procedure A, methyl trans-4-(4-(2-(ethyl(3-ethylphenyl)amino)-2-oxoethyl)-4H-thieno[3,2-b]pyrrole-5-carboxamido)cyclohexane-1-carboxylate (980 mg, 1.98 mmol) was reacted with lithium hydroxide (142 mg, 5.93 mmol) to afford crude product (1.0 g) as a light yellow solid. ESI MS m/z 482 [M+H]$^+$.

Step 2. 4-(2-(Ethyl(3-ethylphenyl)amino)-2-oxoethyl)-N-(trans-4-((6-hydroxyhexyl)carbamoyl)cyclohexyl)-4H-thieno[3,2-b]pyrrole-5-carboxamide (JRW-0429)

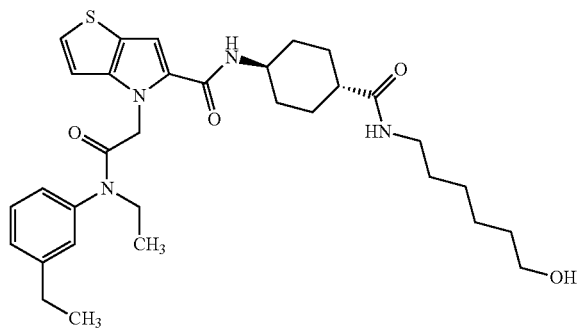 [SMILES: CCc1cccc(N(CC)C(=O)Cn2c(C(=O)N[C@H]3CC[C@H](C(=O)NCCCCCCO)CC3)cc3sccc32)c1]

Following general procedure B, trans-4-(4-(2-(ethyl(3-ethylphenyl)amino)-2-oxoethyl)-4H-thieno[3,2-b]pyrrole-5-carboxamido)cyclohexane-1-carboxylic acid (200 mg, 0.42 mmol) was reacted with 6-aminohexan-1-ol (73 mg, 0.62 mmol) to afford the desired product (200 mg, 83%) as a light yellow foam. $^1$H NMR (300 MHz, DMSO-d$_6$) δ 7.85 (d, J=8.0, 1H), 7.63 (t, J=5.6, 1H), 7.46-7.18 (m, 5H), 7.11-7.04 (m, 2H), 4.96 (s, 2H), 4.27 (t, J=5.2, 1H), 3.72-3.55 (m, 3H), 3.40-3.32 (m, 2H), 3.05-2.95 (m, 2H), 2.72-2.62 (m, 2H), 2.10-1.97 (m, 1H), 1.89-1.68 (m, 4H), 1.53-1.14 (m, 15H), 1.01 (t, J=6.9, 3H); ESI MS m/z 581 [M+H]$^+$; HPLC >99% (AUC), T$_R$ 5.85 min; UV (MeOH) λ$_{max}$ 288 nm, ε 25,165.

Example 64

Sodium 6-(trans-4-(4-(2-(ethyl(3-ethylphenyl)amino)-2-oxoethyl)-4H-thieno[3,2-b]pyrrole-5-carboxamido)cyclohexane-1-carboxamido)hexane-1-sulfonate (JRW-0432)

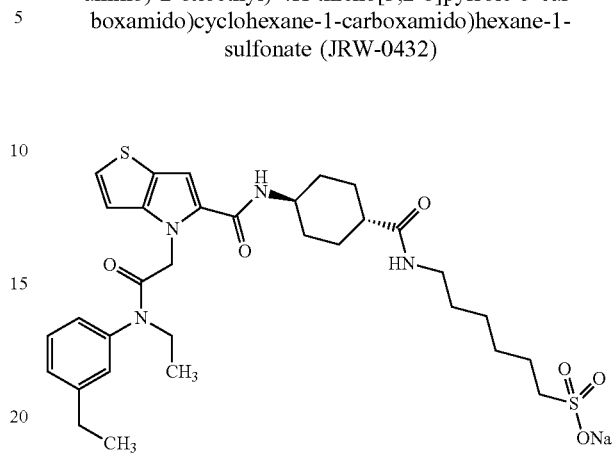

Step 1. 4-(2-(Ethyl(3-ethylphenyl)amino)-2-oxoethyl)-N-(trans-4-((6-iodohexyl)carbamoyl)cyclohexyl)-4H-thieno[3,2-b]pyrrole-5-carboxamide (JRW-0431)

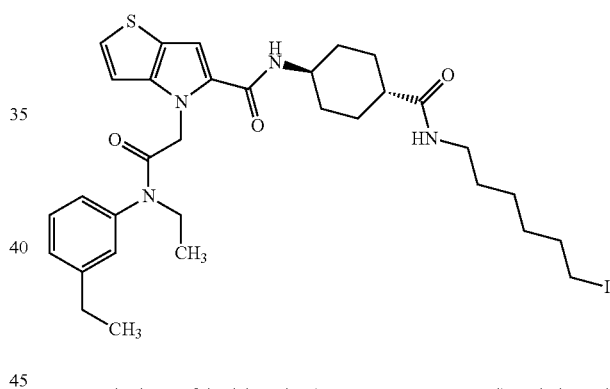

A solution of imidazole (60 mg, 0.88 mmol), triphenylphosphine (230 mg, 0.88 mmol), and iodine (223 mg, 0.88 mmol) in THF (10 mL) stirred at RT for 10 min. 4-(2-(Ethyl (3-ethylphenyl)amino)-2-oxoethyl)-N-(trans-4-((6-hydroxyhexyl)carbamoyl)cyclohexyl)-4H-thieno[3,2-b]pyrrole-5-carboxamide (170 mg, 0.29 mmol) dissolved in THF (5 mL) was added. The solution was stirred for 1 h at RT. The reaction was diluted with ethyl acetate and quenched with a 10% Na$_2$S$_2$O$_3$ solution. The mixture was diluted with ethyl acetate and water, and the layers separated. The organic layer was washed with a 10% Na$_2$S$_2$O$_3$ solution, and the brine dried over anhydrous sodium sulfate and filtered. The filtrate was then concentrated. The residue was partially purified by column chromatography (silica, dichloromethane/methanol) to afford crude product as a white solid. ESI MS m/z 691 [M+H]$^+$.

Step 2. Sodium 6-(trans-4-(4-(2-(ethyl(3-ethylphenyl)amino)-2-oxoethyl)-4H-thieno[3,2-b]pyrrole-5-carboxamido)cyclohexane-1-carboxamido)hexane-1-sulfonate (JRW-0432)

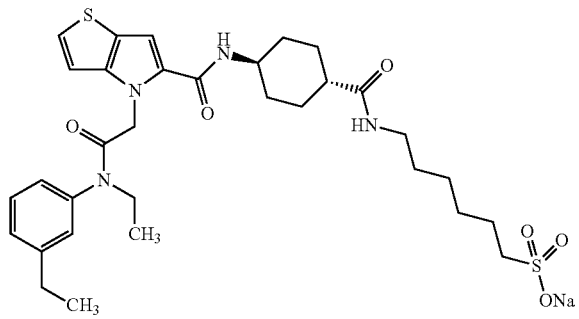

To a solution of 4-(2-(ethyl(3-ethylphenyl)amino)-2-oxoethyl)-N-(trans-4-(6-iodohexyl)carbamoyl)cyclohexyl)-4H-thieno[3,2-b]pyrrole-5-carboxamide (0.29 mmol) in ethanol (10 mL), sodium sulfite (184 mg, 1.46 mmol) and water (10 mL) was added. The mixture was heated to 75° C. for 3.5 h. The reaction was concentrated, and the residue was purified by column chromatography (silica, dichloromethane/methanol) to afford the desired product (205 mg, quant) as a white solid. $^1$H NMR (300 MHz, DMSO-d$_6$) δ 7.88 (d, J=8.3, 1H), 7.68 (t, J=5.4, 1H), 7.48-7.19 (m, 5H), 7.12-7.04 (m, 2H), 4.95 (s, 2H), 3.71-3.55 (m, 3H), 3.04-2.94 (m, 2H), 2.74-2.61 (m, 2H), 2.40-2.32 (m, 2H), 2.11-1.97 (m, 1H), 1.88-1.68 (m, 4H), 1.62-1.14 (m, 15H), 1.00 (t, J=6.7, 3H); ESI MS m/z 645 [M+H]$^+$; HPLC >99% (AUC), T$_R$ 5.07 min; UV (MeOH) λ$_{max}$ 288 nm, ε 18,276.

Example 65

Methyl trans-4-(4-(2-(ethyl(3-methoxyphenyl)amino)-2-oxoethyl)-4H-thieno[3,2-b]pyrrole-5-carboxamido)cyclohexane-1-carboxylate (JRW-0327)

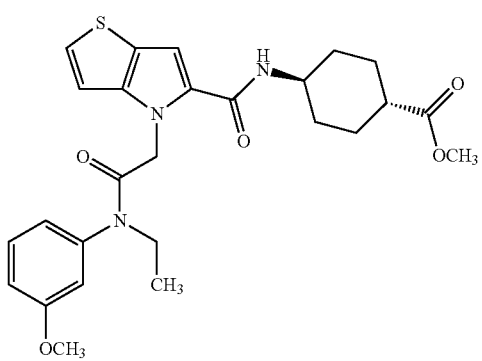

Step 1. Methyl 4-(2-(ethyl(3-methoxyphenyl)amino)-2-oxoethyl)-4H-thieno[3,2-b]pyrrole-5-carboxylate (JRW-0299)

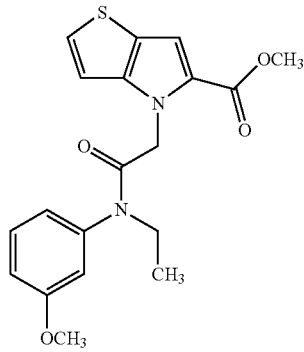

To a solution of 2-(5-(methoxycarbonyl)-4H-thieno[3,2-b]pyrrol-4-yl)acetic acid (100 mg, 0.42 mmol) in DMF (3 mL), N-ethyl-3-methoxyaniline (94 mg, 0.63 mmol), HATU (318 mg, 0.84 mmol), and diisopropylethylamine (162 mg, 1.25 mmol) was added. The reaction was heated to 85° C. for 18 h. The reaction mixture cooled, diluted with ethyl acetate, and washed with water. The organic layer was dried over anhydrous sodium sulfate and filtered. The filtrate was then concentrated. The residue was purified by column chromatography (silica, heptane/ethyl acetate) to afford the desired product (97 mg, 62%) as an orange foam. $^1$H NMR (300 MHz, CDCl$_3$) δ 7.37 (t, J=8.0, 1H), 7.29 (d, J=5.4, 1H), 7.15 (s, 1H), 6.99-6.84 (m, 3H), 6.81 (d, J=5.4, 1H), 5.02 (s, 2H), 3.86 (s, 3H), 3.83-3.69 (m, 5H), 1.14 (t, J=7.2, 3H); ESI MS m/z 373 [M+H]$^+$.

Step 2. 4-(2-(ethyl(3-methoxyphenyl)amino)-2-oxoethyl)-4H-thieno[3,2-b]pyrrole-5-carboxylic acid (JRW-0324)

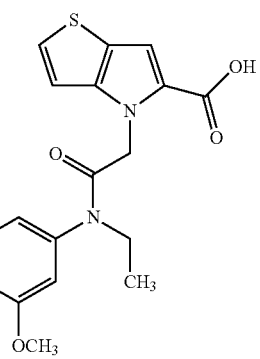

Following general procedure A, methyl 4-(2-(ethyl(3-methoxyphenyl)amino)-2-oxoethyl)-4H-thieno[3,2-b]pyrrole-5-carboxylate (95 mg, 0.26 mmol) was reacted with lithium hydroxide (18 mg, 0.77 mmol) to afford crude product (88 mg) as a light yellow solid. ESI MS m/z 359 [M+H]$^+$.

Step 3. Methyl trans-4-(4-(2-(ethyl(3-methoxyphenyl)amino)-2-oxoethyl)-4H-thieno[3,2-b]pyrrole-5-carboxamido)cyclohexane-1-carboxylate (JRW-0327)

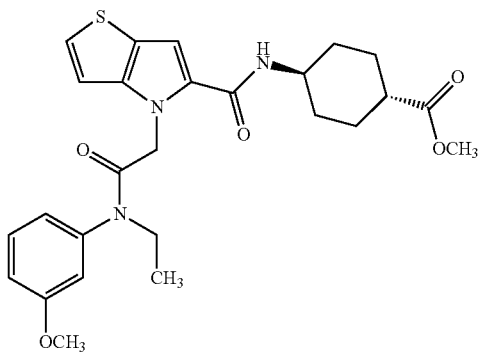 [SMILES: CCN(C(=O)Cn1c(C(=O)N[C@H]2CC[C@H](C(=O)OC)CC2)cc2sccc21)c1cccc(OC)c1]

Following general procedure B, 4-(2-(ethyl(3-methoxyphenyl)amino)-2-oxoethyl)-4H-thieno[3,2-b]pyrrole-5-carboxylic acid (88 mg, 0.25 mmol) was reacted with methyl trans-4-aminocyclohexane-1-carboxylate (48 mg, 0.34 mmol) to afford the desired product (78 mg, 63%) as a white solid. $^1$H NMR (300 MHz, DMSO-$d_6$) δ 7.90 (d, J=8.3, 1H), 7.50-7.31 (m, 2H), 7.16-6.91 (m, 5H), 5.00 (s, 2H), 3.81 (s, 3H), 3.75-3.53 (m, 6H), 2.33-2.18 (m, 1H), 2.01-1.77 (m, 4H), 1.50-1.22 (m, 4H), 1.08-0.95 (m, 3H); ESI MS m/z 498 [M+H]$^+$; HPLC 96.4% (AUC), $T_R$ 6.69 min; UV (MeOH) $\lambda_{max}$ 289 nm, ε 28,671

Example 66

Methyl trans-4-(4-(2-(ethyl(o-tolyl)amino)-2-oxoethyl)-4H-thieno[3,2-b]pyrrole-5-carboxamido)cyclohexane-1-carboxylate (JRW-0330)

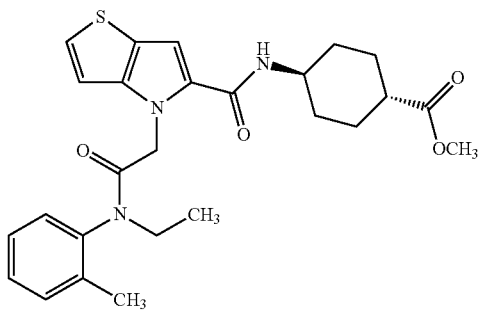

Step 1. Methyl 4-(2-(ethyl(o-tolyl)amino)-2-oxoethyl)-4H-thieno[3,2-b]pyrrole-5-carboxylate (JRW-0300)

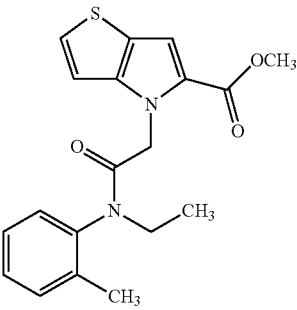 [SMILES: CCN(C(=O)Cn1c(C(=O)OC)cc2sccc21)c1ccccc1C]

To a solution of 2-(5-(methoxycarbonyl)-4H-thieno[3,2-b]pyrrol-4-yl)acetic acid (100 mg, 0.42 mmol) in DMF (3 mL), N-ethyl-2-methylaniline (84 mg, 0.63 mmol), HATU (318 mg, 0.84 mmol), and diisopropylethylamine (162 mg, 1.25 mmol) was added. The reaction was heated to 85° C. for 18 h. The reaction mixture cooled, diluted with ethyl acetate, and washed with water. The organic layer was dried over anhydrous sodium sulfate and filtered. The filtrate was then concentrated. The residue was purified by column chromatography (silica, heptane/ethyl acetate) to afford the desired product (72 mg, 48%) as a white foam. $^1$H NMR (300 MHz, CDCl$_3$) δ 7.43-7.21 (m, 5H), 7.16 (s, 1H), 6.78 (d, J=5.4, 1H), 5.02 (d, J=16.9, 1H), 4.74 (d, J=16.9, 1H), 4.15 (dq, J=7.1, 14.2, 1H), 3.81 (s, 3H), 3.24 (dq, J=7.1, 14.2, 1H), 1.14 (t, J=7.1, 4H); ESI MS m/z 357 [M+H]$^+$.

Step 2. 4-(2-(ethyl(o-tolyl)amino)-2-oxoethyl)-4H-thieno[3,2-b]pyrrole-5-carboxylic acid (JRW-0328)

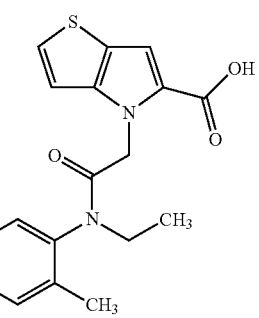

Following general procedure A, methyl 4-(2-(ethyl(o-tolyl)amino)-2-oxoethyl)-4H-thieno[3,2-b]pyrrole-5-carboxylate (70 mg, 0.20 mmol) was reacted with lithium hydroxide (23 mg, 0.98 mmol) to afford crude product (69 mg) as a light yellow solid. ESI MS m/z 343 [M+H]$^+$.

Step 3. methyl trans-4-(4-(2-(ethyl(o-tolyl)amino)-2-oxoethyl)-4H-thieno[3,2-b]pyrrole-5-carboxamido)cyclohexane-1-carboxylate (JRW-0330)

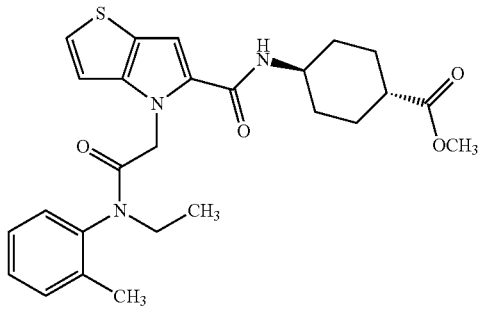 [SMILES: CCN(C(=O)Cn1c(C(=O)N[C@H]2CC[C@H](C(=O)OC)CC2)cc2sccc21)c1ccccc1C]

Following general procedure B, 4-(2-(ethyl(o-tolyl)amino)-2-oxoethyl)-4H-thieno[3,2-b]pyrrole-5-carboxylic acid (69 mg, 0.25 mmol) was reacted with methyl trans-4-aminocyclohexane-1-carboxylate (46 mg, 0.24 mmol) to afford the desired product (77 mg, 79%) as a white foam. $^1$H NMR (300 MHz, DMSO-$d_6$) δ 7.91 (d, J=7.9, 1H), 7.49-7.29 (m, 5H), 7.11-6.98 (m, 2H), 4.91 (d, J=16.7, 1H), 4.79 (d, J=16.7, 1H), 4.06-3.90 (m, 1H), 3.72-3.53 (m, 4H), 3.14-2.99 (m, 1H), 2.34 (s, 3H), 2.31-2.18 (m, 1H), 2.00-1.78 (m, 4H), 1.51-1.14 (m, 4H), 0.99 (t, J=7.1, 3H); ESI MS m/z 482 [M+H]$^+$; HPLC 92.3% (AUC), T$_R$ 6.97 min; UV (MeOH) λ$_{max}$ 288 nm, ε 29,468

Example 67

Methyl trans-4-(4-(2-(6-methyl-3,4-dihydroquinolin-1(2H)-yl)-2-oxoethyl)-4H-thieno[3,2-b]pyrrole-5-carboxamido)cyclohexane-1-carboxylate (JRW-0331)

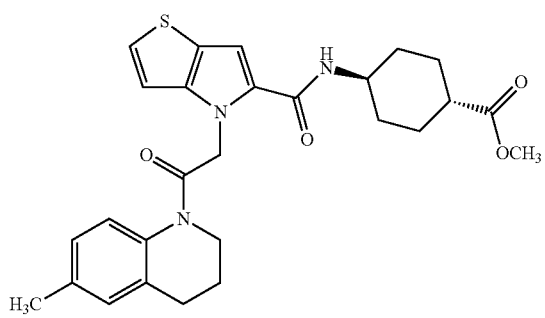 [SMILES: COC(=O)[C@H]1CC[C@H](NC(=O)c2cc3sccc3n2CC(=O)N2CCCc3cc(C)ccc32)CC1]

Step 1. Methyl 4-(2-(6-methyl-3,4-dihydroquinolin-1(2H)-yl)-2-oxoethyl)-4H-thieno[3,2-b]pyrrole-5-carboxylate (JRW-0301)

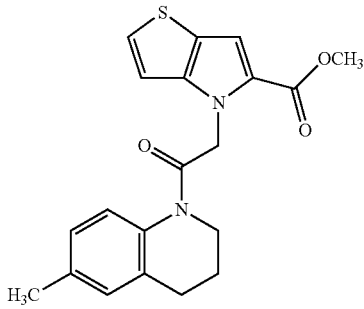 [SMILES: COC(=O)c1cc2sccc2n1CC(=O)N1CCCc2cc(C)ccc21]

To a solution of 2-(5-(methoxycarbonyl)-4H-thieno[3,2-b]pyrrol-4-yl)acetic acid (100 mg, 0.42 mmol) in DMF (3 mL), 6-methyl-1,2,3,4-tetrahydroquinoline (92 mg, 0.63 mmol), HATU (318 mg, 0.84 mmol), and diisopropylethylamine (162 mg, 1.25 mmol) was added. The reaction was heated to 85° C. for 18 h. The reaction mixture cooled, diluted with ethyl acetate, and washed with water. The organic layer was dried over anhydrous sodium sulfate and filtered. The filtrate was then concentrated. The residue was purified by column chromatography (silica, heptane/ethyl acetate) to afford the desired product (140 mg, 90%) as a white foam. $^1$H NMR (300 MHz, CDCl$_3$) δ 7.31 (d, J=5.4, 1H), 7.18 (s, 1H), 7.08-6.96 (m, 3H), 6.82 (d, J=5.4, 1H), 5.39 (s, 2H), 3.86-3.74 (m, 5H), 2.82-2.66 (m, 2H), 2.31 (s, 3H), 2.05-1.89 (m, 2H); ESI MS m/z 367 [M+H]$^+$.

Step 2. 4-(2-(6-methyl-3,4-dihydroquinolin-1(2H)-yl)-2-oxoethyl)-4H-thieno[3,2-b]pyrrole-5-carboxylic acid (JRW-0329)

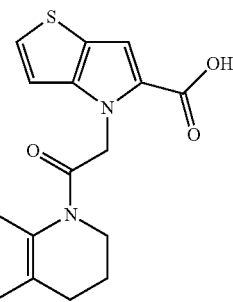

Following general procedure A, methyl 4-(2-(6-methyl-3,4-dihydroquinolin-1(2H)-yl)-2-oxoethyl)-4H-thieno[3,2-b]pyrrole-5-carboxylate (130 mg, 0.35 mmol) was reacted with lithium hydroxide (42 mg, 1.76 mmol) to afford crude product (120 mg) as an orange solid. ESI MS m/z 355 [M+H]$^+$.

Step 3. Methyl trans-4-(4-(2-(6-methyl-3,4-dihydroquinolin-1(2H)-yl)-2-oxoethyl)-4H-thieno[3,2-b]pyrrole-5-carboxamido)cyclohexane-1-carboxylate (JRW-0331)

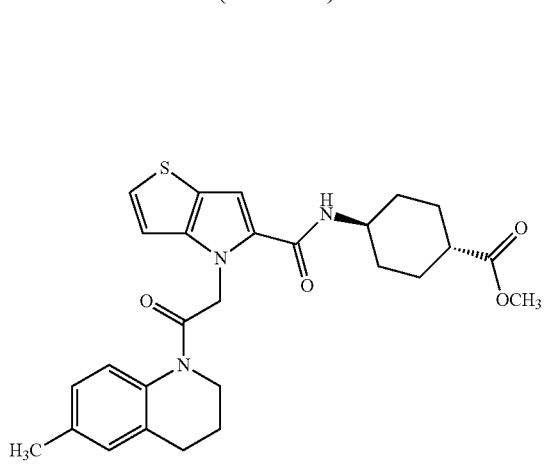

Following general procedure B, 4-(2-(6-methyl-3,4-dihydroquinolin-1(2H)-yl)-2-oxoethyl)-4H-thieno[3,2-b]pyrrole-5-carboxylic acid (140 mg, 0.40 mmol) was reacted with methyl trans-4-aminocyclohexane-1-carboxylate (92 mg, 0.47 mmol) to afford the desired product (130 mg, 67%) as a white solid. $^1$H NMR (300 MHz, DMSO-$d_6$) δ 7.89 (d, J=7.7, 1H), 7.47 (d, J=7.7, 1H), 7.39 (d, J=5.3, 1H), 7.19 (d, J=5.3, 1H), 7.12 (s, 1H), 7.08-6.88 (m, 2H), 5.44 (s, 2H), 3.73-3.53 (m, 6H), 2.72 (t, J=6.6, 2H), 2.33-2.16 (m, 4H), 2.00-1.74 (m, 6H), 1.50-1.20 (m, 4H); ESI MS m/z 494 [M+H]$^+$; HPLC 98.9% (AUC), $T_R$ 7.16 min; UV (MeOH) $\lambda_{max}$ 287 nm, ε 26,027.

Example 68

Methyl trans-4-(4-(2-(ethyl(p-tolyl)amino)-2-oxoethyl)-4H-thieno[3,2-b]pyrrole-5-carboxamido)cyclohexane-1-carboxylate (JRW-0334)

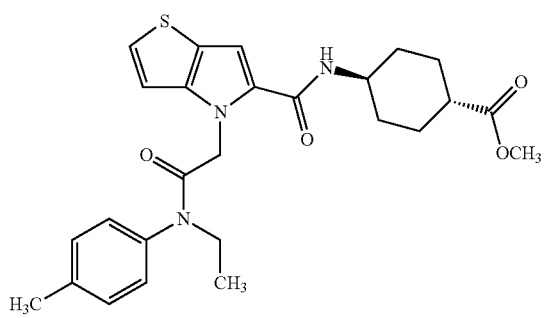 [SMILES: CCN(C(=O)Cn1c(C(=O)N[C@H]2CC[C@H](C(=O)OC)CC2)cc2sccc21)c1ccc(C)cc1]

Step 1. Methyl 4-(2-(ethyl(p-tolyl)amino)-2-oxoethyl)-4H-thieno[3,2-b]pyrrole-5-carboxylate (JRW-0314)

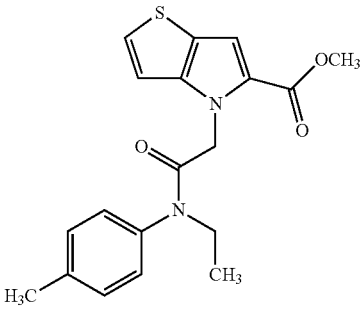 [SMILES: CCN(C(=O)Cn1c(C(=O)OC)cc2sccc21)c1ccc(C)cc1]

To a solution of 2-(5-(methoxycarbonyl)-4H-thieno[3,2-b]pyrrol-4-yl)acetic acid (100 mg, 0.42 mmol) in DMF (3 mL), N-ethyl-4-methylaniline (68 mg, 0.50 mmol), HATU (318 mg, 0.84 mmol), and diisopropylethylamine (162 mg, 1.25 mmol) was added. The reaction was heated to 85° C. for 18 h. The reaction mixture cooled, diluted with ethyl acetate, and washed with water. The organic layer was dried over anhydrous sodium sulfate and filtered. The filtrate was then concentrated. The residue was purified by column chromatography (silica, heptane/ethyl acetate) to afford the desired product (120 mg, 80%) as a white foam. $^1$H NMR (300 MHz, CDCl$_3$) δ 7.33-7.18 (m, 5H), 7.16 (s, 1H), 6.80 (d, J=5.4, 1H), 4.95 (s, 2H), 3.84 (s, 3H), 3.74 (q, J=7.2, 3H), 2.40 (s, 3H), 1.12 (t, J=7.2, 3H); ESI MS m/z 357 [M+H]$^+$.

Step 2. 4-(2-(ethyl(p-tolyl)amino)-2-oxoethyl)-4H-thieno[3,2-b]pyrrole-5-carboxylic acid (JRW-0332)

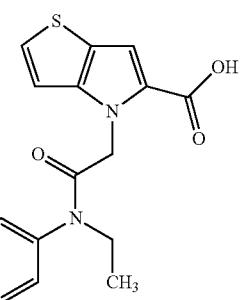

Following general procedure A, methyl 4-(2-(ethyl(p-tolyl)amino)-2-oxoethyl)-4H-thieno[3,2-b]pyrrole-5-carboxylate (120 mg, 0.34 mmol) was reacted with lithium hydroxide (40 mg, 1.68 mmol) to afford crude product (109 mg) as a white solid. ESI MS m/z 343 [M+H]$^+$.

Step 3. methyl trans-4-(4-(2-(ethyl(p-tolyl)amino)-2-oxoethyl)-4H-thieno[3,2-b]pyrrole-5-carboxamido)cyclohexane-1-carboxylate (JRW-0334)

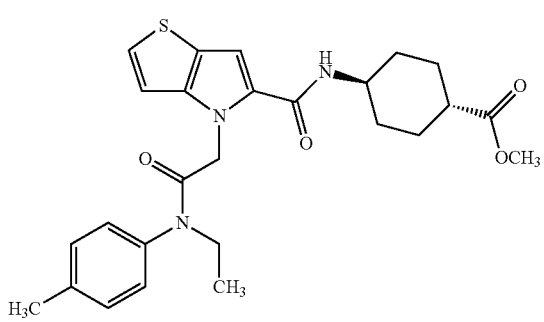 [SMILES: CCN(C(=O)Cn1c(C(=O)N[C@H]2CC[C@H](C(=O)OC)CC2)cc2sccc21)c1ccc(C)cc1]

Following general procedure B, 4-(2-(ethyl(p-tolyl)amino)-2-oxoethyl)-4H-thieno[3,2-b]pyrrole-5-carboxylic acid (109 mg, 0.32 mmol) was reacted with methyl trans-4-aminocyclohexane-1-carboxylate (74 mg, 0.38 mmol) to afford the desired product (131 mg, 85%) as a white foam. $^1$H NMR (300 MHz, DMSO-$d_6$) δ 7.88 (d, J=7.9, 1H), 7.41-7.25 (m, 5H), 7.12-7.03 (m, 2H), 4.95 (s, 2H), 3.72-3.48 (s, 6H), 2.35 (s, 3H), 2.31-2.19 (s, 1H), 2.01-1.77 (m, 4H), 1.52-1.19 (m, 4H), 1.05-0.94 (m, 3H); ESI MS m/z 482 [M+H]$^+$; HPLC 98.0% (AUC), $T_R$ 7.04 min; UV (MeOH) $\lambda_{max}$ 289 nm, ε 27,490.

Example 69

Methyl trans-4-(4-(2-(ethyl(4-(hydroxymethyl)phenyl)amino)-2-oxoethyl)-4H-thieno[3,2-b]pyrrole-5-carboxamido)cyclohexane-1-carboxylate (JRW-0335)

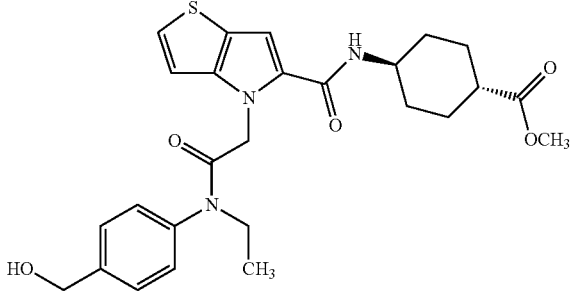 [SMILES: CCN(C(=O)Cn1c(C(=O)N[C@H]2CC[C@H](C(=O)OC)CC2)cc2sccc21)c1ccc(CO)cc1]

Step 1. Methyl 4-(2-((4-(((tert-utyldimethylsilyl)oxy)methyl)phenyl)(ethyl)amino)-2-oxoethyl)-4H-thieno[3,2-b]pyrrole-5-carboxylate (JRW-0320)

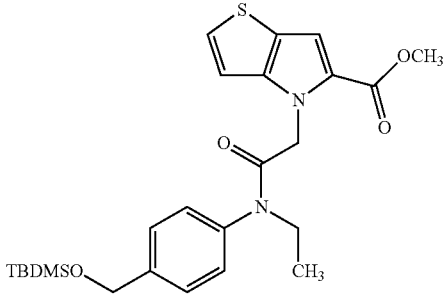 [SMILES: CCN(C(=O)Cn1c(C(=O)OC)cc2sccc21)c1ccc(CO[Si](C)(C)C(C)(C)C)cc1]

To a solution of 2-(5-(methoxycarbonyl)-4H-thieno[3,2-b]pyrrol-4-yl)acetic acid (150 mg, 0.63 mmol) in DMF (3 mL), 4-(((tert-butyldimethylsilyl)oxy)methyl)-N-ethylaniline (166 mg, 0.63 mmol), HATU (477 mg, 1.25 mmol), and diisopropylethylamine (243 mg, 1.88 mmol) was added. The reaction was heated to 85° C. for 30 min. The reaction mixture cooled, diluted with ethyl acetate, and washed with water. The organic layer was dried over anhydrous sodium sulfate and filtered. The filtrate was then concentrated. The residue was purified by column chromatography (silica, heptane/ethyl acetate) to afford the desired product (165 mg, 54%) as a light yellow foam. $^1$H NMR (300 MHz, CDCl$_3$) δ 7.31 (d, J=8.1, 2H), 7.23-7.11 (m, 3H), 7.03 (s, 1H), 6.66 (d, J=5.3, 1H), 4.82 (s, 2H), 4.66 (s, 2H), 3.73-3.55 (m, 5H), 0.99 (t, J=7.2, 3H), 0.83 (s, 9H), 0.00 (s, 6H); ESI MS m/z 487 [M+H]$^+$.

Step 2. 4-(2-(ethyl(4-(hydroxymethyl)phenyl)amino)-2-oxoethyl)-4H-thieno[3,2-b]pyrrole-5-carboxylic acid (JRW-0333)

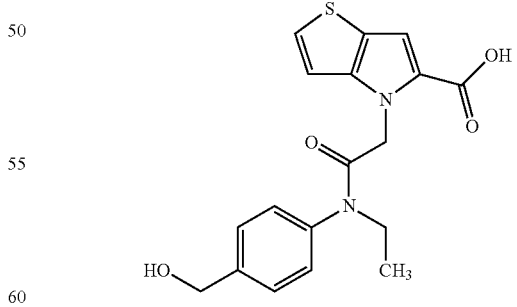

Following general procedure A, methyl 4-(2-((4-(((tert-butyldimethylsilyl)oxy)methyl)phenyl)(ethyl)amino)-2-oxoethyl)-4H-thieno[3,2-b]pyrrole-5-carboxylate (165 mg, 0.34 mmol) was reacted with lithium hydroxide (40 mg, 1.68 mmol) to afford crude product (110 mg) as a white solid. ESI MS m/z 359 [M+H]$^+$.

Step 3. Methyl trans-4-(4-(2-(ethyl(4-(hydroxymethyl)phenyl)amino)-2-oxoethyl)-4H-thieno[3,2-b]pyrrole-5-carboxamido)cyclohexane-1-carboxylate (JRW-0335)

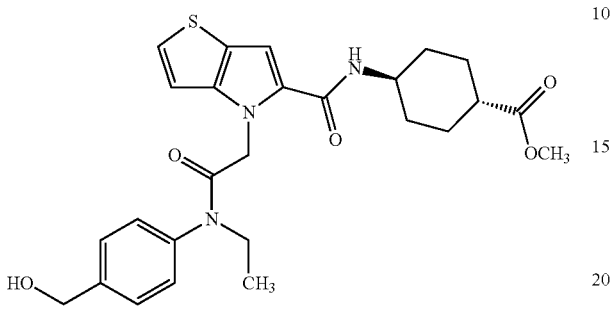

Following general procedure B, 4-(2-(ethyl(4-(hydroxymethyl)phenyl)amino)-2-oxoethyl)-4H-thieno[3,2-b]pyrrole-5-carboxylic acid (110 mg, 0.31 mmol) was reacted with methyl trans-4-aminocyclohexane-1-carboxylate (71 mg, 0.37 mmol) to afford the desired product (169 mg, 91%) as a white solid. $^1$H NMR (300 MHz, DMSO-$d_6$) δ 7.89 (d, J=7.8, 1H), 7.52-7.31 (m, 5H), 7.12-7.05 (m, 2H), 5.30-5.21 (m, 1H), 4.95 (s, 2H), 4.54 (d, J=5.6, 2H), 3.74-3.51 (m, 6H), 2.32-2.18 (m, 1H), 2.00-1.78 (m, 4H), 1.52-1.21 (m, 4H), 1.05-0.94 (m, 3H); ESI MS m/z 498 [M+H]$^+$; HPLC 98.7% (AUC), $T_R$ 5.13 min; UV (MeOH) $\lambda_{max}$ 288 nm, ε 24,103.

Example 70

Methyl trans-4-(4-(2-(ethyl(3-isopropylphenyl)amino)-2-oxoethyl)-4H-thieno[3,2-b]pyrrole-5-carboxamido)cyclohexane-1-carboxylate (JRW-0460)

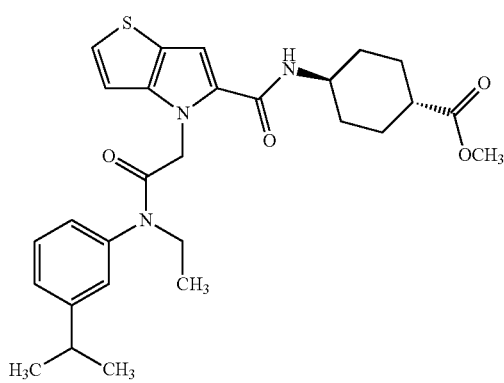 [SMILES: CCN(C(=O)Cn1c(C(=O)N[C@H]2CC[C@H](C(=O)OC)CC2)cc2sccc21)c1cccc(C(C)C)c1]

Step 1. Methyl 4-(2-(ethyl(3-isopropylphenyl)amino)-2-oxoethyl)-4H-thieno[3,2-b]pyrrole-5-carboxylate (JRW-0454)

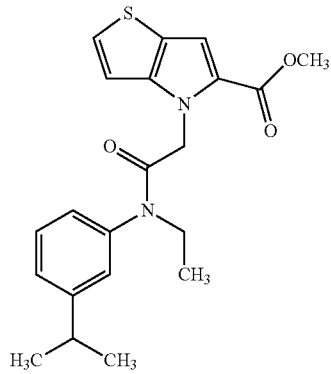 [SMILES: CCN(C(=O)Cn1c(C(=O)OC)cc2sccc21)c1cccc(C(C)C)c1]

To a solution of 2-(5-(methoxycarbonyl)-4H-thieno[3,2-b]pyrrol-4-yl)acetic acid (110 mg, 0.46 mmol) in DMF (5 mL), N-ethyl-3-isopropylaniline (112 mg, 0.69 mmol), HATU (350 mg, 0.92 mmol), and diisopropylethylamine (178 mg, 1.38 mmol) was added. The reaction was heated to 85° C. for 1.5 h. The reaction mixture cooled, diluted with ethyl acetate, and washed with water. The organic layer was dried over anhydrous sodium sulfate and filtered. The filtrate was then concentrated. The residue was purified by column chromatography (silica, heptane/ethyl acetate) to afford the desired product (147 mg, 83%) as a light orange oil. $^1$H NMR (300 MHz, CDCl$_3$) δ 7.45-7.34 (m, 1H), 7.31-7.23 (m, 2H), 7.20-7.11 (m, 3H), 6.80 (d, J=5.4, 1H), 4.96 (s, 2H), 3.83-3.71 (m, 5H), 3.05-2.87 (m, 1H), 1.35-1.25 (m, 6H), 1.18-1.09 (m, 3H); ESI MS m/z 385 [M+H]$^+$.

Step 2. 4-(2-(Ethyl(3-isopropylphenyl)amino)-2-oxoethyl)-4H-thieno[3,2-b]pyrrole-5-carboxylic acid (JRW-0457)

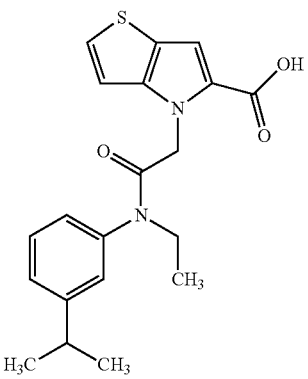 [SMILES: CCN(C(=O)Cn1c(C(=O)O)cc2sccc21)c1cccc(C(C)C)c1]

Following general procedure A, methyl 4-(2-(ethyl(3-isopropylphenyl)amino)-2-oxoethyl)-4H-thieno[3,2-b]pyrrole-5-carboxylate (145 mg, 0.38 mmol) was reacted with lithium hydroxide (45 mg, 1.89 mmol) to afford crude product (134 mg) as a light brown solid. ESI MS m/z 371 [M+H]$^+$.

Step 3. Methyl trans-4-(4-(2-(ethyl(3-isopropylphenyl)amino)-2-oxoethyl)-4H-thieno[3,2-b]pyrrole-5-carboxamido)cyclohexane-1-carboxylate (JRW-0460)

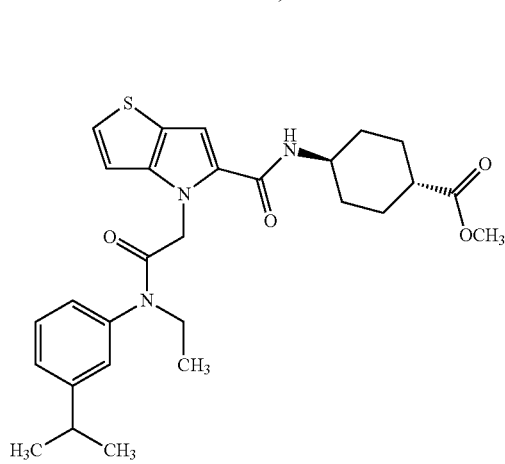

Following general procedure B, 4-(2-(ethyl(3-isopropylphenyl)amino)-2-oxoethyl)-4H-thieno[3,2-b]pyrrole-5-carboxylic acid (130 mg, 0.35 mmol) was reacted with methyl trans-4-aminocyclohexane-1-carboxylate (102 mg, 0.53 mmol) to afford the desired product (135 mg, 75%) as a white solid. $^1$H NMR (300 MHz, DMSO-$d_6$) δ 7.91 (d, J=7.9, 1H), 7.48-7.33 (m, 3H), 7.32-7.19 (m, 2H), 7.12-7.03 (m, 2H), 4.93 (s, 2H), 3.73-3.52 (m, 6H), 3.04-2.87 (m, 1H), 2.33-2.18 (m, 1H), 2.00-1.78 (m, 4H), 1.51-1.18 (m, 10H), 1.08-0.95 (m, 3H); ESI MS m/z 510 [M+H]$^+$; HPLC 98.8% (AUC), $T_R$ 7.61 min; UV (MeOH) $\lambda_{max}$ 289 nm, ε 23,933.

Example 71

Methyl trans-4-(4-(2-(ethyl(3-(hydroxymethyl)phenyl)amino)-2-oxoethyl)-4H-thieno[3,2-b]pyrrole-5-carboxamido)cyclohexane-1-carboxylate (JRW-0461)

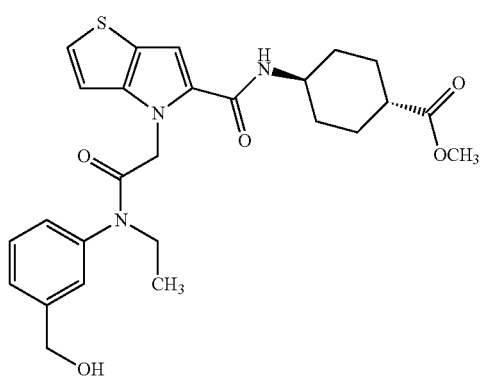 [SMILES: CCN(C(=O)Cn1c(C(=O)N[C@H]2CC[C@H](C(=O)OC)CC2)cc2sccc21)c1cccc(CO)c1]

Step 1. Methyl 4-(2-((3-(((tert-butyldimethylsilyl)oxy)methyl)phenyl)(ethyl)amino)-2-oxoethyl)-4H-thieno[3,2-b]pyrrole-5-carboxylate (JRW-0455)

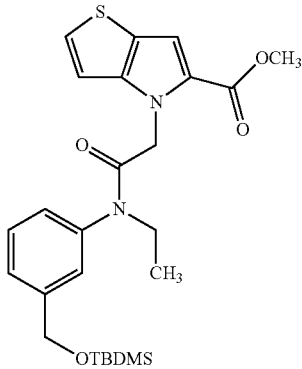 [SMILES: CCN(C(=O)Cn1c(C(=O)OC)cc2sccc21)c1cccc(CO[Si](C)(C)C(C)(C)C)c1]

To a solution of 2-(5-(methoxycarbonyl)-4H-thieno[3,2-b]pyrrol-4-yl)acetic acid (120 mg, 0.50 mmol) in DMF (5 mL), 3-(((tert-butyldimethylsilyl)oxy)methyl)-N-ethylaniline (200 mg, 0.75 mmol), HATU (381 mg, 1.0 mmol), and diisopropylethylamine (194 mg, 1.50 mmol) was added. The reaction was heated to 85° C. for 1.5 h. The reaction mixture cooled, diluted with ethyl acetate, and washed with water. The organic layer was dried over anhydrous sodium sulfate and filtered. The filtrate was then concentrated. The residue was purified by column chromatography (silica, heptane/ethyl acetate) to afford the desired product (156 mg, 63%) as a colorless oil. $^1$H NMR (300 MHz, CDCl$_3$) δ 7.31 (t, J=7.8, 1H), 7.24-7.17 (m, 1H), 7.18-7.06 (m, 3H), 7.02 (s, 1H), 6.66 (d, J=5.2, 1H), 4.82 (s, 2H), 4.66 (s, 2H), 3.71-3.54 (m, 5H), 0.99 (t, J=6.9, 3H), 0.83 (s, 9H), 0.00 (s, 6H); ESI MS m/z 487 [M+H]$^+$.

Step 2. 4-(2-(ethyl(3-(hydroxymethyl)phenyl)amino)-2-oxoethyl)-4H-thieno[3,2-b]pyrrole-5-carboxylic acid (JRW-0458)

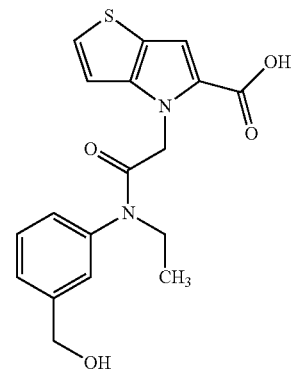 [SMILES: CCN(C(=O)Cn1c(C(=O)O)cc2sccc21)c1cccc(CO)c1]

Following general procedure A, methyl 4-(2-((3-(((tert-butyldimethylsilyl)oxy)methyl)phenyl)(ethyl)amino)-2-oxoethyl)-4H-thieno[3,2-b]pyrrole-5-carboxylate (156 mg, 0.32 mmol) was reacted with lithium hydroxide (38 mg, 1.60 mmol) to afford crude product (150 mg) as a white solid. ESI MS m/z 359 [M+H]$^+$.

Step 3. Methyl trans-4-(4-(2-(ethyl(3-(hydroxymethyl)phenyl)amino)-2-oxoethyl)-4H-thieno[3,2-b]pyrrole-5-carboxamido)cyclohexane-1-carboxylate (JRW-0461)

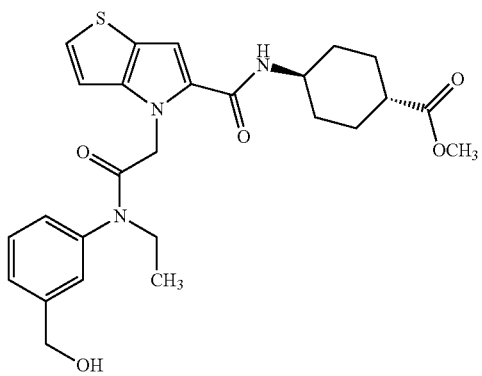 [SMILES: CCN(C(=O)Cn1c(C(=O)N[C@H]2CC[C@H](C(=O)OC)CC2)cc2sccc21)c1cccc(CO)c1]

Following general procedure B, 4-(2-(ethyl(3-(hydroxymethyl)phenyl)amino)-2-oxoethyl)-4H-thieno[3,2-b]pyrrole-5-carboxylic acid (150 mg, 0.42 mmol) was reacted with methyl trans-4-aminocyclohexane-1-carboxylate (121 mg, 0.63 mmol) to afford the desired product (126 mg, 60%) as a white foam. $^1$H NMR (300 MHz, DMSO-$d_6$) δ 7.90 (d, J=8.0, 1H), 7.54-7.27 (m, 5H), 7.13-7.03 (m, 2H), 5.33-5.24 (s, 1H), 4.96 (s, 2H), 4.56 (d, J=5.5, 2H), 3.73-3.52 (m, 6H), 2.31-2.18 (m, 1H), 1.99-1.78 (m, 4H), 1.53-1.21 (m, 4H), 1.07-0.94 (m, 3H); ESI MS m/z 498 [M+H]$^+$; HPLC 97.2% (AUC), $T_R$ 5.23 min; UV (MeOH) $\lambda_{max}$ 289 nm, ε 25,856.

Example 72

Methyl trans-4-(4-(2-((3-(bromomethyl)phenyl)(ethyl)amino)-2-oxoethyl)-4H-thieno[3,2-b]pyrrole-5-carboxamido)cyclohexane-1-carboxylate (JRW-0466)

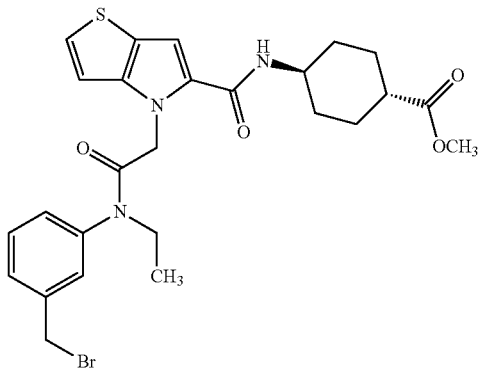 [SMILES: CCN(C(=O)Cn1c(C(=O)N[C@H]2CC[C@H](C(=O)OC)CC2)cc2sccc21)c1cccc(CBr)c1]

To a solution of carbon tetrabromide (333 mg, 1.0 mmol) and triphenylphosphine (263 mg, 1.0 mmol) in THF (5 mL), methyl trans-4-(4-(2-(ethyl(3-(hydroxymethyl)phenyl)amino)-2-oxoethyl)-4H-thieno[3,2-b]pyrrole-5-carboxamido)cyclohexane-1-carboxylate (50 mg, 0.10 mmol) in THF (5 mL) was added. The reaction was stirred at RT for 48 h. The mixture was diluted with DCM and washed with water. The organic layer was dried over anhydrous sodium sulfate and filtered. The filtrate was then concentrated. The residue was purified by column chromatography (silica, dichloromethane/methanol) to afford the desired product (11 mg, 20%) as a white solid. $^1$H NMR (300 MHz, DMSO-$d_6$) δ 7.94-7.86 (m, 1H), 7.72-7.30 (m, 5H), 7.19-6.97 (m, 2H), 4.96 (s, 2H), 4.74 (s, 2H), 3.76-3.49 (m, 6H), 2.37-2.17 (m, 1H), 2.05-1.75 (m, 4H), 1.55-1.19 (m, 4H), 1.10-0.95 (m, 3H); ESI MS m/z 562 [M+H]$^+$; HPLC 87.2% (AUC), $T_R$ 6.96 min; UV (MeOH) $\lambda_{max}$ 289 nm, ε 20,648.

Example 73

Methyl trans-4-(4-(2-((3-(dimethylamino)phenyl)(ethyl)amino)-2-oxoethyl)-4H-thieno[3,2-b]pyrrole-5-carboxamido)cyclohexane-1-carboxylate (JRW-0478)

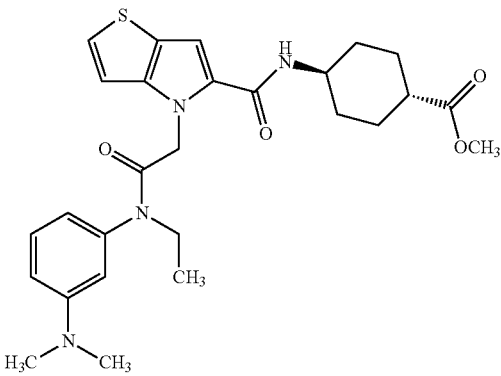 [SMILES: CCN(C(=O)Cn1c(C(=O)N[C@H]2CC[C@H](C(=O)OC)CC2)cc2sccc21)c1cccc(N(C)C)c1]

Step 1. Methyl 4-(2-((3-(dimethylamino)phenyl)(ethyl)amino)-2-oxoethyl)-4H-thieno[3,2-b]pyrrole-5-carboxylate (JRW-0475)

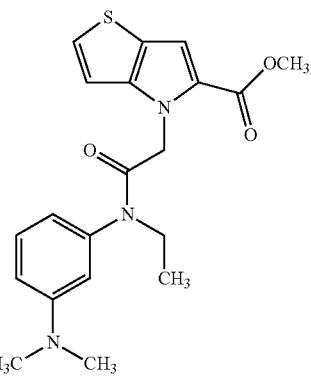

To a solution of 2-(5-(methoxycarbonyl)-4H-thieno[3,2-b]pyrrol-4-yl)acetic acid (115 mg, 0.48 mmol) in DMF (3 mL), N1-ethyl-N3,N3-dimethylbenzene-1,3-diamine (118 mg, 0.72 mmol), HATU (365 mg, 0.96 mmol), and diisopropylethylamine (186 mg, 1.44 mmol) was added. The reaction was heated to 85° C. for 1 h. The reaction mixture cooled, diluted with ethyl acetate, and washed with water. The organic layer was dried over anhydrous sodium sulfate and filtered. The filtrate was then concentrated. The residue was purified by column chromatography (silica, heptane/ ethyl acetate) to afford the desired product (152 mg, 82%) as a yellow solid. ¹H NMR (300 MHz, CDCl₃) δ 7.35-7.23 (m, 2H), 7.14 (s, 1H), 6.85-6.60 (m, 4H), 5.05 (s, 3H), 3.89-3.61 (m, 5H), 3.02 (s, 6H), 1.29-0.97 (m, 3H); ESI MS m/z 386 [M+H]⁺.

Step 2. 4-(2-((3-(Dimethylamino)phenyl)(ethyl) amino)-2-oxoethyl)-4H-thieno[3,2-b]pyrrole-5-carboxylic acid (JRW-0476)

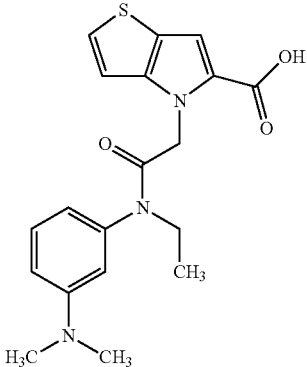

Following general procedure A, methyl 4-(2-((3-(dimethylamino)phenyl)(ethyl)amino)-2-oxoethyl)-4H-thieno[3,2-b]pyrrole-5-carboxylate (160 mg, 0.42 mmol) was reacted with lithium hydroxide (50 mg, 2.1 mmol) to afford crude product (130 mg) as a light green solid. ESI MS m/z 372 [M+H]⁺.

Step 3. Methyl trans-4-(4-(2-((3-(dimethylamino) phenyl)(ethyl)amino)-2-oxoethyl)-4H-thieno[3,2-b] pyrrole-5-carboxamido)cyclohexane-1-carboxylate (JRW-0478)

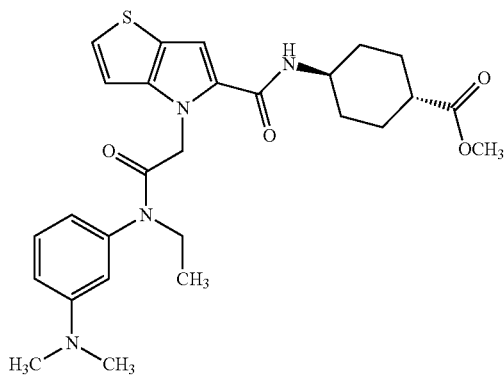

Following general procedure B, 4-(2-((3-(dimethylamino) phenyl)(ethyl)amino)-2-oxoethyl)-4H-thieno[3,2-b]pyrrole-5-carboxylic acid (130 mg, 0.35 mmol) was reacted with methyl trans-4-aminocyclohexane-1-carboxylate (102 mg, 0.53 mmol) to afford the desired product (132 mg, 74%) as an off-white solid. ¹H NMR (300 MHz, DMSO-d₆) δ 7.91 (d, J=7.9, 1H), 7.35 (d, J=5.4, 1H), 7.28 (t, J=7.9, 1H), 7.11-7.04 (m, 2H), 6.86-6.65 (m, 3H), 5.01 (s, 2H), 3.74-3.51 (m, 6H), 2.95 (s, 6H), 2.32-2.19 (s, 1H), 2.01-1.79 (m, 4H), 1.49-1.25 (m, 4H), 1.00 (t, J=7.1, 3H); ESI MS m/z 511 [M+H]⁺; HPLC 97.8% (AUC), T$_R$ 5.21 min; UV (MeOH) λ$_{max}$ 289 nm, ε 29,909.

Example 74

Methyl trans-4-(4-(2-(ethyl(3-isobutylphenyl) amino)-2-oxoethyl)-4H-thieno[3,2-b]pyrrole-5-carboxamido)cyclohexane-1-carboxylate (JRW-0508)

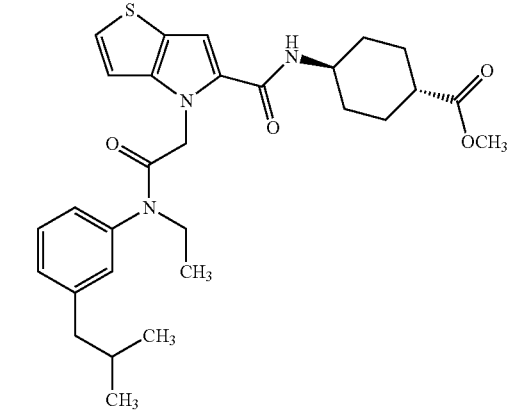 [SMILES: CCN(C(=O)Cn1c(C(=O)N[C@H]2CC[C@H](C(=O)OC)CC2)cc2sccc21)c1cccc(CC(C)C)c1]

Step 1. methyl 4-(2-(ethyl(3-isobutylphenyl)amino)-2-oxoethyl)-4H-thieno[3,2-b]pyrrole-5-carboxylate (JRW-0502)

To a solution of 2-(5-(methoxycarbonyl)-4H-thieno[3,2-b]pyrrol-4-yl)acetic acid (100 mg, 0.42 mmol) in DMF (3 mL), N-ethyl-3-isobutylaniline (89 mg, 0.50 mmol), HATU (318 mg, 0.84 mmol), and diisopropylethylamine (162 mg, 1.25 mmol) was added. The reaction was heated to 85° C. for 4 h. The reaction mixture cooled, diluted with ethyl acetate, and washed with water. The organic layer was dried over anhydrous sodium sulfate and filtered. The filtrate was then concentrated. The residue was purified by column chromatography (silica, heptane/ethyl acetate) to afford the desired product (128 mg, 77%) as a thick oil. ¹H NMR (300 MHz, CDCl₃) δ 7.38 (t, J=7.7, 1H), 7.28 (d, J=5.4, 1H), 7.21-7.13 (m, 3H), 7.13-7.09 (m, 1H), 6.79 (d, J=4.8, 1H), 4.95 (s, 2H), 3.84-3.69 (m, 5H), 2.54 (d, J=7.2, 2H), 1.98-1.82 (m, 1H), 1.13 (t, J=7.2, 3H), 0.92 (t, J=6.1, 6H); ESI MS m/z 399 [M+H]⁺.

Step 2. 4-(2-(ethyl(3-isobutylphenyl)amino)-2-oxoethyl)-4H-thieno[3,2-b]pyrrole-5-carboxylic acid (JRW-0505)

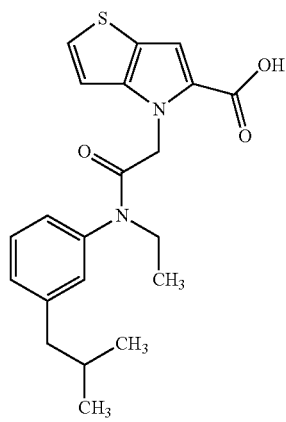 [SMILES: CCN(C(=O)Cn1c(C(=O)O)cc2sccc21)c1cccc(CC(C)C)c1]

Following general procedure A, methyl 4-(2-(ethyl(3-isobutylphenyl)amino)-2-oxoethyl)-4H-thieno[3,2-b]pyrrole-5-carboxylate (120 mg, 0.30 mmol) was reacted with lithium hydroxide (36 mg, 1.5 mmol) to afford crude product (125 mg) as a light yellow solid. ESI MS m/z 385 [M+H]⁺.

Step 3. Methyl trans-4-(4-(2-(ethyl(3-isobutylphenyl)amino)-2-oxoethyl)-4H-thieno[3,2-b]pyrrole-5-carboxamido)cyclohexane-1-carboxylate (JRW-0508)

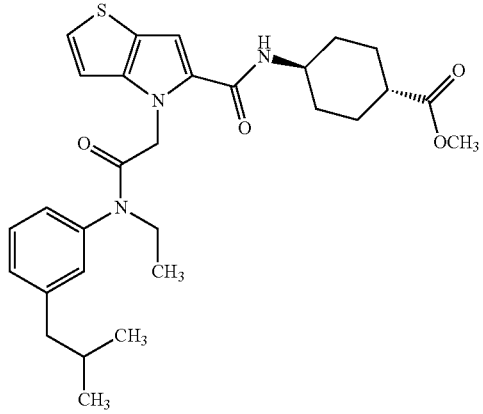 [SMILES: CCN(C(=O)Cn1c(C(=O)N[C@H]2CC[C@H](C(=O)OC)CC2)cc2sccc21)c1cccc(CC(C)C)c1]

Following general procedure B, 4-(2-(ethyl(3-isobutylphenyl)amino)-2-oxoethyl)-4H-thieno[3,2-b]pyrrole-5-carboxylic acid (120 mg, 0.42 mmol) was reacted with methyl trans-4-aminocyclohexane-1-carboxylate (90 mg, 0.47 mmol) to afford the desired product (130 mg, 80%) as a white solid. ¹H NMR (300 MHz, DMSO-d₆) δ 7.90 (d, J=7.9, 1H), 7.47-7.13 (m, 5H), 7.12-7.04 (m, 2H), 4.93 (s, 2H), 3.72-3.52 (m, 6H), 2.57-2.46 (m, 2H), 2.32-2.19 (m, 1H), 2.00-1.79 (m, 5H), 1.50-1.20 (m, 4H), 1.06-0.94 (m, 3H), 0.86 (d, J=6.6, 6H); ESI MS m/z 524 [M+H]⁺; HPLC >99% (AUC), T$_R$ 6.73 min; UV (MeOH) λ$_{max}$ 289 nm, ε 19,115.

Scheme 6.

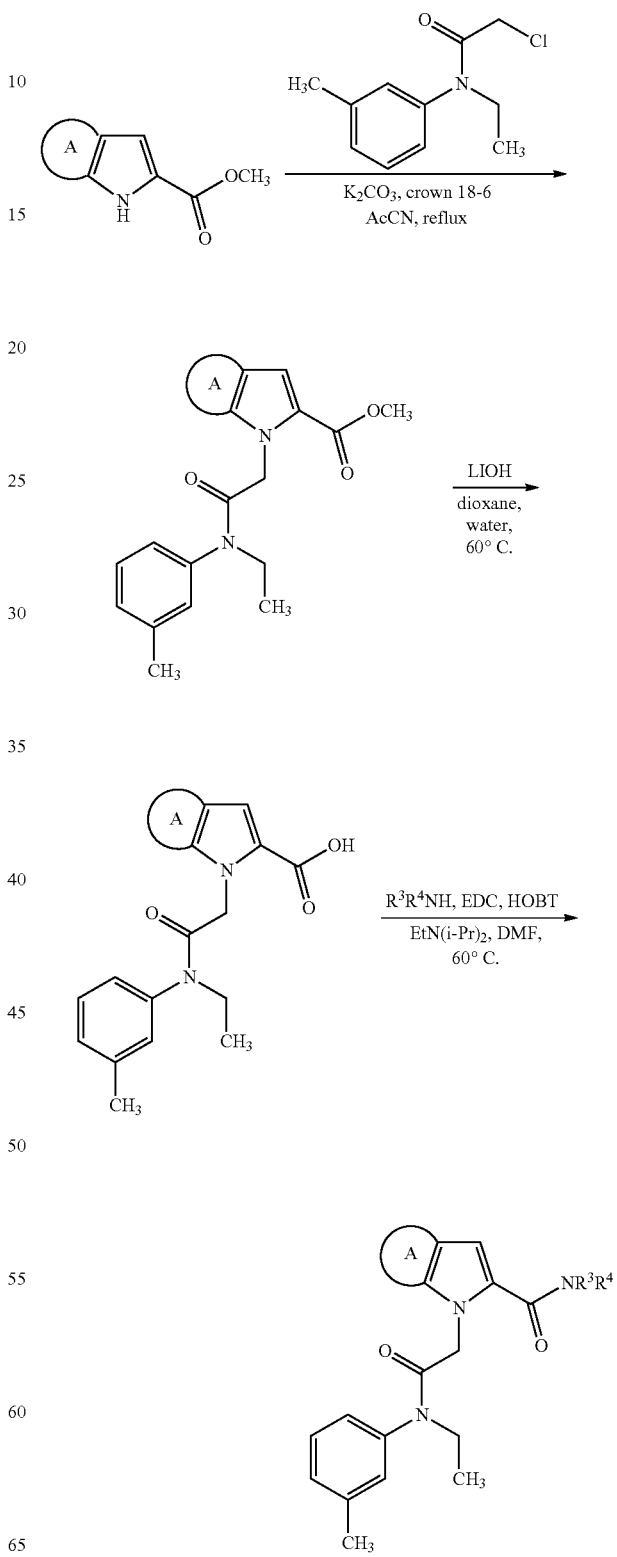

Example 75

Methyl trans-4-(1-(2-(ethyl(m-tolyl)amino)-2-oxo-ethyl)-1H-indole-2-carboxamido)cyclohexane-1-carboxylate (JRW-0355)

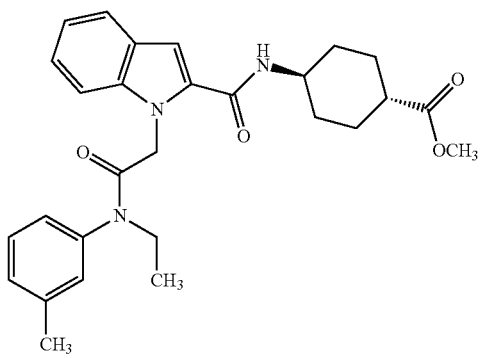 [SMILES: CCN(C(=O)Cn1c(C(=O)N[C@H]2CC[C@H](C(=O)OC)CC2)cc2ccccc21)c1cccc(C)c1]

Step 1. Methyl 1-(2-(ethyl(m-tolyl)amino)-2-oxo-ethyl)-1H-indole-2-carboxylate (JRW-0349)

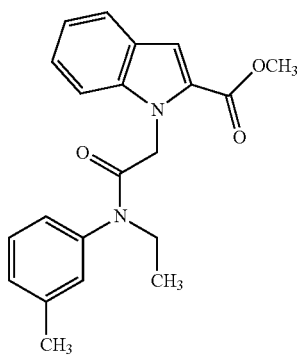 [SMILES: CCN(C(=O)Cn1c(C(=O)OC)cc2ccccc21)c1cccc(C)c1]

To a solution of methyl 1H-indole-2-carboxylate (100 mg, 0.57 mmol) in acetonitrile (5 mL), potassium carbonate (94 mg, 0.68 mmol), 18-crown-6 ether (7 mg, 0.03 mmol), and 2-chloro-N-ethyl-N-(m-tolyl)acetamide (120 mg, 0.57 mmol) was added. The suspension was heated to 75° C. for 18 h. The mixture was diluted with ethyl acetate and water, and the layers were separated. The organic layer was dried over anhydrous sodium sulfate and filtered. The filtrate was then concentrated. The residue was purified by column chromatography (silica, heptane/ethyl acetate) to afford the desired product (108 mg, 54%) as a white solid. $^1$H NMR (300 MHz, CDCl$_3$) δ 7.65 (d, J=8.0, 1H), 7.44-7.07 (m, 8H), 5.05 (s, 2H), 3.88 (s, 3H), 3.78-3.68 (m, 2H), 2.43 (s, 3H), 1.12 (t, J=7.2, 3H); ESI MS m/z 351 [M+H]$^+$.

Step 2. 1-(2-(ethyl(m-tolyl)amino)-2-oxoethyl)-1H-indole-2-carboxylic acid (JRW-0353)

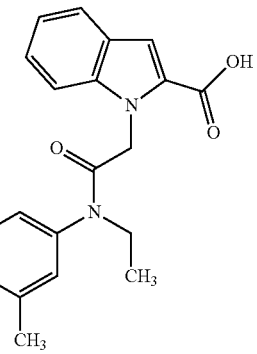

Following general procedure A, methyl 1-(2-(ethyl(m-tolyl)amino)-2-oxoethyl)-1H-indole-2-carboxylate (108 mg, 0.31 mmol) was reacted with lithium hydroxide (37 mg, 1.54 mmol) to afford crude product (103 mg) as a white solid. ESI MS m/z 337 [M+H]$^+$.

Step 3. Methyl trans-4-(1-(2-(ethyl(m-tolyl)amino)-2-oxoethyl)-1H-indole-2-carboxamido)cyclohexane-1-carboxylate (JRW-0355)

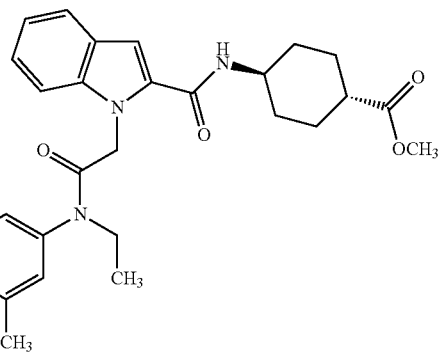

Following general procedure B, 1-(2-(ethyl(m-tolyl)amino)-2-oxoethyl)-1H-indole-2-carboxylic acid (103 mg, 0.31 mmol) was reacted with methyl trans-4-aminocyclohexane-1-carboxylate (71 mg, 0.37 mmol) to afford the desired product (133 mg, 91%) as a white foam. ESI MS m/z 476 [M+H]$^+$.

Example 76

Methyl trans-4-(1-(2-(ethyl(3-ethylphenyl)amino)-2-oxoethyl)-1H-indole-2-carboxamido)cyclohexane-1-carboxylate (JRW-0424)

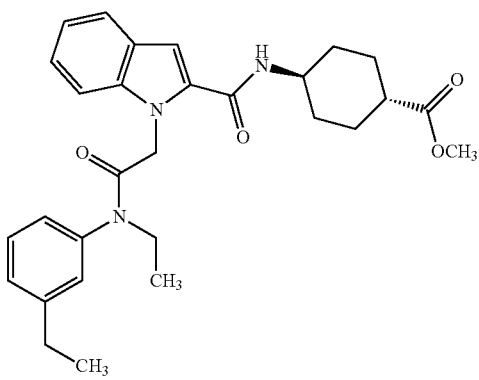 [SMILES: CCc1cccc(N(CC)C(=O)Cn2c(C(=O)N[C@H]3CC[C@H](C(=O)OC)CC3)cc3ccccc32)c1]

Step 1. 2-chloro-N-ethyl-N-(3-ethylphenyl)acetamide (JRW-0413)

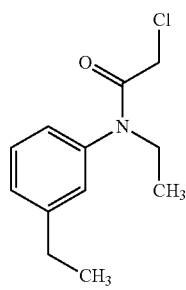

To a solution of N-ethyl-3-ethylaniline (0.97 g, 6.50 mmol) in ethyl acetate (30 mL), water (10 mL) was added. The biphasic solution was cooled to 0° C., and potassium hydroxide (1.09 g, 19.5 mmol) added in one motion. 2-Chloroacetyl chloride (1.10 g, 0.76 mL, 9.75 mmol) was added dropwise over 10 min. The mixture was stirred for 1 h, diluted with water, and extracted with ethyl acetate. The organic layer was dried over anhydrous sodium sulfate and filtered. The filtrate was then concentrated to afford crude product (1.54 g) as a mobile oil. ESI MS m/z 226 [M+H]$^+$.

Step 2. methyl 1-(2-(ethyl(3-ethylphenyl)amino)-2-oxoethyl)-1H-indole-2-carboxylate (JRW-0416)

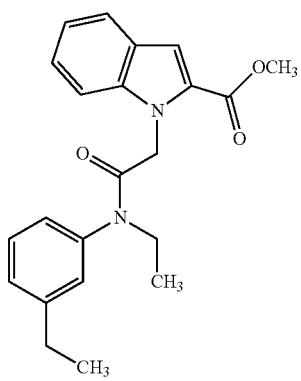 [SMILES: CCc1cccc(N(CC)C(=O)Cn2c(C(=O)OC)cc3ccccc32)c1]

To a solution of methyl 1H-indole-2-carboxylate (582 mg, 3.3 mmol) in acetonitrile (20 mL), potassium carbonate (551 mg, 4.0 mmol), 18-crown-6 ether (44 mg, 0.17 mmol), 2-chloro-N-ethyl-N-(3-ethylphenyl)acetamide (750 mg, 3.3 mmol) was added. The suspension was heated to 75° C. for 18 h. The mixture was diluted with ethyl acetate and water, and the layers were separated. The organic layer was dried over anhydrous sodium sulfate and filtered. The filtrate was then concentrated. The residue was purified by column chromatography (silica, heptane/ethyl acetate) to afford the desired product (0.74 g, 61%) as a light brown solid. $^1$H NMR (300 MHz, CDCl$_3$) δ 7.65 (d, J=8.1, 1H), 7.50-7.07 (m, 8H), 5.06 (s, 2H), 3.87 (s, 3H), 3.82-3.69 (m, 4H), 2.78-2.63 (m, 2H), 1.35-1.24 (m, 3H), 1.18-1.06 (m, 3H); ESI MS m/z 365 [M+H]$^+$.

Step 3. 1-(2-(ethyl(3-ethylphenyl)amino)-2-oxoethyl)-1H-indole-2-carboxylic acid (JRW-0419)

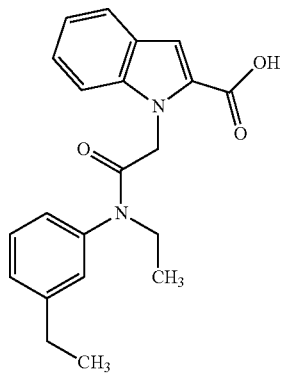 [SMILES: CCc1cccc(N(CC)C(=O)Cn2c(C(=O)O)cc3ccccc32)c1]

Following general procedure A, methyl 1-(2-(ethyl(3-ethylphenyl)amino)-2-oxoethyl)-1H-indole-2-carboxylate (740 mg, 2.0 mmol) was reacted with lithium hydroxide (243 mg, 10.1 mmol) to afford crude product (690 mg) as a white solid. ESI MS m/z 350 [M+H]$^+$.

Step 4. methyl trans-4-(1-(2-(ethyl(3-ethylphenyl)amino)-2-oxoethyl)-1H-indole-2-carboxamido)cyclohexane-1-carboxylate (JRW-0424)

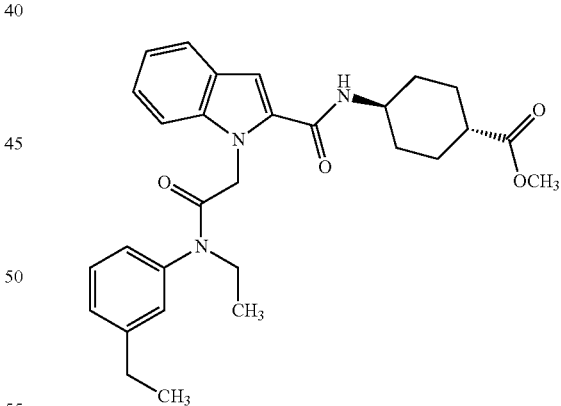

Following general procedure B, 1-(2-(ethyl(3-ethylphenyl)amino)-2-oxoethyl)-1H-indole-2-carboxylic acid (690 mg, 1.97 mmol) was reacted with methyl trans-4-aminocyclohexane-1-carboxylate (457 mg, 2.36 mmol) to afford the desired product (760 mg, 79%) as a white foam. $^1$H NMR (300 MHz, DMSO-d$_6$) δ 8.20 (d, J=7.9, 1H), 7.58 (d, J=7.9, 1H), 7.51-7.13 (m, 6H), 7.13-7.02 (m, 2H), 5.02 (s, 2H), 3.77-3.54 (m, 6H), 2.69 (d, J=7.6, 2H), 2.33-2.21 (m, 1H), 2.02-1.81 (m, 4H), 1.52-1.30 (m, 4H), 1.23 (t, J=7.6, 3H), 1.08-0.95 (m, 3H); ESI MS m/z 490 [M+H]$^+$; HPLC >99% (AUC), T$_R$ 7.56 min; UV (MeOH) λ$_{max}$ 291 nm, ε 15,737

Example 77

1-(2-(Ethyl(3-ethylphenyl)amino)-2-oxoethyl)-N-(trans-4-((6-hydroxyhexyl)carbamoyl)cyclohexyl)-1H-indole-2-carboxamide (JRW-0430)

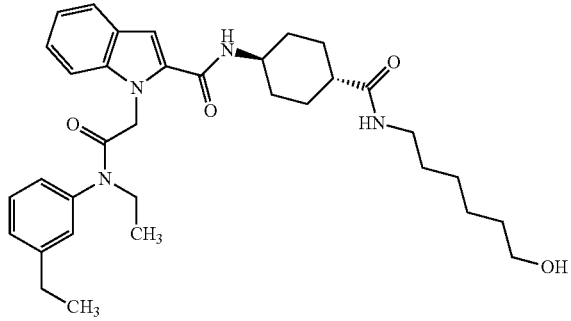 [SMILES: CCc1cccc(N(CC)C(=O)Cn2c(C(=O)N[C@H]3CC[C@H](C(=O)NCCCCCCO)CC3)cc3ccccc32)c1]

Step 1. trans-4-(1-(2-(ethyl(3-ethylphenyl)amino)-2-oxoethyl)-1H-indole-2-carboxamido)cyclohexane-1-carboxylic acid (JRW-0428)

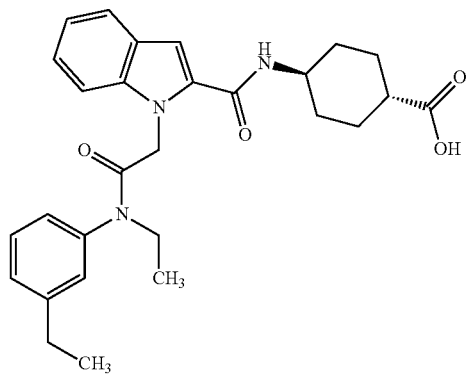 [SMILES: CCc1cccc(N(CC)C(=O)Cn2c(C(=O)N[C@H]3CC[C@H](C(=O)O)CC3)cc3ccccc32)c1]

Following general procedure A, methyl trans-4-(1-(2-(ethyl(3-ethylphenyl)amino)-2-oxoethyl)-1H-indole-2-carboxamido)cyclohexane-1-carboxylate (720 mg, 1.47 mmol) was reacted with lithium hydroxide (105 mg, 4.4 mmol) to afford crude product (680 mg) as a white solid. ESI MS m/z 476 [M+H]$^+$.

Step 2. 1-(2-(ethyl(3-ethylphenyl)amino)-2-oxoethyl)-N-(trans-4-((6-hydroxyhexyl)carbamoyl)cyclohexyl)-1H-indole-2-carboxamide (JRW-0430)

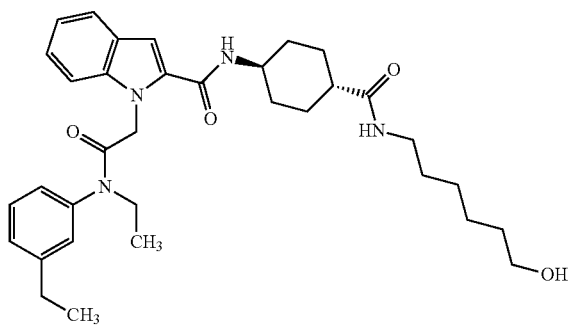 [SMILES: CCc1cccc(N(CC)C(=O)Cn2c(C(=O)N[C@H]3CC[C@H](C(=O)NCCCCCCO)CC3)cc3ccccc32)c1]

Following general procedure B, trans-4-(1-(2-(ethyl(3-ethylphenyl)amino)-2-oxoethyl)-1H-indole-2-carboxamido)cyclohexane-1-carboxylic acid (200 mg, 0.42 mmol) was reacted with 6-aminohexan-1-ol (74 mg, 0.63 mmol) to afford the desired product (218 mg, 79%) as a light yellow foam. $^1$H NMR (300 MHz, DMSO-d$_6$) δ 8.17 (d, J=8.0, 1H), 7.69-7.54 (m, 2H), 7.50-7.14 (m, 6H), 7.13-7.02 (m, 2H), 5.02 (s, 2H), 4.27 (t, J=5.2, 1H), 3.77-3.52 (s, 3H), 3.36 (dd, J=6.4, 11.7, 2H), 3.05-2.95 (m, 2H), 2.74-2.63 (m, 2H), 2.13-1.97 (m, 1H), 1.91-1.69 (m, 4H), 1.54-1.15 (m, 15H), 1.09-0.93 (m, 3H); ESI MS m/z 575 [M+H]$^+$; HPLC >99% (AUC), T$_R$ 6.12 min; UV (MeOH) λ$_{max}$ 291 nm, ε 17,243.

Example 78

Sodium 6-(trans-4-(1-(2-(ethyl(3-ethylphenyl)amino)-2-oxoethyl)-1H-indole-2-carboxamido)cyclohexane-1-carboxamido)hexane-1-sulfonate (JRW-0434)

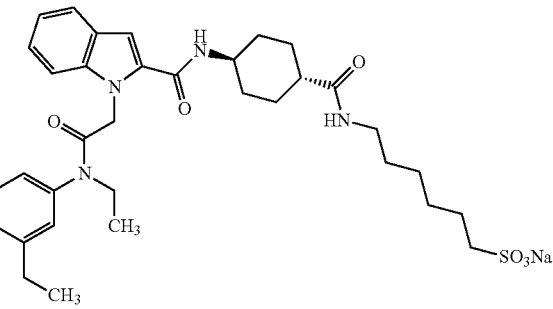

Step 1. 1-(2-(ethyl(3-ethylphenyl)amino)-2-oxoethyl)-N-(trans-4-((6-iodohexyl)carbamoyl)cyclohexyl)-1H-indole-2-carboxamide (JRW-0433)

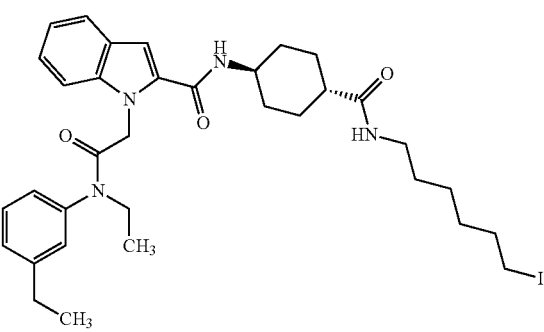

A solution of imidazole (66 mg, 0.97 mmol), triphenylphosphine (254 mg, 0.97 mmol), and iodine (246 mg, 0.97 mmol) in THF (10 mL) stirred at RT for 10 min. 1-(2-(Ethyl(3-ethylphenyl)amino)-2-oxoethyl)-N-(trans-4-((6-hydroxyhexyl)carbamoyl)cyclohexyl)-1H-indole-2-carboxamide (186 mg, 0.32 mmol) dissolved in THF (5 mL) was added. The solution stirred for 1 h at RT. The reaction was diluted with ethyl acetate and quenched with a 10% Na$_2$S$_2$O$_3$ solution. The mixture was diluted with ethyl acetate and water, and the layers were separated. The organic layer was washed with a 10% Na$_2$S$_2$O$_3$ solution, and the brine dried over anhydrous sodium sulfate and filtered. The filtrate was then concentrated. The residue was partially Step 2. sodium 6-(trans-4-(1-(2-(ethyl(3-ethylphenyl)amino)-2-oxoethyl)-1H-indole-2-carboxamido)cyclohexane-1-carboxamido)hexane-1-sulfonate (JRW-0434)

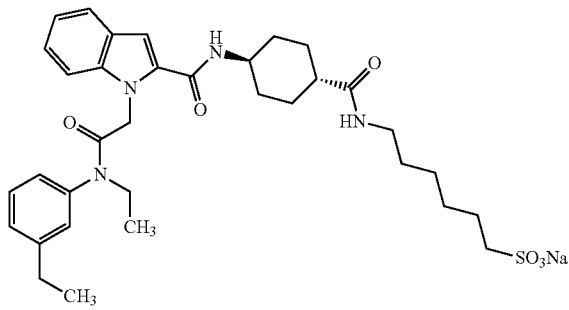

To a solution of 1-(2-(ethyl(3-ethylphenyl)amino)-2-oxoethyl)-N-(trans-4-((6-iodohexyl)carbamoyl)cyclohexyl)-1H-indole-2-carboxamide (0.32 mmol) in ethanol (10 mL), sodium sulfite (203 mg, 1.6 mmol) and water (10 mL) was added. The mixture was heated to 75° C. for 2 h. The reaction was concentrated, and the residue was purified by column chromatography (silica, dichloromethane/methanol) to afford the desired product (190 mg, 89%) as a white solid. $^1$H NMR (300 MHz, DMSO-$d_6$) δ 8.21 (d, J=8.2, 1H), 7.69 (t, J=5.6, 1H), 7.58 (d, J=7.8, 1H), 7.51-7.14 (m, 6H), 7.12-7.03 (m, 2H), 5.02 (s, 2H), 3.76-3.53 (m, 3H), 3.00 (dd, J=6.6, 12.7, 2H), 2.76-2.61 (m, 2H), 2.39-2.32 (m, 2H), 2.12-1.99 (m, 1H), 1.90-1.70 (m, 4H), 1.61-1.14 (m, 15H), 1.08-0.95 (s, 3H); ESI MS m/z 639 [M+H]$^+$; HPLC >99% (AUC), $T_R$ 5.07 min; UV (MeOH) $\lambda_{max}$ 291 nm, ε 15,800.

Example 79

Methyl trans-4-(1-(2-(ethyl(m-tolyl)amino)-2-oxoethyl)-6-methoxy-1H-indole-2-carboxamido)cyclohexane-1-carboxylate (JRW-0359)

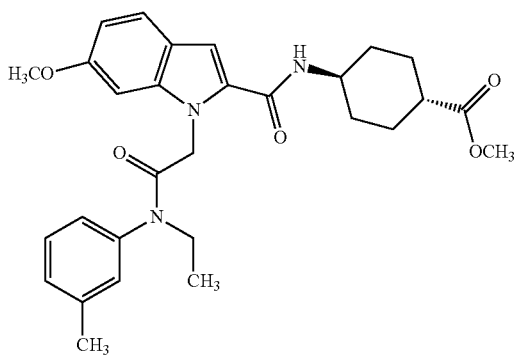 [SMILES: CCN(C(=O)Cn1c(C(=O)N[C@H]2CC[C@H](C(=O)OC)CC2)cc2ccc(OC)cc21)c1cccc(C)c1]

Step 1. Methyl 1-(2-(ethyl(m-tolyl)amino)-2-oxoethyl)-6-methoxy-1H-indole-2-carboxylate (JRW-0351)

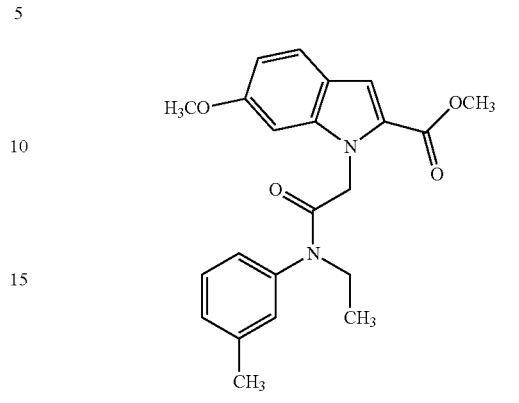

To a solution of methyl 6-methoxy-1H-indole-2-carboxylate (116 mg, 0.57 mmol) in acetonitrile (5 mL), potassium carbonate (94 mg, 0.68 mmol), 18-crown-6 ether (7 mg, 0.03 mmol), and 2-chloro-N-ethyl-N-(m-tolyl)acetamide (120 mg, 0.57 mmol) was added. The suspension was heated to 70° C. for 2 d. The mixture was diluted with ethyl acetate and water, and the layers were separated. The organic layer was dried over anhydrous sodium sulfate and filtered. The filtrate was then concentrated. The residue was purified by column chromatography (silica, heptane/ethyl acetate) to afford the desired product (155 mg, 72%) as a white solid. $^1$H NMR (300 MHz, CDCl$_3$) δ 7.51 (d, J=8.7, 1H), 7.41-7.31 (m, 1H), 7.24-7.08 (m, 4H), 6.79 (dd, J=2.2, 8.7, 1H), 6.62-6.55 (m, 1H), 5.01 (s, 2H), 3.87 (s, 3H), 3.84 (s, 3H), 3.81-3.68 (m, 2H), 2.42 (s, 3H), 1.18-1.09 (m, 3H); ESI MS m/z 381 [M+H]$^+$.

Step 2. 1-(2-(ethyl(m-tolyl)amino)-2-oxoethyl)-6-methoxy-1H-indole-2-carboxylic acid (JRW-0357)

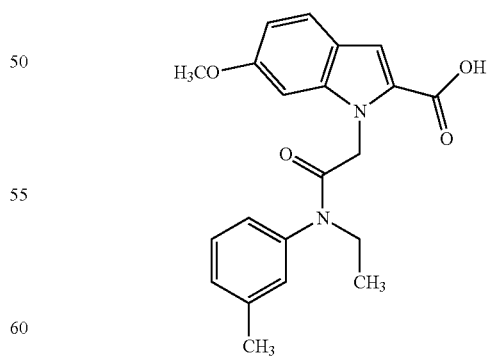

Following general procedure A, methyl 1-(2-(ethyl(m-tolyl)amino)-2-oxoethyl)-6-methoxy-1H-indole-2-carboxylate (150 mg, 0.39 mmol) was reacted with lithium hydroxide (47 mg, 1.97 mmol) to afford crude product (150 mg) as a white solid. ESI MS m/z 367 [M+H]$^+$.

Step 3. Methyl trans-4-(1-(2-(ethyl(m-tolyl)amino)-2-oxoethyl)-6-methoxy-1H-indole-2-carboxamido)cyclohexane-1-carboxylate (JRW-0359)

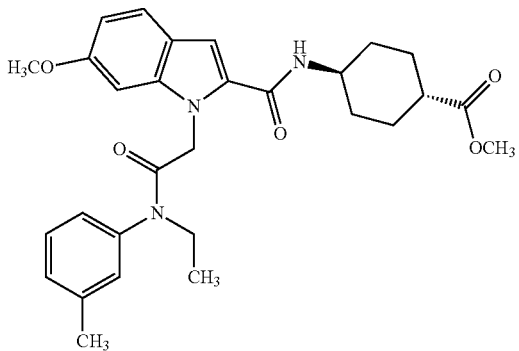 [SMILES: CCN(C(=O)Cn1c(C(=O)N[C@H]2CC[C@H](C(=O)OC)CC2)cc2ccc(OC)cc21)c1cccc(C)c1]

Following general procedure B, 1-(2-(ethyl(m-tolyl)amino)-2-oxoethyl)-6-methoxy-1H-indole-2-carboxylic acid (150 mg, 0.41 mmol) was reacted with methyl trans-4-aminocyclohexane-1-carboxylate (95 mg, 0.49 mmol) to afford the desired product (163 mg, 78%) as a white foam. ESI MS m/z 506 [M+H]$^+$.

Example 80

Methyl trans-4-(4-(2-(ethyl(m-tolyl)amino)-2-oxoethyl)-4H-furo[3,2-b]pyrrole-5-carboxamido)cyclohexane-1-carboxylate (JRW-360)

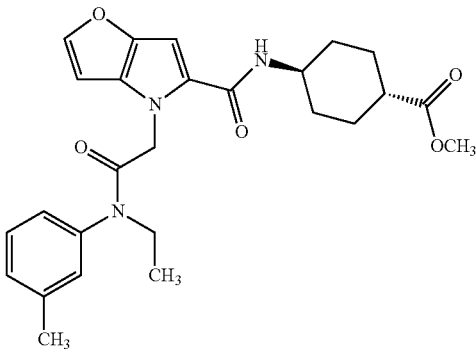

Step 1. Methyl 4-(2-(ethyl(m-tolyl)amino)-2-oxoethyl)-4H-furo[3,2-b]pyrrole-5-carboxylate (JRW-0352)

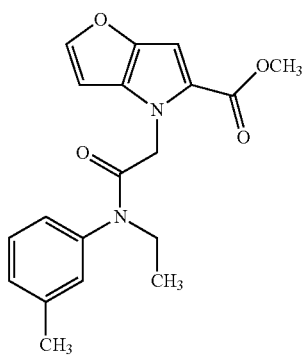

To a solution of methyl 4H-furo[3,2-b]pyrrole-5-carboxylate (94 mg, 0.57 mmol) in acetonitrile (5 mL), potassium carbonate (94 mg, 0.68 mmol), 18-crown-6 ether (7 mg, 0.03 mmol), and 2-chloro-N-ethyl-N-(m-tolyl)acetamide (120 mg, 0.57 mmol) was added. The suspension was heated to 70° C. for 2 d. The mixture was diluted with ethyl acetate and water, and the layers were separated. The organic layer was dried over anhydrous sodium sulfate and filtered. The filtrate was then concentrated. The residue was purified by column chromatography (silica, heptane/ethyl acetate) to afford the desired product (166 mg, 86%) as a white solid. $^1$H NMR (300 MHz, CDCl$_3$) δ 7.47 (d, J=2.2, 1H), 7.35 (t, J=7.7, 1H), 7.24-7.17 (m, 1H), 7.16-7.07 (m, 2H), 6.81-6.78 (m, 1H), 6.38-6.36 (m, 1H), 4.86 (s, 2H), 3.85-3.67 (m, 5H), 2.40 (s, 3H), 1.12 (t, J=7.2, 3H); ESI MS m/z 341 [M+H]$^+$.

Step 2. 4-(2-(ethyl(m-tolyl)amino)-2-oxoethyl)-4H-furo[3,2-b]pyrrole-5-carboxylic acid (JRW-358)

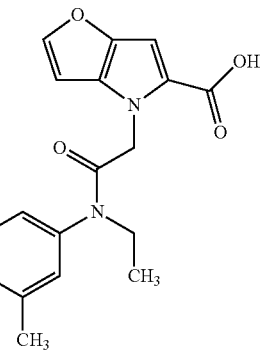

Following general procedure A, methyl 4-(2-(ethyl(m-tolyl)amino)-2-oxoethyl)-4H-furo[3,2-b]pyrrole-5-carboxylate (160 mg, 0.47 mmol) was reacted with lithium hydroxide (56 mg, 2.35 mmol) to afford crude product (150 mg) as a white solid. ESI MS m/z 327 [M+H]$^+$.

Step 3. Methyl trans-4-(4-(2-(ethyl(m-tolyl)amino)-2-oxoethyl)-4H-furo[3,2-b]pyrrole-5-carboxamido)cyclohexane-1-carboxylate (JRW-360)

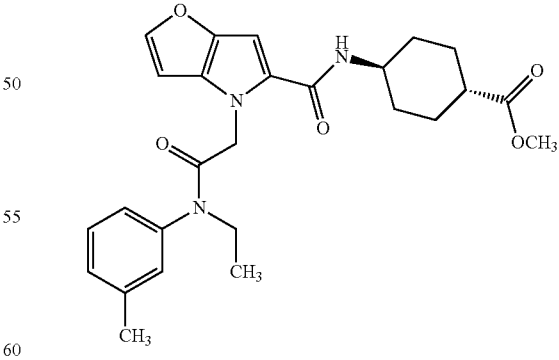

Following general procedure B, 4-(2-(ethyl(m-tolyl)amino)-2-oxoethyl)-4H-furo[3,2-b]pyrrole-5-carboxylic acid (150 mg, 0.46 mmol) was reacted with methyl trans-4-aminocyclohexane-1-carboxylate (106 mg, 0.55 mmol) to afford the desired product (178 mg, 83%) as a white foam. ESI MS m/z 466 [M+H]$^+$.

Example 81

Methyl trans-4-(1-(2-(ethyl(m-tolyl)amino)-2-oxoethyl)-1H-pyrrole-2-carboxamido)cyclohexane-1-carboxylate (JRW-0456)

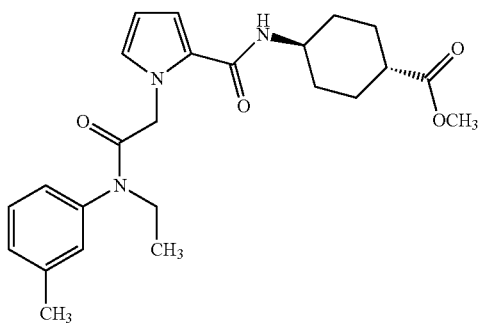 [SMILES: CCN(C(=O)Cn1cccc1C(=O)N[C@H]1CC[C@H](C(=O)OC)CC1)c1cccc(C)c1]

Step 1. methyl 1-(2-(ethyl(m-tolyl)amino)-2-oxoethyl)-1H-pyrrole-2-carboxylate (JRW-0450)

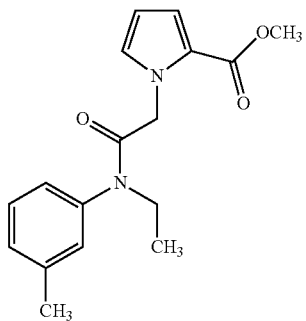 [SMILES: CCN(C(=O)Cn1cccc1C(=O)OC)c1cccc(C)c1]

To a solution of methyl 1H-pyrrole-2-carboxylate (295 mg, 2.36 mmol) in acetonitrile (20 mL), potassium carbonate (391 mg, 2.83 mmol), 18-crown-6 ether (31 mg, 0.12 mmol), and 2-chloro-N-ethyl-N-(m-tolyl)acetamide (500 mg, 2.36 mmol) was added. The suspension was heated to 75° C. for 18 h. The mixture was diluted with ethyl acetate and water, and the layers were separated. The organic layer was dried over anhydrous sodium sulfate and filtered. The filtrate was then concentrated. The residue was purified by column chromatography (silica, heptane/ethyl acetate) to afford the desired product (530 mg, 75%) as a clear oil. $^1$H NMR (300 MHz, CDCl$_3$) δ 7.35 (t, J=7.5, 1H), 7.24-7.10 (m, 3H), 6.93 (dd, J=1.8, 3.9, 1H), 6.78-6.70 (m, 1H), 6.13 (dd, J=2.6, 3.9, 1H), 4.77 (s, 2H), 3.85-3.61 (m, 6H), 2.41 (s, 3H), 1.13 (t, J=7.2, 3H); ESI MS m/z 301 [M+H]$^+$.

Step 2. 1-(2-(ethyl(m-tolyl)amino)-2-oxoethyl)-1H-pyrrole-2-carboxylic acid (JRW-0453)

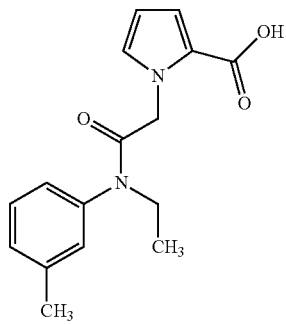 [SMILES: CCN(C(=O)Cn1cccc1C(=O)O)c1cccc(C)c1]

Following general procedure A, methyl 1-(2-(ethyl(m-tolyl)amino)-2-oxoethyl)-1H-pyrrole-2-carboxylate (530 mg, 1.76 mmol) was reacted with lithium hydroxide (211 mg, 8.82 mmol) to afford crude product (475 mg) as a white solid. ESI MS m/z 287 [M+H]$^+$.

Step 3. methyl trans-4-(1-(2-(ethyl(m-tolyl)amino)-2-oxoethyl)-1H-pyrrole-2-carboxamido)cyclohexane-1-carboxylate (JRW-0456)

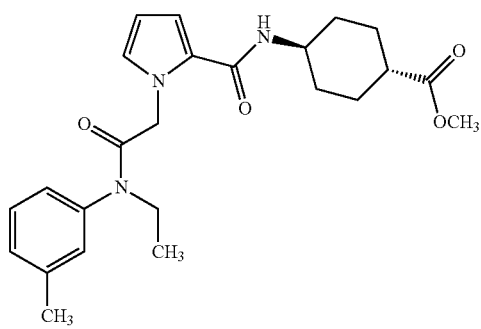 [SMILES: CCN(C(=O)Cn1cccc1C(=O)N[C@H]1CC[C@H](C(=O)OC)CC1)c1cccc(C)c1]

Following general procedure B, 1-(2-(ethyl(m-tolyl)amino)-2-oxoethyl)-1H-pyrrole-2-carboxylic acid (475 mg, 1.66 mmol) was reacted with methyl trans-4-aminocyclohexane-1-carboxylate (482 mg, 2.49 mmol) to afford the desired product (505 mg, 71%) as a white foam. $^1$H NMR (300 MHz, DMSO-d$_6$) δ 7.62 (d, J=8.0, 1H), 7.41-7.30 (m, 1H), 7.26-7.12 (m, 3H), 6.82-6.67 (m, 2H), 5.94 (dd, J=2.6, 3.8, 1H), 4.77 (s, 2H), 3.67-3.54 (m, 6H), 2.34 (s, 3H), 2.29-2.18 (s, 1H), 1.98-1.74 (m, 4H), 1.48-1.26 (m, 4H), 1.09-0.92 (m, 3H); ESI MS m/z 426 [M+H]$^+$; HPLC 97.5% (AUC), T$_R$ 6.05 min; UV (MeOH) λ$_{max}$ 264 nm, ε 11,978.

Example 82

Methyl trans-4-(6-(2-(ethyl(m-tolyl)amino)-2-oxo-ethyl)-6H-thieno[2,3-b]pyrrole-5-carboxamido)cyclohexane-1-carboxylate (JRW-0463)

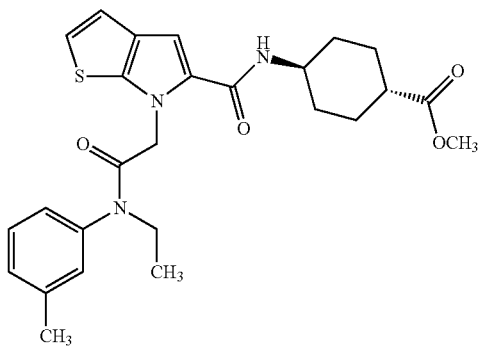 [SMILES: CCN(C(=O)Cn1c(C(=O)N[C@H]2CC[C@H](C(=O)OC)CC2)cc2ccsc21)c1cccc(C)c1]

Step 1. Methyl 6-(2-(ethyl(m-tolyl)amino)-2-oxoethyl)-6H-thieno[2,3-b]pyrrole-5-carboxylate (JRW-0459)

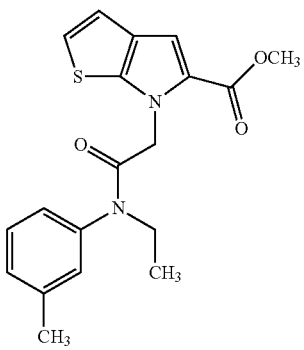 [SMILES: CCN(C(=O)Cn1c(C(=O)OC)cc2ccsc21)c1cccc(C)c1]

To a solution of methyl 6H-thieno[2,3-b]pyrrole-5-carboxylate (171 mg, 0.94 mmol) in acetonitrile (10 mL), potassium carbonate (157 mg, 1.1 mmol), 18-crown-6 ether (13 mg, 0.047 mmol), and 2-chloro-N-ethyl-N-(m-tolyl)acetamide (200 mg, 0.94 mmol) was added. The suspension was heated to 75° C. for 18 h. The mixture was diluted with ethyl acetate and water, and the layers were separated. The organic layer was dried over anhydrous sodium sulfate and filtered. The filtrate was then concentrated. The residue was purified by column chromatography (silica, heptane/ethyl acetate) to afford the desired product (260 mg, 77%) as a white solid. $^1$H NMR (300 MHz, CDCl$_3$) δ 7.37 (t, J=7.6, 1H), 7.25-7.09 (m, 4H), 6.99-6.95 (m, 1H), 6.91-6.85 (m, 1H), 4.93 (s, 2H), 3.92-3.64 (m, 5H), 2.43 (s, 3H), 1.14 (t, J=7.2, 4H); ESI MS m/z 357 [M+H]$^+$.

Step 2. 6-(2-(Ethyl(m-tolyl)amino)-2-oxoethyl)-6H-thieno[2,3-b]pyrrole-5-carboxylic acid (JRW-0462)

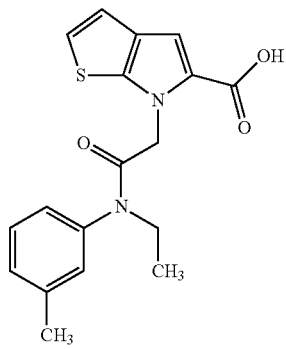 [SMILES: CCN(C(=O)Cn1c(C(=O)O)cc2ccsc21)c1cccc(C)c1]

Following general procedure A, methyl 6-(2-(ethyl(m-tolyl)amino)-2-oxoethyl)-6H-thieno[2,3-b]pyrrole-5-carboxylate (260 mg, 0.73 mmol) was reacted with lithium hydroxide (87 mg, 3.6 mmol) to afford crude product (240 mg) as a white solid. ESI MS m/z 342 [M+H]$^+$.

Step 3. Methyl trans-4-(6-(2-(ethyl(m-tolyl)amino)-2-oxoethyl)-6H-thieno[2,3-b]pyrrole-5-carboxamido)cyclohexane-1-carboxylate (JRW-0463)

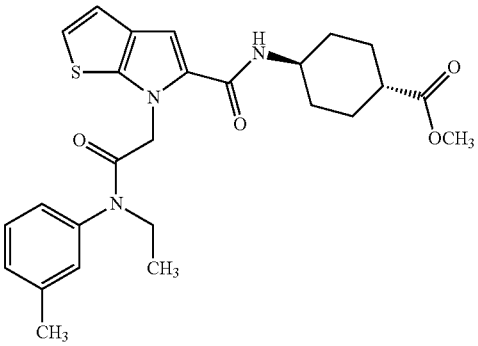 [SMILES: CCN(C(=O)Cn1c(C(=O)N[C@H]2CC[C@H](C(=O)OC)CC2)cc2ccsc21)c1cccc(C)c1]

Following general procedure B, 6-(2-(ethyl(m-tolyl)amino)-2-oxoethyl)-6H-thieno[2,3-b]pyrrole-5-carboxylic acid (240 mg, 0.70 mmol) was reacted with methyl trans-4-aminocyclohexane-1-carboxylate (203 mg, 1.05 mmol) to afford the desired product (320 mg, 95%) as a light yellow foam. $^1$H NMR (300 MHz, DMSO-d$_6$) δ 7.88 (d, J=8.0, 1H), 7.44-7.33 (m, 1H), 7.28-7.14 (m, 3H), 7.11-6.95 (m, 3H), 4.90 (s, 2H), 3.72-3.52 (m, 6H), 2.36 (s, 3H), 2.25 (s, 1H), 2.02-1.76 (m, 4H), 1.51-1.20 (m, 4H), 1.00 (t, J=6.9, 3H); ESI MS m/z 482 [M+H]$^+$; HPLC >99% (AUC), T$_R$ 7.01 min; UV (MeOH) λ$_{max}$ 287 nm, ε 12,894.

Example 83

Inhibition of Nluc Luciferase

K562 were plated into wells of a Corning 3707 assay plate in 20 μL RPMI media at 2000 cells/well and incubated overnight. A Trail titration was prepared in 10 μL RPMI media and added to cells. Then either 10 μL 4× REALTIME-GLO™ MT Cell Viability reagent (RTCV; Promega Corporation) or media (control) was added to each well. The reactions were incubated at 37° C./5% $CO_2$ at various time points, and luminescence was measured on a Tecan M1000 Pro plate reader. At 5 hrs, 40 µL CASPASE-GLO® 3/7 detection reagent (Promega Corporation) was added with or without 200 µM JRW-0004. The reaction was incubated for 2 hrs at room temperature (RT), and luminescence was measured on the Tecan M1000 Pro plate reader. FIG. 1 demonstrates that JRW-0004 can inhibit the Nluc enzyme in REALTIME-GLO™ MT Cell Viability reagent, and therefore recover the CASPASE-GLO® assay window in a multiplex that combines REALTIME-GLO™ assay and CASPASE-GLO®assay.

Example 84

Inhibition of Purified Nluc Luciferase

Figure 2:
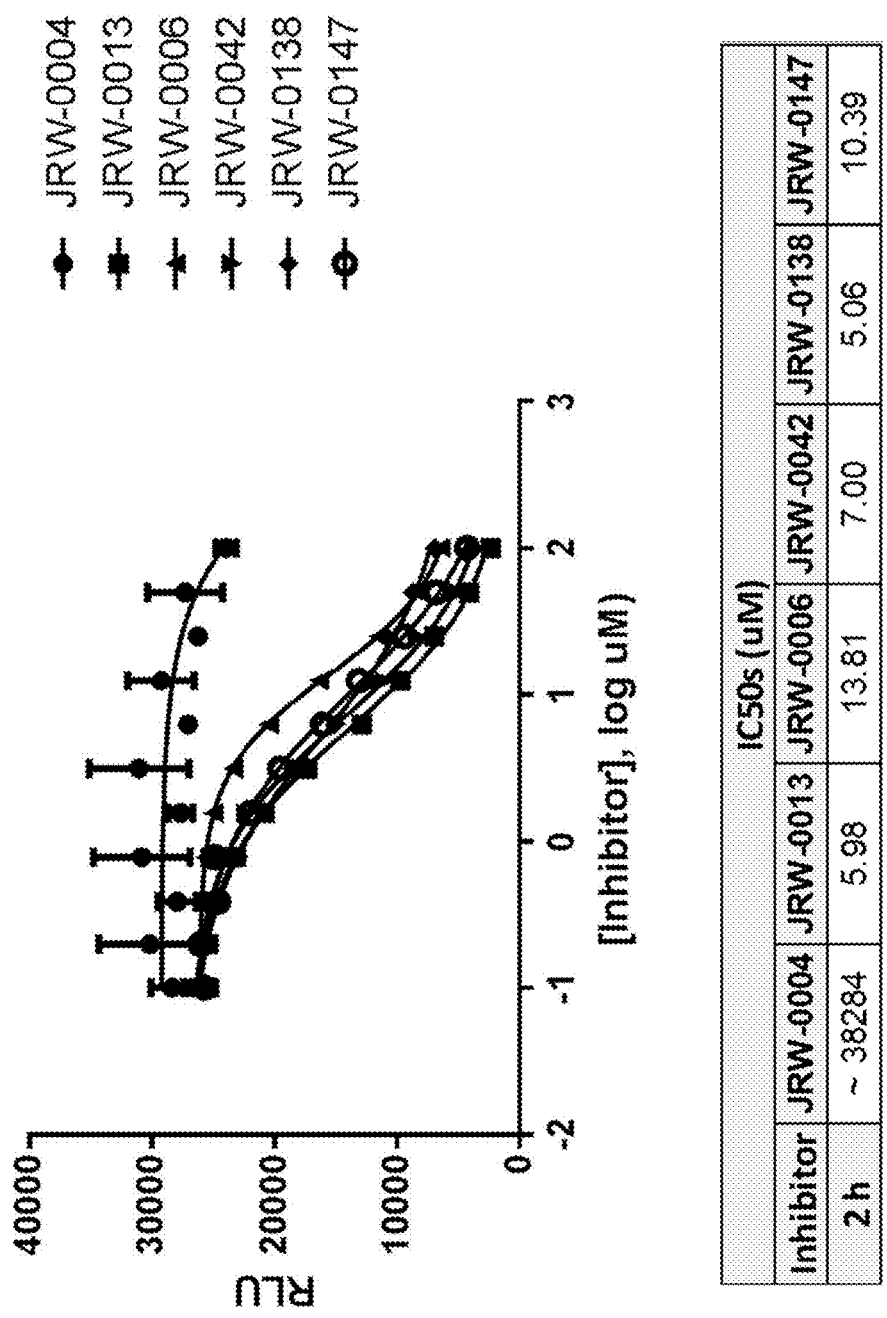
FIG. 2 shows the inhibition of Nluc by thienopyrrole compounds JRW-0004, JRW-0013, JRW-0006, JRW-0042, JRW-0138, and JRW-0147.

In a Corning 3570 assay plate, purified Nluc enzyme (Promega Corporation), 20 mM DTT, and an Nluc pro-substrate (PBI-4442, which is described in US Patent Publication No. 2013/0130289), which is converted to an Nluc substrate upon reduction with DTT, was added. Compound titrations of JRW-0004, JRW-0013, JRW-0006, JRW-0042, JRW-0138, and JRW-0147 were then made (1:2 serial dilution in PBS, 11 points plus no inhibitor control, starting at 200 µM; 100 µM final concentration in reaction). Compound titrations were added in equal volume to the wells of the assay plate. The reactions were incubated at RT for 2 hrs, and luminescence was measured on Tecan M1000 Pro plate reader. Half-maximal inhibitor (thienopyrrole compound) concentrations ($IC_{50}$s) were determined using GraphPad Prism 6.03. FIG. 2 demonstrates that all compounds are capable of inhibiting purified Nluc enzyme.

Example 85

Specificity of Inhibition of Nluc Luciferase

Figure 3:
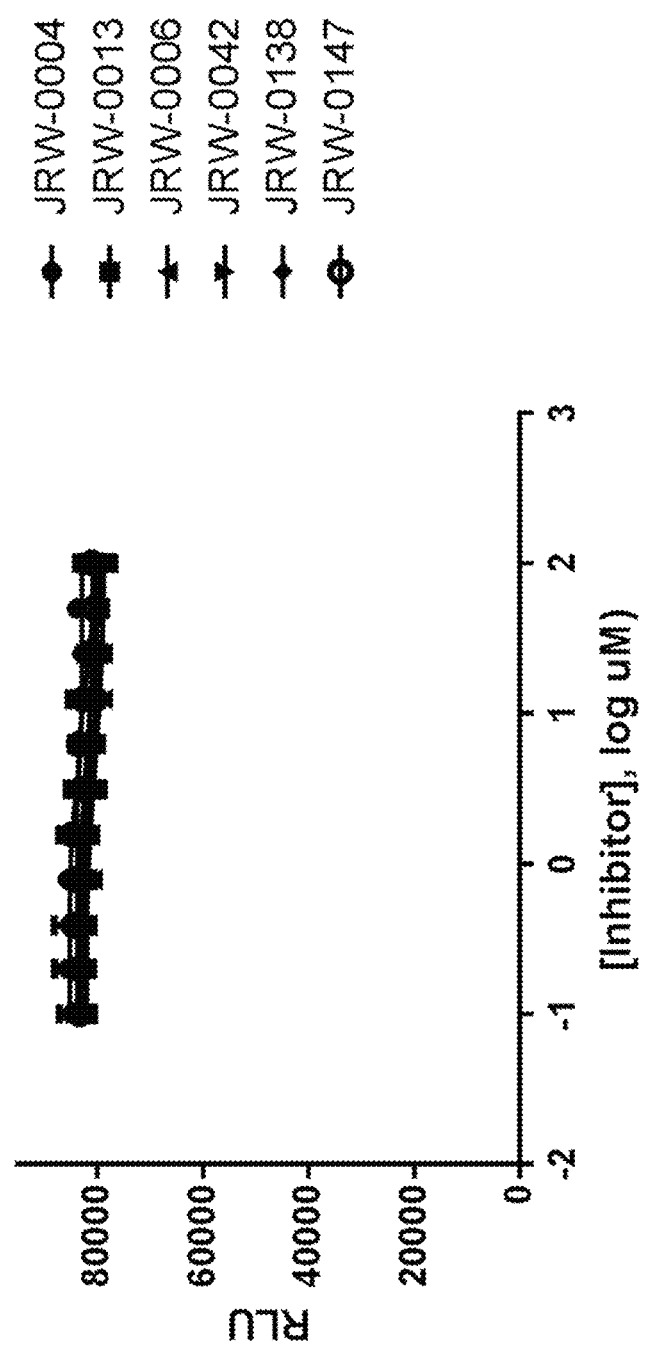
FIG. 3 shows the thienopyrrole compounds JRW-0004, JRW-0013, JRW-0006, JRW-0042, JRW-0138, and JRW-0147 do not inhibit firefly luciferase activity.

The following example describes the specificity of disclosed thienopyrrole compounds, JRW-0004, JRW-0013, JRW-0006, JRW-0042, JRW-0138, and JRW-0147, to inhibit Nluc luciferase activity versus firefly luciferase activity, e.g., ULTRAGLO® luciferase. In a Corning 3570 assay plate, a solution containing 1 µM luciferin in Luciferase Detection Reagent (Promega Corporation V865/859) was added to the assay wells. An equal volume of titrations the thienopyrrole compounds, JRW-0004, JRW-0013, JRW-0006, JRW-0042, JRW-0138, and JRW-0147 were then added to the wells. The reactions were incubated at RT for 2 hrs, and luminescence was measured on Tecan M1000 Pro plate reader. FIG. 3 demonstrates that the thienopyrrole compounds did not inhibit the firefly luciferase activity.

Example 86

Thienopyrrole Compounds Enable Multiplexing

The following examples describe the use of the thienopyrrole compounds of the present invention to allow multiplexing of assays which utilizing Nluc luciferase and another luciferase, e.g., firefly luciferase.

A) In a Corning 3570 assay plate, MCF7 cells were plated at 1,000 cells/well in 20 µL of cell culture media (EMEM supplemented with 0.01 mg/mL human recombinant insulin and 10% fetal bovine serum) and incubated in overnight. 10 µL of 4× REALTIME-GLO™ MT Cell Viability reagents (Promega Corporation) in media or 10 µL media only was added to the cells. 10 µL of 40 µM staurosporine in media or 10 µL media only (control) was added to the cells. The cells were incubated, and caspase activation monitored at 5.5 hrs post-reagent addition. To monitor caspase activation, 40 µL CASPASE-GLO® 3/7 Assay Reagent (Promega Corporation), either on its own (Caspase) or with 200 µM of JRW-0004, JRW-0013, or JRW-0042, was added. Reactions were incubated at RT, and luminescence was measured at 1 hr 10 min post-reagent addition on Tecan M1000 Pro plate reader.

Table 1 shows that the compounds inhibit the background luminescence from REALTIME-GLO™ in the multiplex with CASPASE-GLO® (media containing REALTIME-GLO™). When comparing the signal generated from the CASPASE-GLO® reagent in media only versus the signal generated in media containing REALTIME-GLO™ reagent, the signal is higher in the multiplex reaction. The compounds inhibit the Nluc enzyme and decrease the background luminescence from REALTIME-GLO™ reagent.

TABLE 1

| | MCF7 | | | | | | | |
|---|---|---|---|---|---|---|---|---|
| | Media only | | | | Media containing RealTime-Glo | | | |
| | Control | | 10 µM Stauro | | Control | | 10 µM Stauro | |
| | Avg | SD | Avg | SD | Avg | SD | Avg | SD |
| Caspase | 7448 | 1076 | 51670 | 7299 | 38144 | 3853 | 85801 | 6888 |
| Fold Cont | | | 6.94 | | | | 2.25 | |
| JRW-0004 | 9261 | 1017 | 54589 | 9231 | 9090 | 161 | 50266 | 3766 |
| Fold Cont | | | 5.89 | | | | 5.53 | |
| JRW-0013 | 8069 | 2461 | 55282 | 13491 | 8636 | 1777 | 54338 | 6157 |
| Fold Cont | | | 6.85 | | | | 6.29 | |
| JRW-0042 | 10718 | 1269 | 62280 | 6594 | 10679 | 1747 | 53956 | 4432 |
| Fold Cont | | | 5.81 | | | | 5.05 | |

B) A549 cells were plated at 1,000 cells/well in 20 µL F12K media into wells of a Corning 3570 plate (n-4) and incubated overnight. Then, REALTIME-GLO™ MT Cell Viability assay reagents (Promega Corporation) were added to the wells as a 2× solution in 20 µL media. The reaction was incubated for 1 hr. 40 µL of a titration of JRW-0013 or JRW-0147 in CASPASE-GLO® 3/7 assay reagent (Promega Corporation) at 2× concentrations was added. The reactions were incubated at RT, and luminescence was determined at 1 hr.

Table 2 demonstrates that these compounds can inhibit the Nluc enzyme in REALTIME-GLO™ MT Cell Viability assay in a multiplex with a CASPASE-GLO® assay in a dose-dependent manner.

TABLE 2

| Inhibitor | Caspase, JRW-0013 | | | Caspase, JRW-0147 | | |
|---|---|---|---|---|---|---|
| µM, final | Avg | SD | % remaining | Avg | SD | % remaining |
| 100 | 3619 | 454 | 6.10% | 3389 | 177 | 5.71% |
| 66.67 | 4017 | 450 | 6.77% | 3427 | 51 | 5.78% |
| 44.44 | 4419 | 35 | 7.45% | 4367 | 189 | 7.36% |
| 29.63 | 5132 | 145 | 8.65% | 4394 | 331 | 7.41% |
| 19.75 | 5095 | 330 | 8.59% | 5302 | 223 | 8.94% |
| 13.17 | 6014 | 591 | 10.14% | 5545 | 401 | 9.35% |
| 8.78 | 6703 | 406 | 11.30% | 7125 | 533 | 12.01% |
| 5.85 | 8059 | 801 | 13.59% | 8013 | 375 | 13.51% |
| 3.90 | 9148 | 271 | 15.42% | 9790 | 1213 | 16.51% |
| 2.60 | 11813 | 679 | 19.92% | 11677 | 189 | 19.69% |
| 1.73 | 12879 | 1093 | 21.71% | 15580 | 1288 | 26.27% |
| 0 | 59313 | 1970 | 100.00% | 59313 | 1970 | 100.00% |

Example 87

Figures 4A, 4B, 4C, 4D:
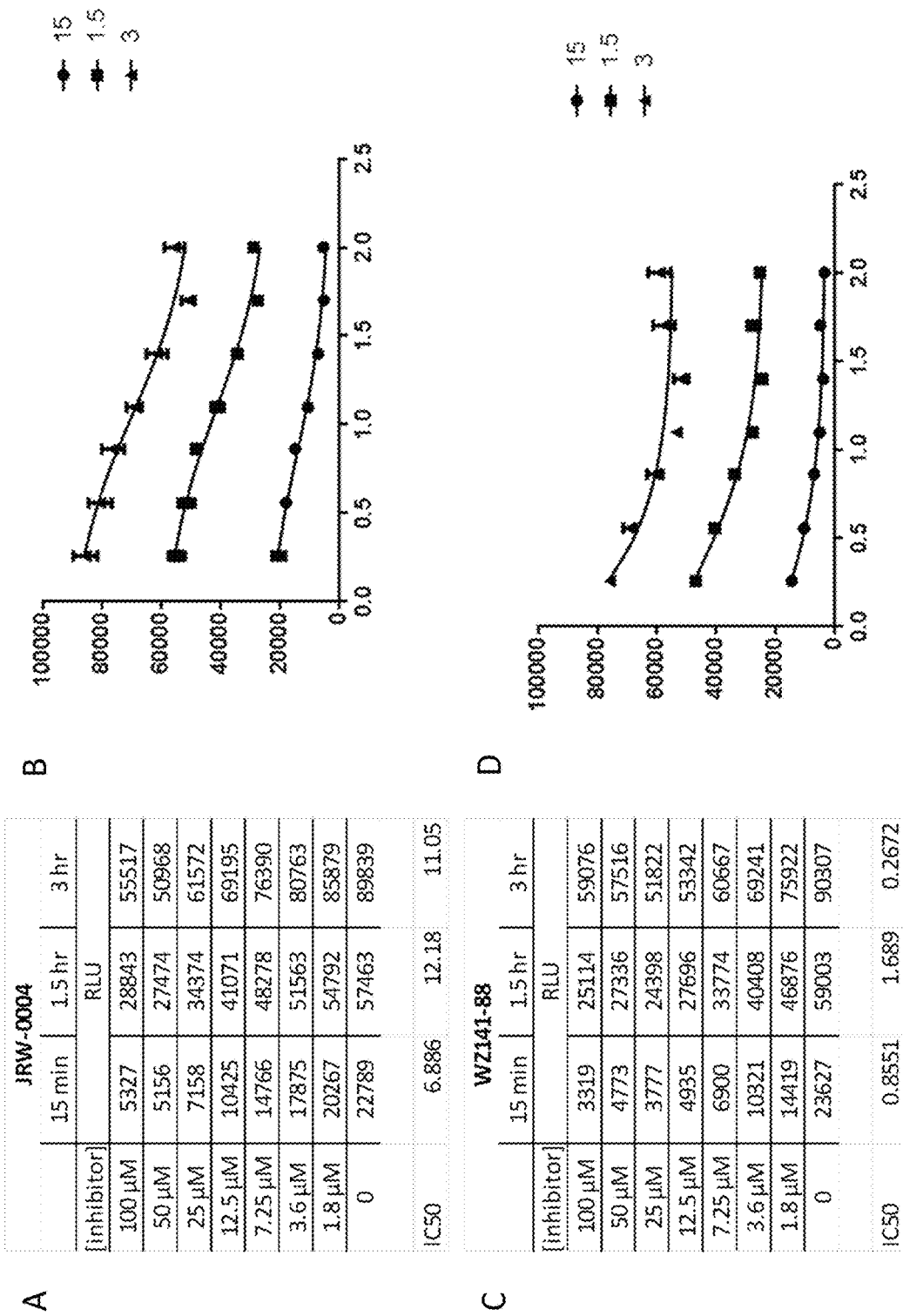
FIGS. 4A-4D show that thienopyrrole compounds JRW-0004 (FIGS. 4A and 4B) and WZ141-88 (FIGS. 4C and 4D) inhibit Nluc in a dose- and time-dependent manner.
Figures 5A, 5B, 5C, 5D:
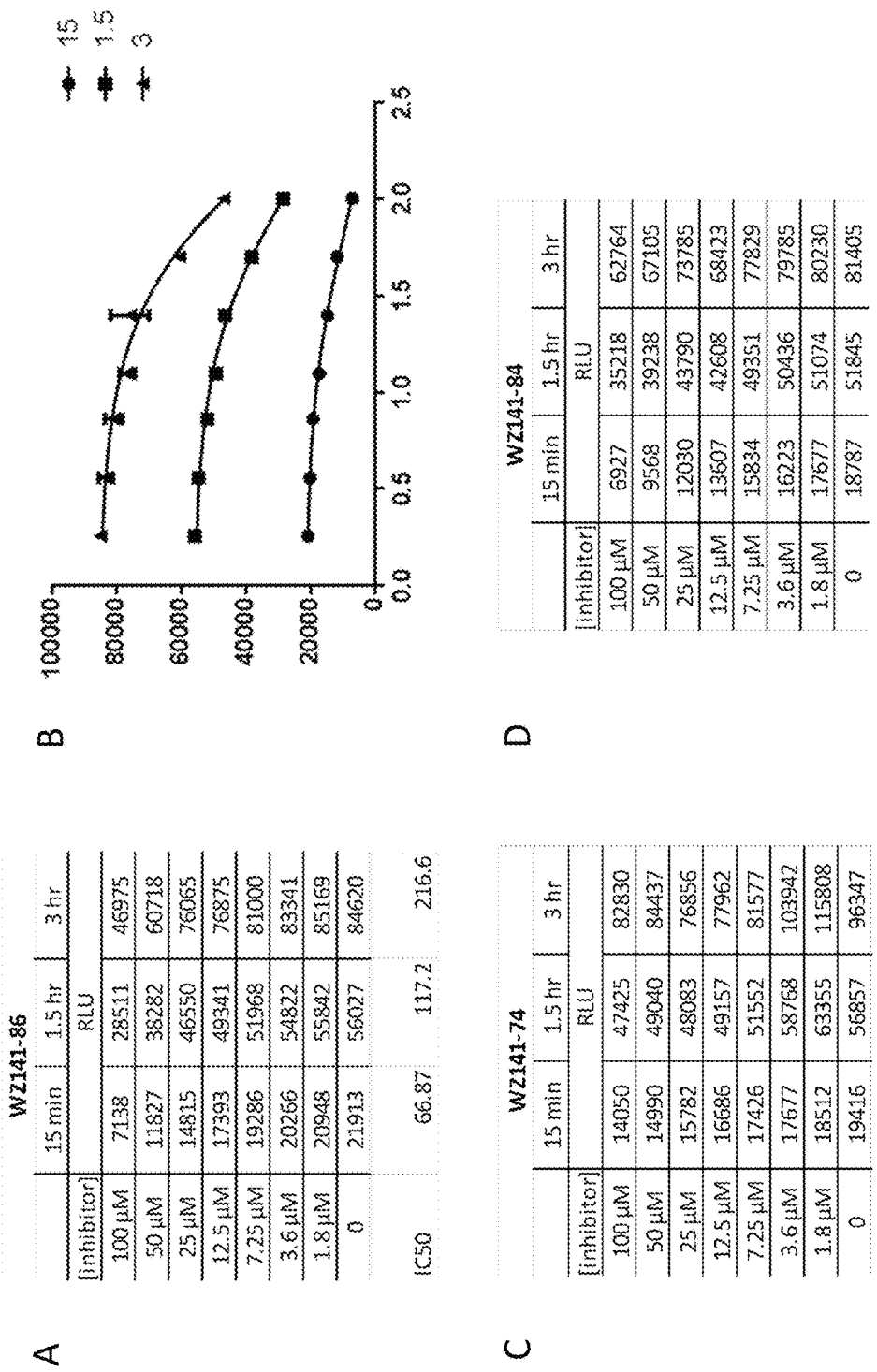
FIGS. 5A-5D show that thienopyrrole compounds WZ141-86 (FIGS. 5A and 5B), WZ141-74 (FIG. 5C), and WZ141-84 (FIG. 5D) inhibit Nluc in a dose- and time-dependent manner.
Figure 7A:
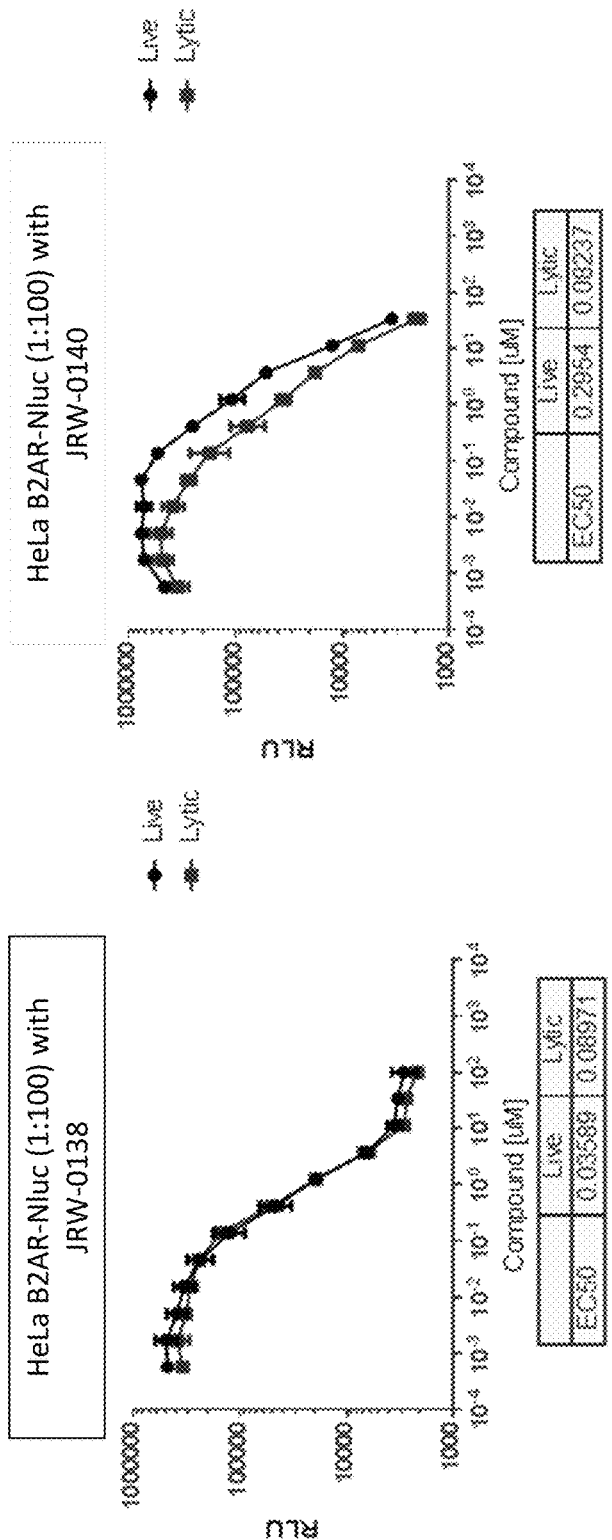
FIGS. 7A-7F show the permeability of the thienopyrrole compounds JRW-0138 (FIG. 7A), JRW-0140 (FIG. 7B), JRW-0142 (FIG. 7C), JRW-0143 (FIG. 7D), JRW-0145 (FIG. 7E), and JRW-0147 (FIG. 7F) using HEK293 or HeLa cells transiently transfected with a Beta-2 Adrenergic Receptor-Nluc fusion protein.
Figure 7B:
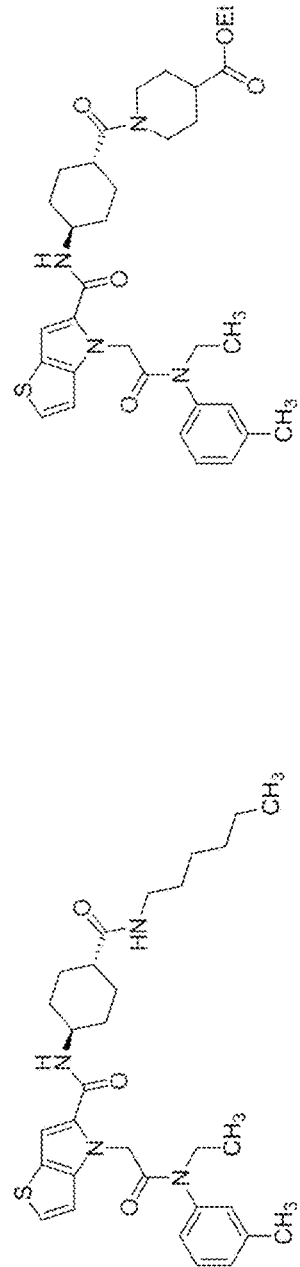
Figures 7C, 7D:
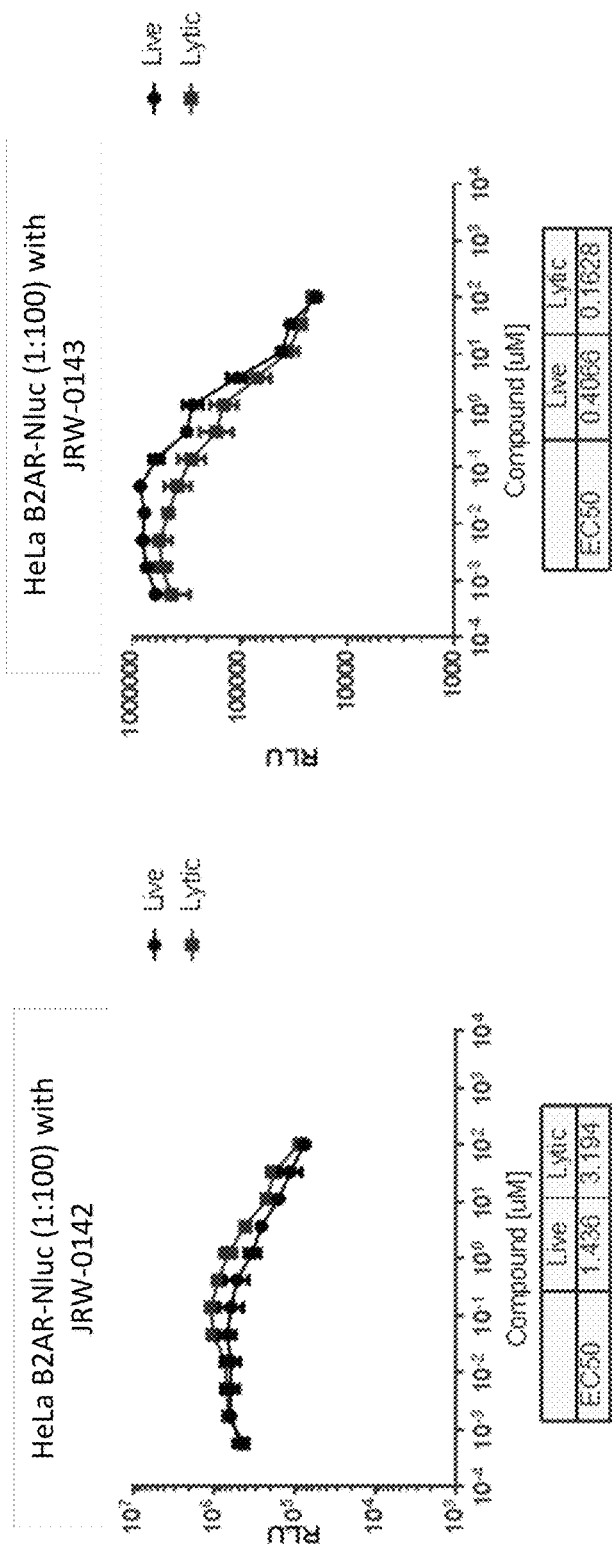
Figures 7E, 7F:
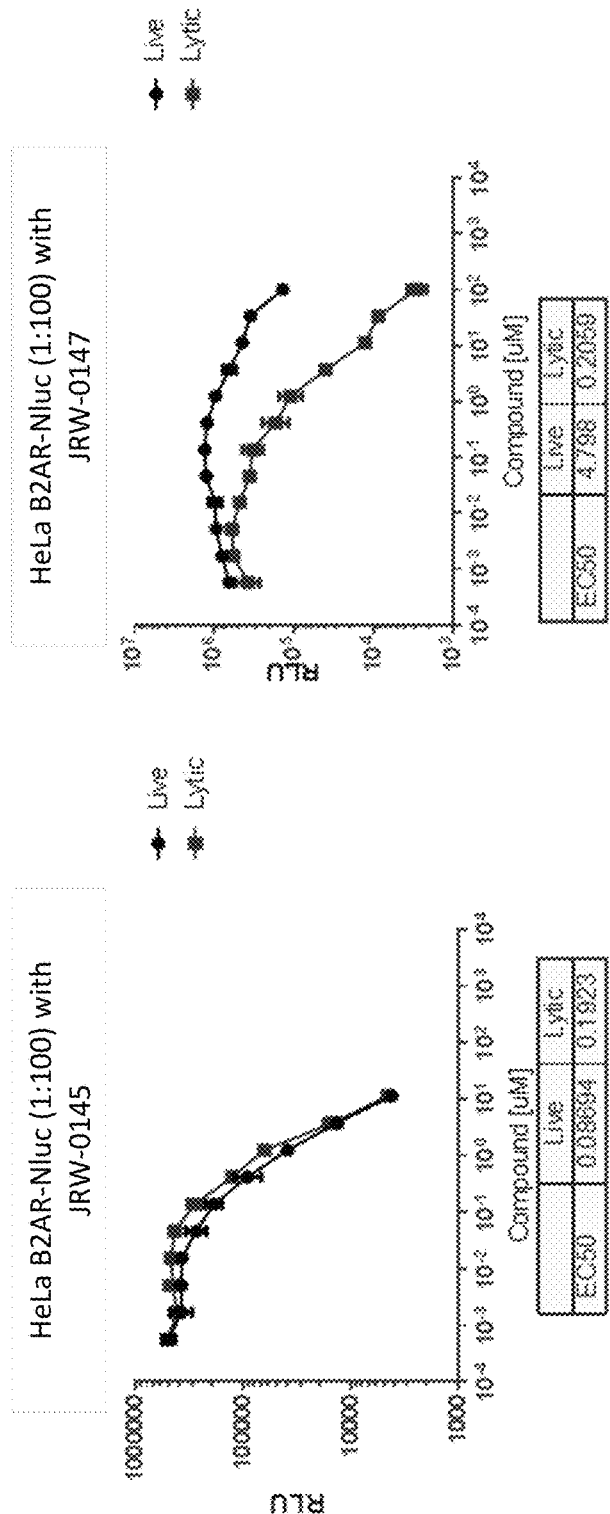
Figure 8A:
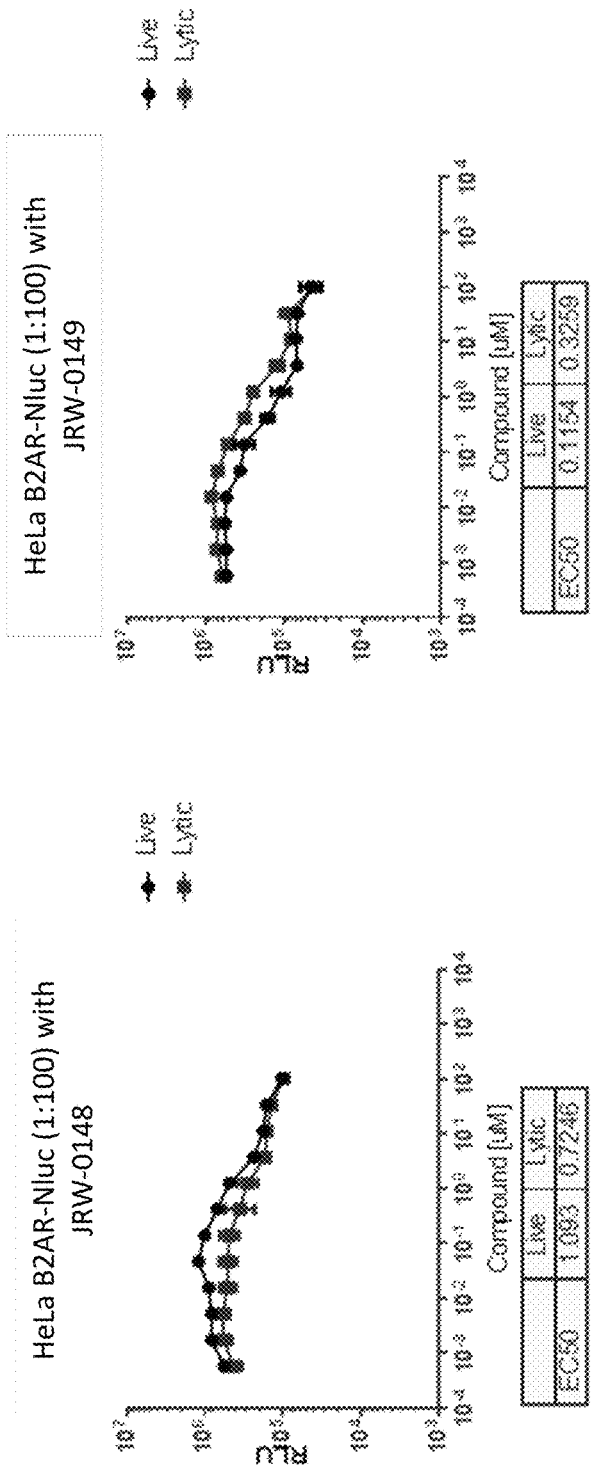
FIGS. 8A-8F show the permeability of the thienopyrrole compounds JRW-0148 (FIG. 8A), JRW-0149 (FIG. 8B), JRW-0151 (FIG. 8C), JRW-0152 (FIG. 8D), JRW-0051 (FIG. 8E), and JRW-0043 (FIG. 8F) using HEK293 or HeLa cells transiently transfected with a Beta-2 Adrenergic Receptor-Nluc fusion protein.
Figure 8B:
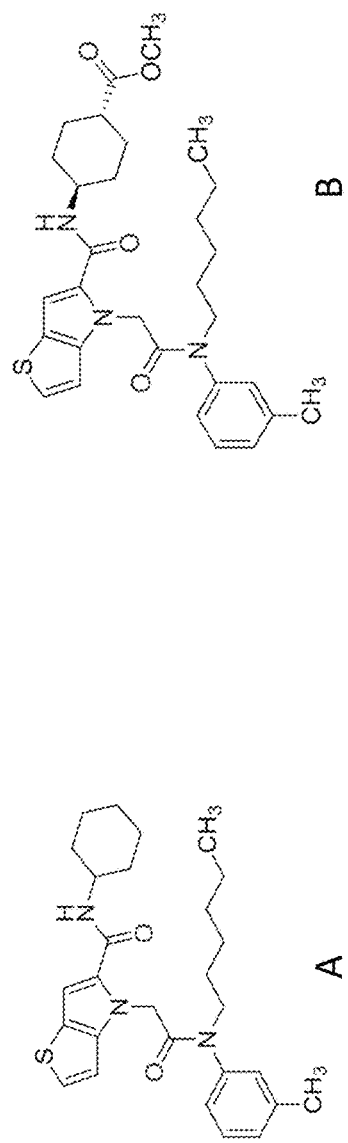
Figure 8C:
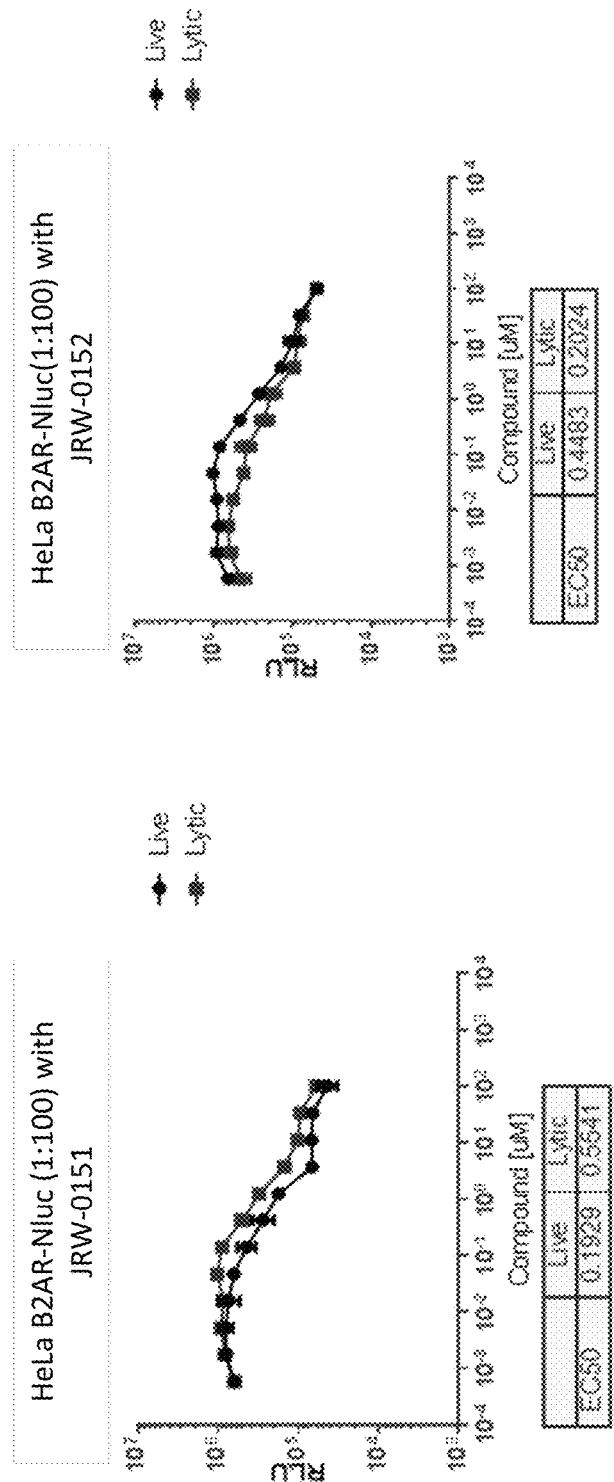
Figure 8D:
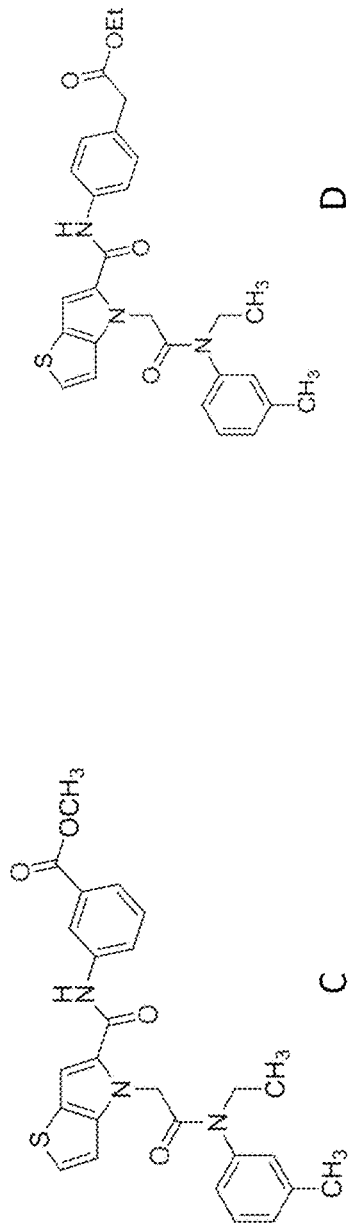
Figure 8E:
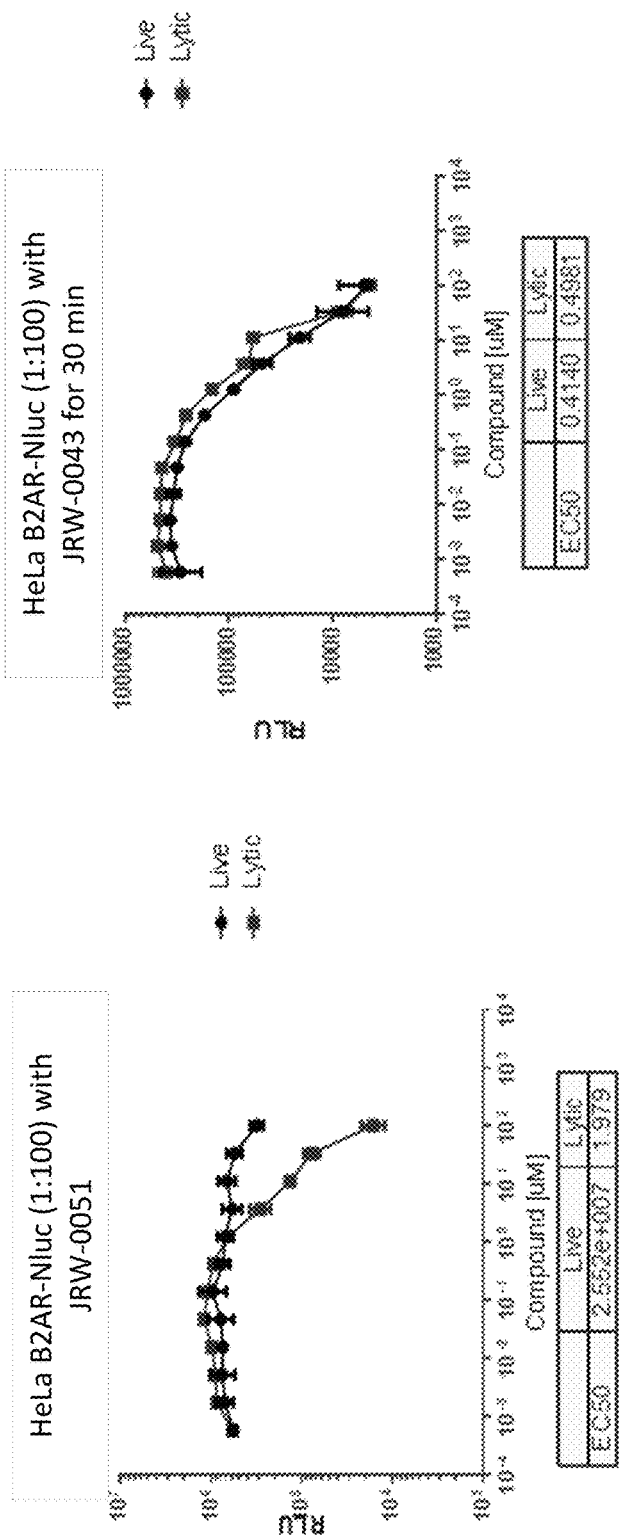
Figure 8F:
Figures 9A, 9B:
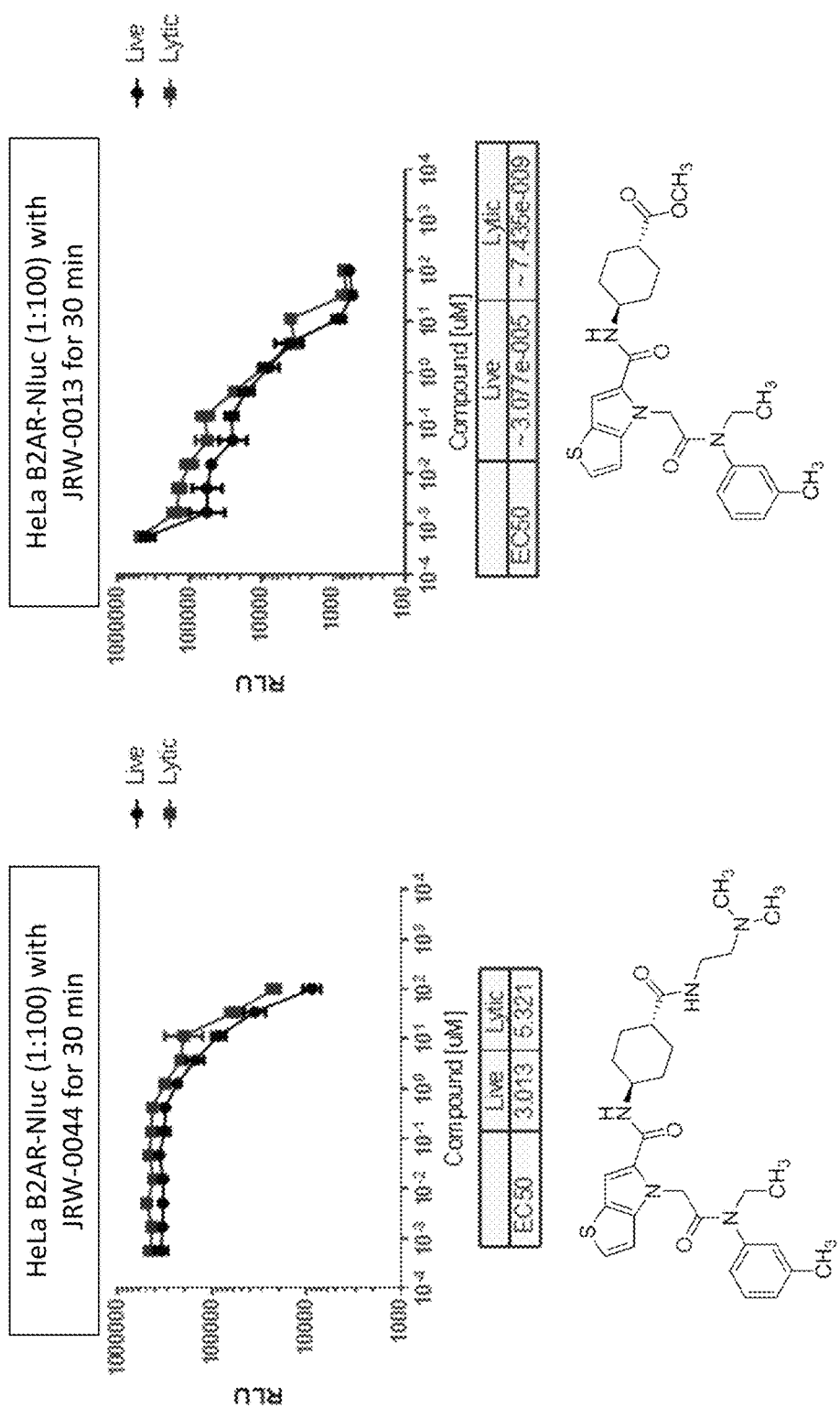
Figures 11A, 11B:
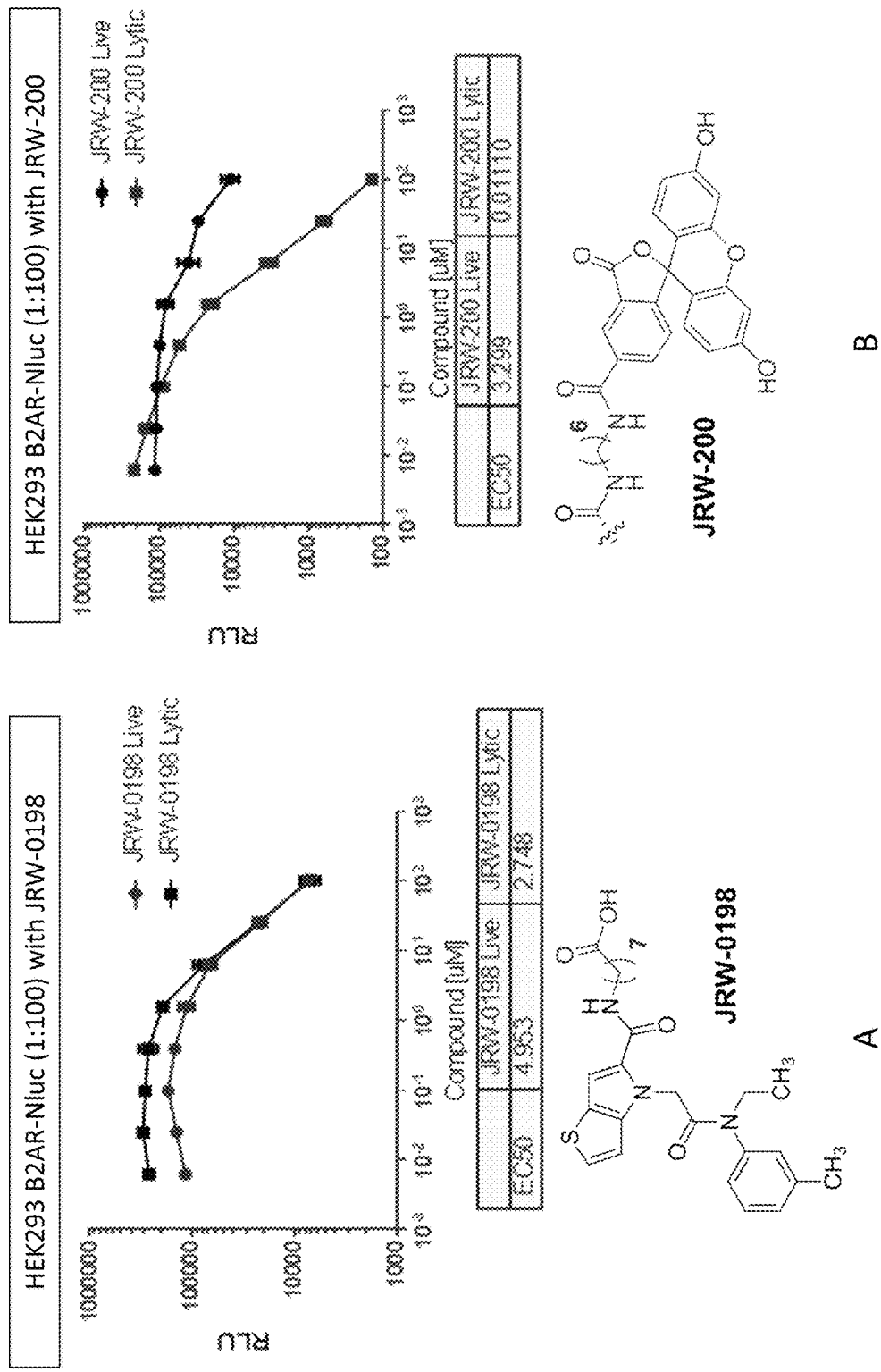
FIGS. 11A-11C show the permeability of the thienopyrrole compounds JRW-0198 (FIG. 11A), JRW-0200 (FIG. 11B), and JRW-0208 (FIG. 11C) using HEK293 or HeLa cells transiently transfected with a Beta-2 Adrenergic Receptor-Nluc fusion protein.
Figure 11C:
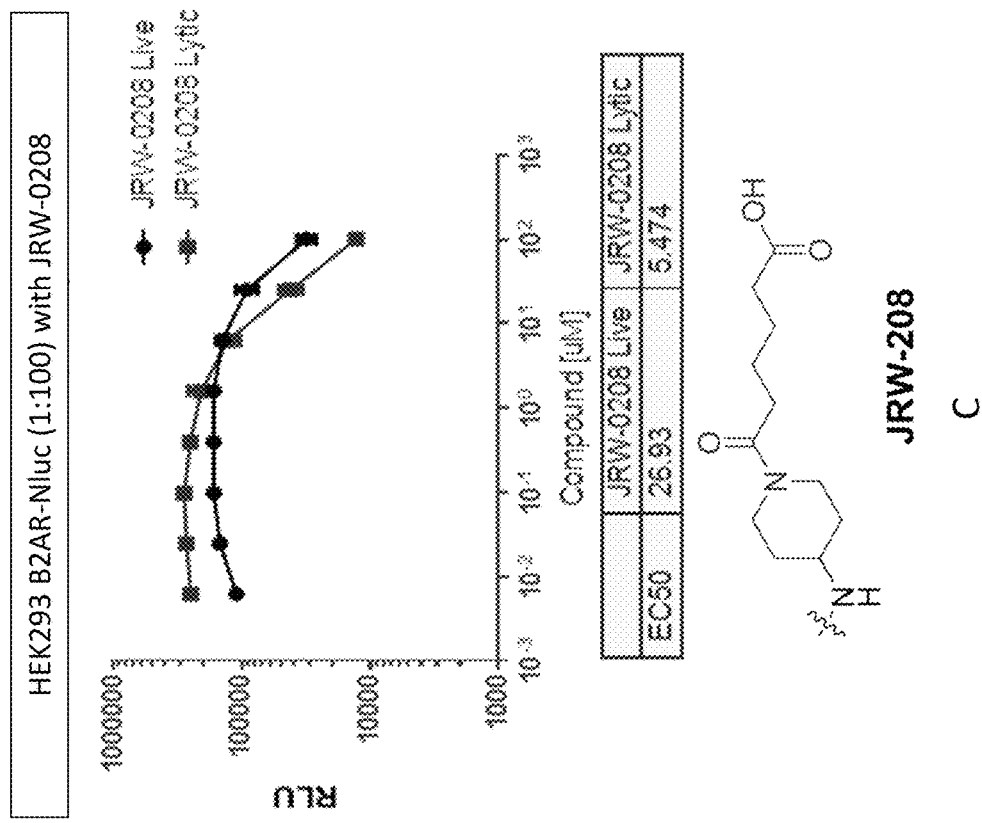

The following example demonstrates that compounds JRW-0004, WZ141-88, WZ141-86, WZ141-74, WZ141-84, WZ141-89, WZ141-90, and WZ141-91 inhibit Nluc luciferase. A solution of purified Nluc and an Nluc pro-substrate (PBI-4442, which is described in US 2013/0130289), which is converted to an Nluc substrate upon reduction with DTT, were prepared in PBS buffer, pH 7.5. A 40 mM solution of DTT in PBS, pH 7.5 containing 1% TERGITOL was also prepared. Titrations of the thienopyrrole compounds JRW-0004, WZ141-88, WZ141-86, WZ141-74, WZ141-84, WZ141-89, WZ141-90, and WZ141-91 in the buffer containing DTT and TERGITOL were then prepared. An equal volume of the Nluc/pro-substrate solution was added to the thienopyrrole compound titrations in wells of an assay plate. The reactions were incubated at RT, and luminescence was measured at various time points on the Tecan M100 Pro plate reader (integration time 200 ms). $IC_{50}$ values were determined using GraphPad Prism 6.03. FIGS. 4-6 demonstrate that all compounds tested inhibit Nluc luciferase in a dose- and time-dependent manner.

Example 88

Cell Permeability

The following example demonstrates the permeability of the thienopyrrole compounds described herein. HEK293 or HeLa cells were transiently transfected with Beta-2 Adrenergic Receptor-Nluc (B2AR-Nluc) fusion protein to anchor and orient Nluc cytosolically. 24 hrs post-transfection, cells were treated with −/+50 µg/mL digitonin to emulate a live and lytic scenario, respectively. Then, intact cells and permeabilized cells were exposed to a compound response curve of thienopyrrole compound up to 2 hrs. 10 µM furimazine (Promega Corp.) was added, and luminescence was measured. If a thienopyrrole compound (inhibitor) was permeable, the dose-response curves for both live and permeabilized cells overlapped. However, if a thienopyrrole compound was impermeable, the $EC_{50}$ was right-shifted in the live cells relative to the permeabilized cells. See FIGS. 7-11.

Example 89

Inhibition of Extracellular BRET

Figure 12A:
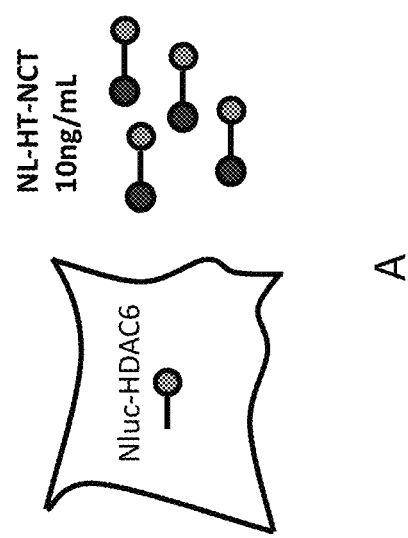
Figures 12, 12B, 13, 13C:
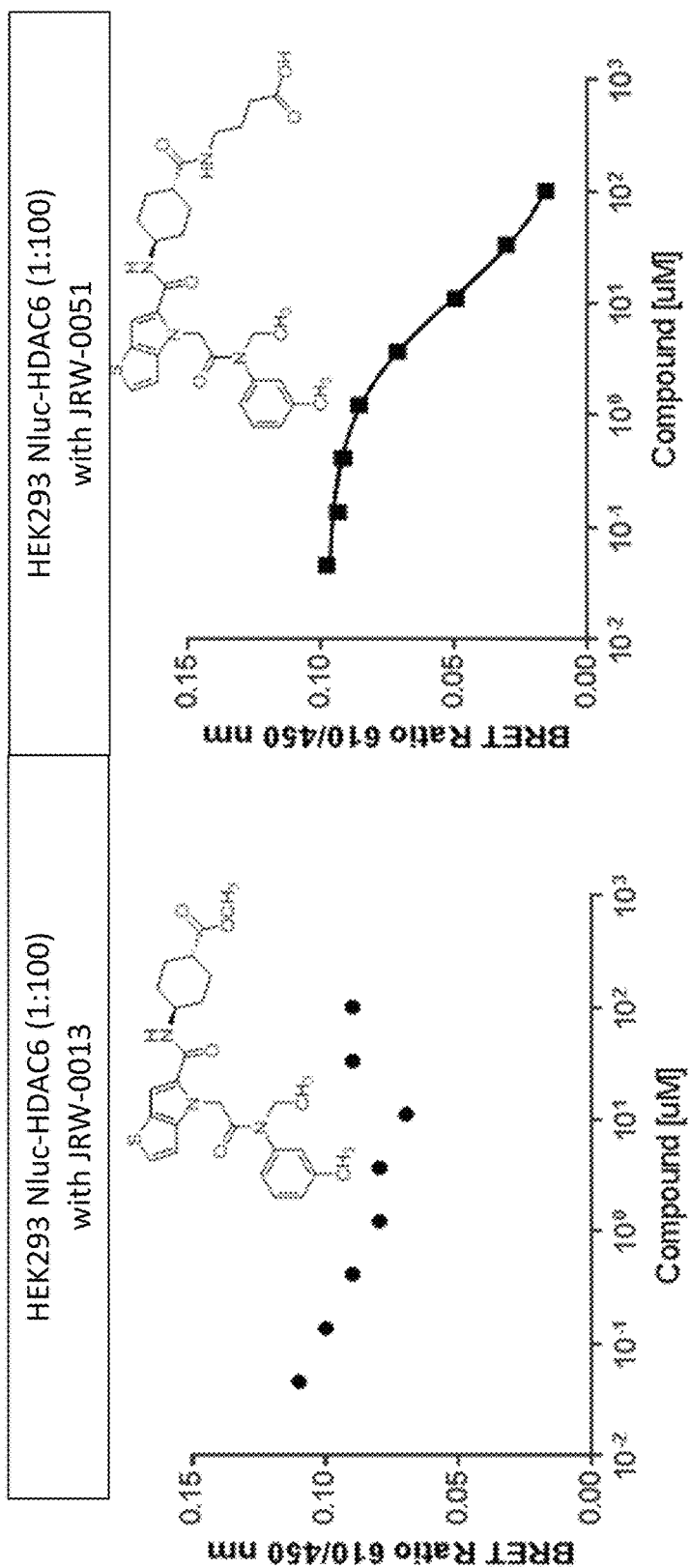
Figures 12D, 12E:
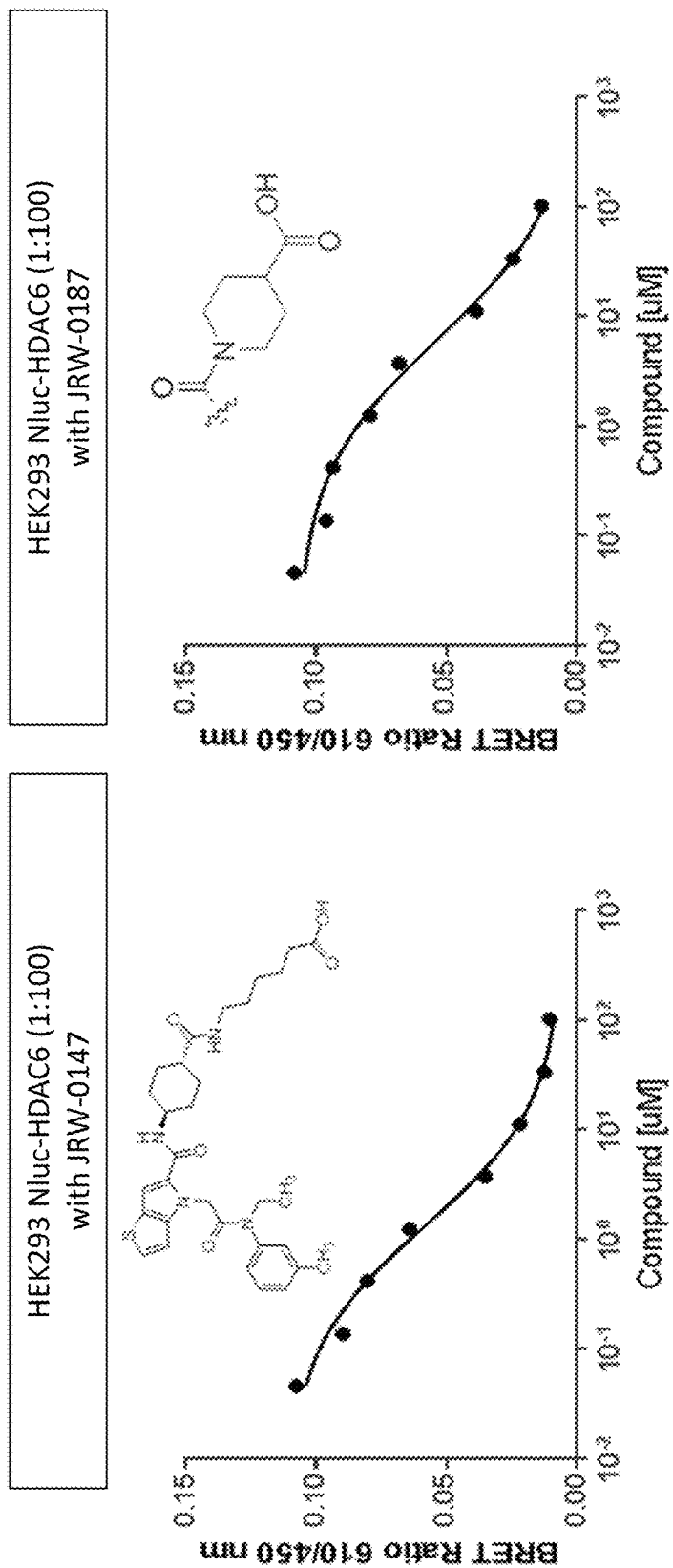

The following example demonstrates the ability of the thienopyrrole compounds described herein to inhibit extracellular BRET. See FIG. 12A. HEK293 were transiently transfected with an Nluc-HDAC6 fusion protein to orient Nluc-HDAC6 inside the cell. 24 hrs post-transfection, cells were treated 10 ng/mL purified Nluc-HALOTAG labeled with NANOBRET 618 ligand to simulate spurious extracellular BRET. Cells were then exposed to a compound response curve of the thienopyrrole compounds, JRW-0013, JRW-0051, JRW-0147, and JRW-0187, for 2 hrs. 10 µM furimazine was then added, and BRET ratio 610/450 nm was measured. If a thienopyrrole compound, such as JRW-0013, was permeable, the BRET ratio remained constant across the compound dose-response curve. If a thienopyrrole compound, such as JRW-0051, JRW-0147, or JRW-0187, was impermeable, the BRET ratio decreased across the compound dose-response curve and enhanced intracellular Nluc signal while inhibiting extracellular BRET. See FIGS. 12B-12E.

Example 90

Figure 13A:
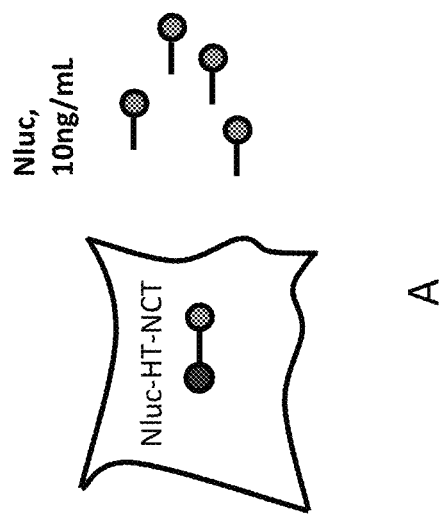
FIGS. 13A-13E show the ability of the thienopyrrole compounds to inhibit extracellular luciferase activity and enhance intracellular BRET.
Figures 13B, 13C:
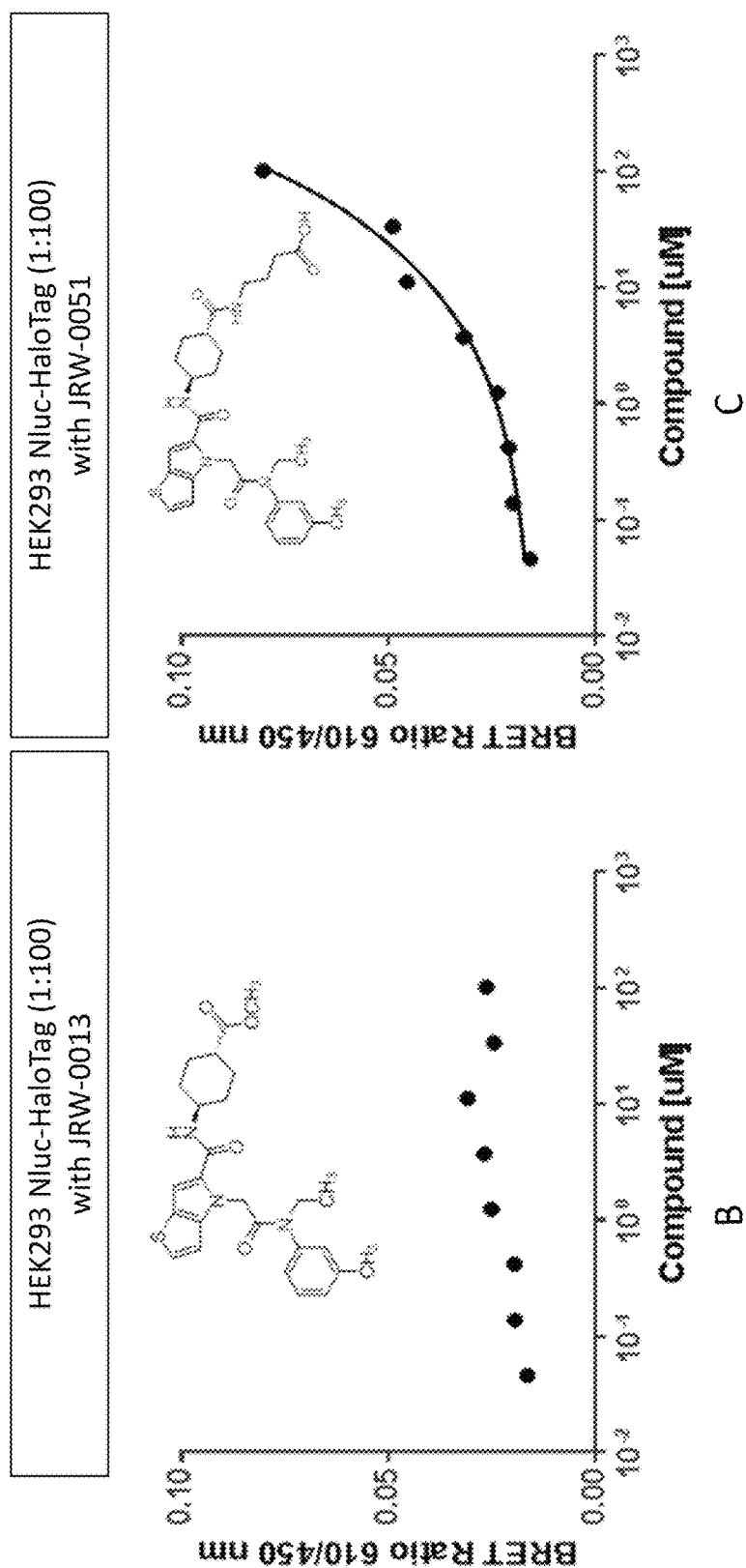
Figure 13D:
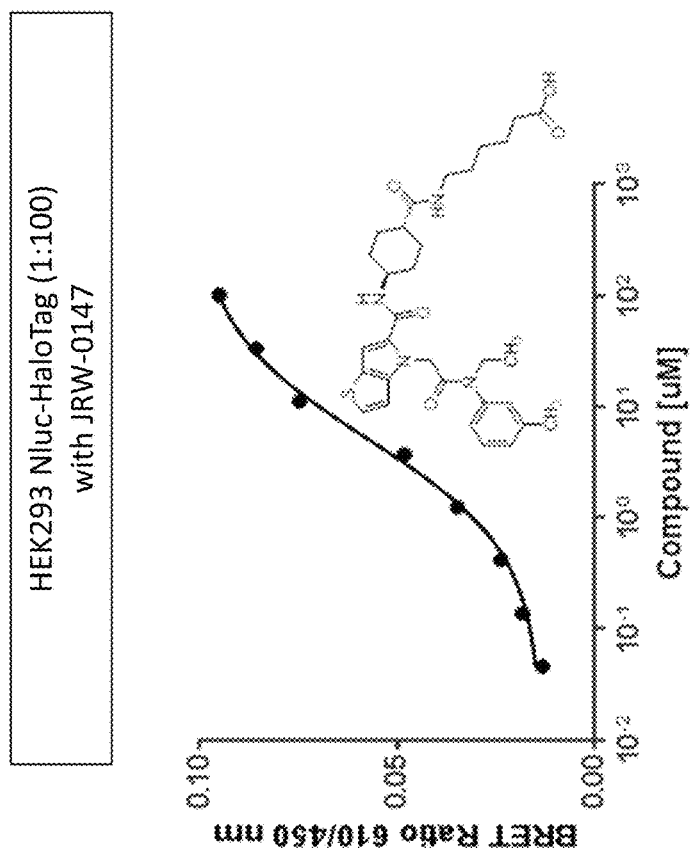
Figure 13E:
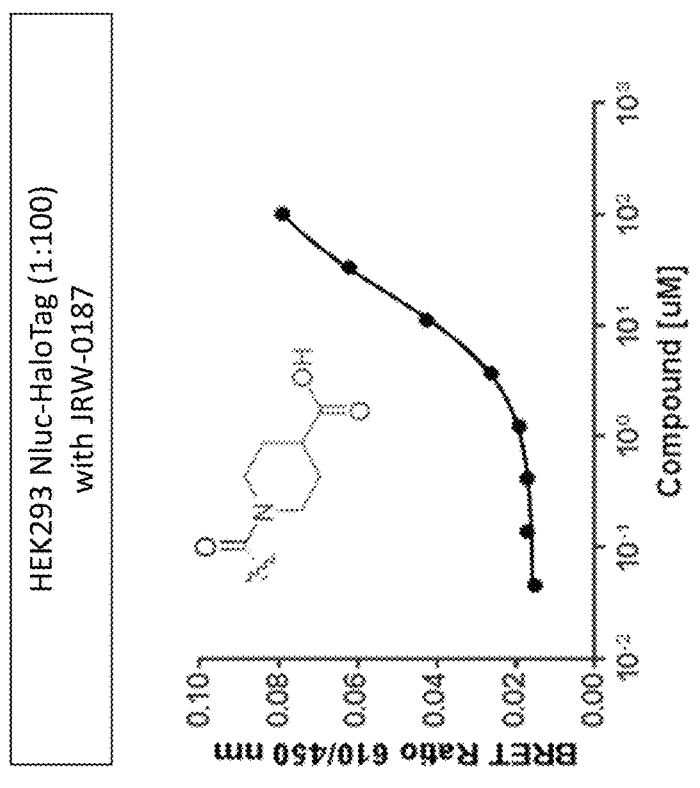

Inhibition of Extracellular Luciferase Activity and Enhancement of Intracellular BRET The following example demonstrates the ability of the thienopyrrole compounds described herein to inhibit extracellular luciferase activity while enhancing intracellular BRET. See FIG. 13A. HEK293 were transiently transfected with Nluc-HALOTAG fusion protein to orient Nluc-HALOTAG inside the cell. 24 hrs post-transfection, cells were labeled with NANOBRET 618 ligand to simulate specific intracellular BRET. Cells were then treated 10 ng/mL purified Nluc to simulate spurious extracellular luminescence. Cells were exposed to a compound response curve of the thienopyrrole compounds, JRW-0013, JRW-0051, JRW-0147, and JRW-0187, for 2 hrs. 10 µM furimazine was added, and the BRET ratio 610/450 nm was measured. If an inhibitor, such as JRW-0013, was permeable, the BRET ratio remained constant across the compound dose-response curve. If an inhibitor, such as JRW-0051, JRW-0147, or JRW-0187, was impermeable, the intracellular BRET ratio was enhanced across the compound dose-response curve while inhibiting spurious extracellular Nluc signal. See FIGS. 13B-13F.

Example 91

Cell Permeability with Bioluminescent Imaging

Figure 14:
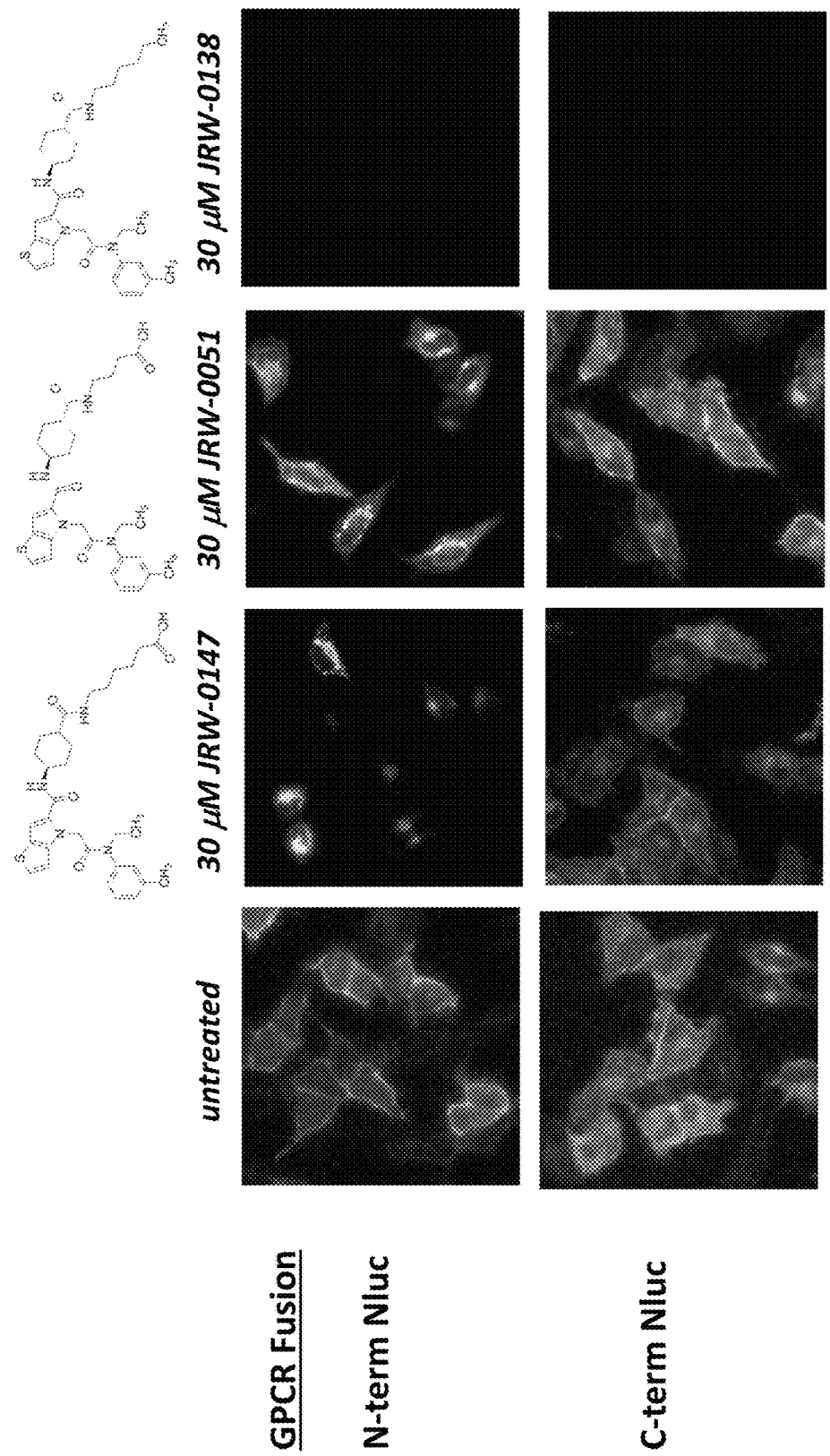
FIG. 14 shows the cell permeability of thienopyrrole compounds JRW-0147, JRW-0051, and JRW-0138.

HeLa cells were transiently transfected with Beta-2 Adrenergic Receptor-Nluc (B2AR-Nluc; C-Terminus Nluc) or Nluc-Beta-2 Adrenergic Receptor (Nluc-B2AR; N-terminus Nluc) fusion protein to anchor and orient Nluc intracellularly or extracellularly, respectively. 24 hrs post-transfection, cells were treated with −/+30 µM of a thienopyrrole compound, JRW-0147, JRW-0051, and JRW-0138. 10 µM furimazine was added, and luminescence was detected by imaging on the Olympus LV200. Thienopyrrole compounds JRW-0147 and JRW-0051 were impermeable and inhibited extracellular Nluc and enhanced intracellular Nluc. Compound JRW-0138 was cell permeable and inhibited both intracellular and extracellular Nluc. See FIG. 14

Example 92

Figure 15A:
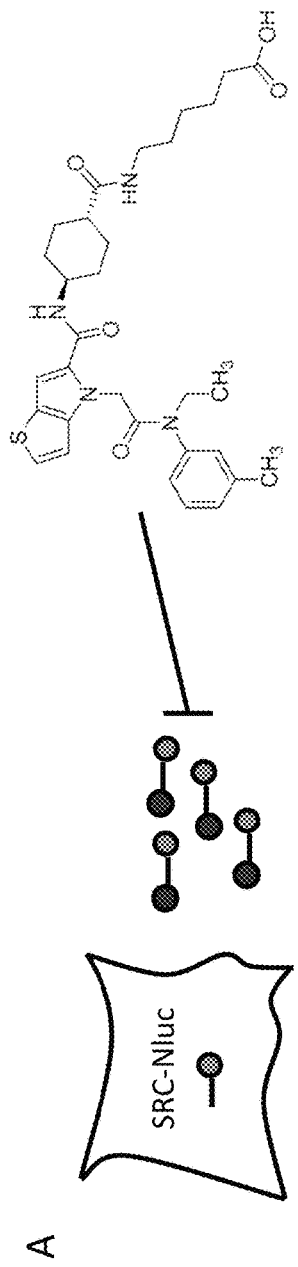
FIGS. 15A-15C show the cell impermeability of thienopyrrole compound JRW-0147 in a target engagement model.
Figure 15B:
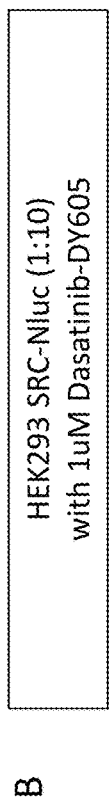
Figure 15C:
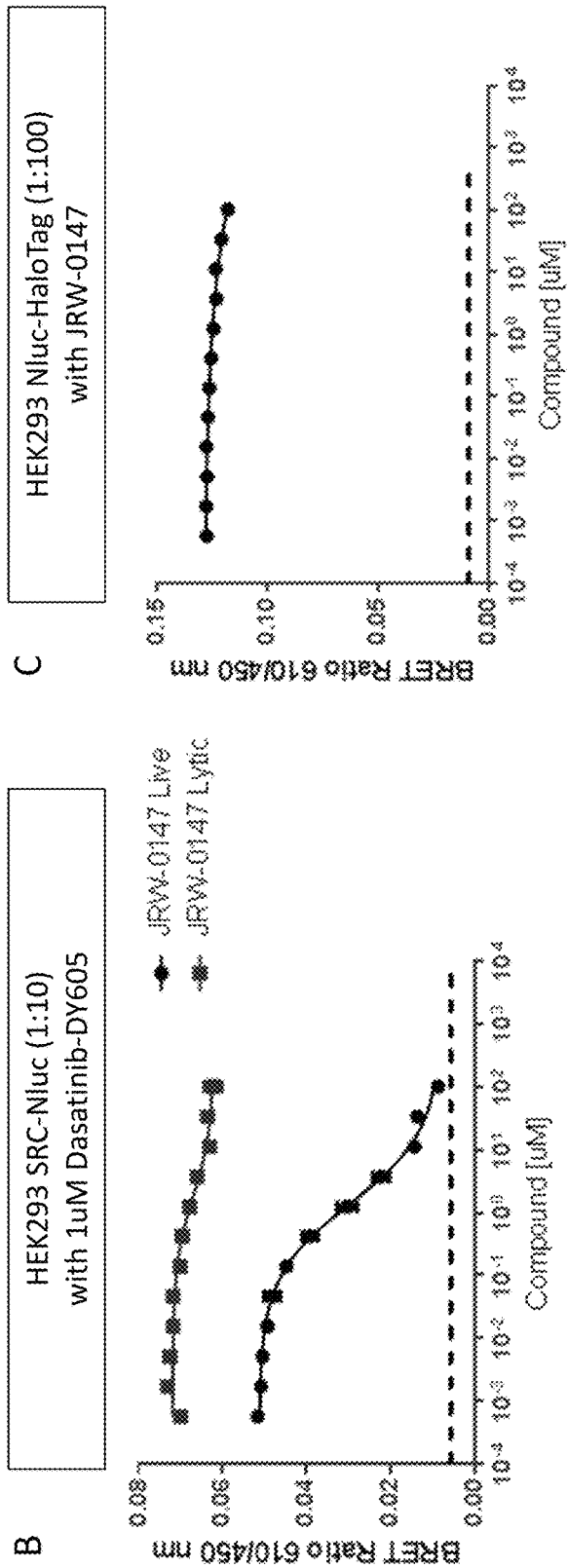

Characterization of an Impermeable Thienopyrrole Compound in a Target Engagement Model HEK293 cells were transiently transfected with Src-Nluc fusion protein. See FIG. 15A. 24 hours post-transfection, cells were treated with −/+50 μg/mL digitonin to simulate a live and lytic scenario, respectively. Intact cells and permeabilized cells were labeled with 1 μM Dasatinib-DY605 tracer (impermeable) and treated with a cell impermeable thienopyrrole compound JRW-0147 response curve for 2 hrs. 10 μM furimazine was added, and a BRET ratio 610/450 nm was recorded. FIGS. 15B-15C demonstrates that JRW-0147 inhibited BRET in cell debris, but not BRET inside cells.

Example 93

Cell Permeability Time Course

The following example demonstrates the permeability of the thienopyrrole compounds described herein. HEK293 cells were transiently transfected with Nluc luciferase to express it cytosolically. Twenty-four hours post-transfection, cells were exposed to a compound response curve of the thienopyrrole compound JRW-0147 or JRW-0013 for 10 minutes, 30 minutes, or 120 minutes. 10 μM furimazine was then added, and luminescence was measured.

Figure 16:
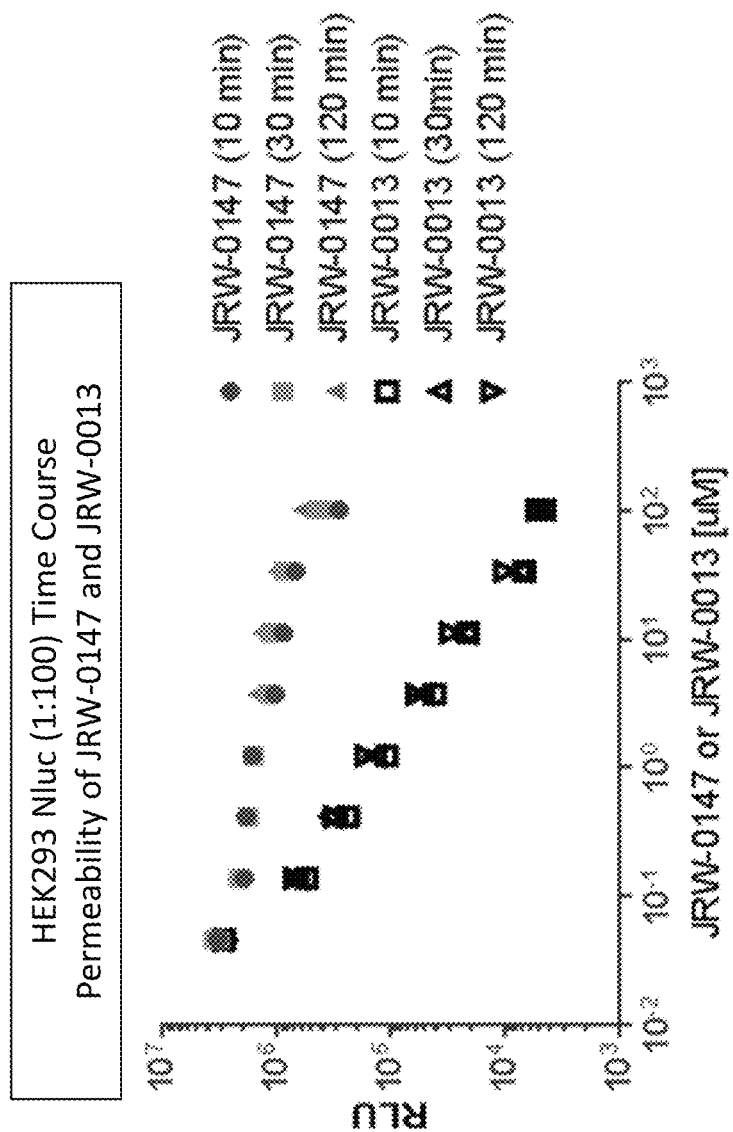
FIG. 16 shows the permeability of the thienopyrrole compounds JRW-0147 and JRW-0013.

If the thienopyrrole compound (inhibitor) was permeable, the compound would passively enter the cell and decrease the RLUs from Nluc in a dose-dependent manner independent of time, such as was seen by JRW-0013 (FIG. 16). If the thienopyrrole compound (inhibitor) was impermeable, the compound would not actively or passively enter the cell, and no significant change in RLUs from Nluc would be observed in a dose-dependent manner independent of time, such as was seen by JRW-0147 (FIG. 16).

Example 94

Measurement of Endocytosis by Chemical Conjugation or Molecular Fusion to Nluc

Antibodies, proteins, receptors, drugs, drug carriers, peptides, sugars, fatty acids, nanoparticles, or other biomolecules could be either chemically conjugated or fused to Nluc to measure endocytosis in combination with the cell impermeable thienopyrrole compound (inhibitor) described herein.

For example, a monoclonal antibody (e.g., Nluc-Trastuzumab) could be chemically conjugated and bound to the HER2 receptor expressed on the surface of SKBR3 cells. Cell impermeable Nluc inhibitor could be applied to inhibit extracellular Nluc-Trastuzumab. Upon addition of a coelenterazine substrate, a gain of signal assay could be used to kinetically measure active/passively internalized Trastuzumab-Nluc-HER2 receptor, which can be extended to other antibodies, proteins, receptors, drugs, drug carriers, peptides, sugars, fatty acids, nanoparticles, or other biomolecules chemically conjugated to Nluc.

In another example, Nluc-GPCRs (e.g., Nluc-B2AR) could be genetically fused and expressed in mammalian cells. A cell impermeable thienopyrrole compound (inhibitor) as described herein could be applied to inhibit extracellular or membrane bound Nluc-B2AR. Upon addition of coelenterazine substrate, a gain of signal assay could be used to kinetically measure active/passively internalized or recycled Nluc-GPCR, which can be extended to other proteins or receptors genetically fused to Nluc.

Example 95

Specificity of Inhibition of Nluc Luciferase

The following example describes the specificity of disclosed thienopyrrole compounds, JRW-0251, JRW-0344, and JRW-0147, to inhibit Nluc luciferase activity versus firefly luciferase activity, e.g., ULTRAGLO® luciferase. In a Corning 3570 assay plate, a solution containing 1 μM luciferin in Luciferase Detection Reagent (Promega Corporation V865/859) was added to the assay wells. An equal volume of titrations the thienopyrrole compounds, JRW-0251, JRW-0344, and JRW-0147 were then added to the wells. The reactions were incubated at RT for 2 hrs, and luminescence was measured on Tecan M1000 Pro plate reader. Table 3 demonstrates that the thienopyrrole compounds did not inhibit the firefly luciferase activity.

TABLE 3

| [cmpd], μM | JRW-0147 | | | JRW-0251 | | | JRW-0344 | | |
|---|---|---|---|---|---|---|---|---|---|
| | Avg | SD | S/B | Avg | SD | S/B | Avg | SD | S/B |
| | Nluc | | | | | | | | |
| 200 | 23722 | 4826 | 0.20 | 23311 | 208 | 0.20 | 16291 | 559 | 0.15 |
| 100 | 32702 | 7220 | 0.27 | 34389 | 977 | 0.30 | 23445 | 1930 | 0.21 |
| 50 | 42630 | 9430 | 0.36 | 44219 | 809 | 0.39 | 32113 | 3215 | 0.29 |
| 25 | 54498 | 13398 | 0.46 | 55210 | 1757 | 0.48 | 40392 | 3250 | 0.36 |
| 12.5 | 66480 | 17301 | 0.56 | 68664 | 2710 | 0.60 | 52627 | 5302 | 0.47 |
| 6.25 | 79191 | 19070 | 0.67 | 81193 | 1762 | 0.71 | 65136 | 4742 | 0.59 |
| 3.125 | 96256 | 5190 | 0.81 | 86555 | 1625 | 0.76 | 71976 | 4730 | 0.65 |
| 1.5625 | 103399 | 1432 | 0.87 | 96602 | 2280 | 0.84 | 83141 | 6007 | 0.75 |
| 0.78125 | 111603 | 2902 | 0.94 | 105881 | 4664 | 0.92 | 95060 | 6457 | 0.86 |
| 0.390625 | 113278 | 2111 | 0.95 | 106075 | 788 | 0.93 | 99851 | 5327 | 0.90 |
| 0.1953125 | 115442 | 1723 | 0.97 | 108634 | 436 | 0.95 | 102409 | 6375 | 0.92 |
| 0 | 119061 | 5586 | 1.00 | 114494 | 1203 | 1.00 | 110876 | 6347 | 1.00 |

TABLE 3-continued

|  | JRW-0147 | | | JRW-0251 | | | JRW-0344 | | |
|---|---|---|---|---|---|---|---|---|---|
| [cmpd], μM | Avg | SD | S/B | Avg | SD | S/B | Avg | SD | S/B |
| | UltraGlo luciferase | | | | | | | | |
| 200 | 78035 | 4010 | 0.90 | 77788 | 618 | 0.92 | 77230.33 | 1326 | 0.93 |
| 100 | 80636 | 3824 | 0.93 | 79556 | 842 | 0.94 | 79847.67 | 842 | 0.96 |
| 50 | 81106 | 3963 | 0.94 | 81930 | 632 | 0.97 | 81805.00 | 791 | 0.98 |
| 25 | 84033 | 3435 | 0.97 | 83382 | 780 | 0.99 | 83084.00 | 711 | 1.00 |
| 12.5 | 83291 | 2687 | 0.97 | 83569 | 583 | 0.99 | 82454.67 | 723 | 0.99 |
| 6.25 | 83282 | 2956 | 0.97 | 83665 | 969 | 0.99 | 83064.33 | 805 | 1.00 |
| 3.125 | 82252 | 1230 | 0.95 | 81125 | 240 | 0.96 | 80134.33 | 350 | 0.96 |
| 1.5625 | 83668 | 949 | 0.97 | 82370 | 308 | 0.98 | 81368.33 | 812 | 0.98 |
| 0.78125 | 84072 | 1686 | 0.97 | 82812 | 745 | 0.98 | 82135.67 | 1203 | 0.99 |
| 0.390625 | 84087 | 1748 | 0.97 | 82723 | 1752 | 0.98 | 82945.67 | 1154 | 1.00 |
| 0.1953125 | 85561 | 2108 | 0.99 | 83059 | 1024 | 0.98 | 83526.33 | 832 | 1.00 |
| 0 | 86300 | 1882 | 1.00 | 84426 | 1289 | 1.00 | 83352.67 | 1781 | 1.00 |

Example 96

Thienopyrrole Compounds Enable Multiplexing

The following examples describe the use of the thienopyrrole compounds of the present invention to allow multiplexing of assays which utilizing Nluc luciferase and another luciferase, e.g., firefly luciferase.

In a Corning 3570 assay plate, 1× REAL-TIME-GLO™ MT Cell Viability assay reagent was prepared in 40 μL DMEM media (n=3) and incubated overnight. Next, 40 μL of a titration of JRW-0147 or JRW-0344 (2× concentration in CASPASE-GLO® 3/7 Assay Reagent (Promega Corporation)) was added. The reactions were incubated at room temperature, and luminescence determined at 1 hour.

Table 4 shows that the compounds inhibit the background luminescence from REALTIME-GLO™ assay in the multiplex with CASPASE-GLO® assay (media containing REALTIME-GLO™ reagent). The compounds inhibit the Nluc enzyme and decrease the background luminescence from REALTIME-GLO™ reagent.

TABLE 4

| 1 hour | JRW-0147 | | | JRW-0344 | | |
|---|---|---|---|---|---|---|
| [cmpd], final μM | Avg | SD | S/B | Avg | SD | S/B |
| 100 | 6568 | 1159 | 0.05 | 5523 | 956 | 0.03 |
| 50 | 8136 | 700 | 0.06 | 6790 | 802 | 0.04 |
| 25 | 10699 | 1130 | 0.08 | 9761 | 674 | 0.06 |
| 12.5 | 17293 | 2129 | 0.12 | 15547 | 3856 | 0.10 |
| 6.25 | 27817 | 3812 | 0.20 | 19560 | 3555 | 0.12 |
| 3.125 | 45167 | 579 | 0.32 | 33523 | 3740 | 0.21 |
| 1.5625 | 65173 | 1320 | 0.47 | 65097 | 6521 | 0.41 |
| 0.78125 | 106867 | 8866 | 0.77 | 95993 | 7772 | 0.61 |
| 0.390625 | 117833 | 5829 | 0.85 | 138900 | 31425 | 0.88 |
| 0.1953125 | 124500 | 7192 | 0.89 | 126333 | 20215 | 0.80 |
| 0.09765625 | 117067 | 8214 | 0.84 | 112533 | 14372 | 0.71 |
| 0 | 139367 | 11254 | 1.00 | 158067 | 13180 | 1.00 |

Example 97

Cell Permeability

Figures 17A, 17B:
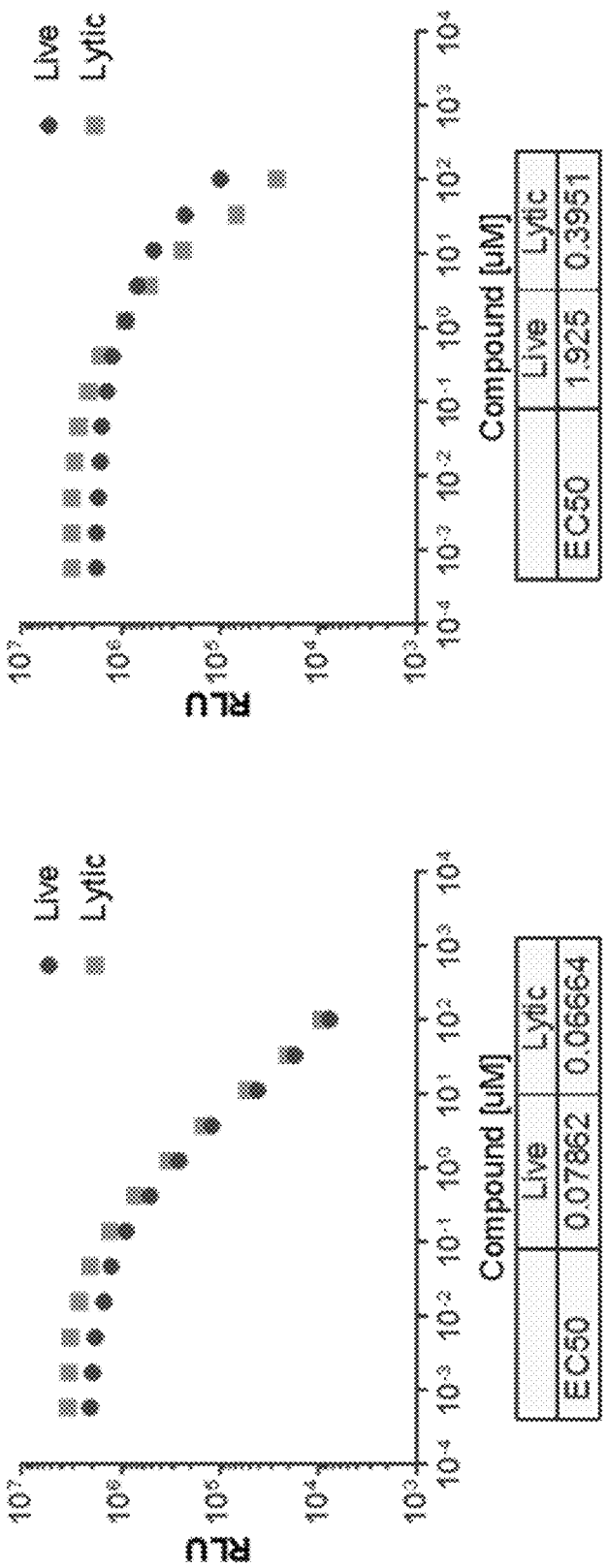
FIGS. 17A-17C show the permeability of the thienopyrrole compounds JRW-0013 (FIG. 17A), JRW-0147 (FIG. 17B), and JRW-0344 (FIG. 17C) using HEK293 cells transiently transfected with a Beta-2 Adrenergic Receptor-Nluc fusion protein.
Figure 17C:
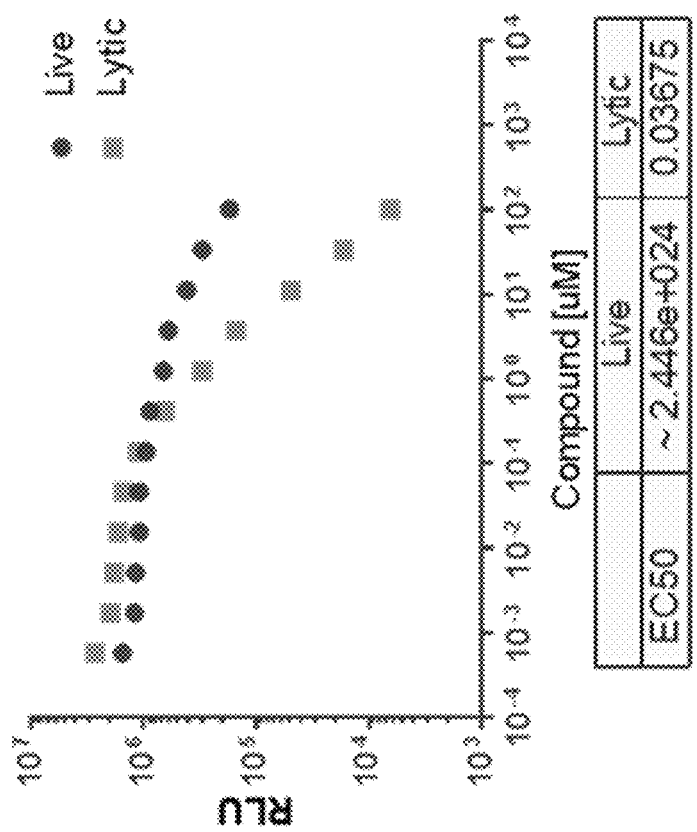

The following example demonstrates the permeability of the thienopyrrole compounds described herein. HEK293 were transiently transfected with Beta-2 Adrenergic Receptor-Nluc (B2AR-Nluc) fusion protein to anchor and orient Nluc cytosolically and pGEM-3z carrier DNA (1:100). 24 hrs post-transfection, cells were treated with −/+50 μg/mL digitonin to emulate a live and lytic scenario, respectively. Then, intact cells and permeabilized cells were exposed to a compound response curve of thienopyrrole compound up to 2 hrs. 10 μM furimazine (Promega Corp.) was added, and luminescence was measured. If a thienopyrrole compound (inhibitor) was permeable, the dose-response curves for both live and permeabilized cells overlapped. However, if a thienopyrrole compound was impermeable, the EC50 was right-shifted in the live cells relative to the permeabilized cells. FIGS. 17A-17C demonstrates that JRW-0147 and JRW-0344 are cell impermeable characterized by right shifted EC50 in Live vs. Lytic cells. JRW-0013 served as a cell permeable control characterized by similar EC50 in Live vs Lytic cells.

Example 98

Cell Viability and Toxicity

Figure 18A:
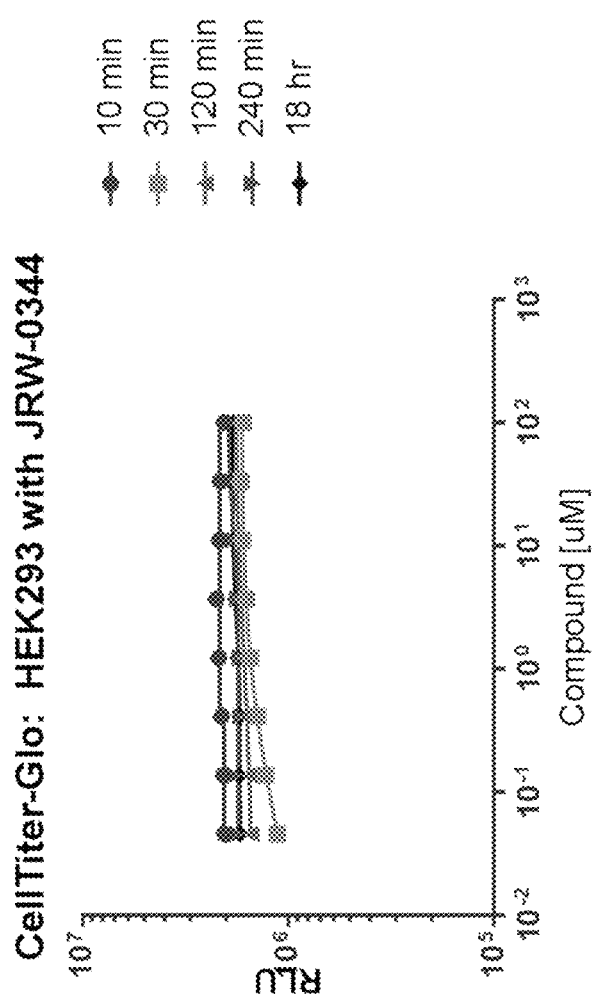
FIGS. 18A-18C show the cell viability and toxicity of JRW-0344 (FIG. 18A) compared to digitonin (FIG. 18B) and DMSO (FIG. 18C).
Figure 18B:
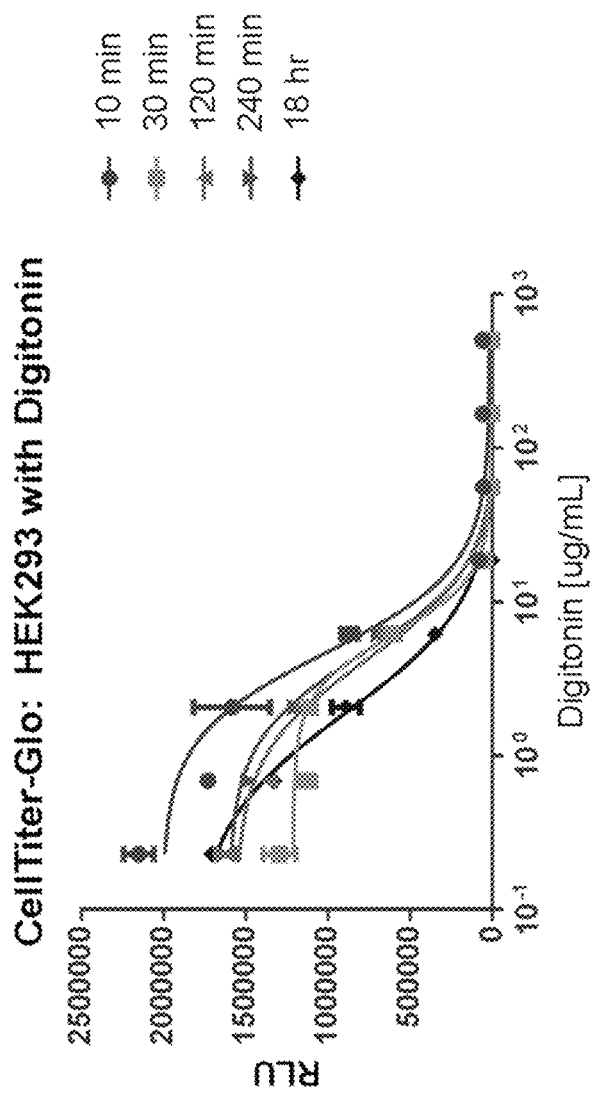
Figure 18C:
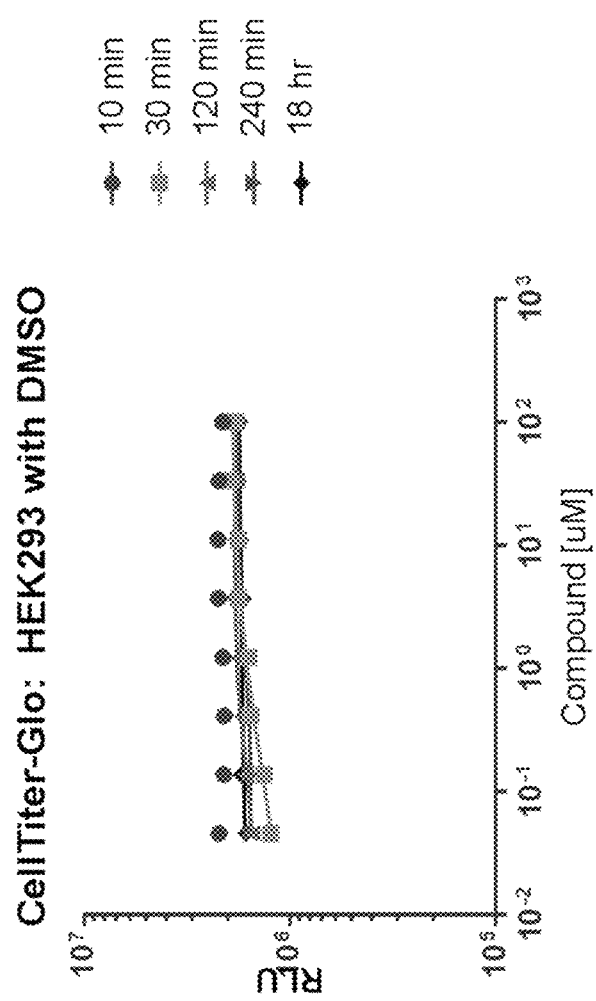

The following example demonstrates the cell viability and toxicity of JRW-0344. HEK293 cells were plated at 20 k cells/well and exposed to vehicle (DMSO), digitonin (positive control for cell death), or JRW-0344 for 10 min/30 min/120 min/240 min/or 18 hrs. CellTiter-Glo (Promega Corp.) was added, and luminescence measured. FIGS. 18A-18C demonstrate that there was no apparent toxicity of vehicle or JRW-0344 up to 100 μM after 18 hrs. Digitonin treated cells experienced almost complete death at concentrations greater than 2 μg/mL.

Example 99

Cell Permeability with Bioluminescent Imaging

Figure 19:
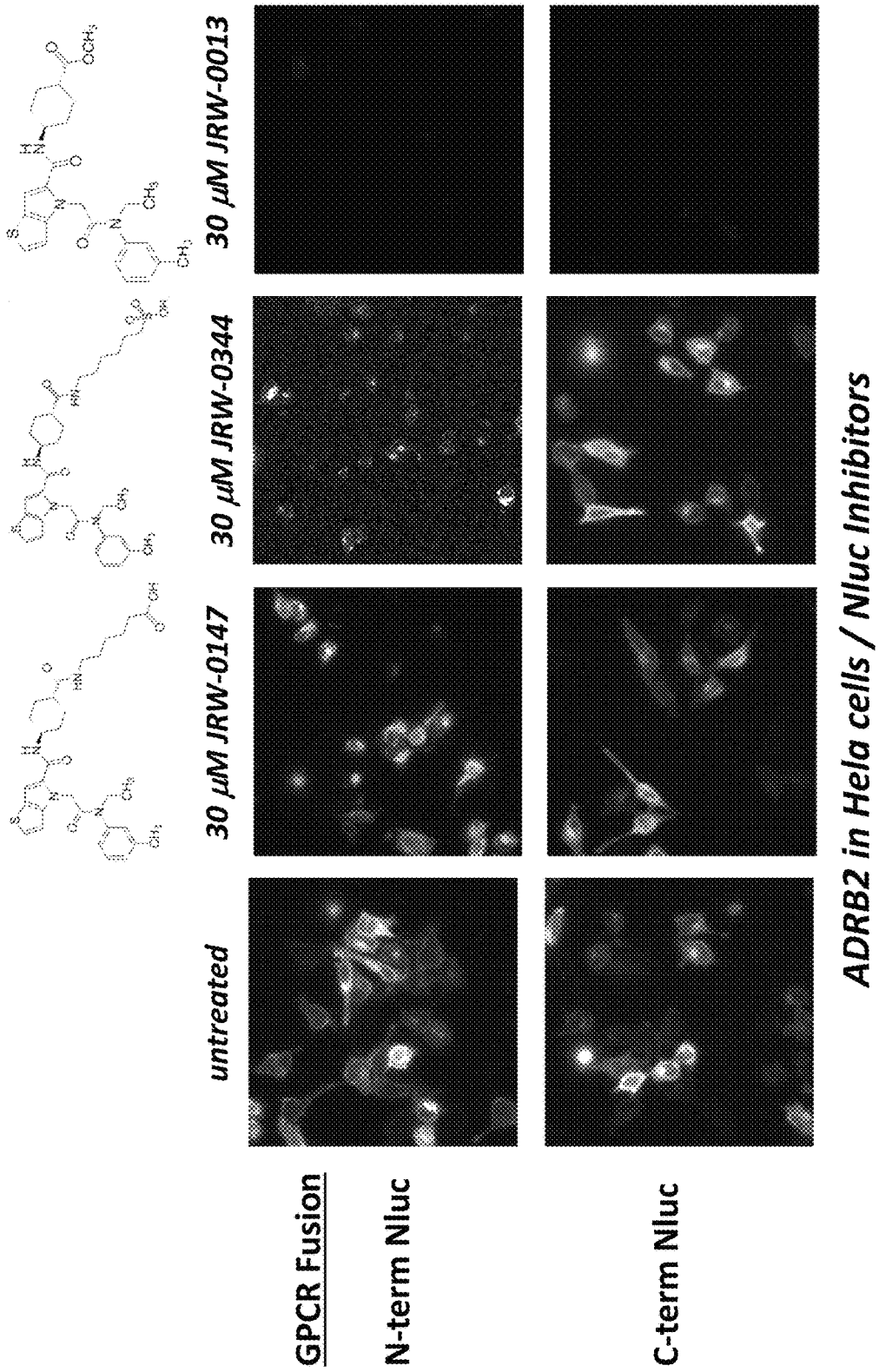
FIG. 19 shows the cell permeability of thienopyrrole compounds JRW-0147, JRW-0344, and JRW-0013.

HeLa cells were transiently transfected with Nluc-ADRB2 (extracellular Nluc) or ADRB2-Nluc (intracellular Nluc) to anchor and orient Nluc extracellularly or intracellularly, respectively. 24 hrs post-transfection, cells were treated with −/+30 μM of a thienopyrrole compound, JRW-0147, JRW-0013, and JRW-0344. 10 μM furimazine was added, and luminescence was detected by imaging on the Olympus LV200. DMSO (untreated) was used as a negative control and did not inhibit Nluc in either orientation. JRW-0013 is a cell permeable positive control and inhibited Nluc in either orientation. However, when Nluc is orientated extracellularly, JRW-0344 or JRW-0147 inhibit the classic ring-like structure, but not when Nluc is orientated intracellularly. See FIG. 19.

Example 100

Inhibition of Extracellular Luciferase Activity

The following example demonstrates the ability of the thienopyrrole compounds described herein to inhibit extracellular luciferase activity while enhancing intracellular BRET. See FIG. 20A. HEK293 were transiently transfected with either SRC-Nluc or Nluc-HaloTag. 24 hrs post-transfection, 20 k/cells were plated into wells of a 96-well plate (Costar 3600). 1 µM of the cell impermeable tracer Dasatinib-DY605 was added to the HEK293 SRC-Nluc expressing cells, and 100 nM of the cell permeable tracer Nano-BRET-618, was added to the Nluc-HaloTag expressing cells. Both HEK293 SRC-Nluc and Nluc-HaloTag cells were exposed to a dose-response curve of JRW-0344. FIGS. 20A-20C demonstrate that JRW-0344 inhibits BRET in cell debris in the HEK293 SRC-Nluc expressing cells, but not in HEK293 Nluc-HaloTag expressing cells.

Example 101

Inhibitor IC50 Determination

The following example provides the IC50 values for the compounds disclosed herein. See Table 5 NANOLUC® enzyme was diluted to 0.4 ng/ml in CO2 independent media+10% FBS to make the detection reagent. A 3× dilution series of each inhibitor was then made in the detection reagent. A "no inhibitor" control was also made for each sample. 50 ul of each inhibitor dilution was mixed with 50 ul of NanoGlo buffer containing 20 uM furimazine. (Final furimazine concentration is 10 uM which is at Km.), and luminescence measured. Each sample was normalized to the "no inhibitor" control. The 1050 values were then determined using GraphPad Prism (log [inhibitor] vs. normalized response).

TABLE 5

| Inhibitor | IC50 (uM) |
| --- | --- |
| jrw-0004 | 1.1 |
| wz-141-74 | 16.4 |
| wz-141-84 | 5.5 |
| wz-141-88 | 0.54 |
| jrw-0013 | 0.14 |
| jrw-0009 | 2.7 |
| jrw-0008 | 1.1 |
| jrw-0006 | 0.26 |
| jrw-0034 | 0.059 |
| jrw-0041 | 0.2 |
| jrw-0042 | 0.31 |
| jrw-0043 | 0.84 |
| jrw-0044 | 16.8 |
| jrw-0051 | 0.74 |
| jrw-0052 | 1.3 |
| jrw-0081 | 19.4 |
| jrw-0109 | 10.1 |
| jrw-0110 | 3 |
| jrw-0138 | 0.13 |
| jrw-0143 | 2.8 |
| jrw-0143 | 2.6 |
| jrw-0145 | 0.12 |
| jrw-0147 | 0.094 |
| jrw-0148 | 5.3 |
| jrw-0149 | 2.5 |
| jrw-0151 | 7 |

TABLE 5-continued

| Inhibitor | IC50 (uM) |
| --- | --- |
| jrw-0152 | 4.3 |
| jrw-0188 | 0.022 |
| jrw-0195 | 0.48 |
| jrw-0198 | 1 |
| jrw-0200 | 0.078 |
| jrw-0208 | 0.82 |
| jrw-0241 | 0.063 |
| jrw-0242 | 0.035 |
| jrw-0243 | 0.21 |
| jrw-0251 | 0.077 |
| jrw-0344 | 0.077 |
| jrw-0264 | 0.24 |
| jrw-0268 | 4.3 |
| jrw-0318 | 0.11 |
| jrw-0321 | 0.16 |
| jrw-0322 | 0.2 |
| jrw-0326 | 0.0039 |
| jrw-0327 | 0.11 |
| jrw-0330 | 0.7 |
| jrw-0331 | 16.9 |
| jrw-0334 | 1.3 |
| jrw-0335 | 1.9 |
| jrw-0355 | 0.052 |
| jrw-0359 | 3 |
| jrw-0360 | 0.61 |
| jrw-0424 | 0.005 |
| jrw-0429 | 0.0021 |
| jrw-0430 | 0.0021 |
| jrw-0432 | 0.0031 |
| jrw-0434 | 0.0019 |
| jrw-0456 | 7.4 |
| jrw-0460 | 0.12 |
| jrw-0461 | 0.077 |
| jrw-0463 | 0.71 |
| jrw-0466 | 0.0018 |
| jrw-0478 | 0.065 |
| jrw-0508 | 0.027 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the present disclosure are set out in the following numbered clauses:

Clause 1. A compound of formula (I), or a salt thereof:

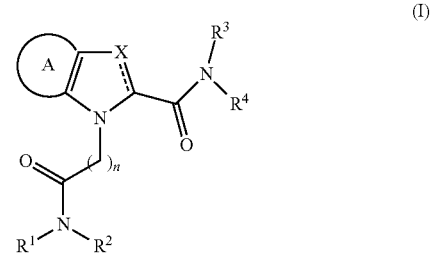

wherein:
the dashed line represents the presence or absence of a bond;
n is 0, 1, 2, 3, 4 or 5;
X is CH, N, O, or S;

wherein, when the dashed line represents the presence of a bond, X is CH or N,
and when the dashed line represents the absence of a bond, X is O or S;

A is an optionally substituted phenyl ring, or an optionally substituted 5- or 6-membered heteroaryl ring;

$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl; and $R^3$ and $R^4$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring.

Clause 2. The compound of clause 1, wherein n is 1.

Clause 3. The compound of any of clauses 1-2, wherein the dashed line represents the presence of a bond, and X is CH.

Clause 4. The compound of any of clauses 1-3, wherein A is a 5-membered heteroaryl ring.

Clause 5. The compound of any of clauses 1-4, wherein A is a thienyl ring or a furanyl ring.

Clause 6. The compound of any of clauses 1-4, wherein A is a phenyl ring.

Clause 7. The compound of any of clauses 1-6, wherein $R^1$ is selected from the group consisting of hydrogen, $C_1$-$C_8$ alkyl, halo-$C_1$-$C_8$-alkyl, alkoxyalkoxyalkyl and arylalkyl.

Clause 8. The compound of any of clauses 1-7, wherein $R^1$ is selected from the group consisting of hydrogen, ethyl, n-hexyl, 2-(2-methoxyethoxy)ethyl and benzyl.

Clause 9. The compound of any of clauses 1-8, wherein $R^1$ is ethyl.

Clause 10. The compound of any of clauses 1-9, wherein $R^2$ is optionally substituted aryl.

Clause 11. The compound of any of clauses 1-10, wherein $R^2$ is substituted phenyl.

Clause 12. The compound of clause 11, wherein $R^2$ is phenyl substituted with one substituent selected from the group consisting of $C_1$-$C_4$ alkyl, cyano, amido, $C_1$-$C_4$ alkoxy, and hydroxyalkyl.

Clause 13. The compound of any of clauses 1-12, wherein $R^2$ is phenyl substituted with one methyl group.

Clause 14. The compound of any of clauses 1-13, wherein $R^3$ and $R^4$, together with the nitrogen atom to which they are attached, together form an optionally substituted ring.

Clause 15. The compound of any of clauses 1-14, wherein $R^3$ and $R^4$, together with the nitrogen atom to which they are attached, together form an optionally substituted monocyclic heterocycle.

Clause 16. The compound of any of clauses 1-15, wherein the optionally substituted monocyclic heterocycle is selected from the group consisting of optionally substituted pyrrolidine, piperidine and piperazine.

Clause 17. The compound of any of clauses 1-16, wherein the optionally substituted monocyclic heterocycle is selected from the group consisting of unsubstituted pyrrolidine, unsubstituted piperidine, piperidine substituted with one substituent, or piperazine substituted with one substituent.

Clause 18. The compound of any of clauses 1-17, wherein $R^3$ is hydrogen.

Clause 19. The compound of any of clauses 1-18, wherein $R^4$ is selected from the group consisting of unsubstituted $C_1$-$C_8$ alkyl, carboxy-$C_1$-$C_8$-alkyl, $C_1$-$C_4$-alkoxycarbonyl-$C_1$-$C_8$-alkyl, optionally substituted phenyl, optionally substituted $C_5$-$C_6$ cycloalkyl, optionally substituted heterocyclyl, optionally substituted heteroarylalkyl, and optionally substituted heterocyclylalkyl.

Clause 20. The compound of any of clauses 1-19, wherein $R^4$ is phenyl that is unsubstituted or substituted with one substituent.

Clause 21. The compound of clause 20, wherein the substituent is selected from the group consisting of $C_1$-$C_4$-alkoxycarbonyl and $C_1$-$C_4$-alkoxycarbonyl-$C_1$-$C_4$-alkyl.

Clause 22. The compound of any of clauses 1-18, wherein $R^4$ is cyclohexyl substituted with one substituent selected from the group consisting of carboxy, $C_1$-$C_4$-alkoxycarbonyl, $C_1$-$C_8$-alkylamido, hydroxy-$C_1$-$C_8$-alkylamido, amido, optionally substituted amino-$C_1$-$C_8$-alkylamido, $C_1$-$C_4$-dialkylamino-$C_1$-$C_8$-alkylamido, carboxy-$C_1$-$C_8$-alkylamido, sulfonic acid-$C_1$-$C_8$-alkylamido, sulfonate-$C_1$-$C_8$-alkylamido, $C_1$-$C_4$-alkylcarbonyl-$C_1$-$C_8$-alkylamido, optionally substituted $C_3$-$C_6$-cycloalkylamido, and optionally substituted heterocyclylamido.

Clause 23. The compound of any of clauses 1-22, wherein the compound has formula (Ia):

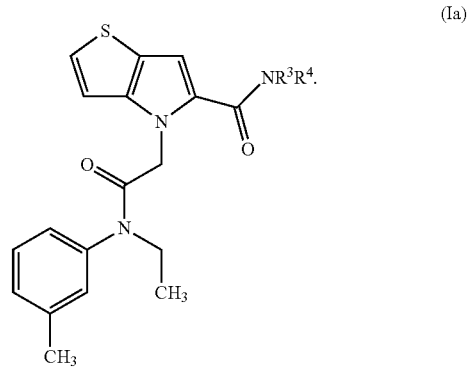

(Ia)

Clause 24. The compound of any of clauses 1-23, wherein the compound has formula (Ib):

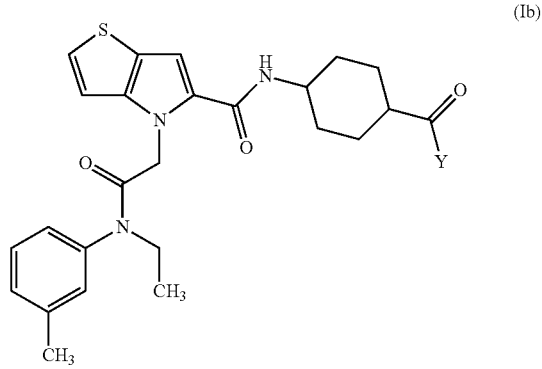

(Ib)

wherein:
Y is selected from the group consisting of —$NR^aR^b$ and —$OR^c$;

$R^a$ and $R^b$ are each independently selected from the group consisting of hydrogen, optionally substituted $C_1$-$C_8$ alkyl, optionally substituted $C_3$-$C_8$-cycloalkyl, and optionally substituted heterocyclyl; or $R^a$ and $R^b$, together with the nitrogen atom to which they are attached, together form an optionally substituted ring; and $R^c$ is selected from the group consisting of hydrogen and optionally substituted $C_1$-$C_4$ alkyl.

Clause 25. The compound of clause 24, wherein Y is —$OR^c$.

Clause 26. The compound of any of clauses 24-25, wherein $R^1$ is selected from the group consisting of hydrogen and methyl.

Clause 27. The compound of clause 24, wherein Y is —$NR^aR^b$.

Clause 28. The compound of clause 27, wherein $R^a$ and $R^b$, together with the nitrogen atom to which they are attached, together form an optionally substituted ring.

Clause 29. The compound of any of clauses 27-28, wherein $R^a$ and $R^b$, together with the nitrogen atom to which they are attached, together form an optionally substituted monocyclic heterocycle.

Clause 30. The compound of clause 29, wherein the optionally substituted monocyclic heterocycle is optionally substituted piperidine.

Clause 31. The compound of any of clauses 29-30, wherein the optionally substituted monocyclic heterocycle is selected from the group consisting of unsubstituted piperidine and piperidine substituted with one substituent.

Clause 32. The compound of clause 27, wherein $R^a$ is hydrogen.

Clause 33. The compound of clause 32, wherein $R^b$ is selected from the group consisting of hydrogen, optionally substituted $C_1$-$C_8$ alkyl, optionally substituted $C_3$-$C_8$-cycloalkyl, and optionally substituted heterocyclyl.

Clause 34. The compound of any of clauses 31-32, wherein $R^b$ is selected from the group consisting of hydrogen, $C_1$-$C_6$ alkyl, hydroxyalkyl, optionally substituted aminoalkyl, carboxyalkyl, sulfonic acid-alkyl, sulfonate-alkyl, alkylcarbonylalkyl, optionally substituted $C_3$-$C_6$-cycloalkyl, and optionally substituted six-membered heterocyclyl.

Clause 35. The compound of any of clauses 1-34, wherein the compound has the following formula (Ib')

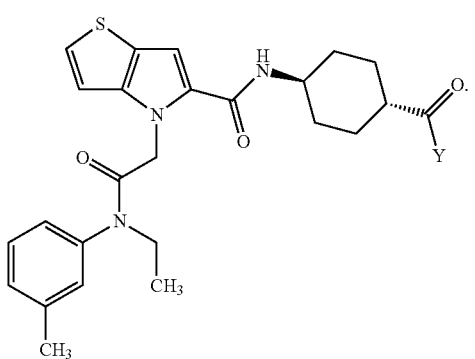

(Ib')

Clause 36. The compound of any of clauses 1-35, wherein the compound is selected from the group consisting of:
N-cyclohexyl-4-(2-(ethyl(m-tolyl)amino)-2-oxoethyl)-4H-thieno[3,2-b]pyrrole-5-carboxamide;
N-ethyl-2-(5-(pyrrolidine-1-carbonyl)-4H-thieno[3,2-b]pyrrol-4-yl)-N-(m-tolyl)acetamide;
N-ethyl-2-(5-(piperidine-1-carbonyl)-4H-thieno[3,2-b]pyrrol-4-yl)-N-(m-tolyl)acetamide;
ethyl 1-(4-(2-(ethyl(m-tolyl)amino)-2-oxoethyl)-4H-thieno[3,2-b]pyrrole-5-carbonyl)piperidine-4-carboxylate;
4-(2-(ethyl(m-tolyl)amino)-2-oxoethyl)-N-phenyl-4H-thieno[3,2-b]pyrrole-5-carboxamide;
ethyl 2-(4-(4-(2-(ethyl(m-tolyl)amino)-2-oxoethyl)-4H-thieno[3,2-b]pyrrole-5-carboxamido)phenyl)acetate;
methyl 3-(4-(2-(ethyl(m-tolyl)amino)-2-oxoethyl)-4H-thieno[3,2-b]pyrrole-5-carboxamido)benzoate;
methyl-cis-4-(4-(2-(ethyl(m-tolyl)amino)-2-oxoethyl)-4H-thieno[3,2-b]pyrrole-5-carboxamido)cyclohexane-1-carboxylate;
8-(4-(2-(ethyl(m-tolyl)amino)-2-oxoethyl)-4H-thieno[3,2-b]pyrrole-5-carboxamido)octanoic acid;
6-(4-(4-(2-(ethyl(m-tolyl)amino)-2-oxoethyl)-4H-thieno[3,2-b]pyrrole-5-carboxamido)piperidin-1-yl)-6-oxohexanoic acid;
trans-methyl-4-(4-(2-(ethyl(m-tolyl)amino)-2-oxoethyl)-4H-thieno[3,2-b]pyrrole-5-carboxamido)cyclohexane-1-carboxylate;
trans-4-(4-(2-(ethyl(m-tolyl)amino)-2-oxoethyl)-4H-thieno[3,2-b]pyrrole-5-carboxamido)cyclohexane-1-carboxylic acid;
N-(trans-4-(butylcarbamoyl)cyclohexyl)-4-(2-(ethyl(m-tolyl)amino)-2-oxoethyl)-4H-thieno[3,2-b]pyrrole-5-carboxamide;
4-(2-(ethyl(m-tolyl)amino)-2-oxoethyl)-N-(trans-4-((2-hydroxyethyl)carbamoyl)cyclohexyl)-4H-thieno[3,2-b]pyrrole-5-carboxamide;
N-(trans-4-((2-(dimethylamino)ethyl)carbamoyl)cyclohexyl)-4-(2-(ethyl(m-tolyl)amino)-2-oxoethyl)-4H-thieno[3,2-b]pyrrole-5-carboxamide;
4-(trans-4-(4-(2-(ethyl(m-tolyl)amino)-2-oxoethyl)-4H-thieno[3,2-b]pyrrole-5-carboxamido)cyclohexane-1-carboxamido)butanoic acid;
N-(trans-4-carbamoylcyclohexyl)-4-(2-(ethyl(m-tolyl)amino)-2-oxoethyl)-4H-thieno[3,2-b]pyrrole-5-carboxamide;
4-(2-(ethyl(m-tolyl)amino)-2-oxoethyl)-N-(trans-4-(hexylcarbamoyl)cyclohexyl)-4H-thieno[3,2-b]pyrrole-5-carboxamide;
ethyl 1-(trans-4-(4-(2-(ethyl(m-tolyl)amino)-2-oxoethyl)-4H-thieno[3,2-b]pyrrole-5-carboxamido)cyclohexane-1-carbonyl)piperidine-4-carboxylate;
methyl 6-(trans-4-(4-(2-(ethyl(m-tolyl)amino)-2-oxoethyl)-4H-thieno[3,2-b]pyrrole-5-carboxamido)cyclohexane-1-carboxamido)hexanoate;
6-(trans-4-(4-(2-(ethyl(m-tolyl)amino)-2-oxoethyl)-4H-thieno[3,2-b]pyrrole-5-carboxamido)cyclohexane-1-carboxamido)hexanoic acid;
1-(trans-4-(4-(2-(ethyl(m-tolyl)amino)-2-oxoethyl)-4H-thieno[3,2-b]pyrrole-5-carboxamido)cyclohexane-1-carbonyl)piperidine-4-carboxylic acid;
8-(trans-4-(4-(2-(ethyl(m-tolyl)amino)-2-oxoethyl)-4H-thieno[3,2-b]pyrrole-5-carboxamido)cyclohexane-1-carboxamido)octanoic acid;
N-(trans-4-(cyclohexylcarbamoyl)cyclohexyl)-4-(2-(ethyl(m-tolyl)amino)-2-oxoethyl)-4H-thieno[3,2-b]pyrrole-5-carboxamide;
4-(2-(ethyl(m-tolyl)amino)-2-oxoethyl)-N-(trans-4-((1-methylpiperidin-4-yl)carbamoyl)cyclohexyl)-4H-thieno[3,2-b]pyrrole-5-carboxamide;

tert-butyl 4-(trans-4-(4-(2-(ethyl(m-tolyl)amino)-2-oxoethyl)-4H-thieno[3,2-b]pyrrole-5-carboxamido)cyclohexane-1-carboxamido)piperidine-1-carboxylate;

4-(2-(ethyl(m-tolyl)amino)-2-oxoethyl)-N-(trans-4-(piperidin-4-ylcarbamoyl)cyclohexyl)-4H-thieno[3,2-b]pyrrole-5-carboxamide;

N-(trans-4-((1-acetylpiperidin-4-yl)carbamoyl)cyclohexyl)-4-(2-(ethyl(m-tolyl)amino)-2-oxoethyl)-4H-thieno[3,2-b]pyrrole-5-carboxamide;

tert-butyl (6-(trans-4-(4-(2-(ethyl(m-tolyl)amino)-2-oxoethyl)-4H-thieno[3,2-b]pyrrole-5-carboxamido)cyclohexane-1-carboxamido)hexyl)carbamate;

N-(trans-4-((6-(3',6'-dihydroxy-3-oxo-3H-spiro[isobenzofuran-1,9'-xanthene]-5(6)-carboxamido)hexyl)carbamoyl)cyclohexyl)-4-(2-(ethyl(m-tolyl)amino)-2-oxoethyl)-4H-thieno[3,2-b]pyrrole-5-carboxamide;

N-(trans-4-((6-aminohexyl)carbamoyl)cyclohexyl)-4-(2-(ethyl(m-tolyl)amino)-2-oxoethyl)-4H-thieno[3,2-b]pyrrole-5-carboxamide hydrochloride;

4-(2-(ethyl(m-tolyl)amino)-2-oxoethyl)-N-(trans-4-((6-hydroxyhexyl)carbamoyl)cyclohexyl)-4H-thieno[3,2-b]pyrrole-5-carboxamide;

methyl-trans-4-(trans-4-(4-(2-(ethyl(m-tolyl)amino)-2-oxoethyl)-4H-thieno[3,2-b]pyrrole-5-carboxamido)cyclohexane-1-carboxamido)cyclohexane-1-carboxylate;

trans-4-(trans-4-(4-(2-(ethyl(m-tolyl)amino)-2-oxoethyl)-4H-thieno[3,2-b]pyrrole-5-carboxamido)cyclohexane-1-carboxamido)cyclohexane-1-carboxylic acid;

(11S,14S,17S)-17-acetamido-11,14-bis(carboxymethyl)-1-(trans-4-(4-(2-(ethyl(m-tolyl)amino)-2-oxoethyl)-4H-thieno[3,2-b]pyrrole-5-carboxamido)cyclohexyl)-1,10,13,16-tetraoxo-2,9,12,15-tetraazanonadecan-19-oic acid;

4-(2-(ethyl(m-tolyl)amino)-2-oxoethyl)-N-methyl-4H-thieno[3,2-b]pyrrole-5-carboxamide;

N-cyclopentyl-4-(2-(ethyl(m-tolyl)amino)-2-oxoethyl)-4H-thieno[3,2-b]pyrrole-5-carboxamide;

4-(2-(ethyl(m-tolyl)amino)-2-oxoethyl)-N-(pyridin-4-ylmethyl)-4H-thieno[3,2-b]pyrrole-5-carboxamide;

4-(2-(ethyl(m-tolyl)amino)-2-oxoethyl)-N-(3-morpholinopropyl)-4H-thieno[3,2-b]pyrrole-5-carboxamide;

N-ethyl-2-(5-(4-methylpiperazine-1-carbonyl)-4H-thieno[3,2-b]pyrrol-4-yl)-N-(m-tolyl)acetamide;

methyl 4-(2-oxo-2-(m-tolylamino)ethyl)-4H-thieno[3,2-b]pyrrole-5-carboxylate;

N-cyclohexyl-4-(2-oxo-2-(m-tolylamino)ethyl)-4H-thieno[3,2-b]pyrrole-5-carboxamide;

N-cyclohexyl-4-(2-((2-(2-methoxyethoxy)ethyl)(m-tolyl)amino)-2-oxoethyl)-4H-thieno[3,2-b]pyrrole-5-carboxamide;

methyl-trans-4-(4-(2-((2-(2-methoxyethoxy)ethyl)(m-tolyl)amino)-2-oxoethyl)-4H-thieno[3,2-b]pyrrole-5-carboxamido)cyclohexane-1-carboxylate;

methyl 4-(2-(hexyl(m-tolyl)amino)-2-oxoethyl)-4H-thieno[3,2-b]pyrrole-5-carboxylate;

N-cyclohexyl-4-(2-(hexyl(m-tolyl)amino)-2-oxoethyl)-4H-thieno[3,2-b]pyrrole-5-carboxamide;

methyl-trans-4-(4-(2-(hexyl(m-tolyl)amino)-2-oxoethyl)-4H-thieno[3,2-b]pyrrole-5-carboxamido)cyclohexane-1-carboxylate;

methyl 4-(2-(benzyl(m-tolyl)amino)-2-oxoethyl)-4H-thieno[3,2-b]pyrrole-5-carboxylate;

6-(cis-4-(4-(2-(ethyl(m-tolyl)amino)-2-oxoethyl)-4H-thieno[3,2-b]pyrrole-5-carboxamido)cyclohexane-1-carboxamido)hexanoic acid;

methyl 6-(trans-4-((4-(2-(ethyl(m-tolyl)amino)-2-oxoethyl)-4H-thieno[3,2-b]pyrrole-5-carboxamido)methyl)cyclohexane-1-carboxamido)hexanoate;

6-(trans-4-((4-(2-(ethyl(m-tolyl)amino)-2-oxoethyl)-4H-thieno[3,2-b]pyrrole-5-carboxamido)methyl)cyclohexane-1-carboxamido)hexanoic acid;

sodium 6-(trans-4-(4-(2-(ethyl(m-tolyl)amino)-2-oxoethyl)-4H-thieno[3,2-b]pyrrole-5-carboxamido)cyclohexane-1-carboxamido)hexane-1-sulfonate;

potassium 6-(trans-4-(4-(2-(ethyl(m-tolyl)amino)-2-oxoethyl)-4H-thieno[3,2-b]pyrrole-5-carboxamido)cyclohexane-1-carboxamido)hexane-1-sulfonate;

trans-4-(4-(2-(hexyl(m-tolyl)amino)-2-oxoethyl)-4H-thieno[3,2-b]pyrrole-5-carboxamido)cyclohexane-1-carboxylic acid;

methyl trans-4-(4-(2-(ethyl(phenyl)amino)-2-oxoethyl)-4H-thieno[3,2-b]pyrrole-5-carboxamido)cyclohexane-1-carboxylate;

methyl trans-4-(4-(2-((3-cyanophenyl)(ethyl)amino)-2-oxoethyl)-4H-thieno[3,2-b]pyrrole-5-carboxamido)cyclohexane-1-carboxylate;

methyl trans-4-(4-(2-((3-carbamoylphenyl)(ethyl)amino)-2-oxoethyl)-4H-thieno[3,2-b]pyrrole-5-carboxamido)cyclohexane-1-carboxylate;

methyl trans-4-(4-(2-(ethyl(3-ethylphenyl)amino)-2-oxoethyl)-4H-thieno[3,2-b]pyrrole-5-carboxamido)cyclohexane-1-carboxylate;

methyl trans-4-(4-(2-(ethyl(3-methoxyphenyl)amino)-2-oxoethyl)-4H-thieno[3,2-b]pyrrole-5-carboxamido)cyclohexane-1-carboxylate;

methyl trans-4-(4-(2-(ethyl(o-tolyl)amino)-2-oxoethyl)-4H-thieno[3,2-b]pyrrole-5-carboxamido)cyclohexane-1-carboxylate;

methyl trans-4-(4-(2-(6-methyl-3,4-dihydroquinolin-1(2H)-yl)-2-oxoethyl)-4H-thieno[3,2-b]pyrrole-5-carboxamido)cyclohexane-1-carboxylate;

methyl trans-4-(4-(2-(ethyl(p-tolyl)amino)-2-oxoethyl)-4H-thieno[3,2-b]pyrrole-5-carboxamido)cyclohexane-1-carboxylate;

methyl trans-4-(4-(2-(ethyl(4-(hydroxymethyl)phenyl)amino)-2-oxoethyl)-4H-thieno[3,2-b]pyrrole-5-carboxamido)cyclohexane-1-carboxylate;

methyl trans-4-(1-(2-(ethyl(m-tolyl)amino)-2-oxoethyl)-1H-indole-2-carboxamido)cyclohexane-1-carboxylate;

methyl trans-4-(1-(2-(ethyl(m-tolyl)amino)-2-oxoethyl)-6-methoxy-1H-indole-2-carboxamido)cyclohexane-1-carboxylate;

methyl trans-4-(4-(2-(ethyl(m-tolyl)amino)-2-oxoethyl)-4H-furo[3,2-b]pyrrole-5-carboxamido)cyclohexane-1-carboxylate;

4-(2-(ethyl(3-ethylphenyl)amino)-2-oxoethyl)-N-(trans-4-((6-hydroxyhexyl)carbamoyl)cyclohexyl)-4H-thieno[3,2-b]pyrrole-5-carboxamide;

sodium 6-(trans-4-(4-(2-(ethyl(3-ethylphenyl)amino)-2-oxoethyl)-4H-thieno[3,2-b]pyrrole-5-carboxamido)cyclohexane-1-carboxamido)hexane-1-sulfonate;

methyl trans-4-(4-(2-(ethyl(3-isopropylphenyl)amino)-2-oxoethyl)-4H-thieno[3,2-b]pyrrole-5-carboxamido)cyclohexane-1-carboxylate;

methyl trans-4-(4-(2-(ethyl(3-(hydroxymethyl)phenyl)amino)-2-oxoethyl)-4H-thieno[3,2-b]pyrrole-5-carboxamido)cyclohexane-1-carboxylate;

methyl trans-4-(4-(2-((3-(bromomethyl)phenyl)(ethyl)amino)-2-oxoethyl)-4H-thieno[3,2-b]pyrrole-5-carboxamido)cyclohexane-1-carboxylate;

methyl trans-4-(4-(2-((3-(dimethylamino)phenyl)(ethyl)amino)-2-oxoethyl)-4H-thieno[3,2-b]pyrrole-5-carboxamido)cyclohexane-1-carboxylate;

methyl trans-4-(4-(2-(ethyl(3-isobutylphenyl)amino)-2-oxoethyl)-4H-thieno[3,2-b]pyrrole-5-carboxamido)cyclohexane-1-carboxylate;
methyl trans-4-(1-(2-(ethyl(3-ethylphenyl)amino)-2-oxoethyl)-1H-indole-2-carboxamido)cyclohexane-1-carboxylate;
1-(2-(ethyl(3-ethylphenyl)amino)-2-oxoethyl)-N-(trans-4-((6-hydroxyhexyl)carbamoyl)cyclohexyl)-1H-indole-2-carboxamide;
sodium 6-(trans-4-(1-(2-(ethyl(3-ethylphenyl)amino)-2-oxoethyl)-1H-indole-2-carboxamido)cyclohexane-1-carboxamido)hexane-1-sulfonate;
methyl trans-4-(1-(2-(ethyl(m-tolyl)amino)-2-oxoethyl)-1H-pyrrole-2-carboxamido)cyclohexane-1-carboxylate; and
methyl trans-4-(6-(2-(ethyl(m-tolyl)amino)-2-oxoethyl)-6H-thieno[2,3-b]pyrrole-5-carboxamido)cyclohexane-1-carboxylate.

Clause 37. A method of inhibiting an *Oplophorus*-derived luciferase the method comprising contacting the *Oplophorus*-derived luciferase with a compound of any of clauses 1-36.

Clause 38. The method of clause 37, wherein the *Oplophorus*-derived luciferase comprises a polypeptide sequence of SEQ ID NO: 2.

Clause 39. A method of inhibiting an *Oplophorus*-derived luciferase, the method comprising contacting the *Oplophorus*-derived luciferase with a compound of formula (II):

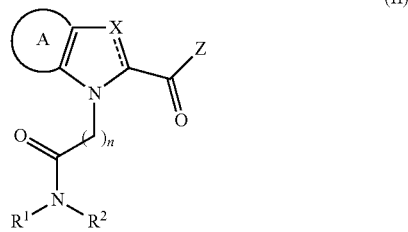

(II)

wherein:
the dashed line represents the presence or absence of a bond;
n is 0, 1, 2, 3, 4 or 5;
X is CH, N, O, or S;
  wherein, when the dashed line represents the presence of a bond, X is CH or N,
  and when the dashed line represents the absence of a bond, X is O or S;
A is an optionally substituted phenyl ring, or an optionally substituted 5- or 6-membered heteroaryl ring;
$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;
Z is selected from the group consisting of —$NR^3R^4$ and —$OR^5$; and
$R^3$, $R^4$ and $R^5$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring.

Clause 40. The method of clause 39, wherein the *Oplophorus*-derived luciferase comprises a polypeptide sequence of SEQ ID NO: 2.

Clause 41. A method for modulating luminescence of an *Oplophorus*-derived luciferase in a sample, the method comprising,
(a) contacting the sample with a coelenterazine substrate and the compound of any of clauses 1-36; and
(b) detecting luminescence in the sample,
wherein the compound of any of clauses 1-36 causes a decrease in the luminescence from the *Oplophorus*-derived luciferase.

Clause 42. A method to detect an interaction between a first protein and a second protein in a sample, the method comprising:
(a) contacting a sample with a coelenterazine substrate and the compound of any one of clauses 1-36, wherein the sample comprises:
  (ix) a first polynucleotide encoding a first fusion protein, wherein the first fusion protein comprises a first fragment of an *Oplophorus*-derived luciferase and a first protein; and
  (x) a second polynucleotide encoding a second fusion protein, wherein the second fusion protein comprises a second fragment of the *Oplophorus*-derived luciferase and a second protein; and
(b) detecting luminescence in the sample,
wherein the detection of luminescence indicates an interaction between the first protein and the second protein.

Clause 43. The method of any of clauses 41-42, comprising contacting the sample with the coelenterazine substrate prior to contacting the sample with the compound of any one of clauses 1-36.

Clause 44. The method of clause 42, wherein when the first protein and second protein interact, the first fragment of the *Oplophorus*-derived luciferase and the second fragment of the *Oplophorus*-derived luciferase reconstitute a full-length enzyme capable of stably binding the coelenterazine substrate.

Clause 45. A method to detect an interaction between a first protein and a second protein in a sample, the method comprising:
(a) contacting a sample with a coelenterazine substrate and the compound of any one of clauses 1-36, wherein the sample comprises:
  (xi) a first polynucleotide encoding a first fusion protein, wherein the first fusion protein comprises an *Oplophorus*-derived luciferase and a first protein, wherein the *Oplophorus*-derived luciferase is a bioluminescent donor; and
  (xii) a second polynucleotide encoding a second fusion protein, wherein the second fusion protein comprises a fluorescent acceptor molecule and a second protein;
(b) detecting bioluminescence resonance energy transfer (BRET) in the sample, indicating an interaction or close proximity of the bioluminescent donor and and the fluorescence acceptor.

Clause 46. The method of any one of clauses 41-45, wherein the sample comprises a cell.

Clause 47. The method of clause 46, wherein the cell comprises the *Oplophorus*-derived luciferase.

Clause 48. The method of clause 46, wherein the cell expresses the *Oplophorus*-derived luciferase.

Clause 49. The method of any one of clauses 41-48, wherein the coelenterazine substrate is a coelenterazine, coelenterazine derivatives, coelenterazine analogs, pro-coelenterazine, or quinone-masked coelenterazine.

Clause 50. A bioluminescence resonance energy transfer (BRET) system comprising: a first fusion protein including a first target protein and a bioluminescence donor molecule, wherein the bioluminescence donor molecule is an *Oplophorus*-derived luciferase; a second fusion protein including a second target protein and a fluorescent acceptor molecule; a coelenterazine substrate, and the compound of any one of clauses 1-36.

Clause 51. A kit comprising:
(a) a compound of any of clauses 1-36; and
(b) an *Oplophorus*-derived luciferase.

Clause 52. The kit of clause 51, wherein the *Oplophorus*-derived luciferase comprises a polypeptide sequence of SEQ ID NO: 2

Clause 53. The kit of any of clauses 51-52, further comprising a coelenterazine substrate.

Clause 54. The kit of any of clauses 51-53, further comprising instructions for carrying out a luminescent assay.

Clause 55. A method for modulating luminescence of an *Oplophorus*-derived luciferase in a sample, the method comprising:
(a) contacting the sample with a coelenterazine substrate and a compound of formula (II):

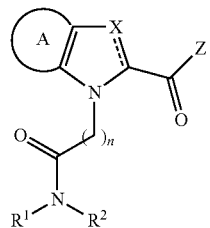

(II)

wherein:
the dashed line represents the presence or absence of a bond;
n is 0, 1, 2, 3, 4 or 5;
X is CH, N, O, or S;
wherein, when the dashed line represents the presence of a bond, X is CH or N,
and when the dashed line represents the absence of a bond, X is O or S;
A is an optionally substituted phenyl ring, or an optionally substituted 5- or 6-membered heteroaryl ring;
$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;
Z is selected from the group consisting of —$NR^3R^4$ and —$OR^5$; and
$R^3$, $R^4$ and $R^5$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring; and
(b) detecting luminescence in the sample,
wherein the compound of formula (II) causes a decrease in the luminescence from the *Oplophorus*-derived luciferase.

Clause 56. A method to detect an interaction between a first protein and a second protein in a sample, the method comprising:
(a) contacting a sample with a coelenterazine substrate and a compound of formula (II):

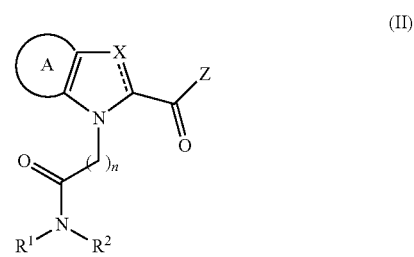

(II)

wherein:
the dashed line represents the presence or absence of a bond;
n is 0, 1, 2, 3, 4 or 5;
X is CH, N, O, or S;
wherein, when the dashed line represents the presence of a bond, X is CH or N,
and when the dashed line represents the absence of a bond, X is O or S;
A is an optionally substituted phenyl ring, or an optionally substituted 5- or 6-membered heteroaryl ring;
$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;
Z is selected from the group consisting of —$NR^3R^4$ and —$OR^5$; and
$R^3$, $R^4$ and $R^5$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring,
p1 wherein the sample comprises:
(xiii) a first polynucleotide encoding a first fusion protein, wherein the first fusion protein comprises a first fragment of an *Oplophorus*-derived luciferase and a first protein; and
(xiv) a second polynucleotide encoding a second fusion protein, wherein the second fusion protein comprises a second fragment of the *Oplophorus*-derived luciferase and a second protein; and
(b) detecting luminescence in the sample,
wherein the detection of luminescence indicates an interaction between the first protein and the second protein.

Clause 57. The method of any of clauses 55-56, comprising contacting the sample with the coelenterazine substrate prior to contacting the sample with the compound of formula (II).

Clause 58. The method of clause 57, wherein when the first protein and second protein interact, the first fragment of the *Oplophorus*-derived luciferase and the second fragment of the *Oplophorus*-derived luciferase reconstitute a full-length enzyme capable of stably binding the coelenterazine substrate.

Clause 59. A method to detect an interaction between a first protein and a second protein in a sample, the method comprising:
(a) contacting a sample with a coelenterazine substrate and a compound of formula (II):

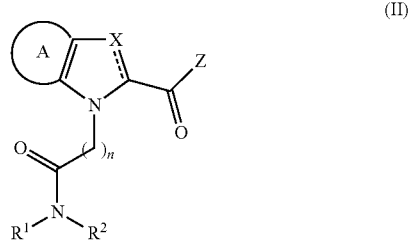

wherein:
the dashed line represents the presence or absence of a bond;
n is 0, 1, 2, 3, 4 or 5;
X is CH, N, O, or S;
wherein, when the dashed line represents the presence of a bond, X is CH or N,
and when the dashed line represents the absence of a bond, X is O or S;
A is an optionally substituted phenyl ring, or an optionally substituted 5- or 6-membered heteroaryl ring;
$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;
Z is selected from the group consisting of —$NR^3R^4$ and —$OR^5$; and
$R^3$, $R^4$ and $R^5$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring,
wherein the sample comprises:
(xv) a first polynucleotide encoding a first fusion protein, wherein the first fusion protein comprises an *Oplophorus*-derived luciferase and a first protein, wherein the *Oplophorus*-derived luciferase is a bioluminescent donor; and
(xvi) a second polynucleotide encoding a second fusion protein, wherein the second fusion protein comprises a fluorescent acceptor molecule and a second protein;

(b) detecting bioluminescence resonance energy transfer (BRET) in the sample, indicating an interaction or close proximity of the bioluminescent donor and the fluorescence acceptor.

Clause 60. The method of any one of clauses 55-59, wherein the sample comprises a cell.

Clause 61. The method of clause 60, wherein the cell comprises the *Oplophorus*-derived luciferase.

Clause 62. The method of clause 60, wherein the cell expresses the *Oplophorus*-derived luciferase.

Clause 63. The method of any one of clauses 54-62, wherein the coelenterazine substrate is coelenterazine substrate is a coelenterazine, coelenterazine derivatives, coelenterazine analogs, pro-coelenterazine, or quinone-masked coelenterazine.

Clause 64. A bioluminescence resonance energy transfer (BRET) system comprising: a first fusion protein including a first target protein and a bioluminescence donor molecule, wherein the bioluminescence donor molecule is an *Oplophorus*-derived luciferase; a second fusion protein including a second target protein and a fluorescent acceptor molecule; a coelenterazine substrate, and a compound of formula (II):

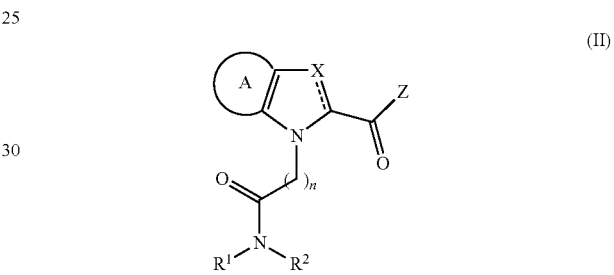

wherein:
the dashed line represents the presence or absence of a bond;
n is 0, 1, 2, 3, 4 or 5;
X is CH, N, O, or S;
wherein, when the dashed line represents the presence of a bond, X is CH or N,
and when the dashed line represents the absence of a bond, X is O or S;
A is an optionally substituted phenyl ring, or an optionally substituted 5- or 6-membered heteroaryl ring;
$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkylyl;
Z is selected from the group consisting of —$NR^3R^4$ and —$OR^5$; and
$R^3$, $R^4$ and $R^5$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring.

Clause 65. A kit comprising:
(a) a compound of formula (II):

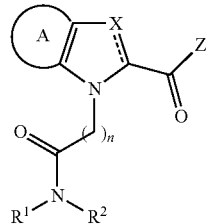

(II)

wherein:
the dashed line represents the presence or absence of a bond;
n is 0, 1, 2, 3, 4 or 5;
X is CH, N, O, or S;
 wherein, when the dashed line represents the presence of a bond, X is CH or N,
 and when the dashed line represents the absence of a bond, X is O or S;
A is an optionally substituted phenyl ring, or an optionally substituted 5- or 6-membered heteroaryl ring;
$R^1$ and $R^2$ are each independently selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;
Z is selected from the group consisting of —$NR^3R^4$ and —$OR^5$; and
$R^3$, $R^4$ and $R^5$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring; and
(b) an *Oplophorus*-derived luciferase.

Clause 66. The kit of clause 65, wherein the *Oplophorus*-derived luciferase comprises a polypeptide sequence of SEQ ID NO: 2.

Clause 67. The kit of any of clauses 65-66, further comprising a coelenterazine substrate.

Clause 68. The kit of any of clauses 65-67, further comprising instructions for carrying out a luminescent assay.

APPENDIX

SEQ ID NO: 1 - Native Mature *Oplophorus* luciferase amino acid sequence
FTLADFVGDWQQTAGYNQDQVLEQGGLSSLFQALGVSVTPIQKVVLSGEN
GLKADIHVIIPYEGLSGFQMGLIEMIFKVVYPVDDHHFKIILHYGTLVID
GVTPNMIDYFGRPYPGIAVFDGKQITVTGTLWNGNKIYDERLINPDGSLL
FR- VTIN GVTGWRLCENILA SEQ ID NO: 2 - Nluc amino acid sequence
MVFTLEDFVGDWRQTAGYNLDQVLEQGGVSSLFQNLGVSVTPIQRIVLSG
ENGLKIDIHVIIPYEGLSGDQMGQIEKIFKVVYPVDDHHFKVILHYGTLV
IDGVTPNMIDYFGRPYEGIAVFDGKKITVTGTLWNGNKIIDERLINPDGS
LLFRVTINGVTGWRLCERILA

The invention claimed is:

1. A compound of formula (I), or a salt thereof:

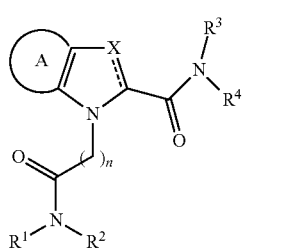

(I)

wherein:
the dashed line represents the presence or absence of a bond;
n is 0, 1, 2, 3, 4 or 5;
X is CH, N, O, or S;

wherein, when the dashed line represents the presence of a bond, X is CH or N, and
when the dashed line represents the absence of a bond, X is O or S;

A is an optionally substituted phenyl ring, or an optionally substituted 5- or 6-membered heteroaryl ring;

$R^1$ is selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;

$R^2$ is optionally substituted aryl; and $R^3$ and $R^4$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, or $R^3$ and $R^4$, together with the nitrogen atom to which they are attached, together form an optionally substituted ring.

2. The compound of claim 1, wherein n is 1.

3. The compound of claim 1, wherein the dashed line represents the presence of a bond, and X is CH.

4. The compound of claim 1, wherein A is a 5-membered heteroaryl ring.

5. The compound of claim 1, wherein A is a thienyl ring, a furanyl ring, or a phenyl ring.

6. The compound of claim 1, wherein $R^1$ is selected from the group consisting of $C_1$-$C_8$ alkyl, halo-$C_1$-$C_8$-alkyl, alkoxyalkoxyalkyl and arylalkyl.

7. The compound of claim 1, wherein $R^3$ and $R^4$, together with the nitrogen atom to which they are attached, together form an optionally substituted ring.

8. The compound of claim 1, wherein $R^3$ is hydrogen.

9. The compound of claim 1, wherein $R^4$ is selected from the group consisting of unsubstituted $C_1$-$C_8$ alkyl, halo-$C_1$-$C_8$ alkyl, carboxy-$C_1$-$C_8$-alkyl, $C_1$-$C_4$-alkoxycarbonyl-$C_1$-$C_8$alkyl, optionally substituted phenyl, optionally substituted $C_5$-$C_6$ cycloalkyl, optionally substituted $C_5$-$C_6$-cycloalkylalkyl, optionally substituted heteroarylalkyl.

10. The compound of claim 1, wherein the compound has formula (Ia):

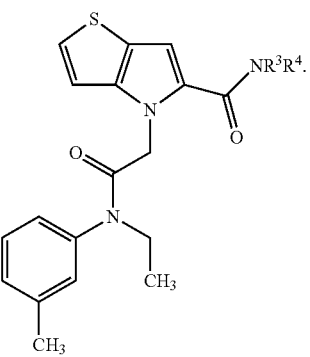

(Ia)

11. The compound of claim 1, wherein the compound has formula (Ib):

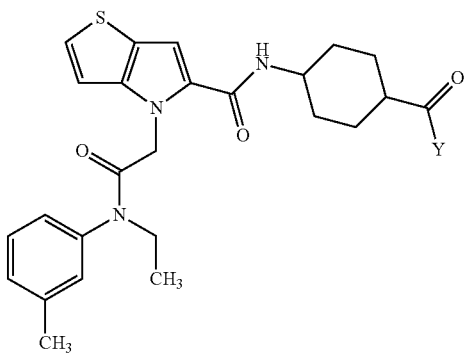

(Ib)

wherein:
Y is selected from the group consisting of —$NR^aR^b$ and —$OR^c$;
$R^a$ and $R^b$ are each independently selected from the group consisting of hydrogen, optionally substituted $C_1$-$C_8$ alkyl, optionally substituted $C_3$-$C_8$-cycloalkyl, and optionally substituted heterocyclyl; or $R^a$ and $R^b$, together with the nitrogen atom to which they are attached, together form an optionally substituted ring; and $R^c$ is selected from the group consisting of hydrogen and optionally substituted $C_1$-$C_4$ alkyl.

12. The compound of claim 11, wherein the compound has the following formula (Ib')

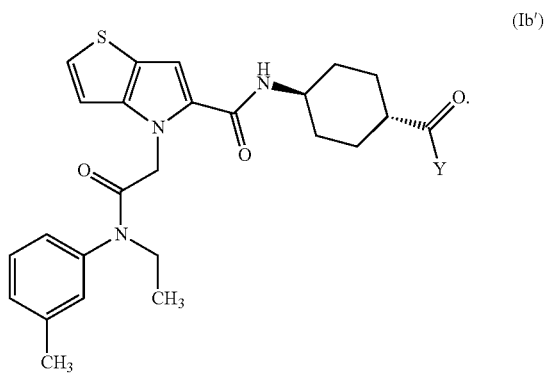

(Ib')

13. The compound of claim 1, wherein the compound is selected from the group consisting of:
N-cyclohexyl-4-(2-(ethyl(m-tolyl)amino)-2-oxoethyl)-4H-thieno[3,2-b]pyrrole-5-carboxamide;
N-ethyl-2-(5-(pyrrolidine-1-carbonyl)-4H-thieno[3,2-b]pyrrol-4-yl)-N-(m-tolyl)acetamide;
N-ethyl-2-(5-(piperidine-1-carbonyl)-4H-thieno[3,2-b]pyrrol-4-yl)-N-(m-tolyl) acetamide;
ethyl 1-(4-(2-(ethyl(m-tolyl)amino)-2-oxoethyl)-4H-thieno[3,2-b]pyrrole-5-carbonyl)piperidine-4-carboxylate;
4-(2-(ethyl(m-tolyl)amino)-2-oxoethyl)-N-phenyl-4H-thieno[3,2-b]pyrrole-5-carboxamide;
ethyl 2-(4-(4-(2-(ethyl(m-tolyl)amino)-2-oxoethyl)-4H-thieno[3,2-b]pyrrole-5-carboxamido)phenyl)acetate;
methyl 3-(4-(2-(ethyl(m-tolyl)amino)-2-oxoethyl)-4H-thieno[3,2-b]pyrrole-5-carboxamido)benzoate;
methyl-cis-4-(4-(2-(ethyl(m-tolyl)amino)-2-oxoethyl)-4H-thieno[3,2-b]pyrrole-5-carboxamido)cyclohexane-1-carboxylate;
8-(4-(2-(ethyl(m-tolyl)amino)-2-oxoethyl)-4H-thieno[3,2-b]pyrrole-5-carboxamido)octanoic acid;
6-(4-(4-(2-(ethyl(m-tolyl)amino)-2-oxoethyl)-4H-thieno[3,2-b]pyrrole-5-carboxamido)piperidin-1-yl)-6-oxohexanoic acid;
trans-methyl-4-(4-(2-(ethyl(m-tolyl)amino)-2-oxoethyl)-4H-thieno[3,2-b]pyrrole-5-carboxamido)cyclohexane-1-carboxylate;
trans-4-(4-(2-(ethyl(m-tolyl)amino)-2-oxoethyl)-4H-thieno[3,2-b]pyrrole-5-carboxamido)cyclohexane-1-carboxylic acid;
N-(trans-4-(butylcarbamoyl)cyclohexyl)-4-(2-(ethyl(m-tolyl)amino)-2-oxoethyl)-4H-thieno[3,2-b]pyrrole-5-carboxamide;
4-(2-(ethyl(m-tolyl)amino)-2-oxoethyl)-N-(trans-4-((2-hydroxyethyl)carbamoyl)cyclohexyl)-4H-thieno[3,2-b]pyrrole-5-carboxamide;
N-(trans-4-((2-(dimethylamino)ethyl)carbamoyl)cyclohexyl)-4-(2-(ethyl(m-tolyl)amino)-2-oxoethyl)-4H-thieno[3,2-b]pyrrole-5-carboxamide;
4-(trans-4-(4-(2-(ethyl(m-tolyl)amino)-2-oxoethyl)-4H-thieno[3,2-b]pyrrole-5-carboxamido)cyclohexane-1-carboxamido)butanoic acid;

N-(trans-4-carbamoylcyclohexyl)-4-(2-(ethyl(m-tolyl) amino)-2-oxoethyl)-4H-thieno[3,2-b]pyrrole-5-carboxamide;
4-(2-(ethyl(m-tolyl)amino)-2-oxoethyl)-N-(trans-4-(hexylcarbamoyl)cyclohexyl)-4H-thieno[3,2-b]pyrrole-5-carboxamide;
ethyl 1-(trans-4-(4-(2-(ethyl(m-tolyl)amino)-2-oxoethyl)-4H-thieno[3,2-b]pyrrole-5-carboxamido)cyclohexane-1-carbonyl)piperidine-4-carboxylate;
methyl 6-(trans-4-(4-(2-(ethyl(m-tolyl)amino)-2-oxoethyl)-4H-thieno[3,2-b]pyrrole-5-carboxamido)cyclohexane-1-carboxamido)hexanoate;
6-(trans-4-(4-(2-(ethyl(m-tolyl)amino)-2-oxoethyl)-4H-thieno[3,2-b]pyrrole-5-carboxamido)cyclohexane-1-carboxamido)hexanoic acid;
1-(trans-4-(4-(2-(ethyl(m-tolyl)amino)-2-oxoethyl)-4H-thieno[3,2-b]pyrrole-5-carboxamido)cyclohexane-1-carbonyl)piperidine-4-carboxylic acid;
8-(trans-4-(4-(2-(ethyl(m-tolyl)amino)-2-oxoethyl)-4H-thieno[3,2-b]pyrrole-5-carboxamido)cyclohexane-1-carboxamido)octanoic acid;
N-(trans-4-(cyclohexylcarbamoyl)cyclohexyl)-4-(2-(ethyl(m-tolyl)amino)-2-oxoethyl)-4H-thieno[3,2-b]pyrrole-5-carboxamide;
4-(2-(ethyl(m-tolyl)amino)-2-oxoethyl)-N-(trans-4-((1-methylpiperidin-4-yl)carbamoyl)cyclohexyl)-4H-thieno[3,2-b]pyrrole-5-carboxamide;
tert-butyl 4-(trans-4-(4-(2-(ethyl(m-tolyl)amino)-2-oxoethyl)-4H-thieno[3,2-b]pyrrole-5-carboxamido)cyclohexane-1-carboxamido)piperidine-1-carboxylate;
4-(2-(ethyl(m-tolyl)amino)-2-oxoethyl)-N-(trans-4-(piperidin-4-ylcarbamoyl)cyclohexyl)-4H-thieno[3,2-b]pyrrole-5-carboxamide;
N-(trans-4-((1-acetylpiperidin-4-yl)carbamoyl)cyclohexyl)-4-(2-(ethyl(m-tolyl)amino)-2-oxoethyl)-4H-thieno[3,2-b]pyrrole-5-carboxamide;
tert-butyl (6-(trans-4-(4-(2-(ethyl(m-tolyl)amino)-2-oxoethyl)-4H-thieno[3,2-b]pyrrole-5-carboxamido)cyclohexane-1-carboxamido)hexyl)carbamate;
N-(trans-4-((6-(3',6'-dihydroxy-3-oxo-3H-spiro[isobenzofuran-1,9'-xanthene]-5(6)-carboxamido)hexyl)carbamoyl)cyclohexyl)-4-(2-(ethyl(m-tolyl)amino)-2-oxoethyl)-4H-thieno[3,2-b]pyrrole-5-carboxamide;
N-(trans-4-((6-aminohexyl)carbamoyl)cyclohexyl)-4-(2-(ethyl(m-tolyl)amino)-2-oxoethyl)-4H-thieno[3,2-b]pyrrole-5-carboxamide hydrochloride;
4-(2-(ethyl(m-tolyl)amino)-2-oxoethyl)-N-(trans-4-((6-hydroxyhexyl) carbamoyl)cyclohexyl)-4H-thieno[3,2-b]pyrrole-5-carboxamide;
methyl-trans-4-(trans-4-(4-(2-(ethcyl(m-tolyl)amino)-2-oxoethyl)-4H-thieno[3,2-b]pyrrole-5-carboxamido)cyclohexane-1-carboxamido)cyclohexane-1-carboxylate;
trans-4-(trans-4-(4-(2-(ethyl(m-tolyl)amino)-2-oxoethyl)-4H-thieno[3,2-b]pyrrole-5-carboxamido)cyclohexane-1-carboxamido)cyclohexane-1-carboxylic acid;
(11S,14S,17S)-17-acetamido-11,14-bis(carboxymethyl)-1-(trans-4-(4-(2-(ethyl(m-tolyl)amino)-2-oxoethyl)-4H-thieno[3,2-b]pyrrole-5-carboxamido)cyclohexyl)-1,10,13,16-tetraoxo-2,9,12,15-tetraazanonadecan-19-oic acid;
4-(2-(ethyl(m-tolyl)amino)-2-oxoethyl)-N-methyl-4H-thieno[3,2-b]pyrrole-5-carboxamide;
N-cyclopentyl-4-(2-(ethyl(m-tolyl)amino)-2-oxoethyl)-4H-thieno[3,2-b]pyrrole-5-carboxamide;
4-(2-(ethyl(m-tolyl)amino)-2-oxoethyl)-N-(pyridin-4-ylmethyl)-4H-thieno[3,2-b]pyrrole-5-carboxamide;
4-(2-(ethyl(m-tolyl)amino)-2-oxoethyl)-N-(3-morpholinopropyl)-4H-thieno[3,2-b]pyrrole-5-carboxamide;
N-ethyl-2-(5-(4-methylpiperazine-1-carbonyl)-4H-thieno[3,2-b]pyrrol-4-yl)-N-(m-tolyl)acetamide;
N-cyclohexyl-4-(2-((2-(2-methoxyethoxy)ethyl)(m-tolyl)amino)-2-oxoethyl)-4H-thieno[3,2-b]pyrrole-5-carboxamide;
methyl-trans-4-(4-(2-((2-(2-methoxyethoxy)ethyl)(m-tolyl)amino)-2-oxoethyl)-4H-thieno[3,2-b]pyrrole-5-carboxamido)cyclohexane-1-carboxylate;
N-cyclohexyl-4-(2-(hexyl(m-tolyl)amino)-2-oxoethyl)-4H-thieno[3,2-b]pyrrole-5-carboxamide;
methyl-trans-4-(4-(2-(hexyl(m-tolyl)amino)-2-oxoethyl)-4H-thieno[3,2-b]pyrrole-5-carboxamido)cyclohexane-1-carboxylate;
6-(cis-4-(4-(2-(ethyl(m-tolyl)amino)-2-oxoethyl)-4H-thieno[3,2-b]pyrrole-5-carboxamido)cyclohexane-1-carboxamido)hexanoic acid;
methyl 6-(trans-4-((4-(2-(ethyl(m-tolyl)amino)-2-oxoethyl)-4H-thieno[3,2-b]pyrrole-5-carboxamido)methyl)cyclohexane-1-carboxamido)hexanoate;
6-(trans-4-((4-(2-(ethyl(m-tolyl)amino)-2-oxoethyl)-4H-thieno[3,2-b]pyrrole-5-carboxamido)methyl)cyclohexane-1-carboxamido)hexanoic acid;
sodium 6-(trans-4-(4-(2-(ethyl(m-tolyl)amino)-2-oxoethyl)-4H-thieno[3,2-b]pyrrole-5-carboxamido)cyclohexane-1-carboxamido)hexane-1-sulfonate;
potassium 6-(trans-4-(4-(2-(ethyl(m-tolyl)amino)-2-oxoethyl)-4H-thieno[3,2-b]pyrrole-5-carboxamido)cyclohexane-1-carboxamido)hexane-1-sulfonate;
trans-4-(4-(2-(hexyl(m-tolyl)amino)-2-oxoethyl)-4H-thieno[3,2-b]pyrrole-5-carboxamido)cyclohexane-1-carboxylic acid;
methyl trans-4-(4-(2-(ethyl(phenyl)amino)-2-oxoethyl)-4H-thieno[3,2-b]pyrrole-5-carboxamido)cyclohexane-1-carboxylate;
methyl trans-4-(4-(2-((3-cyanophenyl)(ethyl)amino)-2-oxoethyl)-4H-thieno[3,2-b]pyrrole-5-carboxamido)cyclohexane-1-carboxylate;
methyl trans-4-(4-(2-((3-carbamoylphenyl)(ethyl)amino)-2-oxoethyl)-4H-thieno[3,2-b]pyrrole-5-carboxamido)cyclohexane-1-carboxylate;
methyl trans-4-(4-(2-(ethyl(3-ethylphenyl)amino)-2-oxoethyl)-4H-thieno[3,2-b]pyrrole-5-carboxamido)cyclohexane-1-carboxylate;
methyl trans-4-(4-(2-(ethyl(3-methoxyphenyl)amino)-2-oxoethyl)-4H-thieno[3,2-b]pyrrole-5-carboxamido)cyclohexane-1-carboxylate;
methyl trans-4-(4-(2-(ethyl(o-tolyl)amino)-2-oxoethyl)-4H-thieno[3,2-b]pyrrole-5-carboxamido)cyclohexane-1-carboxylate;
methyl trans-4-(4-(2-(6-methyl-3,4-dihydroquinolin-1(2H)-yl)-2-oxoethyl)-4H-thieno[3,2-b]pyrrole-5-carboxamido)cyclohexane-1-carboxylate;
methyl trans-4-(4-(2-(ethyl(p-tolyl)amino)-2-oxoethyl)-4H-thieno[3,2-b]pyrrole-5-carboxamido)cyclohexane-1-carboxylate;
methyl trans-4-(4-(2-(ethyl(4-(hydroxymethyl)phenyl)amino)-2-oxoethyl)-4H-thieno[3,2-b]pyrrole-5-carboxamido)cyclohexane-1-carboxylate;
methyl trans-4-(1-(2-(ethyl(m-tolyl)amino)-2-oxoethyl)-1H-indole-2-carboxamido)cyclohexane-1-carboxylate;
methyl trans-4-(1-(2-(ethyl(m-tolyl)amino)-2-oxoethyl)-6-methoxy-1H-indole-2-carboxamido)cyclohexane-1-carboxylate;

methyl trans-4-(4-(2-(ethyl(m-tolyl)amino)-2-oxoethyl)-4H-furo[3,2-b]pyrrole-5-carboxamido)cyclohexane-1-carboxylate;
4-(2-(ethyl(3-ethylphenyl)amino)-2-oxoethyl)-N-(trans-4-((6-hydroxyhexyl)carbamoyl)cyclohexyl)-4H-thieno[3,2-b]pyrrole-5-carboxamide;
sodium 6-(trans-4-(4-(2-(ethyl(3-ethylphenyl)amino)-2-oxoethyl)-4H-thieno[3,2-b]pyrrole-5-carboxamido)cyclohexane-1-carboxamido)hexane-1-sulfonate;
methyl trans-4-(4-(2-(ethyl(3-isopropylphenyl)amino)-2-oxoethyl)-4H-thieno[3,2-b]pyrrole-5-carboxamido)cyclohexane-1-carboxylate;
methyl trans-4-(4-(2-(ethyl(3-(hydroxymethyl)phenyl)amino)-2-oxoethyl)-4H-thieno[3,2-b]pyrrole-5-carboxamido)cyclohexane-1-carboxylate;
methyl trans-4-(4-(2-((3-(bromomethyl)phenyl)(ethyl)amino)-2-oxoethyl)-4H-thieno[3,2-b]pyrrole-5-carboxamido)cyclohexane-1-carboxylate;
methyl trans-4-(4-(2-((3-(dimethylamino)phenyl)(ethyl)amino)-2-oxoethyl)-4H-thieno[3,2-b]pyrrole-5-carboxamido)cyclohexane-1-carboxylate;
methyl trans-4-(4-(2-(ethyl(3-isobutylphenyl)amino)-2-oxoethyl)-4H-thieno[3,2-b]pyrrole-5-carboxamido)cyclohexane-1-carboxylate;
methyl trans-4-(1-(2-(ethyl(3-ethylphenyl)amino)-2-oxoethyl)-1H-indole-2-carboxamido)cyclohexane-1-carboxylate;
1-(2-(ethyl(3-ethylphenyl)amino)-2-oxoethyl)-N-(trans-4-((6-hydroxyhexyl)carbamoyl)cyclohexyl)-1H-indole-2-carboxamide;
sodium 6-(trans-4-(1-(2-(ethyl(3-ethylphenyl)amino)-2-oxoethyl)-1H-indole-2-carboxamido)cyclohexane-1-carboxamido)hexane-1-sulfonate; and
methyl trans-4-(6-(2-(ethyl(m-tolyl)amino)-2-oxoethyl)-6H-thieno[2,3-b]pyrrole-5-carboxamido)cyclohexane-1-carboxylate,
or salt thereof.

14. A method of inhibiting an *Oplophorus*-derived luciferase the method comprising contacting the *Oplophorus*-derived luciferase with a compound of claim 1.

15. The method of claim 14, wherein the *Oplophorus*-derived luciferase comprises a polypeptide sequence of SEQ ID NO: 2.

16. A method for modulating luminescence of an *Oplophorus*-derived luciferase in a sample, the method comprising,
(a) contacting the sample with a coelenterazine substrate and the compound of claim 1; and
(b) detecting luminescence in the sample,
wherein the compound of claim 1 causes a decrease in the luminescence from the *Oplophorus*-derived luciferase.

17. A compound of formula (I), or a salt thereof:

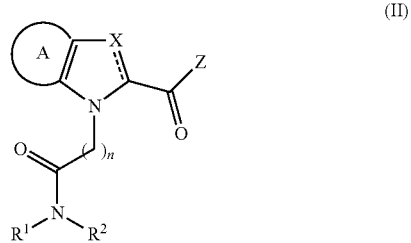

(II)

wherein:
the dashed line represents the presence or absence of a bond;
n is 0, 1, 2, 3, 4 or 5;
X is CH, N, O, or S;
  wherein, when the dashed line represents the presence of a bond, X is CH or N, and
  when the dashed line represents the absence of a bond, X is O or S;
A is an optionally substituted phenyl ring, or an optionally substituted 5or 6-membered heteroaryl ring;
$R^1$ is selected from the group consisting of hydrogen, optionally substituted $C_1$-$C_8$ alkyl, optionally substituted aryl, optionally substituted heteroaryl, optionally substituted arylalkyl, optionally substituted alkoxyalkyl and optionally substituted alkoxyalkoxyalkyl;
$R^2$ is phenyl substituted with one substituent selected from the group consisting of $C_1$-$C_4$ alkyl, cyano, amido, $C_1$-$C_4$ alkoxy, and hydroxyalkyl; and
$R^3$ and $R^4$ are each independently selected from the group consisting of hydrogen, optionally substituted $C_1$-$C_8$ alkyl, optionally substituted $C_3$-$C_8$-cycloalkyl, optionally substituted $C_3$-$C_8$-cycloalkylalkyl, optionally substituted aryl, optionally substituted arylalkyl, optionally substituted heteroaryl, optionally substituted heteroarylalkyl, optionally substituted heterocyclyl, and optionally substituted heterocyclylalkyl; or $R^3$ and $R^4$, together with the nitrogen atom to which they are attached, together form an optionally substituted ring.

18. The compound of claim 1, wherein
n is 1;
the dashed line represents the presence of a bond, X is CH; and
A is an optionally substituted phenyl ring.

19. The compound of claim 18, wherein $R^1$ is $C_1$-$C_8$ alkyl.

20. The compound of claim 19, wherein $R^2$ is optionally substituted phenyl.

21. The compound of claim 20, wherein $R^4$ is optionally substituted $C_3$-$C_8$ cycloalkyl.

22. The compound of claim 1, wherein
n is 1;
the dashed line represents the presence of a bond, X is CH; and
A is a thienyl ring or a furanyl ring.

23. The compound of claim 22, wherein $R^1$ is $C_1$-$C_8$ alkyl.

24. The compound of claim 23, wherein $R^2$ is optionally substituted phenyl.

25. The compound of claim 1, which is sodium 6-(trans-4-(4-(2-(ethyl(m-tolyl)amino)-2-oxoethyl)-4H-thieno[3,2-b]pyrrole-5-carboxamido)cyclohexane-1-carboxamido)hexane-1-sulfonate.

* * * * *

UNITED STATES PATENT AND TRADEMARK OFFICE
CERTIFICATE OF CORRECTION

PATENT NO. : 10,513,694 B2
APPLICATION NO. : 15/192420
DATED : December 24, 2019
INVENTOR(S) : Sarah Duellman et al.

It is certified that error appears in the above-identified patent and that said Letters Patent is hereby corrected as shown below:

In the Claims

Claim 1, Column 158, Line 53, delete "hydrogen,".

Claim 9, Column 159, Line 18, "$C_8$ alkyl" should read -- $C_8$-alkyl --.

Claim 13, Column 160, Lines 25-26, "The compound of claim 1, wherein the compound is selected from the group consisting of:" should read -- A compound, which is selected from the group consisting of: --.

Claim 17, Column 163, Line 53, "(II)" should read -- (I) --.

Claim 17, Column 163, the structure in Lines 54-62, currently reads:

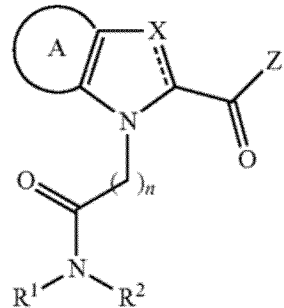

Signed and Sealed this
Nineteenth Day of May, 2020

Andrei Iancu
*Director of the United States Patent and Trademark Office*

CERTIFICATE OF CORRECTION (continued)
U.S. Pat. No. 10,513,694 B2

However, it should read:

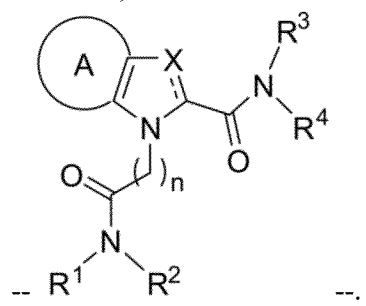

--          --.